US008642256B2

(12) United States Patent
Vogel et al.

(10) Patent No.: US 8,642,256 B2
(45) Date of Patent: Feb. 4, 2014

(54) KINASE AND UBIQUINATION ASSAYS

(75) Inventors: Kurt Vogel, Madison, WI (US); Steven Riddle, Madison, WI (US); Robert Horton, Madison, WI (US); Matthew Robers, Madison, WI (US); Gregory Michaud, Stow, MA (US); Thomas Machleidt, Madison, WI (US); Kevin Vedvik, Sun Prairie, WI (US); Kristin Huwiler, Madison, WI (US)

(73) Assignee: Life Technologies Corporation, Carlsbad, CA (US)

(*) Notice: Subject to any disclaimer, the term of this patent is extended or adjusted under 35 U.S.C. 154(b) by 493 days.

(21) Appl. No.: 12/508,513

(22) Filed: Jul. 23, 2009

(65) Prior Publication Data

US 2010/0151484 A1 Jun. 17, 2010

Related U.S. Application Data

(63) Continuation of application No. 11/554,553, filed on Oct. 30, 2006, now abandoned.

(60) Provisional application No. 60/832,114, filed on Jul. 21, 2006, provisional application No. 60/774,236, filed on Feb. 17, 2006, provisional application No. 60/759,545, filed on Jan. 18, 2006, provisional application No. 60/735,812, filed on Nov. 14, 2005, provisional application No. 60/731,310, filed on Oct. 28, 2005.

(51) Int. Cl.
*C12Q 1/00* (2006.01)

(52) U.S. Cl.
USPC ............................................................. 435/4

(58) Field of Classification Search
USPC ............................................................. 435/4
See application file for complete search history.

(56) References Cited

U.S. PATENT DOCUMENTS

| 4,927,923 | A | 5/1990 | Mathis et al. |
|---|---|---|---|
| 5,162,508 | A | 11/1992 | Lehn et al. |
| 5,220,012 | A | 6/1993 | Mathis et al. |
| 5,534,622 | A | 7/1996 | Lehn |
| 5,571,897 | A | 11/1996 | Takalo |
| 5,622,821 | A | 4/1997 | Selvin et al. |
| 5,639,615 | A | 6/1997 | Selvin et al. |
| 5,656,433 | A | 8/1997 | Selvin et al. |
| 2004/0214227 | A1 | 10/2004 | Joly |
| 2005/0054573 | A1 | 3/2005 | Werner et al. |
| 2005/0064485 | A1 | 3/2005 | Vogel |
| 2005/0170442 | A1 | 8/2005 | Kupcho et al. |

FOREIGN PATENT DOCUMENTS

| EP | 0745690 | 12/1996 |
|---|---|---|
| EP | 1498133 A1 | 1/2005 |
| WO | WO97/39064 | 10/1997 |
| WO | WO-01/08712 | 2/2001 |
| WO | WO-01/09188 | 2/2001 |
| WO | WO-01/36617 | 5/2001 |
| WO | WO-01/75142 | 10/2001 |
| WO | WO-01/96594 | 12/2001 |
| WO | WO-02/066982 | 8/2002 |
| WO | WO-03/011115 | 2/2003 |
| WO | WO-2004/020458 | 3/2004 |
| WO | WO-2005/026730 | 3/2005 |
| WO | WO-2007/051207 | 5/2007 |

OTHER PUBLICATIONS

Belz et al. "In vitro assays to study protein ubiquitination in transcription", Methods, 2002, 26:233-244.*
Mallery et al. "Activation of the E3 ligase function of the BRCA1/BARD1 complex by polyubiquitin chains", The EMBO Journal, 2002, 21(24):6755-6762.*
Tanaka et al. "NUB1-mediated targeting of the ubiquitin precursor UbC1 for its C-terminal hydrolysis" Eur. J. Biochem., 2004, 271:972-982.*
Kus et al. "A high throughput screen to identify substrates for the ubiquitin ligase Rsp5*", JBC, 2005, 280(33):29470-29478.*
Zhu et al. "Global analysis of protein activities using proteome chips", Science, 2001, 293:2101-2105.*
06839622.5, "Supplementary European Search Report", dated Feb. 12, 2009.
U.S. Appl. No. 11/554,553, "Office Action mailed Feb. 23, 2009", 09 pgs.
Amerik, Alexander Y. et al., "Analysis of the Deubiquitinating Enzymes of the yeast *Saccharomyces cerevisiae*", *Biol. Chem.* vol. 381, 2000, 981-992.
Auger, et al., "Quantitative Assays of Mdm2 Ubiquitin Ligase Activity and Other Ubiquitin-Utilizing Enzymes for Inhibitor Discovery", *Methods in Enzymology* vol. 399, 2005, 701-717.
Baker, et al., "Ubiquitin-specific proteases of *Saccharomyces cerevisiae*. Cloning of UBP2 and UBP3, and functional analysis of the UBP gene family", *The Journal of Biological Chemistry* vol. 267, No. 32, 1992, 23364-23375.
Chung, et al., "Deubiquitinating enzymes: their diversity and emerging roles", *Biochem. Biophys. Res. Comm.* 266, 1999, 633-40.
Ciechanover, et al., "Degradation of MyoD by the ubiquitin pathway: regulation by specific DNA-binding and identification of a novel site for ubiquitination", *Mol. Biol. Rep.* 26, 1999, 59-64.
Ciechanover, et al., "The ubiquitin-proteasome pathway: the complexity and myriad functions of proteins death.", *Proceedings of the National Academy of Sciences (PNAS)* vol. 95, 1998, 2727-2730.
Cubitt, Andrew B. et al., "Understanding structure-function relationships in the *Aequorea victoria* green fluorescent protein", *Methods in Cell Biology* vol. 58 1999, 19-30.
Fuchs, et al., "c-Jun NH2-terminal Kinases Target the Ubiquitination of Their Associated Transcription Factors", *The Journal of Biological Chemistry* vol. 272, No. 51 1997, 32163-32168.
Hershko, et al., "The ubiquitin system", *Annu. Rev. Biochem.* 67 1998, 425-479.

(Continued)

*Primary Examiner* — Bin Shen

(57) ABSTRACT

Compositions, including antibodies, polypeptides, and organic molecules, kits, and methods for probing molecular interactions (e.g., deubiquination, ubiquination and kinase activity), e.g., using resonance energy transfer (RET) are provided.

17 Claims, 50 Drawing Sheets

(56) References Cited

OTHER PUBLICATIONS

Hodgins, et al., "The Tail of a Ubiquitin-conjugating Enzyme Redirects Multi-ubiquitin Chain Synthesis from the Lysine 48-linked Configuration to a Novel Nonlysine-linked Form.", *The Journal of Biological Chemistry* vol. 271, No. 46 1996, 28766-28771.

Kuningas, K., "Homogeneous Assay Technology Based on Upconverting Phosphors", *Anal. Chem.* vol. 77, No. 22 2005, 7348-7355.

PCT/US06/060373, "International Search Report mailed Apr. 20, 2007".

PCT/US2006/060373, "International Preliminary Report on Patentablity".

PCT/US2006/060373, "Written Opinion", Apr. 20, 2007.

Perroy, Julie et al., "Real-time monitoring of ubiquitination in living cells by BRET", *Nature Methods* vol. 1, No. 3 Dec. 1, 2004, 203-208.

Pray, et al., "Cell cycle regulatory E3 ubiquitin ligases as anticancer targets", *Drug Resistance Updates* 5 2002, 249-58.

Riddle, Steven M. et al., "Time-resolved fluorescence resonance energy transfer kinase assays using physiological protein substrates: Applications of terbium-fluorescein and terbium-green fluorescent protein fluorescence resonance energy transfer pairs", *Analytical Biochemistry* vol. 356, No. 1 2006, 108-116.

Schmid, J. et al., "Dynamics of NFκB and IκBα studied with green fluorescent protein (GFP) fusion proteins", *The Journal of Biological Chemistry* vol. 275, No. 22 2000, 17035-17042.

Ulrich, "Mutual interactions between the SUMO and ubiquitin systems: a plea of no contest.", *Trends in Cell Biology* vol. 15, No. 10 2005, 525-532.

Voges, et al., "The 26S proteasome: a molecular machine designed for controlled proteolysis.", *Annul. Rev. Biochem.* 68 1999, 1015-1068.

Wilkinson, "Regulation of ubiquitin-dependent processes by deubiquitinating enzymes.", *The FASEB Journal* vol. 11 1997, 1245-1256.

Wilkinson, et al., "Synthesis and Characterization of Ubiquitin Carboxyl-Terminal Hydrolase", *Biochemistry* vol. 25, No. 21 1986, 6644-6649.

Xu, Y. et al., "A bioluminescence resonance energy transfer (BRET) system: application to interacting circadian proteins", *Proceedings of the National Academy of Sciences (PNAS)* vol. 96 1999, 151-156.

Xu, Y. et al., "Bioluminescence resonance energy transfer(BRET) : a new technique for monitoring protein-protein interactions in living cells", *Methods in Enzymol* vol. 360 2003, 289-301.

Yao, et al., "Cyclization of Polyubiquitin by the E2-25K Ubiquitin Conjugating Enzyme", *The Journal of Biological Chemistry* vol. 275, No. 47 2000, 36862-36868.

Zhang, Ji-Hu et al., "A Simple Statistical Parameter for Use in Evaluation and Validation of High Throughout Screening Assays", *Journal of Biomolecular Screening* vol. 4, No. 2 1999, 67-73.

09180259.5, "Extended European Search Report mailed Nov. 3, 2010".

Hong, C. A. et al., "Development of a High Throughout Time-Resolved Fluorescence Resonance Energy Transfer Assay for TRAF6 Ubiquitin Polymerization", *Assay and Drug Development Technologies,*, vol. 1. No. 1-2, 2003, 175-180 pgs.

Takakusa, et al., Design and Synthesis of an Enzyme-Cleavable Sensor Molecule for Phosphodiesterase Activity Based on Fluorescence Resonance Energy Transfer, *J. Am. Chem. Soc.*, vol. 24, No. 8, 2002, 1653-1657.

Boisclair, et al., Development of a ubiquitin transfer assay for high throuphput screening by fluorescence resonance energy transfer, *Journal of Biomolecular Screening*, vol. 5, Issue 5,, Oct. 2000, 319-328.

Horton, Robert A. et al., "A substrate for deubiquitinating enzymes based on time-resolved fluorescence resonance energy transfer between terbium and yellow fluorescent protein", *Analytical Biochemistry*, vol. 360, 2007, 138-143.

\* cited by examiner

LanthaScreen™ Tb-Ubiquitin/GFP    Biotin-Ubiquitin/Tb-Streptavidin/GFP

Expression Clone/pcDNA 6.2 N EmGFP DEST/pENTR221I

GFP-IkBalpha Coding Sequence

ATGGTGAGCAAGGGCGAGGAGCTGTTCACCGGGGTGGTGCCCATCCTGGTCGAGC
TGGACGGCGACGTAAACGGCCACAAGTTCAGCGTGTCCGGCGAGGGCGAGGGCGA
TGCCACCTACGGCAAGCTGACCCTGAAGTTCATCTGCACCACCGGCAAGCTGCCC
GTGCCCTGGCCCACCCTCGTGACCACCTTCACCTACGGCGTGCAGTGCTTCGCCC
GCTACCCCGACCACATGAAGCAGCACGACTTCTTCAAGTCCGCCATGCCCGAAGG
CTACGTCCAGGAGCGCACCATCTTCTTCAAGGACGACGGCAACTACAAGACCCGC
GCCGAGGTGAAGTTCGAGGGCGACACCCTGGTGAACCGCATCGAGCTGAAGGGCA
TCGACTTCAAGGAGGACGGCAACATCCTGGGGCACAAGCTGGAGTACAACTACAA
CAGCCACAAGGTCTATATCACCGCCGACAAGCAGAAGAACGGCATCAAGGTGAAC
TTCAAGACCCGCCACAACATCGAGGACGGCAGCGTGCAGCTCGCCGACCACTACC
AGCAGAACACCCCCATCGGCGACGGCCCCGTGCTGCTGCCCGACAACCACTACCT
GAGCACCCAGTCCGCCCTGAGCAAAGACCCCAACGAGAAGCGCGATCACATGGTC
CTGCTGGAGTTCGTGACCGCCGCCGGGATCACTCTCGGCATGGACGAGCTGTACA
AGGGCTCGAGCCCATCAACAAGTTTGTACAAAAAAGCAGGCACCATGTTCCAGGC
GGCCGAGCGCCCCCAGGAGTGGGCCATGGAGGGCCCCCGCGACGGGCTGAAGAAG
GAGCGGCTACTGGACGACCGCCACGACAGCGGCCTGGACTCCATGAAAGACGAGG
AGTACGAGCAGATGGTCAAGGAGCTGCAGGAGATCCGCCTCGAGCCGCAGGAGGT
GCCGCGCGGCTCGGAGCCCTGGAAGCAGCAGCTCACCGAGGACGGGGACTCGTTC
CTGCACTTGGCCATCATCCATGAAGAAAAGGCACTGACCATGGAAGTGATCCGCC
AGGTGAAGGGAGACCTGGCCTTCCTCAACTTCCAGAACAACCTGCAGCAGACTCC
ACTCCACTTGGCTGTGATCACCAACCAGCCAGAAATTGCTGAGGCACTTCTGGGA
GCTGGCTGTGATCCTGAGCTCCGAGACTTTCGAGGAAATACCCCCCTACACCTTG
CCTGTGAGCAGGGCTGCCTGGCCAGCGTGGGAGTCCTGACTCAGTCCTGCACCAC
CCCGCACCTCCACTCCATCCTGAAGGCTACCAACTACAATGGCCACACGTGTCTA
CACTTAGCCTCTATCCATGGCTACCTGGGCATCGTGGAGCTTTTGGTGTCCTTGG
GTGCTGATGTCAATGCTCAGGAGCCCTGTAATGGCCGGACTGCCCTTCACCTCGC
AGTGGACCTGCAAAATCCTGACCTGGTGTCACTCCTGTTGAAGTGTGGGGCTGAT
GTCAACAGAGTTACCTACCAGGGCTATTCTCCTACCAGCTCACCTGGGGCCGCC
CAAGCACCCGGATACAGCAGCAGCTGGGCCAGCTGACACTAGAAAACCTTCAGAT
GCTGCCAGAGAGTGAGGATGAGGAGAGCTATGACACAGAGTCAGAGTTCACGGAG
TTCACAGAGGACGAGCTGCCCTATGATGACTGTGTGTTTGGAGGCCAGCGTCTGA
CGTTATAG (SEQ ID NO:27)

FIG 32B

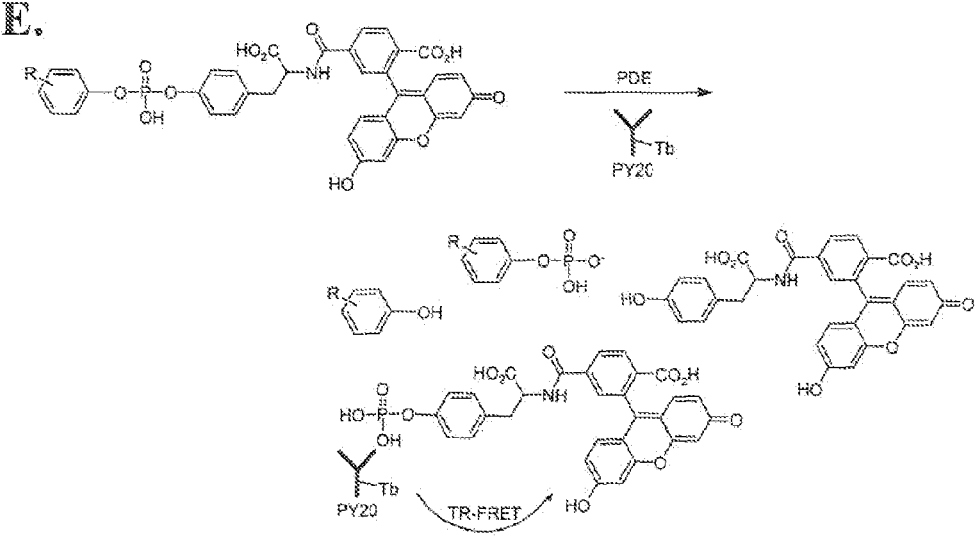
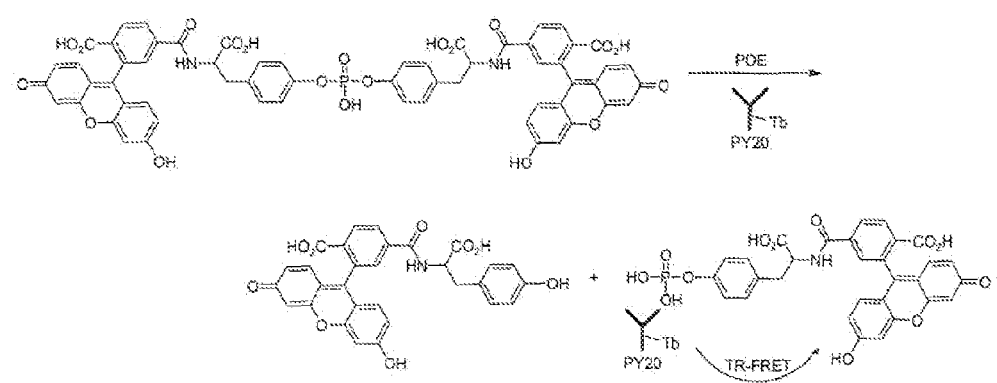
FIG 42

KINASE AND UBIQUINATION ASSAYS

CROSS REFERENCE TO RELATED APPLICATIONS

This application is a continuation of U.S. application Ser. No. 11/554,553, filed Oct. 30, 2006, abandoned, which claims the benefit of U.S. Provisional Application No. 60/832,114, filed Jul. 21, 2006, U.S. Provisional Application No. 60/774,236, filed Feb. 17, 2006, U.S. Provisional Application No. 60/759,545, filed Jan. 18, 2006, U.S. Provisional Application No. 60/735,812, filed Nov. 14, 2005, and U.S. Provisional Application No. 60/731,310, filed Oct. 28, 2005, the disclosures of all of which are incorporated herein by reference in their entireties.

TECHNICAL FIELD

This invention relates to assays employing a fluorescent molecule and a luminescent metal complex and to methods for monitoring and measuring molecular interactions, such as competitive binding or enzymatic activity (e.g., kinase, de-ubiquinating or ubiquination activity).

BACKGROUND

Ubiquitination primarily serves as a targeting signal, and proteins carrying the most common type of poly-Ubiquitin chain are targeted for destruction by the ubiquitin-proteasome pathway, responsible for the majority of cytosolic proteolysis (Ciechanover et al., Proc. Natl. Acad. Sci. USA, 95, 2727-30, 1998), Ubiquitin (Ub) is attached to proteins through an isopeptide linkage, involving the C-terminal carboxylate of Ub and the c-NH2 of a lysine side chain, (Ciechanover et al., Mot Biol Rep, 26, 59-64, 1999; Hodgins et al., J. Biol. Chem., 271, 30 28766-28771, 1996). The enzyme cascade involved in Ub-conjugation and poly-Ub chain formation comprises at least three distinct sets of enzymatic activities including the Ub activating enzyme E1, Ub-conjugating enzymes (E2) and E3 ligases (reviewed in Hershko and Ciechanover, Annu Rev Biochem, 67, 425-79, 1998), Removal of Ub is carried out by deubiquitinating enzymes (DUBs) or deconjugating enzymes (DCEs). These are a large family of proteases that can release poly-Ub chains from proteins to be degraded by the 26S proteasome, recycle monomeric Ub, liberate Ub from the Ub-fusion protein precursors, reverse regulatory ubiquitination and edit inappropriately ubiquitinated proteins (reviewed in Chung et al., Biochem Biophys Res Comm, 266, 633-40, 1999). DUBs can be subdivided into Ub C-terminal hydrolases (UCHs) and Ub-specific processing proteases (UBPs). In vitro, UBPs hydrolyze isopeptide bonds between Ub and folded protein domains, such as additional Ub moieties or target proteins. Thus, UBPs exhibit broad substrate specificity (Wilkinson, FASEBJ, 11, 1245-56, 1997). UCHs generally cleave bonds between Ub and an unfolded polypeptide or Ub and small substituents (Pickart et al., J. Biol. Chem., 260, 7903-10, 1985; Wilkinson, FASEB J, 11, 1245-56, 1997; Wilkinson et al., Biochemistry, 25, 6644-9, 1986). Deletion studies in yeast suggest that the: substrate specificities of UCHs and UBPs overlap (Amerik et al., Biol Chem, 381, 981-92, 15 2000; Baker et al., J Biol Chem, 267, 23364-75, 1992). Both UBPs and UCHs can associate with the 26S proteasome and are involved in the regulation of Ub-dependent proteolysis: (Voges et al., Annul Rev. Biochem, 68, 1999).

Ubiquitination and deubiquitination are emerging as regulatory mechanisms controlling, e.g., proteolysis, protein-protein interactions, DNA repair, and cellular signaling. Recently, USP2 and UCH37 have been shown to deubiquinate tumor-growth-promoting proteins, and other DUBs have been shown to be overexpressed in cancer cells. Therefore inhibition of DUBs is of interest as a potential therapeutic strategy, e.g., for treating cancer. The broad involvement of ubiquitin systems in cellular processes, including proliferation of cancer cells, provides an attractive set of potential drug targets. Most assay formats rely heavily on low throughput methods or customized reagents.

Small Ubiquitin-related Modifier (SUMO) proteins are small proteins that are covalently attached to and detached from other proteins in cells to modify their function. SUMOylation is a post-translational modification involved in various cellular processes, such as nuclear-cytosolic transport, transcriptional regulation, apoptosis, protein stability, response to stress, and progression through the cell cycle. SUMO proteins are similar to ubiquitin (Ulrich, Trends Cell Biol. 2005 Oct.; 15(10):525-32). In contrast to ubiquitin, SUMO is typically not used to tag proteins for degradation. The protein is typically not active until the last four amino acids of the C-terminus have been cleaved off.

The majority of non-radioactive kinase assays depend on phosphorylation of a chemically synthesized peptide substrate of up to approximately 20 residues. Although, it would be preferable to use larger native substrates (such as whole proteins or protein domains) that are "physiologically relevant" (i.e. they can be the "native" substrate of a kinase in a biologically relevant pathway). The use of "native" substrates is a desirable feature for many practitioners of kinase assays. As an example, it is known that some kinases require a "docking" site far removed from the site of phosphorylation in order to be phosphorylated. In some cases, smaller peptide substrates do not function as substrates.

Drug discovery can involve the systematic and/or high-throughput screening of diverse chemical libraries containing thousands of members. The size and complexity of these libraries, when coupled with the expense and length of the FDA approval process, have resulted in the need for simple, efficient, and homogeneous assays for probing molecular interactions.

Luminescence-based techniques, including fluorescence polarization (FP), resonance energy transfer (RET), and luminescence resonance energy transfer methods (LRET) methods, are typically highly sensitive, homogenous methods for probing molecular interactions. Background luminescence (e.g., fluorescence or luminescence from assay components) and non-specific interactions of assay components, however, can limit the sensitivity of luminescence-based assays, particularly when luminophores having short lifetimes are used, resulting in the detection of false positives or false negatives in a drug or compound screen. Follow-up screening of individually-picked compounds or the use of multiple screens may be required to validate screen results. It would be useful to have screening methodologies that could increase the information content of fluorescent or luminescent assays and reduce the number of spurious results encountered in drug screens.

SUMMARY

In various aspects, the invention provides compositions, methods, apparatuses, and kits useful for monitoring molecular interactions, including competitive binding events and those resulting from enzymatic activities. In some aspects, the invention provides compositions and methods for detection and/or identification of molecular modification (e.g., post-translation modification) events, as well as detection and/or identification of molecular modification activities. In many instances, the result of molecular modification events are detected by changes in optical properties (e.g., changes in optical properties of (1) the molecules which are modified or (2) a composition which contains these molecules).

In one embodiment, the invention utilizes a donor moiety (e.g., a luminescent metal complex (e.g. Terbium)) and an acceptor moiety (e.g., a fluorescent protein or polypeptide (e.g. GFP)). In another embodiment, the invention utilizes a luminescent metal complex (e.g. Terbium or Europium) and a fluorophore (e.g. fluorescein). In one embodiment, the invention provides a method of measuring enzymatic activity utilizing a fluorescent molecule and a luminescent metal complex. In one embodiment, the fluorescent molecule and luminescent metal complex are located on two binding partners, respectively. In one embodiment, the fluorescent molecule and luminescent metal complex are located on one molecule, e.g. the substrate for an enzyme. In one embodiment, the activity of an enzyme(s) (e.g. ubiquitination enzymes) "ligates" at least two molecules. In one embodiment, each of the two molecules comprises one part of a resonance energy transfer pair. In one embodiment, one molecule comprises a fluorescent molecule and the other molecule comprises a luminescent metal complex. In one embodiment, one molecule comprises both parts of a RET pair (e.g. creating a RET capable molecule). In one embodiment, this molecule comprises both a fluorescent molecule and a luminescent metal complex. The present invention includes related compositions, for example, a composition comprising two molecules that each comprises one part of a resonance energy transfer pair. The composition can optionally include an enzyme capable of "ligating" the two molecules.

In one embodiment of the invention, the activity of the enzyme disrupts or inhibits a RET capable molecule or the formation of a RET capable complex. In one embodiment, the activity of an enzyme(s) (e.g., deubiquinating enzyme or protease) cleaves a molecule comprised of a fluorescent molecule and a luminescent metal complex (e.g. disrupting a FRET capable molecule). In one embodiment, the activity of an enzyme(s) phosphorylates or dephosphorylates (e.g., modulates phosphorylation) a molecule comprised of a fluorescent molecule or a luminescent metal complex.

In one embodiment, the invention provides a method for measuring the effect of a test compound on binding between a first binding partner and a second binding partner. In one embodiment, the method includes contacting a first binding partner, a second binding partner, and a test compound (e.g., a kinase or small molecule drug candidate) to form a test sample. In some embodiments, the first binding partner and the second binding partner includes a luminescent metal complex, while the other includes a fluorescent acceptor moiety. A first binding partner and a second binding partner are capable of binding to one another to form a complex.

In one method, a test sample is exposed to light and the fluorescent emission from the test sample is measured. In one embodiment, the test sample is exposed to light having a wavelength in the range from 100 nm to 2000 nm and the fluorescence emission of the test sample is measured. In one embodiment, the test compound is identified as affecting binding between the first binding partner and the second binding partner when the fluorescence emission measurement of the test sample is different from the fluorescence emission measurement of a corresponding control sample, e.g., lacking the test compound. In one embodiment, the emission (e.g., fluorescence) measurement(s) involves a ratiometric calculation. In one embodiment, a ratiometric calculation comprises a ratio of the fluorescence emission of a test sample versus a control sample. In another embodiment, a ratiometric calculation comprises a ratio of the fluorescence emission of the acceptor molecule (e.g., fluorescein or GFP) versus the fluorescence emission of the donor molecule of a RET pair (e.g., lanthanide metal complex). In another embodiment, a ratiometric measurement comprises both a ratio of fluorescence emission of the test sample versus the control sample and a ratio of the fluorescence emission of the acceptor molecule (e.g., fluorescein or GFP) versus the fluorescence emission of the donor molecule of a RET pair (e.g., lanthanide metal complex).

A first binding partner and a second binding partner can be independently selected from the group consisting of a protein or polypeptide, a polynucleotide, a lipid, a polysaccharide, a hormone, and a small organic compound. In some embodiments, a polypeptide can be an antibody or antibody fragment. Fluorescent acceptor moieties can be selected from, but not limited to, the group consisting of fluorescein, rhodamine, GFP, GFP derivatives, FITC, 5-FAM, 6-FAM, 7-hydroxycoumarin-3-carboxamide, 6-chloro-7-hydroxycoumarin-3-carboxamide, fluorescein-5-isothiocyanate, dichlorotriazinylaminofluorescein, tetramethylrhodamine-5-isothiocyanate, tetramethylrhodamine-6-isothiocyanate, succinimidyl ester of 5-carboxyfluorescein, succinimidyl ester of 6-carboxyfluorescein, 5-carboxytetramethylrhodamine, 6-carboxymethylrhodamine, and 7-amino-4-methylcoumarin-3-acetic acid.

Examples of donor moieties include a luminescent metal complex such as a lanthanide metal complex. A lanthanide metal complex can include an organic antenna moiety, a metal liganding moiety and a lanthanide metal ion. A lanthanide metal ion can be selected from the group consisting of: Sm(III), Ru(III), Eu (III), Gd(III), Tb(III), and Dy(III). In one embodiment, the lanthanide metal ion is terbium (Tb). An organic antenna moiety can be selected from the group consisting of: rhodamine 560, fluorescein 575, fluorescein 590, 2-quinolone, 4-quinolone, 4-trifluoromethylcoumarin (TFC), 7-diethyl-amino-coumarin-3-carbohydrazide, 7-amino-4-methyl-2-coumarin (carbostyril 124), 7-amino-4-methyl-2-coumarin (coumarin 120), 7-amino-4-trifluoromethyl-2-coumarin (coumarin 124), and aminomethyltrimethylpsoralen. A metal liganding moiety can be a metal chelating moiety selected from the group consisting of: EDTA, DTPA, TTHA, DOTA, NTA, HDTA, DTPP, EDTP, HDTP, NTP, DOTP, DO3A, DOTAGA, and NOTA.

In some embodiments, a lanthanide metal complex has a structure:

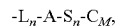

or

-$L_n$-$C_M$-$S_n$-A, where A represents an organic antenna moiety; L represents a linker; S represents a spacer; n can be 0 or 1; C represents a metal chelating moiety; and M represents a lanthanide metal ion coordinated to C.

In another aspect, the invention provides a method for identifying a modulator of an enzymatic activity. In one embodiment, a method includes contacting an enzyme(s) (e.g., kinase, protease, de-ubiquitinating enzyme, ubiquination enzyme) with a substrate(s) for the enzyme and measuring the enzymatic product. In one embodiment, the enzymatic reaction is performed in the presence of a modulator or potential modulator of the enzymatic activity. In one embodiment, the enzyme, substrate(s), and potential modulator are then contacted with a first binding partner and a tracer to form a test sample. The first binding partner has binding specificity for either the enzymatic product or the substrate of the enzymatic activity. In one embodiment, a first binding partner is capable of binding the tracer.

The tracer can be unlabeled or it can include a luminescent metal complex or a fluorescent acceptor moiety, e.g., a "luminescent tracer." For example, in one embodiment of the method, one of a first binding partner or a tracer includes a luminescent metal complex (e.g. Terbium), while the other includes a fluorescent acceptor moiety. In other embodiments, a first binding partner and a substrate includes a luminescent metal complex, while the other includes a fluorescent acceptor moiety (e.g., fluorescein or GFP).

A test sample is then exposed to light and the fluorescent emission from the test sample is measured. In one embodiment, the test sample is exposed to one wavelength of light or a range of wavelengths (e.g., a 10 nm, 15 nm, 20 nm, 30 nm, or 50 nm band or range of wavelength). In one embodiment, the test sample can also be exposed to light having at least one wavelength in the range from 100 nm to 2000 nm (e.g., a wavelength of light in the range from 250 nm to 750 nm, 250 nm to 300 nm, 250 nm to 400 nm, 250 nm to 500 nm, 250 nm to 600 nm, 250 nm to 700 nm, 350 nm to 700 nm, 450 nm to 700 nm, 500 nm to 1000 nm, 1000 nm to 2000 nm, 100 nm to 400 nm, etc.) and the fluorescence emission from the test sample is measured. In one embodiment, a potential modulator is identified as a modulator of the enzymatic activity when the fluorescence emission measurement of the test sample is different from the fluorescence emission measurement of a corresponding control sample lacking or containing less of the potential modulator. The fluorescence emission of a test sample or a control sample can be measured at two or more wavelengths. In one embodiment, a ratio of fluorescence emission measurements of a test sample or a control sample at two wavelengths is calculated.

An enzymatic activity can be selected from the group consisting of kinase activity, phosphatase activity, glucuronidase activity, prenylation, glycosylation, methylation, demethylation, acylation, acetylation, ubiquitination, deubiquitination, sulfation, proteolysis, nuclease activity, nucleic acid polymerase activity, nucleic acid reverse transcriptase activity, nucleotidyl transferase activity, and polynucleotide translation activity.

In some aspects of the invention, components of the assays can be from various sources, e.g., purified, partially purified and/or cell lysates. Each component may be from the same, different or various combinations of sources. In one embodiment, an enzyme (e.g., kinase, ubiquitinase (ubiquitinating enzyme), or DUB, and protease) is from a cell lysate. In one embodiment, the substrate or potential substrate for the enzyme is from a cell lysate.

As in some embodiments of the present invention, preparing protease (e.g., DUB) substrates with a genetically encoded acceptor fluorophore, avoids difficult "orthogonal" labeling strategies to site-specifically incorporate two distinct fluorophores into a single protein. In the case of whole-protein kinase substrates, labeled proteins are typically prepared through a random labeling of surface-accessible amine groups. As in one embodiment of the present invention, preparing enzyme substrates as fluorescent protein fusions, leads to improved lot-to-lot consistency of the substrate, which is a consideration in developing reagents for high-throughput screening applications.

Some embodiments of the invention provide cellular based assays. For example, wherein the cell expresses a fusion protein comprising a label (e.g., an acceptor label, a donor label or a fluorescent protein such as a GFP) and a substrate fbr a post-translational modification (e.g., a substrate for ubiquitination or a potential ubiquitination substrate), wherein the status of the post-translational modification and/or rate of post-translational modification of the substrate or a potential ubiquitination substrate is of interest. In some embodiments, a binding partner (e.g., an antibody) is utilized that preferentially binds the modified or unmodified substrate fusion protein.

Some embodiments provide methods for determining if a compound is a modulator of a post-translational modification. Sonic embodiments provide an assay for determining, monitoring or quantitating the post-translational modification comprising expressing the fusion protein in a cell, lysing the cell and contacting the cell lysate (e.g., a crude, partially purified or purified cell lysate) with a binding partner whose binding is regulated by the post-translational modification. For example, the binding partner may have a greater affinity for the unmodified as compared to the post-translationally modified protein or vice versa. In some embodiments, the binding partner binds a compound (e.g., a peptide or a polypeptide) that is added, attached to or associated with the substrate fusion protein as part of the post-translational modification. In some embodiments, the binding partner binds a compound (e.g., a peptide or a polypeptide) that is removed or disassociated from the substrate fusion protein as part of the post-translational modification.

In some embodiments, the binding partner is labeled. In some embodiments, the binding partner comprises a label that is capable of forming a RET pair with the label on the fusion protein. In some embodiments, the binding partner (e.g., an antibody) is not labeled. in some aspects of the invention, the binding partner is utilized to preferentially immobilize the modified or un-modified substrate/label fusion protein. Then the binding can be detected, e.g., by exciting and detecting the label of the fusion protein.

Most if not all ubiquitination assays are either performed without intact/living cells or use lysed-cell starting points or semi-purified systems to assay protein ubiquitination. The inventors describe herein assays that utilize a living cell (starting point), Additionally, these cellular based assays can be used, inter alia, to test the ability of a compound to diffuse into a living cell or act on the cell surface (e.g., bind and/or block a receptor) and inhibit, enhance/up-regulate or modulate an activity of a ubiquitination machinery or a pathway in the context of the living cell. This provides the user a means to dissecting a ubiquitin-related pathway, e.g., in a context that is less "artificial" than other technologies. The cellular assays of the invention can be utilized fbr high-throughput and in some embodiments take advantage of the user friendly qualities of existing TR-FRET assays.

Some embodiments of the invention involve a set of generic TR-FRET ubiquitin reagents for both ubiquitination and deubiquitination. By selectively incorporating the TR-FRET donor (e.g., terbium) and acceptors (e.g., fluorescein or fluorescent proteins) onto ubiquitin, universal high throughput screening reagents were created that enable robust HTS assays with high Z' values (>0.7) with either kinetic or endpoint readout. In addition, the time resolved signal from the terbium donor reduces the amount of interference from color quenchers and autofluorescent compounds that are frequently encountered in compound libraries. In some embodiments of the invention, TR-FRET ubiquitin platforms are provided herein as a simple, flexible set of reagents to accelerate compound screening to identify specific inhibitors of ubiquitin conjugating and deubiquitinating enzymes.

The invention also provides articles of manufacture. An article of manufacture, such as a kit, can include packaging material; and a first binding partner and/or a second binding partner, where the second binding partner is capable of binding the first binding partner, in one embodiment, a binding partner can comprise a luminescent metal complex or a fluorescent acceptor moiety. In one embodiment, the article of manufacture comprises a fusion protein comprised of a fluorescent peptide domain (e.g. GFP) and a ubiquitin domain, wherein said ubiquitin domain is linked to a luminescent metal complex (e.g., Terbium).

In another aspect, the invention provides compositions. In one embodiment, a composition can be a first binding partner, a second binding partner, or a mixture thereof In one embodiment, a binding partner can include a fluorescent acceptor moiety or a luminescent metal chelate. In one embodiment, a composition comprises a fusion protein comprised of a fluorescent peptide domain (e.g. GFP) and a ubiquitin domain, wherein said ubiquitin domain is linked to a luminescent metal complex (e.g., Terbium).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

For the purpose of illustrating the invention, there are depicted in the drawings certain embodiments on the invention. However, the invention is not limited to the precise arrangements and instrumentalities of the embodiments depicted in the drawings.

FIGS. 11E & 11F utilize a terbium labeled antibody. One skilled in the art will recognize other similar variations and combinations of attaching/binding a lanthanide metal complex and a fluorescent acceptor (e.g., a GFP polypeptide or protein), which are all contemplated by the present invention. GFP is depicted as an example of a label and as an example of an acceptor label. Terbium (Tb) is depicted as an example of a label and as an example of a donor label. The invention is not meant to be limited to GFP or Tb but contemplates the use of essentially any labels including any compatible donor or acceptor labels for RET. Additionally, any time the term ubiquitin is used in the figure it can refer to either mono-ubiquitin or poly-ubiquitin or any ubiquiton. Abbreviations: SA-Streptavidin; B-Biotin

FIG. 32B shows a coding sequence for an EmGFP-IkBa (SEQ ID NO:27).

DETAILED DESCRIPTION

Definitions

Figure 1:
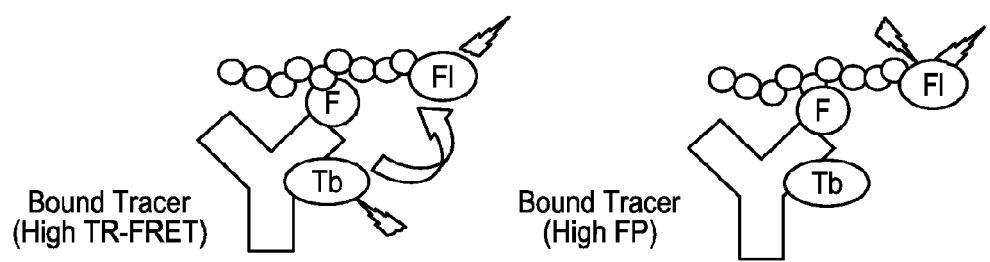
FIG. 1 is a schematic indicating one embodiment of a TR-RET assay.

Generally, the nomenclature used herein and many of the fluorescence, luminescence, computer, detection, chemistry, and laboratory procedures described herein are commonly employed in the art. Standard techniques are generally used for chemical synthesis, fluorescence or luminescence monitoring and detection, optics, molecular biology, and computer software and integration. Chemical reactions, cell assays, and enzymatic reactions are typically performed according to the manufacturer's specifications where appropriate. See, generally, Lakowicz, J. R. *Topics in Fluorescence Spectroscopy*, (3 volumes) New York: Plenum Press (1991), and Lakowicz, J. R. *Emerging applications of florescence spectroscopy to cellular imaging: lifetime imaging, metal-ligand probes, multi photon excitation and light quenching*, Scanning Microsc. Suppl. Vol. 10 (1996) pages 213-24, for fluorescence techniques; Sambrook et al., *Molecular Cloning: A Laboratory Manual*, 2ed. (1989) Cold Spring Harbor Laboratory Press, Cold Spring Harbor, N.Y., for molecular biology methods; *Cells: A Laboratory Manual*, 1st edition (1998) Cold Spring Harbor Laboratory Press, Cold Spring Harbor, N.Y., for cell biology methods; and *Optics Guide* 5 Melles Griot® Irvine Calif., and *Optical Waveguide Theory*, Snyder & Love (published by Chapman & Hall) for general optical methods, all of which are incorporated herein by reference. General methods for performing a variety of fluorescent or luminescent assays on luminescent materials are known in the art and are described in, e.g., Lakowicz, J. R., Topics in Fluorescence Spectroscopy, volumes 1 to 3, New York: Plenum Press (1991); Herman, B., Resonance Energy Transfer Microscopy, in Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361; and Bernard Valeur, "Molecular Fluorescence: Principles and Applications" Wiley VCH, 2002. Guidance in the selection and use of specific resonance acceptor moieties is available at, for example, Berlman, I. B., Energy transfer parameters of aromatic compounds, Academic Press, New York and London (1973), which contains tables of spectral overlap integrals for the selection of resonance energy transfer pairs. Additional information sources include the Molecular Probes Catalog (2003) and website; and Tsien et al., 1990 Handbook of Biological Confocal Microscopy, pp. 169-178. Instruments useful for performing FP and/or RET and TR-RET applications are available from Tecan Group Ltd. (Switzerland) (Ultra, Ultra 384, Ultra Evolution); Perkin-Elmer (Boston, Mass.) (Fusion, EnVision, Victor V, and ViewLux); Amersham Bioscience (Piscataway, N.J.) (LeadSeeker); and Molecular Devices Corporation (Sunnyvale, Calif.) (Analyst AD, GT, and HT).

Commonly used chemical abbreviations that are not explicitly defined in this disclosure may be found in The American Chemical Society Style Guide, Second Edition; American Chemical Society, Washington, D.C. (1997), "2001 Guidelines for Authors" J. Org. Chem. 66(1), 24A (2001), and "A Short Guide to Abbreviations and Their Use in Peptide Science" J. Peptide. Sci. 5, 465-471 (1999).

Abbreviations: t-Boc, tert-butyloxycarbonyl; Bzl, benzyl; PTK, protein tyrosine kinase; Fmoc, fluorenylmethyloxycarbonyl; ELISA, enzyme-linked immuno absorbant assay; FP, fluorescence polarization; FITC, fluorescein isothiocyanate; RET, resonance energy transfer; FRET, fluorescence resonance energy transfer or Forster resonance energy transfer; TR, time resolved; FAM, carboxyfluorescein.

As employed throughout the disclosure, the following terms, unless otherwise indicated, shall be understood to have the following meanings:

The terms "antibody" and "antibodies" include polyclonal antibodies, monoclonal antibodies, humanized or chimeric antibodies, single chain Fv antibody fragments, Fab fragments, and F(ab)$_2$ fragments. Polyclonal antibodies are heterogeneous populations of antibody molecules that are specific for a particular antigen, while monoclonal antibodies are homogeneous populations of antibodies to a particular epitope contained within an antigen. A chimeric antibody is a molecule in which different portions are derived from different animal species, such as those having a variable region derived from a mouse monoclonal antibody and a human immunoglobulin constant region. The term "epitope" refers to an antigenic determinant on an antigen to which an antibody binds. Epitopes usually consist of chemically active surface groupings of molecules such as amino acids, sugar side chains, or chemical moieties (e.g., from organic compounds) and typically have specific three-dimensional structural characteristics as well as specific charge characteristics. Epitopes can consist of a series of contiguous amino acids, e.g., 5 contiguous amino acids. In other embodiments, an epitope can be a discontinuous epitope, e.g., the epitope is a particular arrangement of amino acids in space that results from the secondary, tertiary, and/or quaternary folding of a protein or polypeptide. In yet other embodiments, an epitope can consist of a modified amino acid side chain, e.g., a phosphorylated tyrosine, serine, or threonine. Monoclonal antibodies are particularly useful in the present invention.

The term "RET" means resonance energy transfer, and refers to the radiationless transmission of an energy quantum from its site of absorption (the donor) to the site of its utilization (the acceptor) in a molecule, or system of molecules, by resonance interaction between donor and acceptor species, over distances considerably greater than interatomic, without substantial conversion to thermal energy, and without the donor and acceptor coming into kinetic collision. A donor is a moiety that initially absorbs energy (e.g., optical energy or electronic energy). A luminescent metal complex as described herein can comprise two donors: 1) an organic antenna moiety, which absorbs optical energy (e.g., from a photon); and 2) a lanthanide metal ion, which absorbs electronic energy (e.g., transferred from an organic antenna moiety). RET is sometimes referred to as fluorescent resonance energy transfer or Forster resonance energy transfer (both abbreviated FRET). FRET can be used to detect proximity between fluorescent molecules. If the emission spectrum of the donor overlaps with the excitation spectrum of the acceptor (for example, in the case of a terbium chelate and a fluorescent protein or polypeptide), energy transfer takes place when the molecules are proximal. Because of the long fluorescent lifetime of terbium chelates, energy transfer can be detected after interferences from other fluorescent molecules or from scattered light has dissipated.

The term "acceptor" refers to a chemical or biological moiety that accepts energy via resonance energy transfer. In RET applications, acceptors may re-emit energy transferred from a donor fluorescent or luminescent moiety as fluorescence (e.g., RET or TR-RET) and are "fluorescent acceptor moieties." As used herein, such a donor fluorescent or luminescent moiety and an acceptor fluorescent moiety are referred to as a "RET pair." Examples of acceptors include coumarins and related fluorophores; xanthenes such as fluoresceins and fluorescein derivatives; fluorescent proteins such as GFP and GFP derivatives; rhodols, rhodamines, and derivatives thereof; resorufins; cyanines; difluoroboradiazaindacenes; and phthalocyanines The terms "label" or "labeled" refer to the inclusion of a luminescent metal complex or a fluorescent acceptor moiety on a first binding partner, second binding partner, tracer, test compound, potential modulator, substrate, or product, as described herein. Methods for incorporation of labels include expression as fusion proteins, covalent attachment through chemical ligation, and non covalent attachment such as those mediated by ligand-protein domain interactions such as biotin-avidin or FKBP ligands and FKBP, or through antibody mediated interactions with antibody targets.

The term "modulates" refers to partial or complete enhancement or inhibition of an activity or process (e.g., by attenuation of rate or efficiency).

The term "modulator" refers to a chemical compound (naturally occurring or non-naturally occurring), such as a biological macromolecule (e.g., polynucleotide, protein or polypeptide, hormone, polysaccharide, lipid), an organic molecule (e.g., a small organic molecule), or an extract made from biological materials such as bacteria, plants, fungi, or animal (particularly mammalian, including human) cells or tissues. Modulators may be evaluated for potential activity as inhibitors or enhancers (directly or indirectly) of a biological process or processes (e.g., agonist, partial antagonist, partial agonist, inverse agonist, antagonist, antineoplastic agents, cytotoxic agents, inhibitors of neoplastic transformation or cell proliferation, cell proliferation-promoting agents, and the like) by inclusion in screening assays described herein. The activity of a modulator may be known, unknown, or partially known.

The term "non-naturally occurring" refers to the fact that an object, compound, or chemical cannot be found in nature. For example, a polypeptide, protein or polynucleotide that is present in an organism (including viruses) that can be isolated from a source in nature and which has not been intentionally modified by man in the laboratory is naturally-occurring, while such a polypeptide or polynucleotide that has been intentionally modified by man is non-naturally occurring.

The term "organic molecule" refers to compounds having a molecular skeleton containing a covalent arrangement of one or more of the elements C, N, H, O, S, and P, and typically having a molecular weight less than 10000 Daltons. Organic molecules having a molecular weight less than 5000 Daltons may be referred to as "small organic molecules."

The term "polypeptide" refers to a polymer of two or more amino acids joined together through amide bonds. A polypeptide can be an entire protein (e.g., isolated from a natural source or an expression system), a fragment of a protein, an enzymatically or chemically synthesized and/or modified version of a protein or protein fragment, or an amino acid sequence designed de novo (e.g., not based on a known protein sequence). Polypeptides can be 2-1000 amino acids in length (e.g., 2-900, 2-800, 2-700, 2-600, 2-500, 2-480, 2-450, 2-300, 2-200, 2-100, 2-50, 2-25, 5-900, 5-800, 5-700, 5-600, 5-500, 5-450, 5-300, 5-200, 5-100, 5-50, 5-25, 10-900, 10-800, 10-700, 10-600, 10-500, 10-450, 10-300, 10-200, 10-100, 10-50, 20-900, 20-800, 20-700, 20-600, 20-500, 20-450, 20-300, 20-200, 20-100, or 20-50 amino acids in length). Amino acids may be natural or unnatural amino acids, including, for example, beta-alanine, phenylglycine, and homoarginine. For a review, see Spatola, A. F., in *Chemistry and Biochemistry of Amino Acids, Peptides and Proteins*, B. Weinstein, eds., Marcel Dekker, New York, p. 267 (1983). All of the amino acids used in the present invention may be either the D- or L-isomer. Particularly useful chemically modified or substituted amino acids including phosphorylated (e.g., phospho-serine (phosphorylated at the hydroxyl of the side chain), phospho-tyrosine (phosphorylated at the OH of the side-chain phenyl ring), and phospho-threonine (phosphorylated at the hydroxyl of the size chain)), sulfated, methylated, or prenylated amino acids.

The terms "post-translational modification" and "post-translational type modification" are used interchangeably and refer to enzymatic or non-enzymatic modification of one or more amino acid residues in a protein or polypeptide. Typical modifications include phosphorylation, dephosphorylation, glycosylation, methylation, sulfation, ubiquitination, acylation, acetylation, prenylation, and ADP-ribosylation. Preferred post-translational type modifications include phosphorylation and dephosphorylation. The term post-translational modification includes non-covalent modifications that may affect protein or polypeptide activity, structure, or function, such as polypeptide-polypeptide interactions or the binding of ligands, allosteric modulators, other modulators, or second messengers such as calcium, cAMP, or inositol phosphates.

The term "test compound" refers to a compound to be tested by one or more screening method(s) of the invention, e.g., to determine if it is a putative modulator of an enzymatic activity such as a kinase activity. A test compound can be any chemical, such as an inorganic chemical, an organic molecule, a protein or polypeptide, a carbohydrate, a polynucleotide, a polysaccharide, a lipid, a phospholipid, or a combination thereof. Typically, various predetermined concentrations (e.g., various dilutions) of test compounds are used for screening, such as 0.01 micromolar, 1 micromolar, or 10 micromolar. Experimental controls for a test compound can include measuring a signal for an assay performed in the absence of the test compound or comparing a signal obtained using a compound known to modulate a target activity with a signal obtained with the test compound. The test compound can be substantially or partially purified or a cell lysate.

The terms "ubiquination" and "ubiquitination" are used interchangeably.

Kinase Assays

Figure 28:
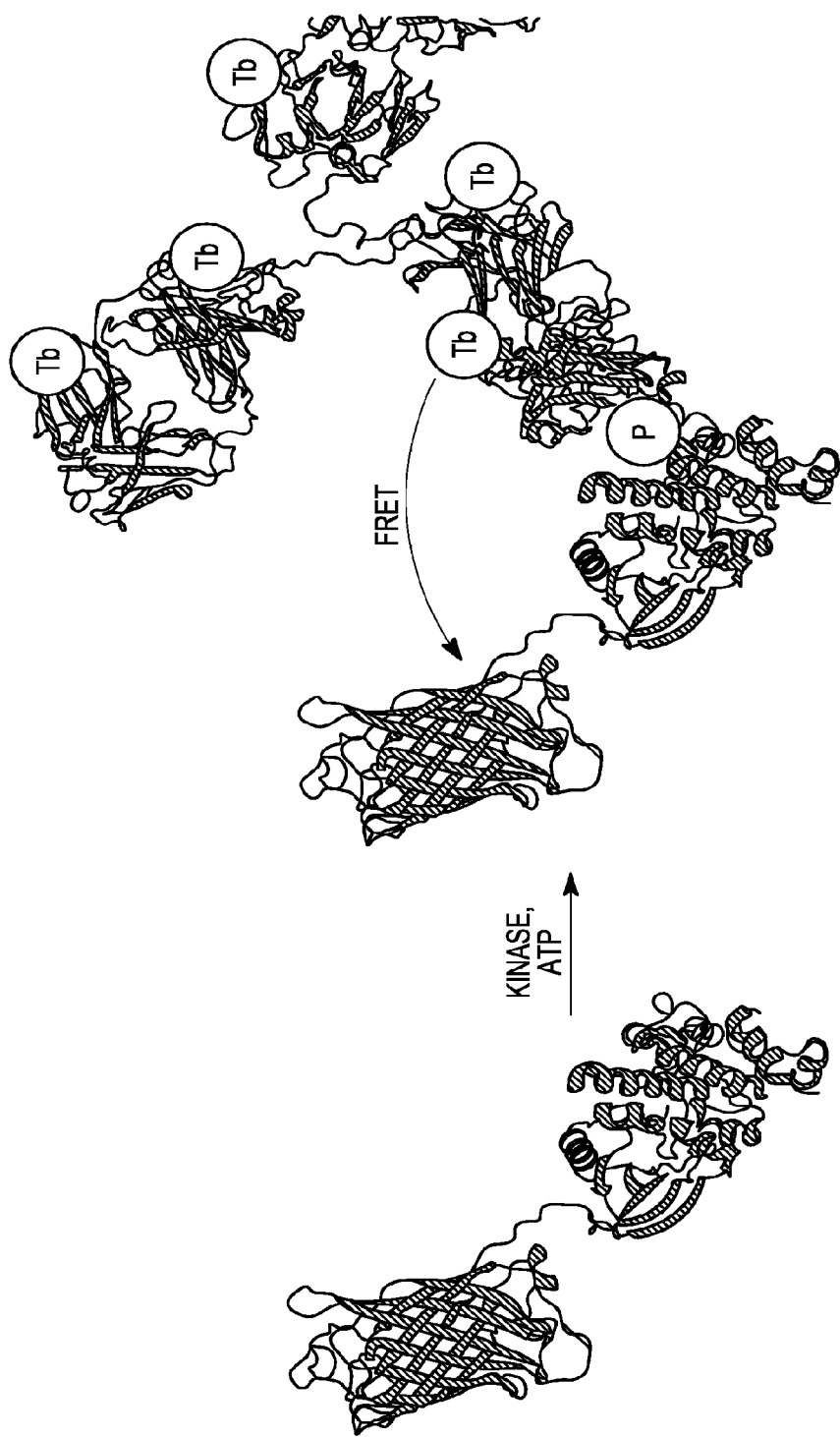
FIG. 28 shows a general principle for a fluorescent protein-based TR-FRET kinase assay.
Figure 29:
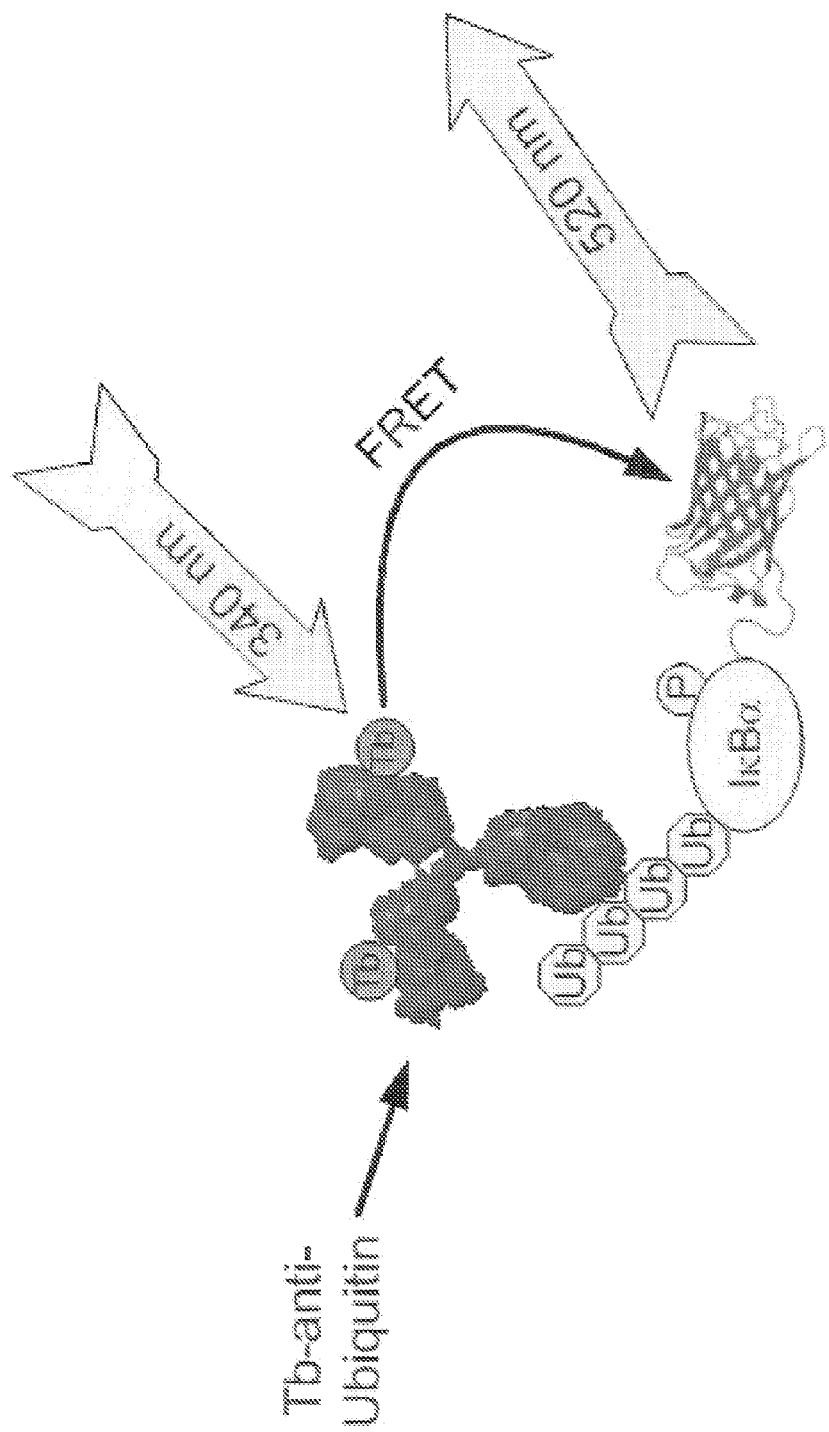
FIG. 29 depicts detection of ubiquitination of a fusion protein comprising a ubiquitination substrate (e.g., IκBα) and an acceptor label (e.g., GFP). In some embodiments, the fusion protein is expressed in a cell. Optionally the cell is exposed to conditions and/or compounds to determine if they modulate (e.g., the rate of) ubiquitination of the substrate. The cell is then lysed and exposed to a binding partner which binds ubiquitin (e.g., poly-ubiquitin) and wherein the binding partner is labeled with a donor label that forms a FRET pair with the acceptor label of the fusion protein. Ubiquitination is detected via FRET, e.g., a change in emission of the acceptor and/or donor.

TR-FRET kinase assays are often performed using fluorophore-labeled peptide substrates. Although some tyrosine kinases phosphorylate such substrates, many (e.g., serine/threonine kinases) show poor activity against such substrates, and show higher activity against native protein substrates. By expressing native protein kinase substrates as fluorescent protein (e.g., CiFP) fusions, the inventors have developed robust kinase assays for which peptide-based substrates, e.g., those that are unacceptable or work with low efficiency. Such assays allow for routine analysis of "difficult" kinases, and are useful in identifying compounds that act on the substrate (e.g., potentially by binding to a "docking" site rather than the kinase itself).One embodiment of the invention provides a method to assay kinase activity using a fluorescent polypeptide fusion of a substrate. in one embodiment, the invention provides a method to assay kinase activity using a GFP fusion substrate. The substrate moiety can be a polypeptide sequence, a protein or a protein domain. In one embodiment, the protein or protein domain comprises a site for phosphorylation. In some embodiments of the invention, a GFP fusion protein of >20 residues is used as the substrate. Such substrates can be produced recombinantly in bacteria or in insect cells. These larger substrates (such as whole proteins or protein domains) can be "physiologically relevant" (e.g., they can be the "native" substrate of a kinase in a biologically relevant pathway). Thus, this invention increases the number of kinases that can be assayed and increases the potential biological relevance of studies of kinase activity, since the present invention is not limited to small peptide substrates, FIG. 28 represents a fluorescent protein-based TR-FRET kinase assay of the invention. The kinase's protein substrate (or a fragment thereof containing the phosphorylation site) is produced as a fusion to a fluorescent protein (e.g., GFP). If the substrate is phosphorylated, it can bind to an antibody specific for the phosphorylated substrate. In one embodiment, this antibody is labeled with a fluorescent and/or luminescent label that can act as a RET partner with the fluorescent protein/peptide, which is part of the substrate fusion protein. In some aspects of the invention, the antibody is labeled with a lanthanide metal. In some embodiments, the lanthanide metal is Terbium or Europium. In some aspects of the invention, the antibody specifically binds the unphosphorylated substrate. In this case, RET signal will be reduced as more substrate is phosphorylated. If the antibody is specific for the phosphorylated substrate, then FRET signal increases as more substrate is phosphorylated. In some aspects of the invention, a TR-FRET signal is measured.

The fluorescent label can be a compatible fluorescent protein or polypeptide, for example Green Fluorescent Protein (GFP) or a GFP variant. The substrate protein or polypeptide may be expressed recombinantly and isolated as a fusion with the GFP protein or polypeptide. The substrate protein or polypeptide may be expressed within a cell and then used in a non-purified form from a cell lysate or may be used in a substantially pure form. In one embodiment, the kinase phosphorylated substrate is recognized by a labeled phosphospecific antibody labeled with a lanthanide metal complex (e.g., comprising Tb). This association is detected by an increase in RET between terbium and the fluorescent label. The invention can be used to assess enzymatic activity, such as that of a kinase. The kinase and/or the kinase's protein substrate can be either purified or present in a complex matrix such as that of a cell lysate. Further, the invention can be used to assess the ability of a compound to affect enzymatic activity, such as after treating a purified kinase or cell containing a kinase with a test compound. In some embodiments, the assay is cell based with the kinase's substrate fusion protein being expressed by the cell.

The majority of non-radioactive kinase assays depend on phosphorylation of a chemically synthesized peptide substrate of up to approximately 20 residues. This assay format uses, as an example, a GFP fusion protein of >20 residues as the substrate.

Figure 9:
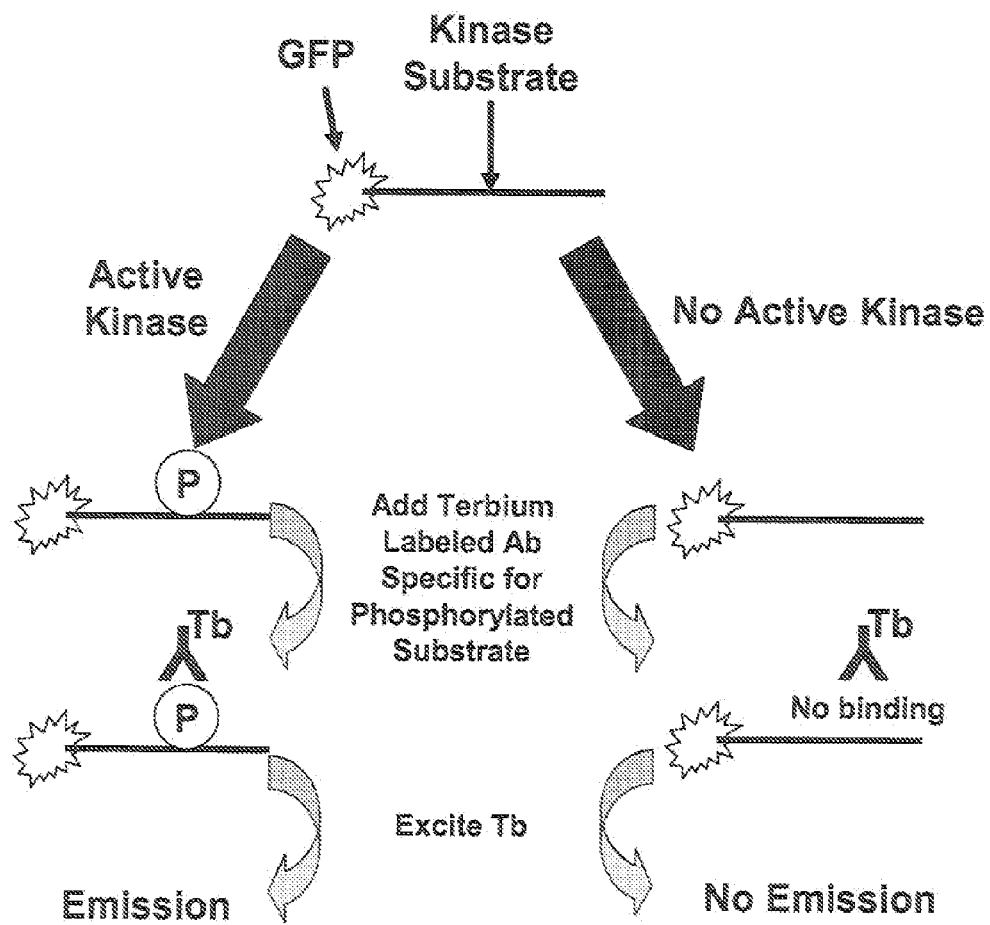
FIG. 9 depicts embodiments of the invention which relates to methods of measuring kinase activity.
Figure 10:
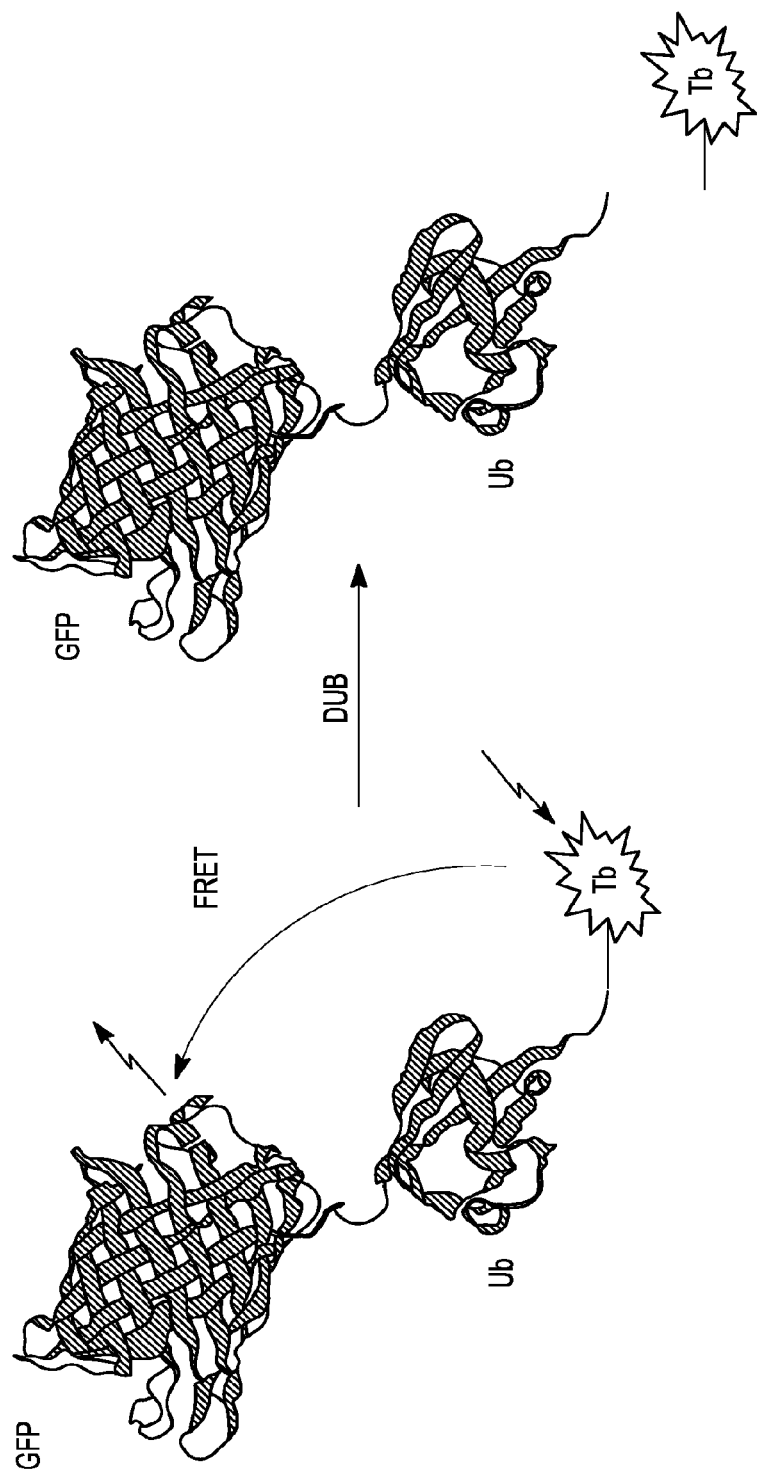
FIG. 10 depicts one embodiment of the invention which relates to methods of measuring de-ubiquinating activity.
Figure 11:
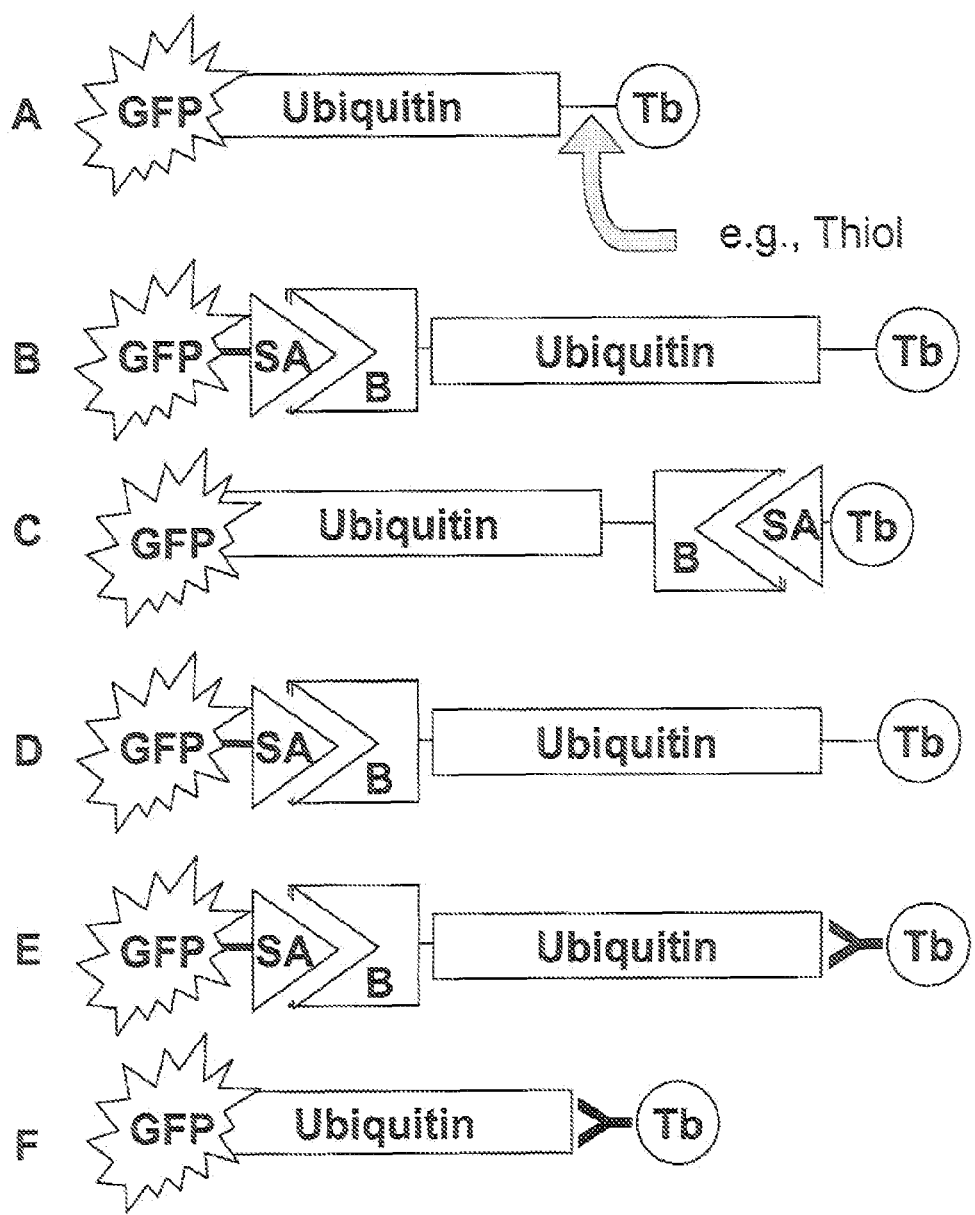
FIGS. 11A-11F depict non-limiting examples of ubiquitin substrates that can be utilized in the present invention.
Figure 12A:
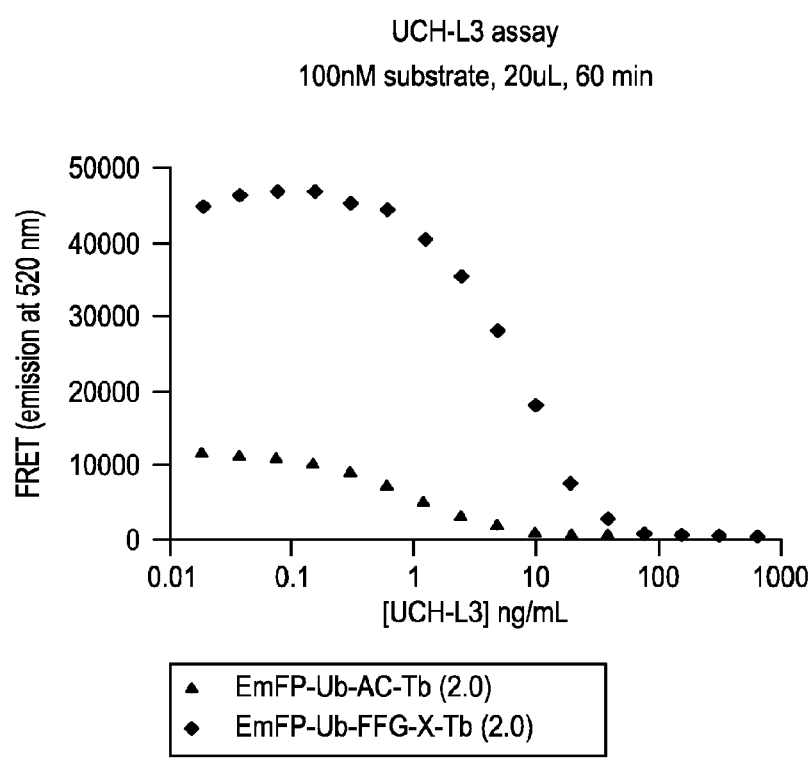
FIGS. 12A and 12B show the results of assays measuring deubiquinating activity.
Figure 12B:
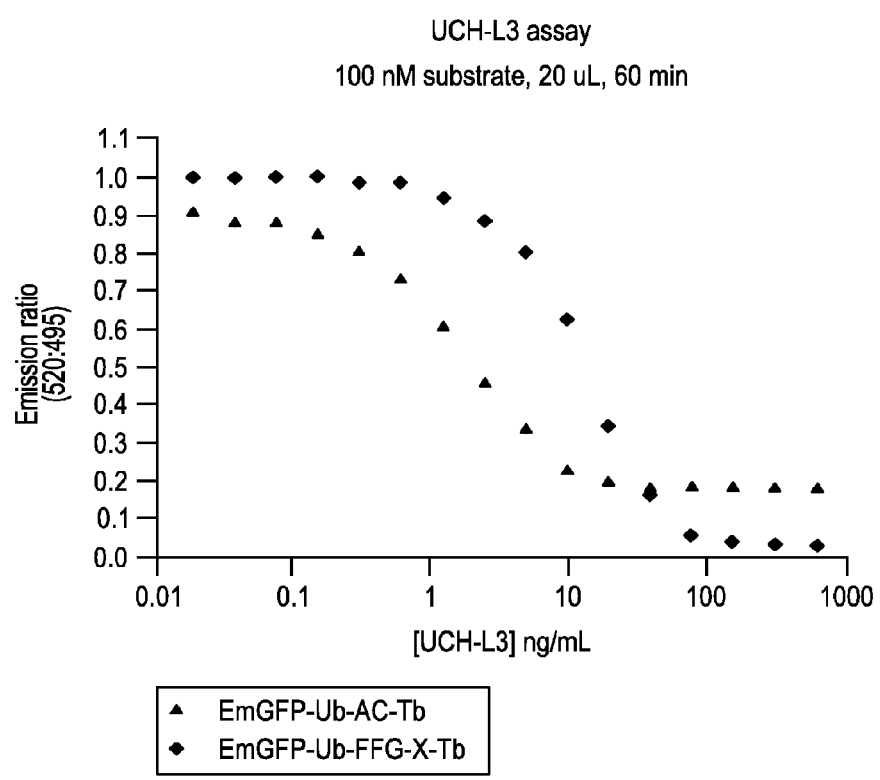
Figure 13:
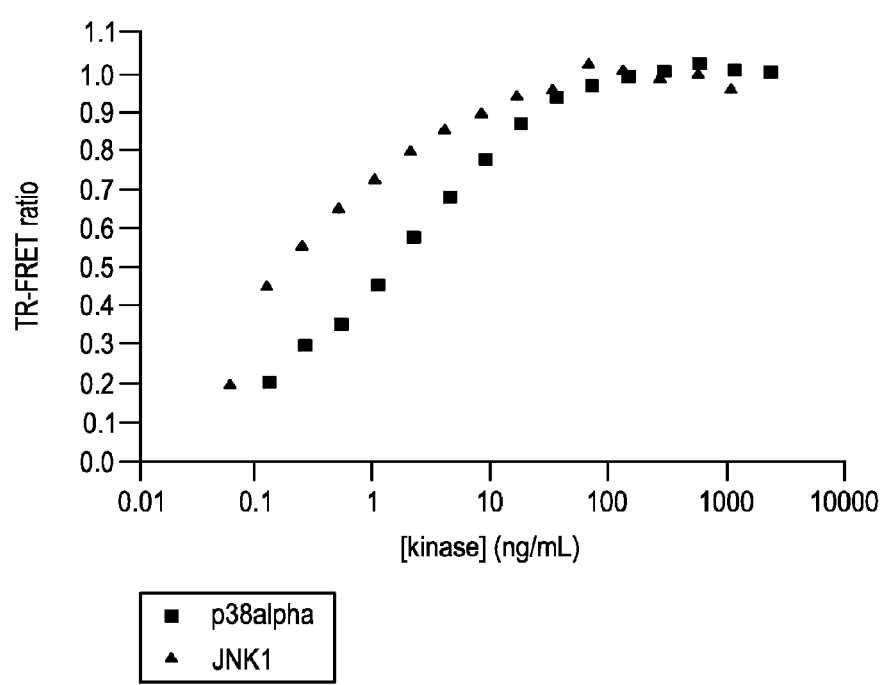
FIGS. 13-19 shows the results of assays measuring kinase activity.
Figure 14:
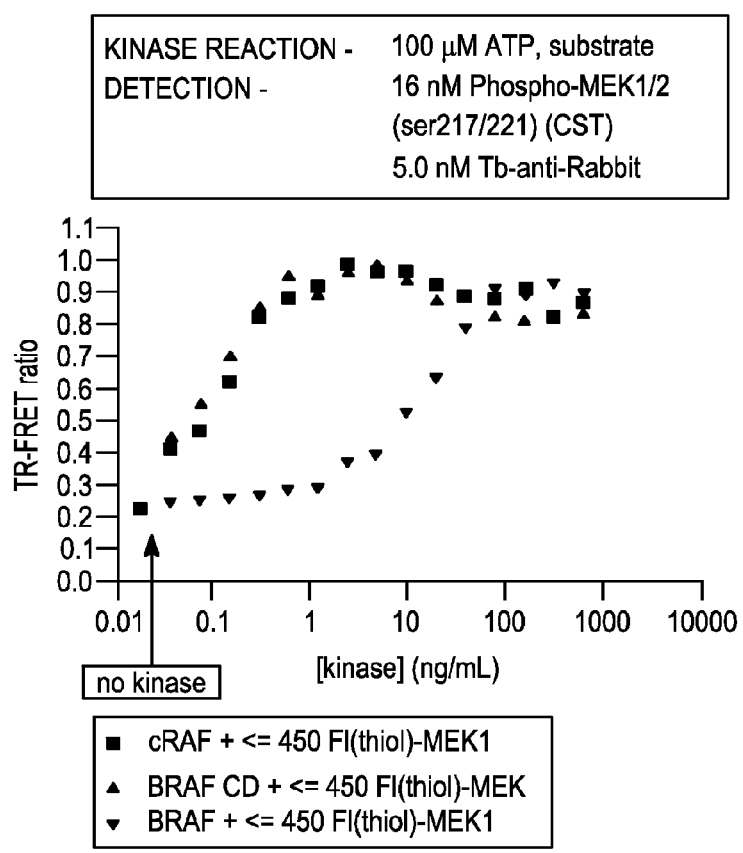
Figure 15:
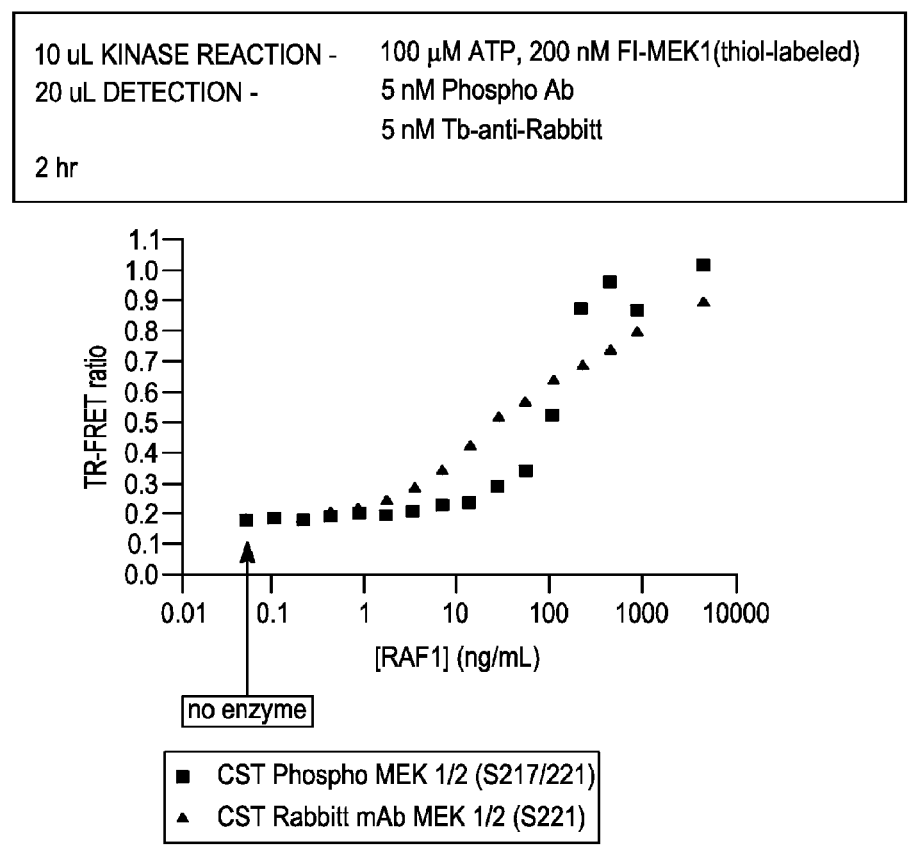
Figure 16:
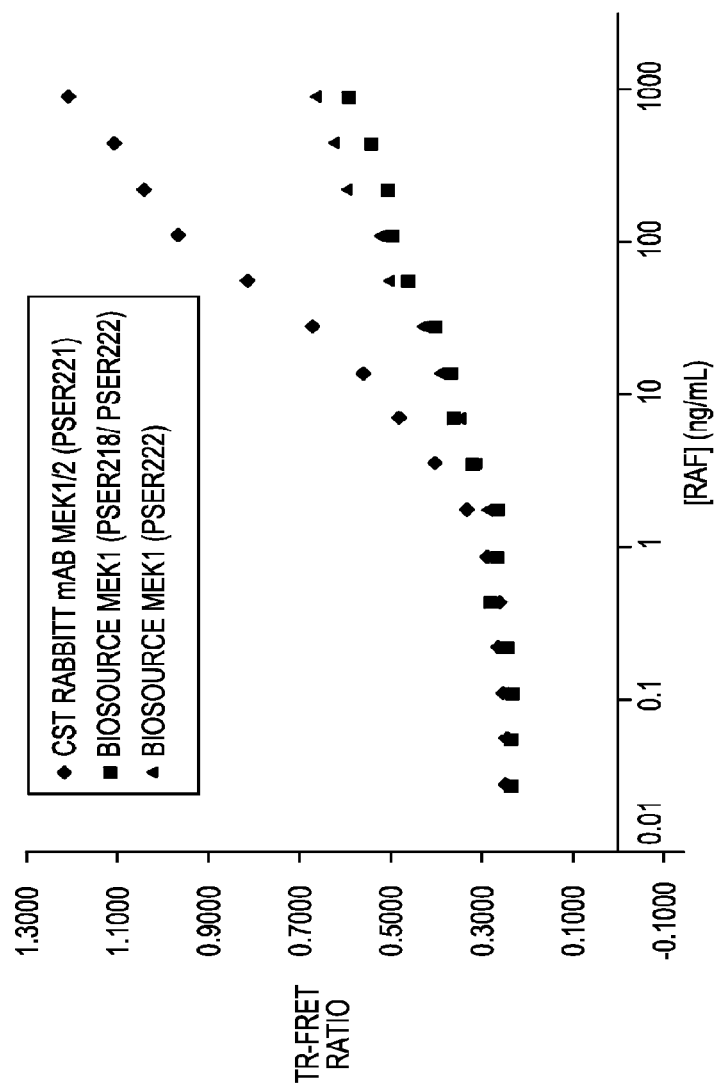
Figure 17:
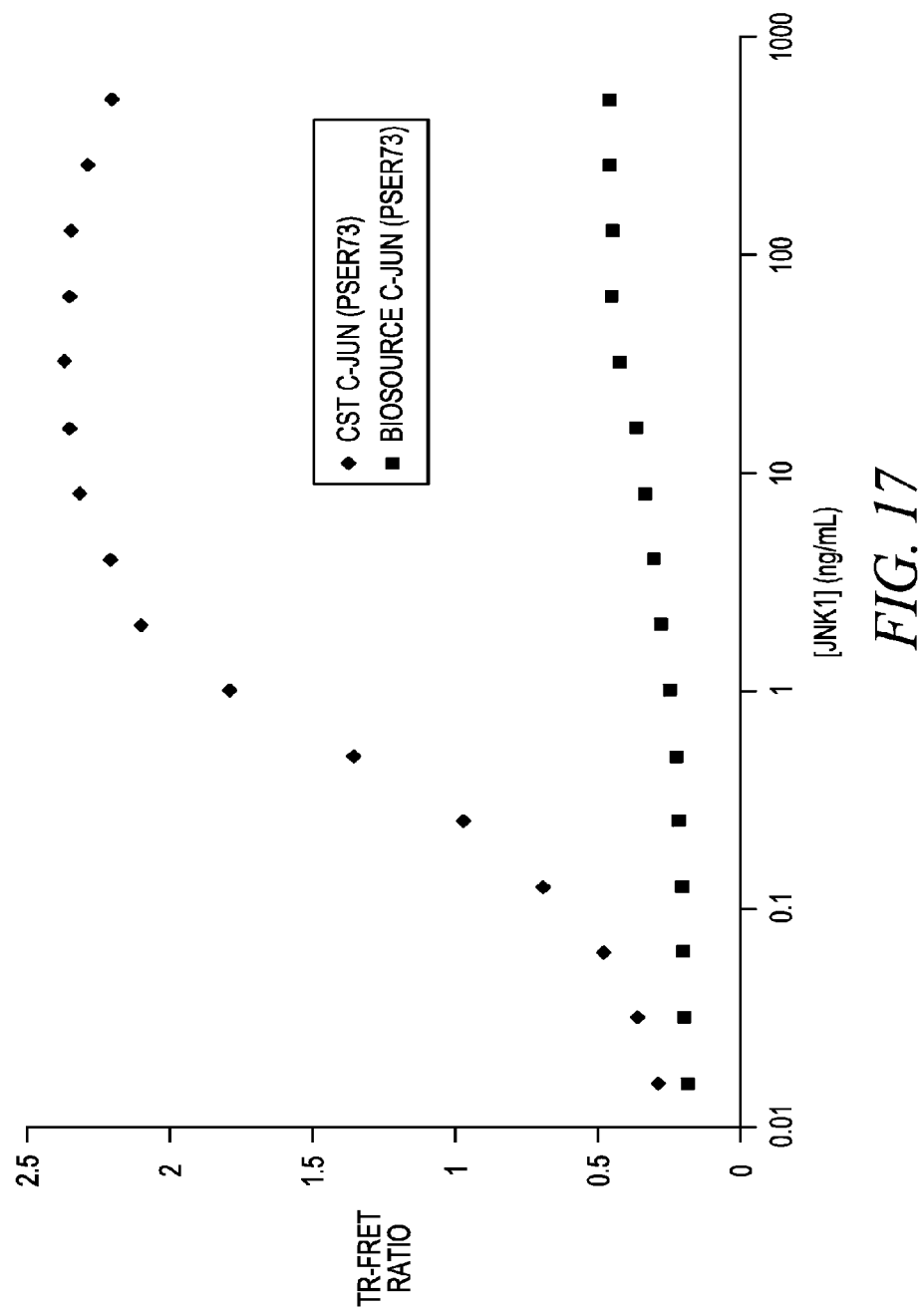
Figure 18:
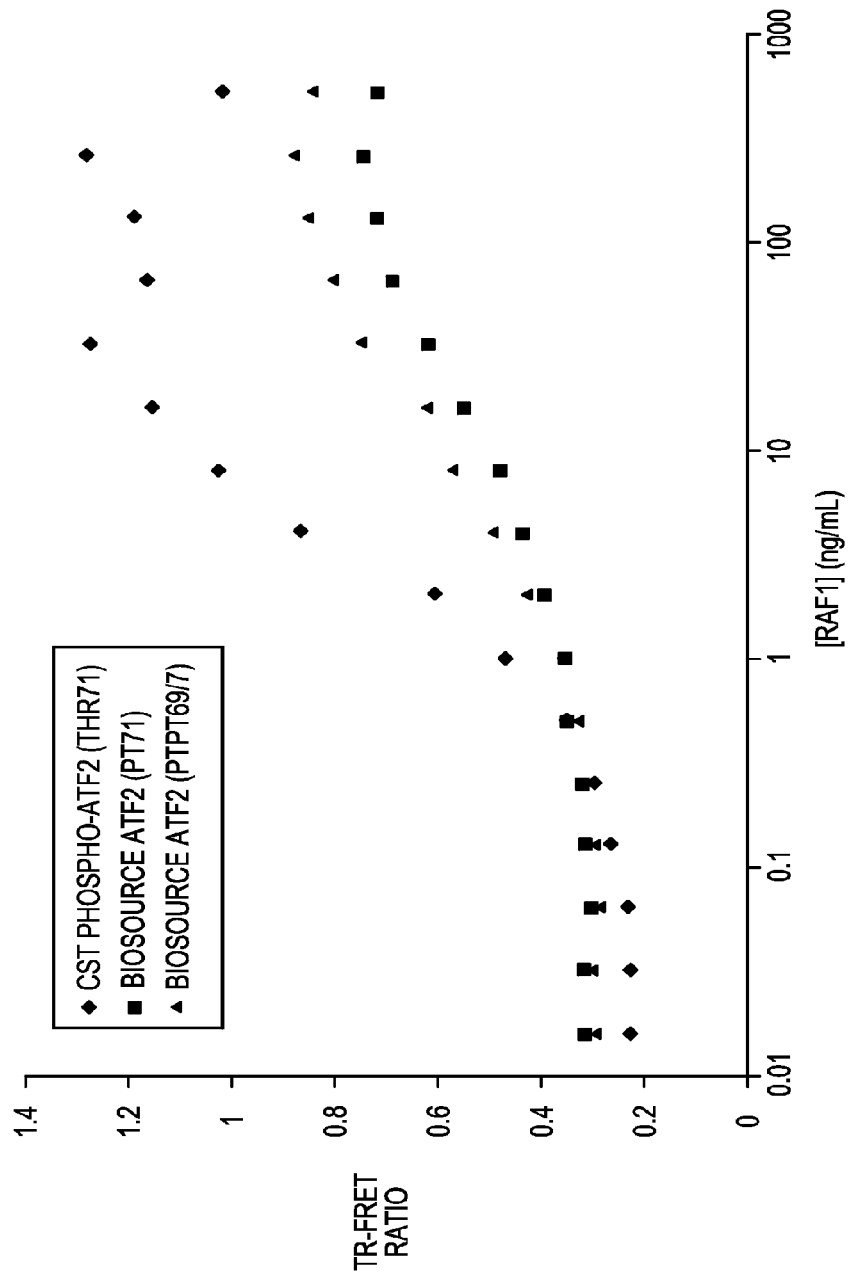
Figure 19:
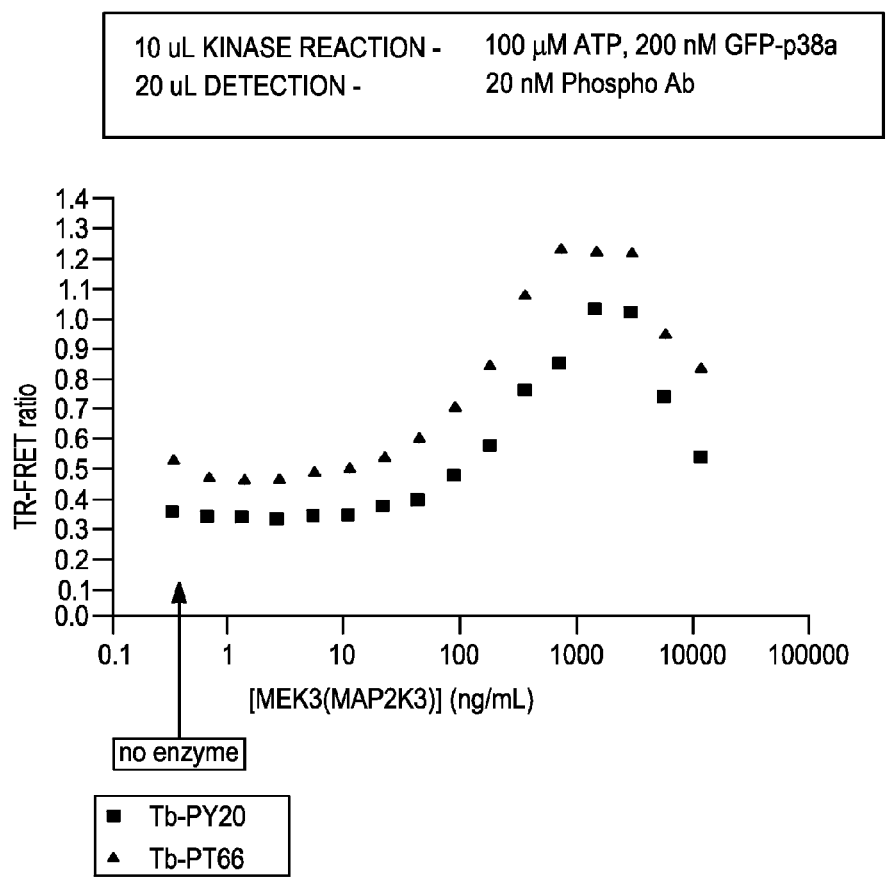

In one embodiment of the invention, substrates are produced recombinantly in bacteria or in insect cells. These larger substrates (such as whole proteins or protein domains) can be "physiologically relevant" (e.g., they can be the "native" substrate of a kinase in a biologically relevant pathway). The use of "native" substrates is a desirable feature for many practitioners of kinase assays. As an example, it is known that some kinases require a "docking" site far removed from the site of phosphorylation in order to be phosphorylated. In many such cases, smaller peptide substrates may not function as substrates. For examples of related assay formats and compositions, see FIG. 9. In some embodiments, the "native" substrate or fragment thereof is expressed as a fusion comprising a fluorescent polypeptide.

One embodiment of the invention, provides a method for measuring kinase activity of a compound comprising: a) contacting the compound and a fusion protein to form a test sample, wherein the fusion protein comprises a fluorescent protein or polypeptide and a kinase substrate polypeptide; b) contacting said fusion protein with a binding molecule labeled with a luminescent metal complex, wherein said binding molecule specifically binds either the unphosphorylated or phosphorylated substrate; exposing said test sample to light (e.g., having a wavelength in the range from 250 nm to 750 nm) and measuring the fluorescence emission from said test sample.

Another embodiment of the invention provides a method for identifying a modulator of kinase activity comprising: a) contacting a kinase and a fusion protein to form a test sample, wherein the fusion protein comprises a fluorescent protein or polypeptide and a kinase substrate polypeptide and said contacting is carried out in the presence of a potential modulator of said kinase activity; b) contacting said fusion protein with a binding molecule labeled with a luminescent metal complex, wherein said binding molecule specifically binds either the unphosphorylated or phosphorylated substrate; c) exposing said test sample to light (e.g., having a wavelength in the range from 250 nm to 750 nm) and measuring the fluorescence emission from said test sample.

Another embodiment of the invention provides a method for measuring kinase activity of at least one compound comprising: a) contacting the compound and at least one fusion protein to form a test sample, wherein the fusion protein comprises a fluorescent protein or polypeptide and a kinase substrate polypeptide; b) contacting the fusion protein with a binding molecule labeled with a luminescent metal complex, wherein the binding molecule specifically binds either the unphosphorylated or phosphorylated substrate; c) exposing the test sample to at least one wavelength of light; and d) measuring the fluorescence emission from the test sample.

In some embodiments, the kinase is measured from a cell lysate. The cell lysate can be a crude cell lysate, partially purified or substantially purified. Substantially purified refers to about 95% purity. In some embodiments, the kinase (or other enzyme depending on the particular embodiment of the invention e.g. de-ubiquitinase or ubiquitinase) is about 90, 91, 92, 93, 94, 95, 96, 99, 99.9 or 100% pure, such as 90% to 99.9%, 93% to 99.9%, 95% to 99.9%, or 90% to 96% pure. In some embodiments, the enzyme is from a cell lysate that has been centrifuged to remove cellular debris. In some embodiments, the enzyme is in the presence of at least one protease inhibitor, e.g., to reduce degradation in a cell lysate or during purification.

Another embodiment of the invention provides a method for identifying a modulator of kinase activity comprising: a) contacting a kinase and a fusion protein to form a test sample, wherein the fusion protein comprises a fluorescent protein or polypeptide and a kinase substrate polypeptide and the contacting is carried out in the presence of at least one potential modulator of the kinase activity; b) contacting the fusion protein with a binding molecule labeled with a luminescent metal complex, wherein the binding molecule specifically binds either the unphosphorylated or phosphorylated substrate; c) exposing the test sample to at least one wavelength of light; and d) measuring the fluorescence emission from the test sample.

Another embodiment of the invention provides a method for measuring a kinase activity of at least one compound, the method comprising: a) contacting the at least one compound and at least one fusion protein to form a test sample, wherein the fusion protein comprises a fluorescent polypeptide and a kinase substrate polypeptide; b) incubating the test sample under conditions suitable for the kinase activity; c) contacting the test sample, before, during or after (b), with a binding molecule comprising a label, wherein the binding molecule binds with specificity to the at least one fusion protein containing either an unphosphorylated or phosphorylated substrate and wherein the fluorescent polypeptide and the label are a RET pair; d) exposing the test sample to at least one wavelength of light; and e) measuring fluorescence emission from the test sample.

Another embodiment of the invention provides a method for determining if at least one compound modulates a kinase activity, the method comprising: a) contacting the at least one compound, at least one kinase and at least one fusion protein to form a test sample, wherein the fusion protein comprises a fluorescent polypeptide and a kinase substrate polypeptide; b) incubating the test sample under conditions suitable for the kinase activity; c) contacting the test sample, before, during or after (b), with a binding molecule comprising a label, wherein the binding molecule binds with specificity to the at least one fusion protein containing either an unphosphorylated or phosphorylated substrate and wherein the fluorescent polypeptide and the label are a RET pair; d) exposing the test sample to at least one wavelength of light; and e) measuring fluorescence emission from the test sample.

Another embodiment of the invention provides an article of manufacture comprising: a) packaging material; b) at least one fusion protein comprising a fluorescent protein or polypeptide and a kinase substrate polypeptide; and c) at least one binding molecule labeled with a luminescent metal complex. Another embodiment of the invention provides a fusion protein comprising: i) a fluorescent protein or polypeptide; and ii) a kinase substrate polypeptide.

Another embodiment of the invention provides an article of manufacture comprising: a) packaging material; b) at least one fusion protein comprising a fluorescent polypeptide and a kinase substrate polypeptide; and c) at least one binding molecule comprising a label, wherein the fluorescent polypeptide and the label are a RET pair.

In one embodiment, the fluorescent protein or polypeptide is GFP. In some embodiments, the fluorescent protein or polypeptide is a fluorescent polypeptide the amino acid sequence of any of the fluorescent polypeptide sequences as described herein. In some embodiments, the fluorescent protein or polypeptide is a fluorescent polypeptide with an amino acid sequence that is at least 70%, 80%, 90%, 95% or 98% homology to any of the fluorescent polypeptide sequences as described herein. In one embodiment, the luminescent metal complex comprises terbium. In one embodiment, the binding molecule is an antibody or antibody fragment. In one embodiment, the binding molecule binds an unphosphorylated form of the fusion protein. In one embodiment, the binding molecule binds a phosphorylated form of the fusion protein. In one embodiment, the luminescent metal complex comprises an organic antenna moiety, a metal liganding moiety and a terbium metal ion. In one embodiment, the luminescent metal complex comprises Tb(III). In one embodiment, the luminescent metal complex comprises an organic antenna moiety, a metal liganding moiety and a terbium metal ion. In one embodiment, the luminescent metal complex comprises a metal chelating moiety selected from the group consisting of: EDTA, DTPA, TTHA, DOTA, NTA, HDTA, DTPP, EDTP, HDTP, NTP, DOTP, DO3A, DOTAGA, and NOTA. In one embodiment, the compound is in a cell lysate. In one embodiment, the compound is substantially purified. In one embodiment, the potential modulator is in a cell lysate. In one embodiment, the potential modulator is substantially purified. In one embodiment, the compound is a kinase enzyme. In one embodiment, the kinase enzyme is in a cell lysate. In one embodiment, the kinase is purified. In one embodiment, the fusion protein is substantially purified. In one embodiment, the fusion protein is in a cell lysate. In one embodiment, measuring the fluorescence emission from the test sample comprises measuring time resolved fluorescence. In one embodiment, the method further comprises contacting the kinase and the fusion protein to form a control sample, wherein the concentration of the potential modulator of the kinase activity is less than the concentration in the test sample. In another embodiment, the potential modulator of the kinase activity is absent from the control sample. In one embodiment, measuring the fluorescent emission comprises a ratiometric measurement.

It is understood that in most cases where a luminescent metal complex is used that it could be substituted with any donor moiety that forms a RET pair with the acceptor moiety (e.g., fluorescein or a GFP).

Also see, Riddle et al., Anal. Biochem. 2006. 356(1) pp 108-116.

De-ubiquination Assays

Another embodiment of the invention provides the use of TR-RET with protein-based substrates that can enable sensitive detection of deubiquitinating enzyme (DUB) activity. Methods of the invention allow the use of both standard RET (resonance energy transfer) or time-resolved resonance energy transfer (TR-RET). Use of TR-RET or RET enables sensitive detection of this type of enzyme activity, for example for use in screening for modulators, activators or inhibitors. Use of TR-RET is of particular utility in high throughput screening due to the robustness of the assay signal and the resistance to interference from test compounds. Use of intact protein substrates containing whole proteins (or domains), such as ubiquitin, enables sensitive measurements of DUB activity not often possible with typical peptide-based substrates. The present invention also includes the use of protein fragments or peptides comprised of a de-ubiquination domain (e.g., de-ubiquination protein or polypeptide substrate) e.g., an amino acid sequence cleaved by a de-ubiquinating enzyme(s). Furthermore, use of a genetically encoded fluorophore such as green fluorescent protein, enables facile production of labeled substrates. Compositions suitable for use in the presently described methods are also described, including mixtures of compositions.

Some embodiments of the invention are based on the fact that many proteases cleave at specific amino acid sequences, but also recognize substrate structure distant in amino acid sequence, and therefore preferentially cleave folded protein substrates rather than typical short peptide substrates. The protease recognition site could be ubiquitin, a ubiquitin-like protein such as SUMO, Nedd8, ISG15, or others.

In one embodiment, methods of measuring and detecting DUB activity can be employed using a protein substrate with both donor and acceptor fluorophores covalently attached. In one embodiment, a method can be employed using a protein substrate with either one donor or acceptor fluorophore covalently attached, and the other provided by its association to a binding partner. Likewise, both donor and acceptor fluorophores can be present on binding partners, e.g., see FIGS. 10 and 11A-11F. In some embodiment, the donor and acceptor fluorophores can be standard organic fluorophores, luminescent molecules, lanthanide chelates, or genetically encoded fluorescent protein or polypeptides. The binding partners could be, but are not limited to, antibodies, streptavidin, small molecules attached to a fluorophore (tracers), or other molecules. In one embodiment, the fluorophores would be chosen such that RET would occur in the intact substrate. However, after cleavage with a ubiquitin-specific protein (e.g., a DUB or a DCE), RET would be disrupted. Some embodiments of the invention use a Terbium chelate and a suitable accepter fluorophore (e.g., GFP). Some embodiments of the invention, utilize a terbium labeled ubiquitin. In one embodiment, the terbium is labeled via attachment to a cysteine residue or residues. The cysteine residue may be a cysteine residue naturally found in ubiquitin or a cysteine residue engineered into a ubiquitin protein. Some embodiments of the invention, utilize an N-terminal fusion of ubiquitin with a short C-terminal extension containing an engineered cysteine residue that has been labeled with a terbium chelate. In these embodiments, the intact substrate shows a high degree of FRET, whereas DUB-dependant or DCE-dependent cleavage leads to a decrease in FRET. For examples of various substrates and methods of the invention see FIGS. 11A-11F.

In one embodiment the invention provides a method for measuring de-ubiquinating activity of a compound comprising: a) contacting the compound and a fusion protein to form a test sample, wherein the fusion protein comprises i) a fluorescent protein or polypeptide; ii) a de-ubiquinating enzyme polypeptide substrate; and iii) a luminescent metal complex, wherein ii) is positioned between i) and ii); b) exposing said test sample to light having a wavelength (e.g., in the range from 250 nm to 750 nm) and measuring the fluorescence emission from said test sample.

Another embodiment of the invention provides a method for identifying a modulator of de-ubiquinating activity comprising: a) contacting a de-ubiquinating compound and a fusion protein to form a test sample and said contacting is carried out in the presence of a potential modulator of said kinase activity, wherein the fusion protein comprises: i) a fluorescent protein or polypeptide; ii) a ubiquitin or ubiquitin like protein or polypeptide; and iii) a luminescent metal complex, wherein ii) is positioned between i) and iii); c) exposing said test sample to light having a wavelength (e.g., in the range from 250 nm to 750 nm) and measuring the fluorescence emission from said test sample.

Another embodiment of the invention provides a method for measuring de-ubiquinating activity of at least one compound comprising: a) contacting the compound and a fusion protein to form a test sample, wherein the fusion protein comprises: i) a fluorescent protein or polypeptide; ii) a de-ubiquinating enzyme polypeptide substrate; and iii) a luminescent metal complex, wherein upon cleavage of the de-ubiquinating enzyme polypeptide substrate, resonance energy transfer between (i) and (iii) is decreased; c) exposing the test sample to at least one wavelength of light; and d) measuring the fluorescence emission from the test sample. In one embodiment, the at least one compound is a de-ubiquinating enzyme.

Another embodiment of the invention provides a method for measuring de-ubiquinating activity of at least one compound, the method comprising: a) contacting the compound and at least one fusion protein to form a test sample, wherein the at least one fusion protein comprises: i) a fluorescent polypeptide; ii) a de-ubiquinating enzyme polypeptide substrate; and iii) a label, wherein the fluorescent polypeptide and the label are a RET pair and wherein upon cleavage of the de-ubiquinating enzyme polypeptide substrate, resonance energy transfer between (i) and (iii) is decreased; b) exposing the test sample to at least one wavelength of light; andc) measuring fluorescence emission from the test sample.

Another embodiment of the invention provides a method for determining if at least one compound modulates a de-ubiquinating activity, the method comprising: a) contacting the at least one compound, at least one de-ubiquinating enzyme and at least one fusion protein to form a test sample, wherein the fusion protein comprises: i) a fluorescent polypeptide; ii) a de-ubiquinating enzyme polypeptide substrate; and iii) a label, wherein the fluorescent polypeptide and the label are a RET pair and wherein upon cleavage of the de-ubiquinating enzyme polypeptide substrate, resonance energy transfer between (i) and (iii) is decreased; b) exposing the test sample to at least one wavelength of light; and c) measuring fluorescence emission from the test sample.

Another embodiment of the invention provides a method for identifying a modulator of de-ubiquinating activity, the method comprising: a) contacting at least one de-ubiquinating enzyme and a fusion protein to form a test sample in the presence of at least one potential modulator of the de-ubiquinating activity, wherein the fusion protein comprises: i) a fluorescent protein or polypeptide ii) a de-ubiquinating enzyme polypeptide substrate; and iii) a luminescent metal complex, wherein upon cleavage with the at least one de-ubiquinating enzyme, resonance energy transfer between (i) and (iii) is decreased; c) exposing the test sample to at least one wavelength of light; and d) measuring the fluorescence emission from the test sample.

Another embodiment of the invention provides a article of manufacture comprising: a) packaging material; b) at least one fusion protein comprising: i) a fluorescent protein or polypeptide; ii) a de-ubiquinating enzyme polypeptide substrate; and iii) a luminescent metal complex, wherein upon cleavage with the at least one de-ubiquinating enzyme, resonance energy transfer between (i) and (iii) is decreased. Another embodiment of the invention provides an article of manufacture comprising: a) packaging material; and b) at least one fusion protein comprising: i) a fluorescent polypeptide; ii) a de-ubiquinating enzyme polypeptide substrate; and iii) a label, wherein the fluorescent polypeptide and the label are a RET pair and wherein upon cleavage of the de-ubiquinating enzyme polypeptide substrate, resonance energy transfer between (i) and (iii) is decreased.

In one embodiment, the article of manufacture further comprises at least one de-ubiquinating enzyme. In one embodiment, the de-ubiquinating enzyme is selected from the group consisting of POH1 (also known as Rpn11); UCHL3; ubiquitin carboxyl-terminal esterase L1 (UCHL1); SUMO1/sentrin specific protease 1 (SENP1); ubiquitin carboxyl-terminal esterase L1 (UCHL1); ubiquitin specific protease 1 (USP1); ubiquitin specific protease 10 (USP10); ubiquitin specific protease 12 (USP12); ubiquitin specific protease 14 (USP14); ubiquitin specific protease 15 (USP15); ubiquitin specific protease 16 (USP16); ubiquitin specific protease 18 (USP18); ubiquitin specific protease 2 (USP2); ubiquitin specific protease 28 (USP28); ubiquitin specific protease 3 (USP3); ubiquitin specific protease 30 (USP30); ubiquitin specific protease 33 (USP33); ubiquitin specific protease 4 (USP4); ubiquitin specific protease 44 (USP44); ubiquitin specific protease 45 (USP45); ubiquitin specific protease 46 (USP46); and ubiquitin specific protease 49 (USP49); and ubiquitin specific protease 5 (isopeptidase T) (USP5).

In some embodiments, the DUB is measured from a cell lysate. The cell lysate can be a crude cell lysate, partially purified or substantially purified. Substantially purified refers to about 95% purity. In some embodiments, the DUB is about 90, 91, 92, 93, 94, 95, 96, 99, 99.9 or 100% pure, such as 90% to 99.9%, 93% to 99.9%, 95% to 99.9%, or 90% to 96% pure. In some embodiments, the enzyme is from a cell lysate that has been centrifuged to remove cellular debris. In some embodiments, the enzyme is in the presence of at least one protease inhibitor, e.g., to reduce degradation in a cell lysate or during purification.

Another embodiment of the invention provides a fusion protein comprising: i) a fluorescent protein or polypeptide; ii) a de-ubiquinating enzyme polypeptide substrate; and iii) a luminescent metal complex, wherein upon cleavage with the at least one de-ubiquinating enzyme, resonance energy transfer between (i) and (iii) is decreased. Some embodiments of the invention comprise an N-terminal fluorescent protein (e.g., GFP) fusion of ubiquitin with a short C-terminal extension containing an engineered cysteine residue that has been labeled with a terbium chelate. In some embodiments, an intact substrate demonstrates FRET, whereas DUB-dependant cleavage leads to a decrease in FRET. Another embodiment of the invention provides a fusion protein comprising: i) a fluorescent polypeptide; ii) a de-ubiquinating enzyme polypeptide substrate; and iii) a label, wherein the fluorescent polypeptide and the label are a RET pair and wherein upon cleavage of the de-ubiquinating enzyme polypeptide substrate, resonance energy transfer between (i) and (iii) is decreased.

In one embodiment, the compound is a de-ubiquinating enzyme. In one embodiment, the de-ubiquinating enzyme polypeptide substrate is a ubiquitin protein or polypeptide, a ubiquitin like polypeptide, protein or fragments thereof. In one embodiment, measuring the fluorescence emission from the test sample comprises determining a ratiometric measurement. In one embodiment, the method further comprises contacting the de-ubiquitinating and the fusion protein to form a control sample, wherein the concentration of the potential modulator of the de-ubiquitinating activity is less than the concentration in the test sample. In another embodiment, the potential modulator of the de-ubiquitinating activity is absent from the control sample. In one embodiment, measuring the fluorescent emission comprises a ratiometric measurement.

Described herein are various assays and methods for ubiquitination. These ubiquitination assays and methods can also be used in conjunction with or coupled to deubiquitination assays as described herein. For example, cellular based (e.g., living cell) assays and methods are described herein. In one embodiment, a fusion protein is expressed in a cell, wherein the fusion protein comprises a label (e.g., a GFP) and a ubiquitination substrate. This type of assay or method can be coupled to a deubiquitination assay of the invention. In one embodiment, the fusion protein can be expressed in a cell under conditions that cause ubiquitination, the cells can then be lysed and the ubiquitinated fusion protein can be utilized in deubiquitination assays and methods as described herein.

In another embodiment, the fusion protein can be expressed in a cell under conditions that cause ubiquitination. Then the cells are exposed to compounds and/or conditions of interest. In some embodiments, the cells are then lysed and ubiquitination/deubiquitination is measured as described herein, e.g., as described for some of the cellular based ubiquitination assay. For example, the cell lysate can then be contacted with a labeled binding partner that preferentially binds the ubiquitinated substrate or the un-ubiquitinated substrate. In some embodiments, the labeled binding partner is labeled with a RET partner (e.g., comprising terbium) compatible with the label (e.g., a GFP) of the fusion protein. In some embodiments, the labeled binding partner binds a ubiquitin or ubiquitin like protein (e.g., anti-ubiquitin or anti-polyubiquitin). In some embodiments, the labeled binding partner binds polyubiquitin (e.g., anti-polyubiquitin). In some embodiments, the labeled binding partner binds preferentially binds a non-ubiquitinated substrate, e.g., ubiquitination decrease RET measurements.

In some embodiments, the deubiquitination assays and methods of the present invention a fluorescent protein as a label, e.g., a fluorescent protein and ubiquitin fusion protein. In some embodiments, the fluorescent protein is a GFP. In some embodiments, the fluorescent protein is a YFP. In some embodiments, a fusion protein comprises the following amino acid sequence:

(SEQ ID NO: 25)
MRGSHHHHHHGMASMTGGQQMGRDLYDDDDKDRWGSEFATMVSKGEELFT

GVVPILVELDGDVNGHKFSVSGEGEGDATYGKLTLKFICTTGKLPVPWPT

LVTTFGYGVQCFARYPDHMRQHDFFKSAMPEGYVQERTIFFKDDGNYKTR

AEVKFEGDTLVNRIELKGIDFKEDGNILGHKLEYNYNSHNVYIMADKQKN

GIKVNFKIRHNIEDGSVQLADHYQQNTPIGDGPVLLPDNHYLSYQSALSK

DPNEKRDHMVLLEFVTAAGITLGMDELYKLETDQTSLYKKAGTMQIFVKT

LTGKTITLEVEPSDTIENVKAKIQDKEGIPPDQQRLIFAGKQLEDGRTLS

DYNIQKESTLHLVLRLRGG.

In some embodiments, a fusion protein comprises the previous amino acid sequence with the amino acid sequence "AC" added to the C-terminus. In some embodiments, a fusion protein comprises an amino acid sequence that has at least 70%, 80%, 90%, 95%, or 98% homology to the fluorescent polypeptides described herein. In some embodiments, the fusion protein does not comprise a tag, e.g., a histidine tag.

This section generally refers to de-ubiquitination as an exemplary embodiment of the invention. The invention also contemplates and provides similar assays and methods utilizing any protease, e.g., a protease that uses a SUMO protein as a substrate. In other words, the methods and assays described herein can also be performed using another protein in place of a de-ubiquitination assay and another substrate protein in place of ubiquitin, such as a SUMO specific protease and a SUMO protein. In some embodiments, the SUMO specific protease is a Ulp (e.g., catalog #12588-018, Invitrogen, Carlsbad, Calif.). A fusion protein containing a SUMO protein can be produced recombinantly for assays and methods of the invention. For example, to express a protein of interest as a fusion to the SUMO protein, one can use the Champion™ pET SUMO expression vector (Cat. no. K300-01) available from Invitrogen. In some embodiments, the SUMO fusion protein comprises a poly-histidine tag.

Also, see Horton et al., Analytical Chemistry, available online 10 Aug. 2006, doi:10.1016/j.ab.2006.06.031.

Ubiquination and Ubiquination-like Enzymes

Ubiquinating enzymes include, but are not limited to, E1, E2 and E3 enzymes. E1 and E2 are structurally related and well characterized enzymes. There are several species of E2, some of which act in preferred pairs with specific E3 enzymes to confer specificity for different target proteins. E3 enzymes contain two separate activities: a ubiquitin ligase activity to conjugate ubiquitin to substrates and form polyubiquitin chains via isopeptide bonds, and a targeting activity to physically bring the ligase and substrate together. Substrate specificity of different E3 enzymes is the major determinant in the selectivity of the ubiquitin-dependent protein degradation process.

E3 ligases that have been characterized include the HECT (homologous to E6-AP carboxy terminus) domain proteins, represented by the mammalian E6AP-E6 complex which functions as a ubiquitin ligase for the tumor suppressor p53 and which is activated by papillomavirus in cervical cancer (Huang et al., Science 286:1321-26 (1999)). One well characterized E3 ligase is the APC (anaphase promoting complex), which is a multi-subunit complex that is involved in both entry into anaphase as well as exit from mitosis (see King et al., Science 274:1652-59 (1996) for review). Most proteins known to be degraded by the APC contain a conserved nine amino acid motif known as the "destruction box" that targets them for ubiquitination and subsequent degradation. However, proteins that are degraded during G1, including G1 cyclins, CDK inhibitors, transcription factors and signaling intermediates, do not contain this conserved amino acid motif. Instead, substrate phosphorylation appears to play an important role in targeting their interaction with an E3 ligase for ubiquitination (see Hershko et al., Ann. Rev. Biochem. 67:429-75 (1998)).

Because the E3 complex is an important determinant of selection for protein degradation by the ubiquitin-dependent proteolytic process, modulators of E3 ligase activity may be used to upregulate or downregulate specific molecules involved in cellular signal transduction. Disease processes can be treated by such up- or down regulation of signal transducers to enhance or dampen specific cellular responses. This principle has been used in the design of a number of therapeutics, including phosphodiesterase inhibitors for airway disease and vascular insufficiency, kinase inhibitors for malignant transformation and proteasome inhibitors for inflammatory conditions such as arthritis.

Due to the importance of ubiquitination in cellular regulation and the wide array of different possible components in ubiquitin-dependent proteolysis, there is a need for a fast and simple means for assaying E3 ligase activity. Furthermore, such an assay would be very useful for the identification of modulators of E3 ligase. Accordingly, it is an object of the present invention to provide methods of assaying ubiquitin ligase activity, which methods may further be used to identify modulators of ubiquitin ligase activity.

Ubiquitin and Ubiquitination enzyme are described herein in exemplary embodiments of the invention. The invention also contemplates the use of Ubiquitin-like proteins and Ubiquitin-like enzymes, many of which are described herein e.g., those related to ubiquitination, SUMOylation, NEDDylation and ISGylation. As described herein, one skilled in the art will readily recognize comparable assays and methods related to ubiquitin-like proteins, enzymes and pathways.

Ubiquitin and Ubiquitin Like Proteins and Polypeptides

Ubiquitin and ubiquitin-like proteins are collectively known as "ubiquitons". Some ubiquitons comprise a central structural element of these post-translational modifications which is a ubiquitin superfold and, as well as being small conjugatable protein modifiers, ubiquitin superfolds can be domains that are genetically built into much larger proteins. An encompassing term for each of these structural folds is 'ubiquiton'. Ubiquitons have various functions, some of which are unrelated to protein degradation, and some ubiquitons have little homology to ubiquitin.

There are many ubiquitin like proteins, including but not limited to: NEDD8; SUMO-1; UCHL3; SUMO-2; SUMO-3; SUMO4; ISG15a; ISG15b; FAT10a; FAT10b; FUB1; UBL5; URM1; ATG8; Rub1; Smt3; Hub1; Urm1; and ATG12. Embodiments of the invention contemplate fluorescent protein-fusions (e.g., GFP) of any of these proteins or active fragments thereof All of these ubiquitin like polypeptides, proteins or fragments thereof are contemplated in the present invention. In one embodiment, the ubiquitin like polypeptide/protein is UCHL3.

There are many proteins that proteolytically remove ubiquitin and/or ubiquitin-like polypeptides from protein substrates, including but not limited to: POH1 (also known as Rpn11); UCHL3; ubiquitin carboxyl-terminal esterase L1 (UCHL1); SUMO1/sentrin specific protease 1 (SENP1); ubiquitin carboxyl-terminal esterase L1 (UCHL1); ubiquitin specific protease 1 (USP1); ubiquitin specific protease 10 (USP10); ubiquitin specific protease 12 (USP12); ubiquitin specific protease 14 (USP14); ubiquitin specific protease 15 (USP15);

ubiquitin specific protease 16 (USP16); ubiquitin specific protease 18 (USP18); ubiquitin specific protease 2 (USP2); ubiquitin specific protease 28 (USP28); ubiquitin specific protease 3 (USP3); ubiquitin specific protease 30 (USP30); ubiquitin specific protease 33 (USP33); ubiquitin specific protease 4 (USP4); ubiquitin specific protease 44 (USP44); ubiquitin specific protease 45 (USP45); ubiquitin specific protease 46 (USP46); and ubiquitin specific protease 49 (USP49); ubiquitin specific protease 5 (isopeptidase T) (USP5). One skilled in the art will recognize, that they are broadly defined as UCHs (ubiquitin-c terminal hydrolases) or USPs (ubiquitin specific proteases), as well as a family of metalloproteases of which POH1 is a member. All of these proteins that proteolytically remove ubiquitin and/or ubiquitin-like proteins from polypeptide substrates are contemplated in the present invention. They may be used individually or in any combination.

NEDD8/Rub1 is a ubiquitin (Ub)-like post-translational modifier. NEDD8/Rub1 is thought to be covalently linked to cullin (Cul)-family proteins in a manner analogous to ubiquitination. NEDD8 is thought to enhance the ubiquitinating activity of the SCF complex (composed of Skp1, Cul-1, ROC1 and F-box protein). It is also thought that NEDD8 modification of Cul-1 enhances recruitment of Ub-conjugating enzyme Ubc4 (E2) to the SCF complex (E3) and that the NEDD8-modifying system accelerates the formation of the E2-E3 complex, which stimulates protein polyubiquitination. It is believed that the NEDD8 system positively regulates SCF activity, possibly through a conformational change of Cul-1 that promotes the E2-E3 complex formation. For more information regarding NEDD8, NEDDylation or de-NEDDylation, see, e.g., Kawakami et al. EMBO J. 2001 Aug. 1; 20(15):4003-12; Osaka et al. Genes Dev. 12 (15), 2263-2268 (1998); Whitby et al. J. Biol. Chem. 273 (52), 34983-34991 (1998); and Kito et al. J. Biol. Chem. 276 (23), 20603-20609 (2001).

The C-terminal glycine of ubiquitin can be utilized for activation by E1, and glycine residues are typically found at the C-termini of ubiquitin-like proteins, such as SUMO, NEDD8 and ISG15. This C-terminal residue can eventually become conjugated to the lysyl e-amino group of target proteins to form isopeptide linkages and subsequent conjugates.

There can be cross-regulation between the various conjugation pathways since some proteins can become modified by more than one ubiquination-like enzyme, and sometimes even at the same lysine residue.

In some instances, SUMO modification acts antagonistically to that of ubiquitination. In some instances, SUMO modification serves to stabilize protein substrates.

Attachment of ubiquitin-like proteins might alter substrate conformation, affect the affinity for ligands or other interacting molecules, alter substrate localization and influence protein stability.

Figure 22:
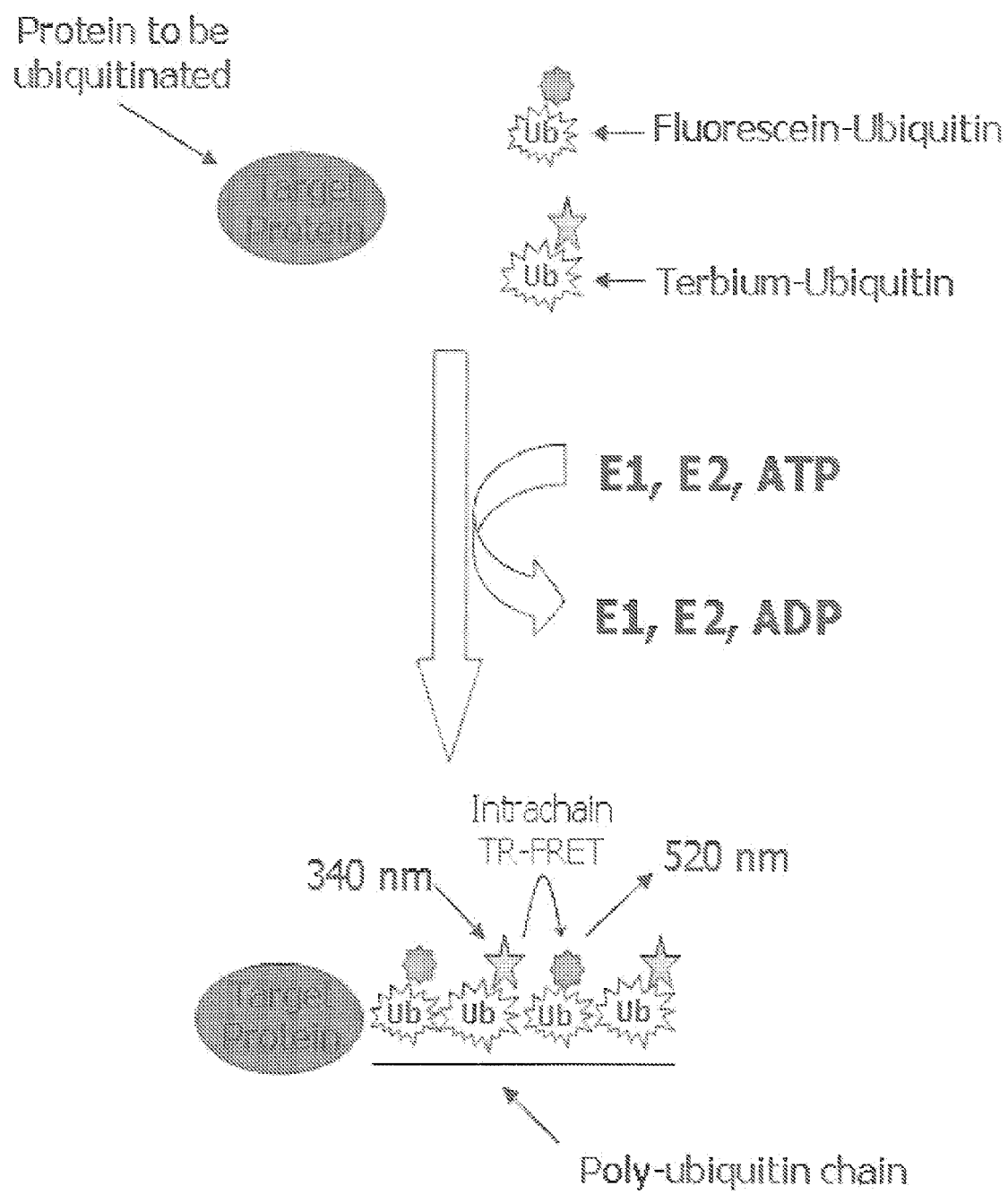
FIG. 22 shows a graphical representation of an Intrachain TR-FRET Ubiquitination Assay.
Figure 26A:
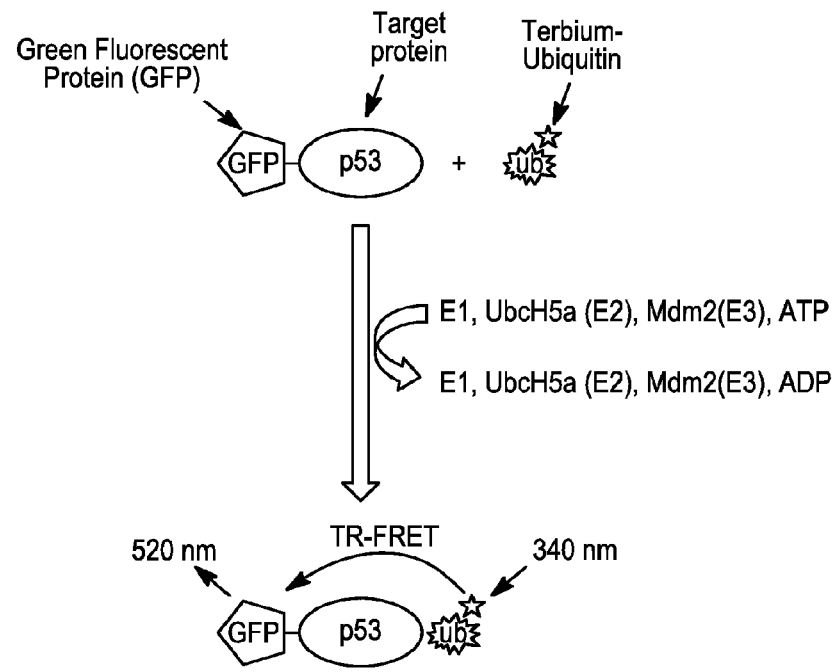
FIG. 26A shows an example of a ubiquitination assay with a GFP/P53 fusion protein and terbium-ubiquitin (terbium labeled ubiquitin). If the DNA sequence of the target protein (in this case p53) is known, a fusion product with a fluorescent protein or polypeptide (e.g., GFP) can be formed. For example a p53-GFP fusion protein can be used in a ubiquitination assay with terbium-ubiquitin to monitor the ubiquitination of p53.
Figure 26B:
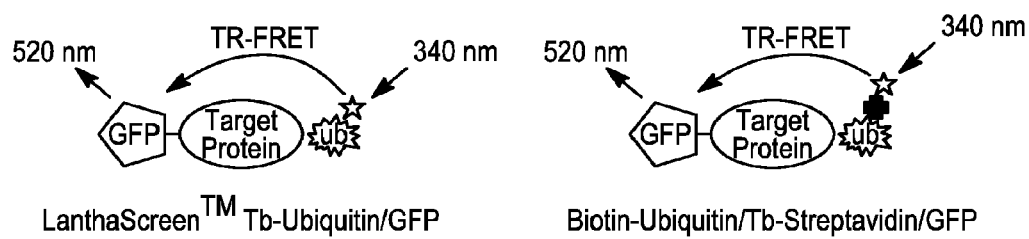
FIG. 26B shows a Tb-Streptavidin/Biotin-Ubiquitin format. When GFP fusions of the target protein are available, ubiquitination assays utilizing LanthaScreen™ Tb-Ubiquitin or Tb-Streptavidin/Biotin-Ubiquitin are possible. GFP acts as the TR-FRET acceptor and can be read with standard filter sets, e.g., LanthaScreen™ standard filter sets (Invitrogen, Carlsbad, Calif.).
Figure 27:
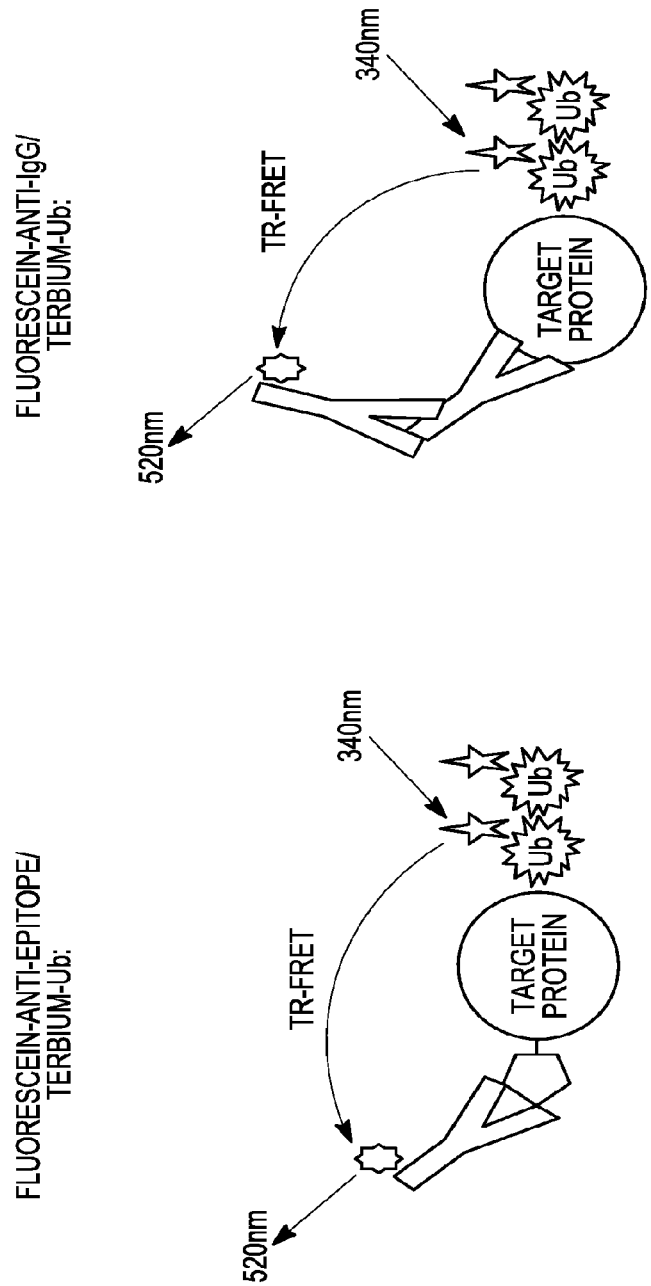
FIG. 27 shows examples of various ubiquination assay formats utilizing fluorescein labeled antibodies. A similar format may be utilized wherein the antibody is labeled with terbium and the ubiquitin is labeled with fluorescein. A similar format may be utilized wherein the antibody is labeled with an acceptor moiety of a RET pair and the ubiquitin is labeled a donor moiety of the RET pair. Another similar format can be utilized wherein a labeled antibody binds directly to the protein to be ubiquitinated, e.g., instead of binding to a "tag" or indirectly binding through a primary antibody.

Assays Related to Ubiquitination Proteins, Enzymes and Pathways and Ubiquitination-like Proteins, Enzymes and Pathways The invention provides various methods for the detection of ubiquination and various methods to identifying a modulator of a ubiquination reaction, e.g., see FIGS. 22, 26 and 27. The methods and assays of the invention can be in a high throughput format, cellular based, in vitro based or a combination thereof Ubiquinating enzymes include, but are not limited to E1, E2 and E3 enzymes.

There are several different classes of ubiquitination. One is poly-ubiquitination which typically results in a chain of ubiquitin or ubiquitin like molecules being attached to a protein. Mono-ubiquitination results in only one ubiquitin or ubiquitin like molecule being attached to a protein. Multi-ubiquitination results in ubiquitin or ubiquitin like molecules being attached to a protein at different sites on the protein. N-terminal ubiquitination results in a ubiquitin or ubiquitin like molecule being attached to the N-terminus of a protein.

One embodiment of the invention provides a sensitive screening assay to monitor a change in the rate or amount of poly-ubiquitination of a protein. In one embodiment, the assay is a HTS assay. In one embodiment, the assay is used to identify and develop pharmaceuticals for the treatment of disorders where ubiquitin-mediated protein degradation participates in the disease process (e.g. in diseases related to protein misfolding).

With regards to the present invention, ubiquitination assays and related methods are disclosed as examples of post-translation modification assays. The invention also contemplates related assays and methods, e.g., those related to SUMOylation.

SUMOylation involves SUMO isoforms being conjugated to lysine residues that are found within a sequence (e.g., a consensus sequence) in a target protein. For example, the consensus sequence may comprise ΨKXE, in which Ψ represents a large hydrophobic amino acid and X represents any amino acid. However, many attachment sites do not conform to this consensus sequence. A SUMOylation motif is found surrounding K11 of SUMO-2 and -3 but not SUMO-1. Therefore, like ubiquitin, SUMO-2 and -3 are capable of forming polySUMO chains. SUMO-1 can be conjugated to SUMO-2 and -3 but it functions as a chain terminator.

The Nedd8 conjugation process, called NEDDylation, is similar to ubiquitination. NEDDylation can utilize the E1 activating-enzyme complex composed of two subunits, APP-BP1 and UBA3, and the E2 conjugating-enzyme, UBC12 (e.g., Yeh et al. 2000). Known substrates of NEDDylation include, but are not limited to, Cullin family proteins, Cul1, Cul2, Cul3, Cul4A, Cul4B, and Cul5 (e.g., Osaka et al. 1998; Hori et al. 1999). NEDD8 and related proteins are also known as Rub1, ISG15 (UCRP), APG8, APG12, FAT10, URM1, Hub1, MGC104393, MGC125896 and MGC125897. A Nedd-8 gene can be found at Chromosome: 14; Location: 14q12 (MIM: 603171 GeneID: 4738)

In some embodiments, the assays and methods of the invention attach one protein to another as a post-translational modification, e.g. ubiquitination, SUMOylation and NEDDylation. In some embodiments, a labeled antibody which binds an epitope from a SUMO protein is utilized.

For further details and information related to ubiquitons, refer to the review by Rebecca L. Welchman, Colin Gordon and R. John Mayer, Nat Rev Mol Cell Biol. 2005 August; 6(8):599-609.

In one embodiment of the invention, the assay is an intrachain TR-FRET ubiquitin assay. In one embodiment, a portion of the ubiquitin (Ub) in the reaction is labeled with a RET donor, and another portion is labeled with a RET acceptor, wherein the donor and acceptor are compatible for RET. In one embodiment, a portion of the ubiquitin (Ub) in the reaction is labeled with fluorescein, and another portion is labeled with a terbium chelate. In one embodiment, a portion of the ubiquitin (Ub) in the reaction is labeled with a fluorescent protein, and another portion is labeled with a terbium chelate. The fluorescein and terbium ubiquitin portions are mixed with the ubiquitination enzymes (E1, E2, and E3), the target protein to be ubiquitinated, and an ATP solution to fuel the reaction. In one embodiment, the target protein is a ubiquitin protein or polypeptide. In another embodiment, the target protein is not ubiquitin. In one embodiment, ubiquitination enzymes incorporate a fluorescein labeled ubiquitin and a terbium labeled ubiquitin into poly-ubiquitin chains on the target protein. See FIG. 22. Following the ubiquitination of the protein of interest, both the RET donor and acceptor are present on the ubiquitin chain itself, allowing for the detection of the ubiquitination event without requiring the addition of a secondary reagent to complete the RET pairing. The percent incorporation of the fluorescein and terbium ubiquitin on the target protein may be controlled, in part, by the initial concentrations of each ubiquitin analogue at the start of the reaction. In one embodiment, the percent of target protein ubiquitinated is determined by measuring the RET ratio upon exciting the reaction mixture at 340 nm, and measuring the intensity of light emitted at 520 nm as compared to the light emitted at 495 nm. A significant increase in the RET ratio signifies ubiquitination of the target protein, whereas no significant increase in the RET ratio indicates that the target protein was not poly-ubiquitinated.

In one embodiment, the substrate is polyubiquitinated, but not by forming polyubiquitin chains. For example, multiple ubiquitin molecules are added to at least two sites on the substrate, e.g., multi-ubiquitinated.

For a HTS assay, a compound(s) (e.g., a drug or drug candidate) is introduced to measure the effectiveness of the compound(s) to inhibit or promote the ubiquitination of the target protein. In some embodiments, if the compound(s) inhibits the ubiquitination reaction, a decrease in the RET ratio (e.g., compared to control wells) is observed due to a decrease in the ubiquitination of the target protein. Conversely, an increase in the TR-FRET ratio is observed if the compound(s) promotes the ubiquitination of the target protein.

Because the RET donor and acceptor are located on a ubiquiton, the intrachain ubiquitination assay can be used with target proteins of which the encoding DNA sequence is unknown (therefore unable to encode epitope tags) or that do not have an antibody to selectively label the target protein. The assay can also be used to monitor the kinetics of the ubiquitination of a target protein in real time. In some embodiments, an intrachain TR-FRET ubiquitination assay incorporates both TR-FRET partners (e.g., Fluorescein-ubiquitin and Terbium-ubiquitin) in the ubiquitin chain, eliminating the requirement for the addition of a secondary reagent for analysis.

In some embodiments, a ubiquitin addition mutant is synthesized, e.g., with the addition of four amino acids (e.g., methionine-cysteine-glycine-glycine) to the N-terminus of the wildtype protein. In one embodiment, a cysteine is introduced to allow for the site specific labeling of the ubiquitin mutant with thiol reactive forms of fluorescein or the terbium chelate. Following purification of ubiquitin from cellular homogenate, the ubiquitin addition mutant is labeled with either the fluorescein or terbium chelate thiol reactive dyes to produce the corresponding fluorescein-ubiquitin or terbium-ubiquitin.

If a binding partner (e.g. an antibody) is available that recognizes the target protein, a ubiquitination assay that utilizes 1) an acceptor labeled (e.g. fluorescent label) binding partner (e.g. an antibody) with a donor labeled (e.g., terbium) ubiquitin or 2) a donor labeled (e.g., terbium) binding partner (e.g. an antibody) and an acceptor labeled (e.g. fluorescent label) ubiquitin can be established. A basic outline of these assay formats is provided in FIG. 27. In one embodiment, the labeled antibody binds a native epitope of the protein to be ubiquitinated. In some embodiments, the labeled binding partner binds a non-native epitope of the protein to be ubiquitinated, e.g., a tag such as GST.

With regards to the related assays and methods as described herein, one skilled in the art can recognize and select an appropriate binding molecule (e.g., an antibody) that binds ubiquitin and/or ubiquitin chains. In some methods, not all antibodies that bind ubiquitin will be useful or optimal. For example, some antibodies may, as an example, 1) have a higher affinity for a free ubiquiton as compared to a ubiquiton that is part of a ubiquitoned protein, 2) have a lower affinity for a free ubiquiton as compared to a ubiquiton that is part of a ubiquitoned protein, or 3) have relatively the same affinity for a free ubiquiton as compared to a ubiquiton that is part of a ubiquitoned protein. Some antibodies that bind a free ubiquiton may bind to an epitope that is not available or is altered when the ubiquiton is part of a ubiquitonated protein/substrate. In some embodiments of the invention, a binding molecule (e.g., an antibody) is utilized that binds a ubiquiton or ubiquiton chains that are a part of a ubiquitonated protein/substrate. In some embodiments, the binding molecule is an antibody. In some embodiments, an antibody preferentially binds a ubiquitin or ubiquiton that is associated with a ubiquitonated protein/substrate. In some embodiments, an antibody preferentially binds a free ubiquitin or ubiquiton, e.g., that is not associated with a ubiquitonated protein/substrate. In some embodiments of the invention, an antibody is a FK1 or FK2 antibody or binds the same epitopes (Fujimuro et al.,

*Methods Enzymol.* 399:75-86 (2005). In some embodiments of the invention, the antibody is FK-1 (e.g., recognizing polyubiquitin chains), for example, from BioMol (Plymouth Meeting, Pa.) represented by Catalog #PW8805 or an antibody comprising the CDRs of this antibody. In some embodiments of the invention, the antibody is FK-2 (e.g., recognizing ubiquitin), for example, from BioMol represented by Catalog #PW8810 or an antibody comprising the CDRs of this antibody.

Some embodiments of the invention provide an anti-epitope ubiquitination assay which utilizes an acceptor (e.g., fluorescein) labeled ubiquitin and a donor (e.g., a terbium) labeled anti-epitope antibody to complete the TR-FRET pairing. Some embodiments of the invention provide an anti-epitope ubiquitination assay which utilizes a donor (e.g., a terbium) labeled ubiquitin and an acceptor (e.g., fluorescein) labeled anti-epitope antibody to complete the TR-FRET pairing. The anti-epitope format can detect both mono- and poly-ubiquitination of a target protein. The anti-epitope ubiquitination assay has an acceptable signal-to-background compared to controls, and methylated ubiquitin will compete with fluorescein-ubiquitin for attachment to a GST-UbcH1.

Some embodiments of the invention provide detection of poly-ubiquitin chain formation. Since both the TR-FRET donor (e.g., Tb-ubiquitin) and acceptor (e.g., fluorescein-ubiquitin) are present in the polyubiquitin chain, no development step is required for the intrachain assay. This makes the intrachain assay especially useful when real-time kinetic information on ubiquitination is desired. As with the epitope method, the intrachain ubiquitination assay has an acceptable signal-to-background compared to controls, and methylated ubiquitin will compete with terbium and fluorescein-ubiquitin to inhibit the reaction.

In another embodiment, a ubiquination assay utilizes a protein which is a fusion between a fluorescent protein or polypeptide (e.g., GFP) and the target protein or polypeptide to be ubiquitinated (see FIG. 26). A fluorescent protein or polypeptide (e.g., a GFP) can be fused to the target protein or polypeptide providing an alternative to the intrachain ubiquitination reaction. An example of a ubiquitination assay with a GFP fusion protein or polypeptide with p53 and terbium-ubiquitin is outlined in FIG. 26. In this embodiment, both monoubiquitinated and polyubiquitinated proteins can be detected and/or measured. Real time kinetic analysis of the ubiquitination of the target protein can still be collected. This assay can be used in a high throughput screening format to identify compounds that can modulate (e.g., inhibit, maintain or enhance) the function of a ubiquitination enzyme(s) (e.g., Mdm2, the ubiquitin ligase enzymes (E3)) or compounds that can modulate the interaction between a ubiquitinating enzyme and a target protein (e.g., Mdm2 and p53).

In some embodiments, the ubiquitinating enzyme is measured from a cell lysate.

The cell lysate can be a crude cell lysate, partially purified or substantially purified. Substantially purified refers to about 95% purity. In some embodiments, the ubiquitinating enzyme is about 90, 91, 92, 93, 94, 95, 96, 99, 99.9 or 100% pure, such as 90% to 99.9%, 93% to 99.9%, 95% to 99.9%, or 90% to 96% pure. In some embodiments, the enzyme is from a cell lysate that has been centrifuged to remove cellular debris. In some embodiments, the enzyme is in the presence of at least one protease inhibitor, e.g., to reduce degradation in a cell lysate or during purification.

Some embodiments of the invention provide a cellular based assay. One embodiment of the invention provides a cell expressing a fusion protein wherein the fusion protein comprises a substrate for an enzymatic activity (e.g., ubiquitination) and the fusion protein comprises a label (e.g., a fluorescent protein, such as GFP). In some embodiments, the label can act as a donor or acceptor label for RET. In some embodiments, the enzymatic activity is ubiquitination. In some embodiments, the ubiquitination is poly-ubiquitination. In some embodiments, the ubiquitination is mono-ubiquitination. The fusion protein can be expressed in any cell, e.g., an eukaryotic or mammalian cell.

The ability to express GFP/ubiquitination substrate fusion proteins within a cell allows the cell's own ubiquitin machinery to modify a target protein. This can be especially useful with ubiquitin-protein ligases (e.g., E3) that consist of multiple subunits, such as APC, that might otherwise be difficult to express and purify for an assay (e.g., an in vitro assay). Some embodiments of the invention related to cellular ubiquitination assays utilize a cell endogenously expressing a GFP fusion of IκBα, e.g., in 293 cells. In some embodiments, a TNFR receptor can be stimulated with TNFα to induce the ubiquitination of the GFP-IκBα. In some embodiments, following the lysis of the cell to release the ubiquitinated fusion protein (e.g., GFP-IκBα), a labeled (e.g., terbium) anti-ubiquitin antibody is introduced to detect the ubiquitinated fusion protein, e.g., by completing FRET pairing and in some cases stimulating emission from the acceptor (e.g., GFP) and/or decreasing emission from the donor.

Some embodiments of the invention, e.g., the cellular based assays described herein, can be used to monitor the ubiquitination status of a target protein(s) in a cellular environment. This can enable a user to conduct high-throughput screens to test the functionality of, for example, a related ubiquitin pathway. In some embodiments, the invention provides means to screen compounds, e.g., for cell permeability as well as for effective inhibition of ubiquitination in the cellular milieu.

The cellular based assays of the invention provide one with the ability examine or determine various aspects of a pathway with regards to an enzymatic activity, such as ubiquitination. For example, one can screen compounds and/or conditions (e.g., radiation, temperature change, change in oxygen concentrations, etc.) that effect ubiquitination of a specific polypeptide that is a substrate for ubiquitination. The compound may exert its effect directly on a ubiquitinating enzyme(s) or it may exert its effect indirectly by affecting another protein in a pathway related to ubiquitination. In some embodiments, the effect(s) exerted by the compound or condition is modulation of the rate of ubiquitination of at least one protein substrate. In some embodiments, the rate of ubiquitination of a substrate is decreased. In some embodiments, the rate of ubiquitination of a substrate is increased. Any cellular pathway related to ubiquitination may be utilized and examined in the assays of the invention.

In some embodiments, a fusion protein (e.g., comprising a ubiquitination substrate and a label (e.g., GFP) is expressed by the cell. In some aspects of the invention, these cells are utilized in an assay of the invention. In some embodiments, after the cells have been exposed to a condition and/or compound the cells are lysed. The cell lysate may optionally be purified or partially purified with regards to the labeled ubiquitination substrate fusion protein, e.g., as described herein. The cell lysate can then be contacted with a labeled binding partner that binds the ubiquitinated substrate. In some embodiments, the labeled binding partner is labeled with a FRET partner (e.g., comprising terbium) compatible with the label (e.g., a GFP) of the fusion protein. In some embodiments, the labeled binding partner binds a ubiquitin or ubiquitin like protein (e.g., anti-ubiquitin or anti-polyubiquitin). In some embodiments, the labeled binding partner binds polyubiquitin (e.g., anti-polyubiquitin). In some embodiments, the labeled binding partner binds preferentially binds a non-ubiquitinated substrate, e.g., ubiquitination decrease RET measurements.

In some embodiments, the amount of ubiquitinated GFP-IκBα is measured as a dose response with TNFα (a known activator of TNFR). In some embodiments, either Tb-anti-polyubiquitin and/or Tb-anti-ubiquitin are used to bind the ubiquitinated fusion protein (e.g., GFP-IκBα) from the cellular lysate, e.g., to complete the FRET pairing.

In some embodiments, the pathway related to ubiquitination is the NF-κB pathway. For example, stimulation of the TNF receptor (TNFR) activates TNFR-associated factor (TRAF) and subsequently TGFb-activated kinase 1 (TAK1). The active TAK1 regulates the phosphorylation of IKKβ that is responsible for phosphorylating IκBα. The ubiquitin-ligase complex, SCF-bTrCP, poly-ubiquitinates the phosphorylated IκBα, signaling the protein for degradation.

Some embodiments of the invention provide methods for determining if a compound is a modulator of a post-translational modification, the method comprising: (a) contacting the compound and a cell expressing at least one fusion protein, wherein the fusion protein comprises a first label and a substrate for the post-translational modification to form a test sample; (b) contacting the test sample with a binding partner that exhibits discriminate binding based on the presence or absence of the post-translational modification, wherein the binding partner comprises a second label and wherein the first and second label are a RET pair; and (c) measuring the fluorescence emission from the test sample. In some embodiments, the method additionally comprises a control sample, e.g., lacking the compound or the fusion protein. In some embodiments, a fluorescence property of the test sample is compared to a fluorescence property of a control sample.

One embodiment of the invention provides a method for measuring ubiquination activity of at least one compound comprising: a) contacting the compound with at least one protein and labeled ubiquiton to form a test sample, wherein the labeled ubiquiton comprises at least two populations, wherein the first population is labeled with an acceptor molecule of a compatible RET pair and the second population is labeled with a donor molecule of a compatible RET pair; b) exposing the test sample to at least one wavelength of light; and c) measuring the fluorescence emission from the test sample.

Another embodiment of the invention provides a method for identifying at least one modulator of ubiquination activity, the method comprising: a) contacting at least one potential modulator of the ubiquination activity, at least one protein and labeled ubiquiton to form a test sample, wherein the labeled ubiquiton comprises at least two populations, wherein the first population is labeled with an acceptor molecule of a compatible RET pair and the second population is labeled with a donor molecule of a compatible RET pair; b) exposing the test sample to at least one wavelength of light; and c) measuring the fluorescence emission from the test sample. In one embodiment, the method further comprises contacting the at least one protein and the labeled ubiquitin to form a control sample, wherein the concentration of the potential modulator of the ubiquination activity is less than the concentration in the test sample. In one embodiment, the potential modulator of the ubiquination activity is absent from the control sample.

Another embodiment of the invention provides an article of manufacture comprising: a) packaging material; and b) at least two populations of labeled ubiquiton, wherein the first population is labeled with an acceptor molecule of a compatible RET pair and the second population is labeled with a donor molecule of a compatible RET pair. In one embodiment, the article of manufacture further comprises at least one ubiquinating enzyme. In one embodiment, the article of manufacture further comprises at least one ubiquinating enzyme is selected from an E1, E2, and E3. In one embodiment, the article of manufacture further comprises ubiquinating enzymes E1, E2, and E3.

Another embodiment of the invention provides a method for measuring a ubiquitination activity of at least one compound comprising: a) contacting i) the at least one compound with ii) a ubiquitin and iii) a protein to form a test sample, wherein the protein comprises a ubiquitination substrate and a first moiety of a RET pair; b) incubating the test sample under conditions suitable for ubiquitination; c) contacting the test sample either before, during or after (b) with a binding molecule that binds the ubiquitin, wherein the binding molecule is labeled with a second moiety of a FRET pair; d) exposing the test sample to at least one wavelength of light; and e) measuring the fluorescence emission from the test sample.

Another embodiment of the invention provides a method for determining if at least one compound is a modulator of ubiquination activity, the method comprising: a) contacting i) the at least one compound with ii) a ubiquitin, iii) a protein, and iv) a ubiquitinating enzyme to form a test sample, wherein the protein comprises a ubiquitination substrate and a first moiety of a RET pair; b) incubating the test sample under conditions suitable for ubiquitination; c) contacting the test sample, either before, during or after (b), with a binding molecule that binds the ubiquitin, wherein the binding molecule is labeled with a second moiety of a FRET pair; d) exposing the test sample to at least one wavelength of light; e) measuring the fluorescence emission from the test sample; and f) comparing the fluorescence emission to a control sample.

Another embodiment of the invention provides ubiquitin or ubiquitin like protein or polypeptide labeled with a terbium metal ion. In one embodiment, the terbium ion labeled ubiquitin or ubiquitin like protein or polypeptide is as described in example 17 below.

In one embodiment, the second labeled ubiquitin population is labeled with a lanthanide metal complex. In one embodiment, the lanthanide metal complex comprises terbium. In one embodiment, the lanthanide metal complex comprises an organic antenna moiety, a metal liganding moiety and a lanthanide metal ion. In one embodiment, the lanthanide metal complex comprises Tb(III). In one embodiment, the lanthanide metal complex comprises a metal chelating moiety selected from the group consisting of: EDTA, DTPA, TTHA, DOTA, NTA, HDTA, DTPP, EDTP, HDTP, NTP, DOTP, DO3A, DOTAGA, and NOTA.

In one embodiment, the at least one wavelength of light is in the range from 250 nm to 750 nm. In one embodiment, the first labeled ubiquitin population is labeled with fluorescein or a fluorescent protein or polypeptide. In one embodiment, the fluorescent protein or polypeptide is a GFP. In one embodiment, the at least one protein is ubiquitin. In one embodiment, the at least one protein is not ubiquitin. In one embodiment, at least one member from the group selected of the compound, the at least one protein and the labeled ubiquitin is in a cell lysate. In one embodiment, at least one member from the group selected of the compound, the at least one protein and the labeled ubiquitin is substantially purified. In one embodiment, at least one member from the group selected of the potential modulator, the at least one protein and the labeled ubiquitin is in a cell lysate. In one embodiment, at least one member from the group selected of the potential modulator, the at least one protein and the labeled ubiquitin is substantially purified. In one embodiment, measuring the fluorescence emission from the test sample comprises determining a ratiometric measurement.

Reaction Volumes of the Assays of the Invention

The assays described herein can be run in various volumes. In some embodiments, the volumes of the reactions can be reduced significantly. In some embodiments, the reaction volumes are between about 1 nanoliter (nl) to about 200 ul; about 10 nl to about 200 ul; about 100 nl to about 200 ul; about 1 ul to about 200 ul; about 10 ul to about 200 ul; about 10 nl to about 100 ul; about 10 nl to about 20 ul; about 100 nl to about 20 ul; about 1 ul to about 20 ul; about 1 ul to about 10 ul; about 1 ul to about 5 ul; about 5 ul to about 10 ul; or about 10 ul to about 20 ul. In some embodiments, the reaction volume is about 4 or 20 ul.

In some embodiments, the assays of the invention can be run in relatively small reaction volumes. This lends the advantage of being able to reduce the amount and cost of assay reagents, some of which may be in limited supply. The miniaturization of the assay can also increase the number of samples screened at a time, e.g., increasing high throughput efficiency.

Fluorescent Measurements and Calculations for the Assays of the Invention

In some cases, when assessing the quality of a ratiometric assay and its ability to reliably identify compounds that have biological activity, it can be tempting (but sometimes misleading) to look at the "fold change" between maximal and minimal assay values. In practice, the robustness of a ratiometric assay is not actually determined by the relative difference in these values, but by the magnitude of the absolute difference in these values relative to the magnitude of the errors associated with these values. With TR-FRET assays in particular, the magnitude of these errors can be quite small relative to the separation between maximal and minimal TR-FRET values, and as a result, a large "window" is not necessary for the assay to be robust.

Competitive equilibrium binding assays are typically performed at a concentration of tracer and receptor that provides a signal that is 80% between that of the fully bound and fully competed tracer. This provides a balance between the magnitude of the signal change and the ability of the assay to report changes in analyte concentration, which decreases as the initial concentration of complex in the uncompeted state increases. As an example, TR-FRET kinase assays are often run at or near the EC80 concentration of the kinase (under a given set of substrate and ATP concentrations), so that small changes in the amount of active kinase present will result in appreciable changes in the TR-FRET value, while maintaining a suitable separation between the readouts of active and inactive kinase.

Binding Partners

One embodiment of the invention is based on monitoring and/or measuring a molecular interaction (e.g., complex formation or disruption) between two binding partners. A "binding partner" is a compound (e.g., a first binding partner) that has affinity for another compound (e.g., a second binding partner) (or vice versa) such that the two binding partners are capable of forming a complex when bound. Two binding partners can be members of a specific binding pair. For example, a first binding partner can be a monoclonal antibody and a second binding partner can be a composition having the epitope recognized by that monoclonal antibody.

One embodiment related to kinase or phosphatase activity, utilizes anti-phospho-specific antibodies labeled with a lanthanide metal complex (e.g., comprising a Tb chelate) following standard protocols (e.g., supplied with a commercial chelate reagent). Alternatively, phospho-specific antibodies are labeled "in situ" through association with species-specific antibodies (e.g., Tb-labeled anti-IgG) that bind to the anti-phosphospecific antibodies. In one embodiment, these reagents are added to a kinase reaction in which the GFP- or fluorescein-labeled protein or polypeptide substrate has been used. The GFP fusion may be produced in E coli using standard molecular biology, recombinant protein expression, and protein purification techniques. After a brief incubation the assay may be read using standard "LanthaScreen™" settings, e.g., as described in the "LanthaScreen™ User's Guide" (Invitrogen, California).

Accordingly, in one aspect, the invention provides compositions that include a binding partner. The binding partner can be labeled with a luminescent metal complex (e.g., Tb or Europium). Alternatively, the binding partner can be labeled with a fluorescent acceptor moiety. Examples of binding partners labeled with luminescent metal complexes or fluorescent acceptor moieties are set forth in the Examples, below. The present invention also provides mixtures of binding partners. For example, a composition can include a first binding partner and a second binding partner. The first binding partner can comprise a luminescent metal complex while the second binding partner can comprise a fluorescent acceptor moiety. Alternatively, the first binding partner can comprise a fluorescent acceptor moiety, while the second binding partner can comprise a luminescent metal complex.

Typically, the affinity (apparent $K_d$) of a first binding partner for a second binding partner is about 1 mM or less, e.g., about 10 µM or less, or about 1 µM or less, or about 0.1 µM or less, or 10 nM or less, or 1 nM or less, or 0.1 nM or less. As one of skill in the art will recognize, one can systematically adjust experimental parameters, e.g., concentrations of assay components, reaction times, temperatures, and buffers, depending on the $K_d$ of the first binding partner for the second binding partner, to obtain a desired combination of conditions and cost-effectiveness.

A second binding partner need not be an optimal binding partner for a first binding partner. The term encompasses all binding partners whose binding interactions can be probed using the methods of the present invention. A second binding partner is sometimes referred to herein as a "tracer," and if it includes a luminescent metal complex or a fluorescent acceptor moiety, a "luminescent tracer."

A binding partner can be a protein, polypeptide, a polynucleotide, a lipid, a phospholipid, a polysaccharide, or an organic molecule. Examples of specific protein or polypeptide binding partners include an antibody, a protein, or an enzymatically or chemically-synthesized or modified polypeptide sequence (e.g., a polypeptide sequence derived from a protein, modified from a protein, or designed and synthesized de novo.) A protein or polypeptide binding partner may be linear or cyclic. An organic molecule binding partner can be a small organic molecule.

Typical examples of first and second binding partners that form complexes include an antibody and a composition having an epitope or epitope mimetic recognized by that antibody; a polypeptide and a ligand (e.g., receptor-ligand interactions); a polypeptide and another polypeptide (e.g., protein-protein interactions); a polypeptide and a polynucleotide (e.g., protein-DNA or protein-RNA interactions); a polynucleotide and another polynucleotide (e.g., DNA-DNA, DNA-RNA, or RNA-RNA interactions); a polypeptide and an organic molecule (e.g., protein-drug interactions); a polypeptide and a lipid (e.g., protein-phospholipid interactions); a polynucleotide and an organic molecule; and an organic molecule and another organic molecule.

A binding partner can comprise either a luminescent metal complex or a fluorescent acceptor moiety. In some embodiments of the methods described herein, one binding partner can comprise a luminescent metal complex and the other can comprise a fluorescent acceptor moiety, e.g., a first binding partner comprises a luminescent metal complex and a second binding partner comprises a fluorescent acceptor moiety. Inclusion of a luminescent metal complex and fluorescent acceptor moiety on a binding partner pair allows an interaction of first and second binding partners to be monitored by one or more fluorescent techniques (e.g., TR-RET, or multiplex modes). For example, when a first binding partner and second binding partner are bound to one another, the complex will typically exhibit a characteristic TR-RET signal. Disruption of the molecular interaction between the first binding partner and the second binding partner (e.g., by the addition of a competitor of the second binding partner) alters the TR-RET signal, allowing the monitoring of the molecular interaction in either TR-RET modes.

In one embodiment, an antibody can be labeled with a luminescent metal chelate and a protein or polypeptide binding partner for the antibody can be labeled with a fluorescent acceptor moiety. When the antibody and polypeptide are bound to one another, the sample typically exhibits a fluorescence emission measurement characteristic of RET between the luminescent metal chelate and the acceptor moiety. Addition of a competitor at a suitable concentration and with a suitable $K_d$ for the antibody results in displacement of the second binding partner, with a change in the fluorescence emission measurement as a result of a loss of RET between the luminescent metal chelate on the antibody and the fluorescent acceptor moiety on the protein or polypeptide.

Binding partners can be prepared and purified by a number of methods known to those of ordinary skill in the art. For example, antibodies, including monoclonal antibodies and antibody fragments, can be prepared by a number of methods known to those of skill in the art, or can be purchased from a variety of commercial vendors, including Serotec (Raleigh, N.C.), Abcam (Cambridge, Mass.), R&D Systems, Cambridge Antibody Technologies, and Covance Research Products (Denver, Colo.).

In general, an antigen for which an antibody is desired is prepared, e.g., recombinantly, by chemical synthesis, or by purification of a native protein, and then used to immunize animals. For example, polypeptides or proteins containing a particular amino acid sequence and/or post-translational modification (e.g., phosphorylation) can be prepared by solid-phase chemical synthesis in order to raise an antibody specific for the sequence and/or post-translational modification. Various host animals including, for example, rabbits, chickens, mice, guinea pigs, goats, and rats, can be immunized by injection of the antigen of interest. Depending on the host species, adjuvants can be used to increase the immunological response and include Freund's adjuvant (complete and/or incomplete), mineral gels such as aluminum hydroxide, surface-active substances such as lysolecithin, pluronic polyols, polyanions, peptides, oil emulsions, keyhole limpet hemocyanin, and dinitrophenol. Polyclonal antibodies are contained in the sera of the immunized animals. Monoclonal antibodies can be prepared using standard hybridoma technology. In particular, monoclonal antibodies can be obtained by any technique that provides for the production of antibody molecules by continuous cell lines in culture as described, for example, by Kohler et al. (1975) Nature 256:495-497, the human B-cell hybridoma technique of Kosbor et al. (1983) Immunology Today 4:72, and Cote et al. (1983) Proc. Natl. Acad. Sci. USA 80:2026-2030, and the EBV-hybridoma technique of Cole et al., Monoclonal Antibodies and Cancer Therapy, Alan R. Liss, Inc. pp. 77-96 (1983). Such antibodies can be of any immunoglobulin class including IgM, IgG, IgE, IgA, IgD, and any subclass thereof. The hybridoma producing the monoclonal antibodies of the invention can be cultivated in vitro or in vivo. Chimeric antibodies can be produced through standard techniques.

Antibody fragments that have specific binding affinity for an antigen can be generated by known techniques. Such antibody fragments include, but are not limited to, F(ab')$_2$ fragments that can be produced by pepsin digestion of an antibody molecule, and Fab fragments that can be generated by reducing the disulfide bridges of F(ab')$_2$ fragments. Alternatively, Fab expression libraries can be constructed. See, for example, Huse et al. (1989) Science 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

Once produced, antibodies or fragments thereof can be tested for recognition of (and affinity for) a second binding partner by standard immunoassay methods including, for example, enzyme-linked immunosorbent assay (ELISA) or radioimmuno assay (RIA). See, Short Protocols in Molecular Biology, eds. Ausubel et al., Green Publishing Associates and John Wiley & Sons (1992). Suitable antibodies typically will have a $K_d$ for a second binding partner of about 1 mM or less, e.g., about 10 μM or less, or about 1 μM or less, or about 0.1 μM or less, or about 10 nM or less, or about 1 nM or less, or about 0.1 nM or less. For example, if a post-translationally modified protein is used to immunize an animal to produce an antibody specific for the particular post-translational modification, the second binding partner can be a protein or polypeptide containing the same post-translational modification. In other embodiments, a second binding partner will have the same chemical structure as an antigen used to immunize.

Other polypeptides in addition to antibodies are useful as first or second binding partners and can also be prepared and analyzed using standard methods. By way of example and not limitation, polypeptides or proteins can be obtained by extraction from a natural source (e.g., from isolated cells, tissues or bodily fluids), by expression of a recombinant nucleic acid encoding the protein or polypeptide, or by chemical synthesis. Polypeptides or proteins can be produced by, for example, standard recombinant technology, using expression vectors encoding the proteins or polypeptides. The resulting polypeptides then can be purified. Expression systems that can be used for small or large scale production of polypeptides include, without limitation, microorganisms such as bacteria (e.g., E. coli and B. subtilis) transformed with recombinant bacteriophage DNA, plasmid DNA, or cosmid DNA expression vectors; yeast (e.g., S. cerevisiae) transformed with recombinant yeast expression vectors; insect cell systems infected with recombinant virus expression vectors (e.g., baculovirus); plant cell systems infected with recombinant virus expression vectors (e.g., tobacco mosaic virus) or transformed with recombinant plasmid expression vectors (e.g., Ti plasmid); or mammalian cell systems (e.g., primary cells or immortalized cell lines such as COS cells, Chinese hamster ovary cells, HeLa cells, human embryonic kidney 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter).

Suitable methods for purifying the polypeptides or proteins of the invention can include, for example, affinity chromatography, immunoprecipitation, size exclusion chromatography, and ion exchange chromatography. See, for example, Flohe et al. (1970) *Biochim. Biophys. Acta.* 220:469-476, or Tilgmann et al. (1990) *FEBS* 264:95-99. The extent of purification can be measured by any appropriate method, including but not limited to: column chromatography, polyacrylamide gel electrophoresis, or high-performance liquid chromatography.

Polypeptides and proteins as first or second binding partners can also be prepared using solid phase synthesis methods, see, e.g., WO 03/01115 and 6,410,255. For ease of synthesis and cost considerations, it is preferred that polypeptides synthesized chemically have between 3 to 50 amino acids (e.g., 3 to 30, 3 to 20, 3 to 15, 5 to 30, 5 to 20, 5 to 15, 8 to 20, 8 to 15, 10 to 10, 10 to 15 or 10 to 12 amino acids in length). In the polypeptides and proteins of the invention, a great variety of amino acids can be used. Suitable amino acids include natural, non-natural, and modified (e.g., phosphorylated) amino acids. Amino acids with many different protecting groups appropriate for immediate use in the solid phase synthesis of peptides are commercially available.

Polynucleotides useful as binding partners can be produced by standard techniques, including, without limitation, common molecular cloning and chemical nucleic acid synthesis techniques. For example, polymerase chain reaction (PCR) techniques can be used. PCR refers to a procedure or technique in which target nucleic acids are enzymatically amplified. Sequence information from the ends of the region of interest or beyond typically is employed to design polynucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in PCR Primer: A Laboratory Manual, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis Genetic Engineering News, 12(9):1 (1992); Guatelli et al., Proc. Natl. Acad. Sci. USA, 87:1874-1878 (1990); and Weiss, Science, 254:1292 (1991).

Polynucleotides of the invention also can be chemically synthesized, either as a single nucleic acid molecule (e.g., using automated DNA synthesis in the 3' to 5' direction using phosphoramidite technology) or as a series of smaller polynucleotides. For example, one or more pairs of long polynucleotides (e.g., >100 nucleotides) can be synthesized that contain the desired sequence, with each pair containing a short segment of complementarity (e.g., about 15 nucleotides) such that a duplex is formed when the polynucleotide pair is annealed. DNA polymerase is used to extend the polynucleotides, resulting in a single, double-stranded polynucleotide.

Polynucleotides of the invention also can be obtained by mutagenesis. For example, polynucleotides can be mutated using standard techniques including polynucleotide-directed mutagenesis and site-directed mutagenesis through PCR. See Short Protocols in Molecular Biology, Chapter 8, Green Publishing Associates and John Wiley & Sons, edited by Ausubel et al., 1992.

In some embodiments of the invention, binding partners are utilized to label substrates with the enzymatic reaction of interest. For examples see FIGS. 9, 11*b-f* and 27.

Luminescent Metal Complex

A binding partner can comprise a luminescent metal complex. A luminescent metal complex can act as a donor fluorophore in a RET or TR-RET assay. A luminescent metal complex is useful in the present methods because its excited state lifetime is typically on the order of milliseconds or hundreds of microseconds rather than nanoseconds; a long excited state lifetime allows detection of a molecular interaction between binding partners to be monitored after the decay of background fluorescence and/or interference from light-scattering.

Methods for covalently linking a luminescent metal complex to a variety of binding partners are known to those of skill in the art, see, e.g., WO 96/23526; WO 01/09188, WO 01/08712, and WO 03/011115; and U.S. Pat. Nos. 5,639,615; 5,656,433; 5,622,821; 5,571,897; 5,534,622; 5,220,012; 5,162,508; and 4,927,923.

A luminescent metal complex includes a metal ligating moiety, one or more lanthanide metal ions, and optionally linkers, spacers, and organic antenna moieties.

Metal Liganding Moiety

A metal liganding moiety coordinates one or more lanthanide metal ions to form a metal complex. Typically, a metal ligating moiety includes one or more metal coordinating moieties X, where X is a heteroatom electron-donating group capable of coordinating a metal cation, such as $O^-$, $OH$, $NH_2$, $OPO_3^{2-}$, $NHR$, or $OR$ where R is an aliphatic group.

A metal ligating moiety can be a chelating moiety or a cryptand moiety. If a lanthanide metal ion is coordinated to a chelating moiety, the complex is referred to as a "metal chelate." If a lanthanide metal ion is coordinated to a cryptand moiety, the complex is referred to as a "metal cryptand."

A metal chelate should be stable to exchange of the lanthanide ion. Metal chelates preferably have a formation constant ($K_f$) of greater than $10^{10}$ $M^{-1}$. A variety of useful chelating moieties are known to those of skill in the art. Typical examples of chelating moieties include: EDTA, DTPA, TTHA, DOTA, NTA, HDTA, DTPP, EDTP, HDTP, NTP, DOTP, DO3A, DOTAGA, and NOTA.

In some embodiments, a luminescent metal chelate can have the following structures:

or

wherein A represents an organic antenna moiety;
L represents a linker;
S represents a spacer;
n can be 0 or 1;
C represents a metal chelating moiety; and
M represents a lanthanide metal ion coordinated to C.

Figure 2:
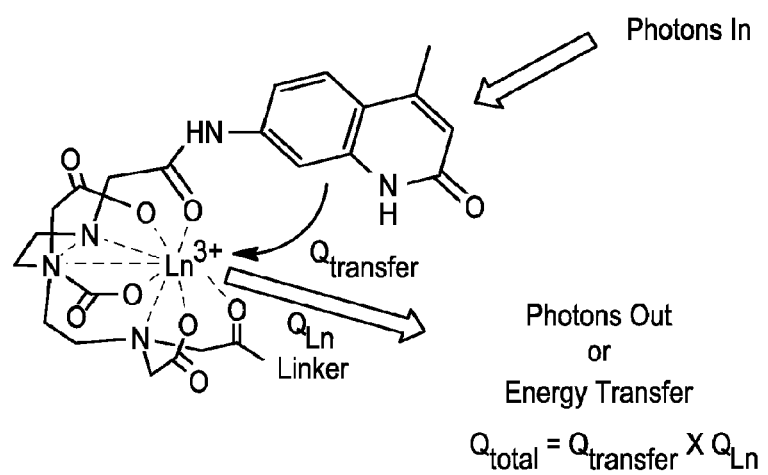
FIG. 2 demonstrates the structure of a lanthanide metal chelate comprising an organic antenna moiety and the transfer of energy from the organic antenna moiety to the lanthanide metal ion.
Figure 3A:
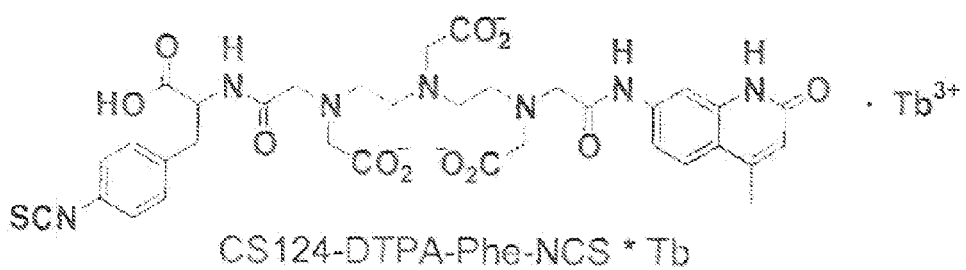
FIG. 3 demonstrates the chemical structure of two luminescent metal chelates comprising organic antenna moieties.
Figure 3B:
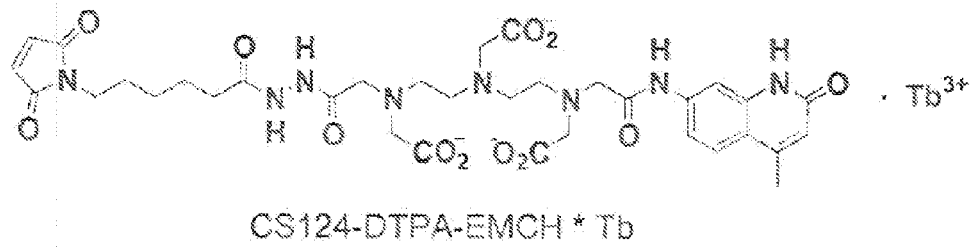

For illustrative examples of luminescent metal chelates, see FIGS. 2 and 3. FIG. 3 also demonstrates luminescent metal chelates useful for conjugating to amine moieties (top structure) or thiol moieties (bottom structure) on binding partners.

Cryptates are formed by the inclusion of a lanthanide cation into a tridimensional organic cavity, leading to highly stable complexes. A variety of useful cryptand moieties are known to those of skill in the art. Examples of cryptand moieties useful in the present methods include: trisbypyridine (TBP, e.g., TBP pentacarboxylate), and pyridine bipyridine (e.g., pyridine bipyridine tetracarboxylate).

Chelating and cryptand moieties can be synthesized by a variety of methods known to those of skill in the art or may be purchased commercially. See U.S. Pat. Nos. 5,639,615; 5,656,433; 5,622,821; 5,571,897; 5,534,622; 5,220,012; 5,162,508; and 4,927,923; and WO 96/23526 and WO 03/011115.

Lanthanide Metal Ions

Metal liganding moieties coordinate one or more lanthanide metal ions to form a metal complex. Lanthanide metal ions are useful because their special electronic configuration shields the optically active electrons, resulting in characteristic line type emissions. As the electronic transitions of the metal ions are forbidden by quantum mechanics rules, the emission lifetimes of these ions are typically long (from μs to msec).

Useful lanthanide metal ions include Sm(III), Ru(III), Eu (III), Gd(III), Tb(III), and Dy(III). Methods for complexing a metal ion to a chelating or cryptand moiety are known to those of skill in the art, see, e.g., WO 96/23526 and WO 03/011115.

Organic Antenna Moiety

Figure 4:
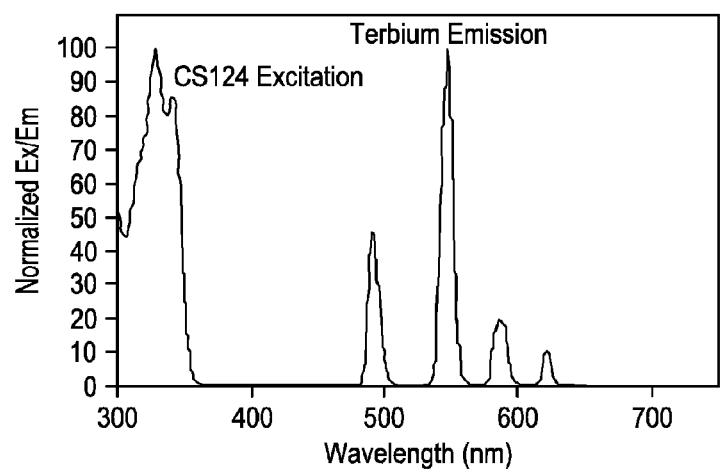
FIG. 4 demonstrates the normalized excitation/emission spectrum for a terbium chelate comprising an organic antenna moiety (CS124).
Figure 5:
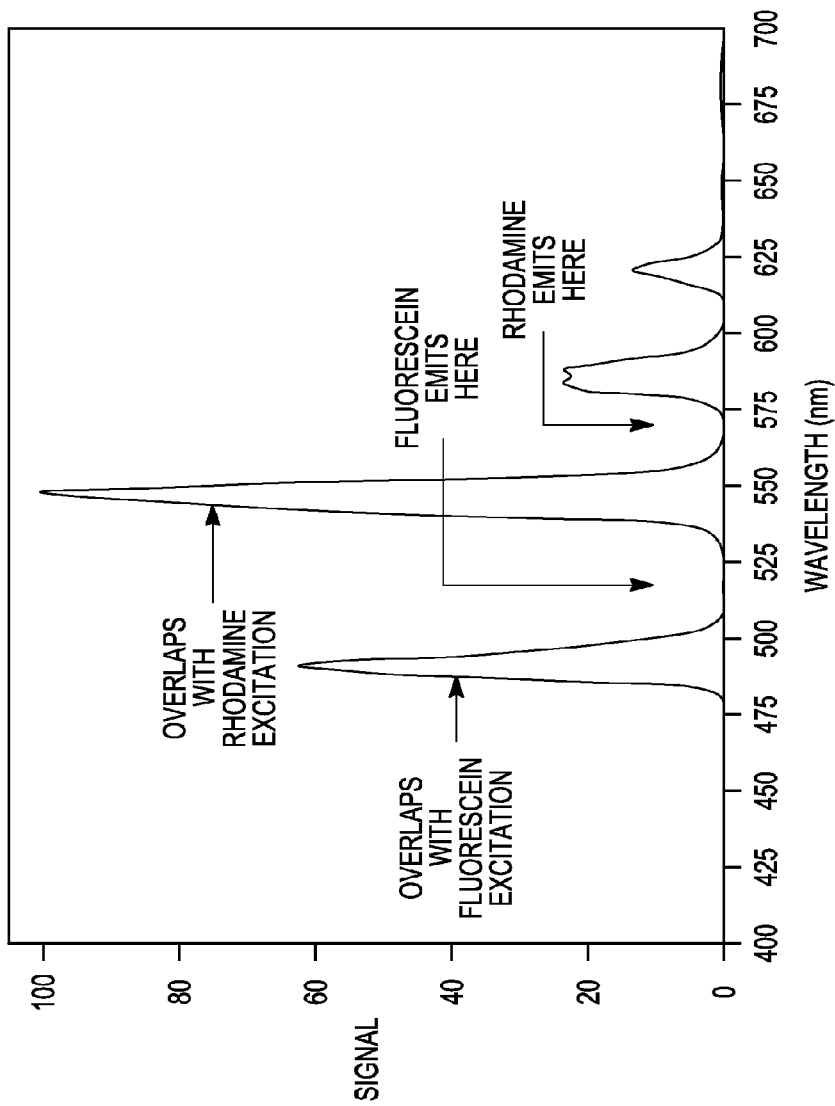
FIG. 5 is a terbium chelate emission spectrum, demonstrating the overlap of terbium emission bands with fluorescein and rhodamine excitation bands and the location of fluorescein and rhodamine emission bands in regions having minimal terbium emission.

A luminescent metal complex can optionally include an organic antenna moiety. An organic antenna moiety typically has a conjugated electronic structure so that it can absorb light. The absorbed light is transferred by intramolecular non-radiative processes from the singlet to the triplet excited state of the antenna moiety, then from the triplet state to the emissive level of the lanthanide ion, which then emits characteristically long-lived luminescence. See FIGS. 2 and 4. It should be noted that some metal liganding moieties can absorb light without the inclusion of an organic antenna moiety. For example, certain cryptand moieties that contain conjugated organic moieties, such as tribipyridine pentacarboxylate, do not require the inclusion of a discrete organic antenna moiety.

In some embodiments, an organic antenna moiety can be a polynuclear heterocyclic aromatic compound. The polynuclear heterocylic aromatic compound can have two or more fused ring structures. Examples of useful organic antenna moieties include rhodamine 560, fluorescein 575, fluorescein 590, 2-quinolone, 4-quinolone, 4-trifluoromethylcoumarin (TFC), 7-diethyl-amino-coumarin-3-carbohydrazide, 7-amino-4-methyl-2-coumarin (carbostyril 124, CS124), 7-amino-4-methyl-2-coumarin (coumarin 120), 7-amino-4-trifluoromethyl-2-coumarin (coumarin 124), and aminomethyltrimethylpsoralen. See FIGS. 2 and 3.

Compounds useful as organic antenna moieties can be synthesized by methods known to those of skill in the art or purchased commercially. See U.S. Pat. Nos. 5,639,615; 5,656,433; 5,622,821; 5,571,897; 5,534,622; 5,220,012; 5,162,508; and 4,927,923.

Linkers, Spacers

Linkers and Spacers can optionally be included in a luminescent metal complex. A Linker (L) functions to link a luminescent metal complex to a first or second binding partner. In some embodiments, a L can link an acetate, amine, amide, carboxylate, or methylene functionality on a metal liganding moiety to a first or second binding partner.

One of skill in the art can design Ls to react with a number of functionalities on binding partners, including, without limitation, amines, acetates, thiols, alcohols, ethers, esters, ketones, and carboxylates. In embodiments where the binding partner is a protein or polypeptide, a L can cap the N-terminus, the C-terminus, or both N- and C-termini, as an amide moiety. Other exemplary L capping moieties include sulfonamides, ureas, thioureas and carbamates. Ls can also include linear, branched, or cyclic alkanes, alkenes, or alkynes, and phosphodiester moieties. The L may be substituted with one or more functional groups, including ketone, ester, amide, ether, carbonate, sulfonamide, or carbamate functionalities. Specific Ls contemplated also include NH—CO—NH—; —CO—$(CH_2)_n$—NH—, where n=1 to 10; —NH-Ph-; —NH—$(CH_2)_n$—, where n=1 to 10; —CO—NH—; —$(CH_2)_n$—NH—, where n=1 to 10; —CO—$(CH_2)_n$—NH—, where n=1 to 10; and —CS—NH—. Additional examples of Ls and synthetic methodologies for incorporating them into metal complexes, particularly metal complexes linked to polypeptides or proteins, are set forth in WO 01/09188, WO 01/08712, and WO 03/011115.

A Spacer (S) can connect an organic antenna moiety to a metal liganding moiety. In some embodiments, a S can link an acetate, amine, or methylene functionality on a metal liganding moiety to an organic antenna moiety. One of skill in the art can design Ss to react with a number of functionalities on organic antenna moieties and on metal liganding moieties, including, without limitation, amines, acetates, thiols, alcohols, ethers, esters, ketones, and carboxylates. Ss can include linear, branched, or cyclic alkanes, alkenes, or alkynes, and phosphodiester moieties. The S may be substituted with one or more functional groups, including ketone, ester, amide, ether, carbonate, sulfonamide, or carbamate functionalities. Specific Ss contemplated also include NH—CO—NH—; —CO—$(CH_2)_n$—NH—, where n=1 to 10; —NH-Ph-; —NH—$(CH_2)_n$—, where n=1 to 10; —CO—NH—; —$(CH_2)_n$—NH—, where n=1 to 10; —CO—$(CH_2)_n$—NH—, where n=1 to 10; and —CS—NH—.

Fluorescent Acceptor Moiety

A binding partner can include a fluorescent acceptor moiety. A fluorescent acceptor moiety can act as an acceptor in RET or TR-RET-based assays.

In general, an optimal fluorescent acceptor moiety should exhibit a good quantum yield and a large extinction coefficient; should be resistant to collisional quenching and bleaching; and should be easily conjugated to a variety of first and second binding partners by methods known to those having ordinary skill in the art. Suitable fluorophores include, without limitation, fluorescein, rhodamine, FITCs (e.g., fluorescein-5-isothiocyanate), 5-FAM, 6-FAM, 5,6-FAM, 7-hydroxycoumarin-3-carboxamide, 6-chloro-7-hydroxycoumarin-3-carboxamide, dichlorotriazinylaminofluorescein, tetramethylrhodamine-5-isothiocyanate, tetramethylrhodamine-6-isothiocyanate, succinimidyl ester of 5-carboxyfluorescein, succinimidyl ester of 6-carboxyfluorescein, 5-carboxytetramethylrhodamine, 6-carboxymethylrhodamine, and 7-amino-4-methylcoumarin-3-acetic acid. Other suitable fluorophores include the Cy family of fluorophores (Cy 3, Cy3B, Cy3.5, Cy5; available from Amersham Biosciences, Piscataway, N.J.); the Alexa Fluor family (available from Molecular Probes, Eugene, Oreg.); the BODIPY family (available from Molecular Probes, Eugene, Oreg.); carbopyronins; squarines; cyanine/indocyanines; benzopyrylium heterocyles; and amide-bridged benzopyryliums.

Fluorescent polypeptides, proteins and mutants can also be used as fluorescent acceptor moieties. Examples include firefly, bacterial, or click beetle luciferases, aequorins, and other photoproteins (for example as described in U.S. Pat. No. 5,221,623, issued Jun. 22, 1989 to Thompson et al., U.S. Pat. No. 5,683,888 issued Nov. 4, 1997 to Campbell; U.S. Pat. No. 5,674,713 issued Sep. 7, 1997 to DeLuca et al.; U.S. Pat. No. 5,650,289 issued Jul. 22, 1997 to Wood; and U.S. Pat. No.

5,843,746 issued Dec. 1, 1998 to Tatsumi et al.). GFP and GFP mutants are particularly useful in applications using Tb(III)-containing metal complexes. A variety of mutants of GFP from *Aequorea victoria* have been created that have distinct spectral properties, improved brightness, and enhanced expression and folding in mammalian cells compared to the native GFP (e.g., see Table 7 of U.S. Pat. No. 6,410,255 and also Green Fluorescent Proteins, Chapter 2, pages 19 to 47, edited by Sullivan and Kay, Academic Press; U.S. Pat. No. 5,625,048 to Tsien et al., issued Apr. 29, 1997; U.S. Pat. No. 5,777,079 to Tsien et al., issued Jul. 7, 1998; and U.S. Pat. No. 5,804,387 to Cormack et al., issued Sep. 8, 1998).

Fluorescent proteins and their color variants are excellent tools for cell biology and are important tools for biochemical HTS (high throughput screening) assay development. In some embodiments of the present invention, a fluorescent protein is utilized as a FRET partner, e.g., with a lanthanide metal complex. These embodiments of the invention can utilize any fluorescent protein that when utilized with the corresponding lanthanide metal complex can act together as a FRET pair. For example, if the emission spectrum of the donor overlaps with the excitation spectrum of the acceptor (e.g., in the case of a terbium chelate and a fluorescent protein), energy transfer takes place when the molecules are proximal. Because of the long fluorescent lifetime of terbium chelates, energy transfer can be detected after interferences from other fluorescent molecules or from scattered light has dissipated. Some embodiments of the invention are generally described with GFP as an example of a fluorescent protein. GFP is only an example and any other fluorescent protein may be utilized that meets the above criteria. (e.g. capable of FRET with the corresponding lanthanide metal complex). In some embodiments of the invention, avGFP fusion proteins or polypeptides in combination with terbium chelates is utilized to create a general strategy for time-resolved fluorescence resonance energy transfer (TR-FRET) assays for kinase and ubiquitin-related pathways. Unlike europium, terbium can be paired with GFP, enabling TR-FRET assays using a genetically encoded acceptor fluorophore. In some embodiments of the invention, the general strategy consists of making a fusion between GFP and a protein or polypeptide of interest. After purification of the fusion protein, either a terbium labeled antibody or terbium labeled fusion protein provides the TR-FRET signal. Finally the assay functions by disruption or association of the terbium donor with the GFP acceptor. GFP enables biochemical assay development by providing for example 1) a soluble fluorescent label for easy protein purification, 2) a fully labeled substrate, and 3) a well matched acceptor fluorophore for TR-FRET. In some embodiments, a topaz GFP is utilized. Labeling kinase substrate as a GFP fusion has some advantages such as improving batch-to-batch consistency as compared to when a substrate protein is randomly labeled through accessible amino groups and lower cost when compared to using an acceptor-labeled antibody.

A fluorescent acceptor moiety for use in multiplex assays should exhibit characteristics useful for RET/TR-RET applications. For TR-RET applications, a region of the fluorophore's absorbance spectra should overlap with a region of a luminescent metal chelate's emission spectra, while a region of the fluorophore's emission spectra preferably overlaps substantially with a region of the luminescent metal chelate's emission spectra.

Examples of suitable acceptor fluorophores in TR-RET assays using Tb(III)-containing luminescent metal complexes include, but are not limited to, fluorescein (and its derivatives); rhodamine (and its derivatives); Alexa Fluors 488, 500, 514, 532, 546, 555, 568 (available from Molecular Probes); BODIPYs FL, R6G, and TMR (available from Molecular Probes); Cy3 and Cy3B (available from Amersham Biosciences), and IC3 (available from Dojindo Molecular Technologies, Gaithersburg, Md.). Examples of suitable acceptor fluorophores in TR-RET assays using Eu(III)-containing luminescent metal complexes include: Alexa Fluors 594, 610, 633, 647, and 660 (available from Molecular Probes); BODIPYs TR, 630/650, and 650/665 (available from Molecular Probes); Cy5 (available from Amersham Biosciences) and IC5 (available from Dojindo Molecular Technologies).

Suitable fluorophores for use in the present invention are commercially available, e.g., from Molecular Probes (Eugene, Oreg.), Attotec (Germany), Amersham, and Biosearch Technologies (Novato, Calif.). Methods for incorporating fluorophores into a variety of binding partners are known to those of skill in the art: see, e.g., U.S. Pat. No. 6,410,255.

RET and TR-RET

Methods of the present invention also take advantage of resonance energy transfer (RET) between a donor moiety (e.g., a luminescent metal chelate) and an acceptor moiety (e.g., a fluorescent acceptor moiety). In one embodiment, a donor luminescent metal chelate is excited by light of appropriate wavelength and intensity (e.g., within the donor antenna moiety's excitation spectrum) and under preferable conditions in which direct excitation of the acceptor fluorophore is minimized. The donor luminescent chelate then transfers the absorbed energy by non-radiative means to the acceptor fluorescent moiety, which subsequently re-emits some of the absorbed energy as fluorescence emission at one or more characteristic wavelengths. In TR-RET applications, the re-emitted radiation is not measured until after a suitable delay time, e.g., 25, 50, 75, 100, 150, 200, or 300 microseconds to allow decay of background fluorescence, light scattering, or other luminescence, such as that caused by the plastics used in microtiter plates.

In some RET applications, a first binding partner can comprise either a luminescent metal complex or a fluorescent acceptor moiety, while the second binding partner comprises the other. For example, an antibody first binding partner can be labeled with a Tb(III)-chelate-organic antenna moiety (luminescent metal chelate), while a protein or polypeptide for which the antibody is specific can be labeled with a fluorescein (fluorescent acceptor moiety). In this case, disruption of the complex formed by the antibody and protein or polypeptide (e.g., by a compound that affects binding between the two) results in an alteration in energy transfer between the luminescent metal chelate on the antibody and the fluorescent acceptor moiety on the polypeptide that may be used to monitor and measure the binding between the first and second binding partners. A compound that affects binding of a second binding partner (or tracer) to a first binding partner can be, for example, a test compound, an enzyme product (e.g., for which the first binding partner has specificity), or an enzyme substrate (e.g., for which the first binding partner has specificity).

In other RET embodiments, a compound that affects binding of a second binding partner (or tracer) to a first binding partner can comprise either a luminescent metal chelate or fluorescent acceptor moiety while the first binding partner comprises the other. In these embodiments, disruption of the complex formed between the first binding partner and the second binding partner by the labeled compound that affects binding can result in an increase in RET.

RET can be manifested as a reduction in the intensity of the luminescent signal from the donor luminescent metal complex and/or an increase in emission of fluorescence from the acceptor fluorescent moiety. For example, when a complex between an antibody having a donor luminescent metal complex and a protein or polypeptide having an acceptor fluorescent moiety is disrupted, e.g., by a competitor for the protein or polypeptide, such as an unlabeled protein or polypeptide, the donor luminescent metal complex and the acceptor fluorescent moiety physically separate, and RET is diminished or eliminated. Under these circumstances, luminescence emission from the donor luminescent metal complex increases and fluorescence emission from the acceptor fluorescent moiety decreases. Accordingly, a ratio of emission amplitudes at wavelengths characteristic (e.g., the emission maximum) of the donor luminescent metal complex relative to the acceptor fluorescent moiety should increase as compared to the same ratio under RET conditions (e.g., when emission of the donor luminescent metal complex is quenched by the acceptor).

The efficiency of RET is dependent on the separation distance and the orientation of the donor luminescent metal complex and acceptor fluorescent moiety, the luminescent quantum yield of the donor metal ion, the spectral overlap with the acceptor fluorescent moiety, and the extinction coefficient of the acceptor fluorophore at the wavelengths that overlap with the donor's emission spectra. Forster derived the relationship:

$$E=(F°-F)/F°=Ro^6/(R^6+Ro^6)$$

where E is the efficiency of RET, F and F° are the fluorescence intensities of the donor in the presence and absence of the acceptor, respectively, and R is the distance between the donor and the acceptor. Ro, the distance at which the energy transfer efficiency is 50% of maximum is given (in Å) by:

$$Ro=9.79\times 10^3(K^2QJn^{-4})^{1/6}$$

where $K^2$ is an orientation factor having an average value close to 0.67 for freely mobile donors and acceptors, Q is the quantum yield of the unquenched fluorescent donor, n is the refractive index of the intervening medium, and J is the overlap integral, which expresses in quantitative terms the degree of spectral overlap. The characteristic distance Ro at which RET is 50% efficient depends on the quantum yield of the donor, the extinction coefficient of the acceptor, the overlap between the donor's emission spectrum and the acceptor's excitation spectrum, and the orientation factor between the two fluorophores.

Changes in the degree of RET can be determined as a function of a change in a ratio of the amount of luminescence from the donor and acceptor moieties, a process referred to as "ratioing." By calculating a ratio, the assay is less sensitive to, for example, well-to-well fluctuations in substrate concentration, photobleaching and excitation intensity, thus making the assay more robust. This is of particular importance in automated screening applications where the quality of the data produced is important for its subsequent analysis and interpretation. See, e.g., U.S. Pat. Nos. 6,410,255; 4,822,733; 5,527,684; and 6,352,672.

In some embodiments, the emission from the donor moiety is measured. In some embodiments, the emission from the acceptor moiety is measured. In some embodiments, an increase in RET is measured by a decrease in emission from the donor moiety.

For example, in some embodiments of the method, a ratiometric analysis is performed, wherein a ratio of luminescence emission at two different wavelengths is compared between a test sample and a control sample. In a typical TR-RET-based assay, the two wavelengths can correspond to an emission maximum for a luminescent metal complex and a fluorescent acceptor moiety. In some embodiments, an emissions ratio of the control sample will be about 1.5, 2, 3, 4, 5, 7, 10, 15, 20, 25, 30, 40, 50, or 100 times larger or smaller than the emissions ratio of a test sample.

For further description of RET and related methods see: U.S. patent publications US20050064485, US20050170442, US20050054573 and the U.S. provisional applications 60/731,310, 60/735,812, 60/759,545, 60/774,236, and 60/832,114.

Methods for Measuring Effects of Test Compounds on Binding Between Binding Partners Methods of the present invention can be used to measure the effect of a test compound or compounds on binding between a first binding partner and a second binding partner. For example, the present methods may be used to identify competitive binders to first or second binding partners, or to identify compounds that physically (e.g., allosterically) or chemically affect a first or second binding partner so as to consequently affect binding of its partner. Accordingly, assays to identify effects of test compounds on such binding partner interactions as protein-protein interactions, protein-ligand interactions, protein-DNA interactions, and polynucleotide hybridizations may be designed using the present methods.

In one method, a first binding partner, a second binding partner, and a test compound are contacted to form a test sample. In some embodiments, one of the binding partners comprises a luminescent metal complex, while the other comprises a fluorescent acceptor moiety. See FIG. 1. As described previously, the first and second binding partner is capable of binding to one another to form a complex. In some embodiments, the test sample is exposed to light (e.g., at a wavelength in an absorbance band of the luminescent metal complex or of the antenna moiety), typically in the wavelength range of 250 nm to 750 nm, and the fluorescence emission from the test sample is measured. In one embodiment, fluorescence emission may be measured after a suitable time delay, as indicated above, to result in a time-resolved fluorescence emission measurement.

In other embodiments, as explained above, a test compound can comprise either a luminescent metal complex or a fluorescent acceptor moiety and a first binding partner can comprise the other. For example, a first binding partner receptor can be labeled with a luminescent metal chelate while a test ligand for the first binding partner receptor can be labeled with a fluorescent acceptor moiety. Disruption of a complex formed between the first binding partner receptor and an unlabeled second binding partner (e.g., a ligand for the receptor) by the labeled test ligand can lead to an increase in RET.

A test compound is identified as affecting binding between first and second binding partners when the fluorescence emission measurement of the test sample is different from the fluorescence emission measurement of a control sample lacking the test compound. Generally, there should be a statistically significant difference in measurements as compared to the control sample. As one of skill in the art will recognize, whether or not a difference is statistically significant will depend on the type of measurement and the experimental conditions. It is understood that when comparing measurements, a statistically significant difference indicates that the test compound may warrant further study. Typically, a difference is considered statistically significant at $p<0.05$ with an appropriate parametric or non-parametric statistic, e.g., Chi-square test, Student's t-test, Mann-Whitney test, or F-test. In some embodiments, a difference is statistically significant at $p<0.01$, $p<0.005$, or $p<0.001$.

Methods for Identifying Modulators of Enzymatic Activity

Methods of the invention can also be used to identify a modulator of enzymatic activity. In some embodiments, a first binding partner is selected based on specificity for either a substrate or a product of an enzymatic activity. For example, an antibody with specificity for a phosphorylated tyrosine as compared to an unmodified tyrosine can be a first binding partner with specificity for a product of tyrosine kinase activity. In one embodiment, a tracer is then selected based partially on the specificity of the first binding partner for the substrate or product of the enzymatic activity. For example, a tracer can include the purported epitope recognized by an antibody first binding partner, or a recognition site or chemical structure recognized by a protein or polypeptide first binding partner. In other embodiments, a tracer can have the same chemical structure as an antigen used to immunize an animal to generate a first binding partner antibody. Typically, the first binding partner will bind to a tracer with a similar $K_d$ as to the enzymatic product or substrate for which it has specificity, e.g., about 0.001 to 1000 times, or 0.01 to 100 times, or 0.1 to 10 times the $K_d$ of the first binding partner for the product or substrate.

A tracer may be labeled (e.g., include a luminescent metal complex or a fluorescent acceptor moiety; referred to herein as a "luminescent tracer") or the tracer may be unlabeled. For example, if the first binding partner is an antibody with specificity for a phosphorylated tyrosine, a product of tyrosine kinase activity, a luminescent tracer can be selected that includes the epitope (or an epitope mimetic) recognized by the antibody (in this case, a phosphorylated tyrosine) so that the antibody binds the luminescent tracer. The inclusion of a fluorescent acceptor moiety or luminescent metal complex on the tracer should not substantially affect the $K_d$ of the first binding partner for the tracer.

Because the assay is based on the selection of a first binding partner having specificity for a product or substrate of an enzymatic activity, a wide variety of enzymatic activities may be probed, including, without limitation, kinase activity, phosphatase activity, glucuronidase activity, prenylation, glycosylation, methylation, demethylation, acylation, acetylation, ubiquitination, deubiquination, sulfation, proteolysis, nuclease activity, nucleic acid polymerase activity, nucleic acid reverse transcriptase activity, nucleotidyl transferase activity, polynucleotide transcription activity, and polynucleotide translation activity.

In some methods of the invention, an enzyme is contacted with a substrate for the enzyme under conditions effective for an enzymatic activity of the enzyme to form a product from the substrate. As one of skill in the art will recognize, conditions effective for enzymatic activity will vary with the enzyme, enzymatic activity, and substrate chosen. For kinase reactions, ATP is generally included. Incubation conditions for a contacting step can vary, e.g., in enzyme concentration, substrate concentration, temperature, and length of time. In one embodiment, an incubation temperature conditions typically are from about 15 to about 40° C.; in some embodiments, the temperature may be about room temperature, e.g., about 20-25° C.

A contacting step is carried out in the presence of a potential modulator of the enzymatic activity. In some embodiments, the enzyme, substrate, and potential modulator mixture is then contacted with a first binding partner and luminescent tracer, as described above, to form a test sample. As indicated previously, in these embodiments, either the first binding partner or the luminescent tracer includes a luminescent metal complex, while the other includes a fluorescent acceptor moiety.

In other embodiments, the enzyme, substrate, and potential modulator mixture is contacted with a first binding partner and optionally a tracer to form a test sample. In these embodiments, either the first binding partner or the substrate includes a luminescent metal complex, while the other includes a fluorescent acceptor moiety. In such cases, enzymatic activity can result in the conversion of the labeled substrate to a labeled product. The inclusion of a fluorescent acceptor moiety or luminescent metal complex on the substrate should not substantially affect the ability of the enzyme to form a product from the labeled substrate. In addition, the inclusion of a fluorescent acceptor moiety or luminescent metal complex on the substrate (or product) should not substantially affect the $K_d$ of the first binding partner for the substrate (or product) for which it has specificity.

In some embodiments, the test sample is also exposed to at least one wavelength of light (e.g., at a wavelength in an absorbance band of the luminescent metal complex), typically in the wavelength range of 250 nm to 750 nm, and the fluorescence emission from the test sample is measured. Fluorescence emission may be measured after a suitable time delay, as indicated above, to result in a time-resolved fluorescence emission measurement.

In some embodiments a tracer may be unlabeled, e.g., in embodiments where a first binding partner is labeled with a luminescent metal complex and a substrate is labeled with a fluorescent acceptor moiety. Disruption of a complex formed between an unlabeled tracer and a labeled first binding partner by an appropriately labeled compound (e.g., labeled substrate, labeled product, labeled test compound) that affects binding between the unlabeled tracer and first binding partner can lead to an increase or decrease in RET.

A potential modulator is identified as a modulator of enzymatic activity when the fluorescence emission measurement of the test sample is different from the fluorescence emission measurement of a control sample lacking the potential modulator. As indicated above, there should be a statistically significant difference as compared to the control sample. As one of skill in the art will recognize, whether or not a difference is statistically significant will depend on the type of measurement and the experimental conditions. It is understood that when comparing measurements, a statistically significant difference indicates that that potential modulator may warrant further study. Typically, a difference is considered statistically significant at $p<0.05$ with an appropriate parametric or non-parametric statistic, e.g., Chi-square test, Student's t-test, Mann-Whitney test, or F-test. In some embodiments, a difference is statistically significant at $p<0.01$, $p<0.005$, or $p<0.001$.

Any of the methods of the present invention can be modified to be performed in a high-throughput or ultra-high-throughput manner. For example, a method to identify a modulator of activity of an enzyme may be modified to contact a plurality of substrates, independently, with a particular enzyme(s) and potential modulator(s), to form a plurality of enzyme mixtures. Each enzyme mixture is then contacted with an appropriate first binding partner and luminescent tracer to form a test sample, with the excitation and measurement steps as described previously. As one of skill in the art will appreciate, such high-throughput methods are particularly amenable to multi-well plate or 2-D array panel formats. Devices for incubating and monitoring multi-well plates are known in the art.

The dynamic range, quality, and robustness of the methods of the present invention can be evaluated statistically. For example, the Z'-Factor is a statistic designed to reflect both assay signal dynamic range and the variation associated with signal measurements. Signal-to-noise (S/N) or signal-to-background (S/B) ratios alone are unsatisfactory in this regard because they do not take into account the variability in sample and background measurements and signal dynamic range. The Z'-Factor takes into account these factors, and because it is dimensionless, it can be used to compare similar assays. Typically, assays of the present invention yield Z'-factors of greater than or equal to 0.5. Methods for determining Z'-factor are known to those of skill in the art. A Z'-factor may be determined by evaluating the dynamic range of a method.

Articles of Manufacture and Apparatuses

The invention also provides articles of manufacture, such as kits, and apparatuses useful for performing the described inventions. Typically, a kit includes packaging material, such as a container, and one or more compositions useful as first and/or second binding partners. In some embodiments, a kit can include one or more of the following: a multi-well plate, one or more enzymes, buffers, and directions for use of the kit.

Kits of the invention may be designed to perform one or more methods of the invention. Further these kits may contain one or more composition described herein. Appendix A contains protocols which may be included in, for example, kits of the invention.

An apparatus will generally include a sample chamber and means for illuminating the sample chamber with at least one wavelength of light (e.g., in the range of 250 nm to 750 nm). In addition, an apparatus will include means for detecting light (e.g., fluorescence) emitted from the sample chamber.

Methods for Providing Products and Services

The invention further provides methods for providing various aspects of the invention to others (e.g., customers). These methods will typically involve at least one of the following steps: (a) advertising a product or service, (b) receiving one or more orders for the product or service, (c) supplying the product or performing the service with, optionally, delivering tangible material or data resulting from the service, (d) providing a bill to the party which placed the order, (e) ensuring that payment of the bill occurs, and (f) processing the payment (e.g., cashing a payment check, debiting a bank account, etc.).

In certain aspects, the method is a method for generating revenue by providing a purchasing function to a customer to purchase a product or service provided herein. For example, the purchasing function can include providing a telephonic ordering system, a direct sales representative, or by utilizing a computer system that displays a visual representation on a monitor, of a link to purchase a product or service disclosed herein. The method can further include providing a computer-based ordering function that is activated when the visual representation is selected.

In a specific embodiment, the invention is directed, in part to performing a service for a party, providing data derived from that service to the party and collecting payment for the service. These services will often be directed to assays related to the detection and/or identification of molecular modifications, e.g., utilizing the methods and assays as described herein.

Methods that Use Protein Arrays

Provided herein are methods for detecting substrates for ubiquitinating enzymes or other enzymes that conjugate a ubiquiton to a polypeptide by contacting a ubiquitinating enzyme(s) with polypeptides immobilized on a substrate.

Also provided herein are methods for detecting substrates for a ubiquitination-like enzyme(s) (or other enzymes that conjugate a ubiquitin-like protein to a polypeptide) by contacting a ubiquitination-like enzyme(s) with polypeptides immobilized on a substrate. The methods can include contacting a positionally addressable array comprising a plurality of polypeptides immobilized on a substrate, with ubiquitin that is associated with a detectable moiety (or a ubiquitin-like protein(s) associated with a detectable moiety) and a ubiquitinating enzyme(s) and detecting the detectable moiety. Typically, the detecting includes identifying polypeptides of the plurality of polypeptides that are associated with a ubiquiton such as ubiquitin, SUMO or NEDD8, for example, by identifying positions on the array at which the detectable moiety is detected. The reaction conditions for the ubiquitination reaction are provided herein including those for other methods for the addition of a ubiquiton to a substrate. In illustrative aspects the ubiquitinating enzymes include E1, E2, and E3.

Certain aspects of the invention provide methods for identifying substrates for deubiquitinating enzymes. Accordingly, the method can further include incubating a positionally addressable array with a deubiquitinating enzyme, detecting the detectable moiety and identifying substrates for the deubiquitinating enzyme by comparing polypeptides that were labeled with the detectable moiety before and after contact with the deubiquitinating enzyme. The contacting typically includes incubating for an effective period of time to allow the enzyme to remove ubiquitin from substrates. For clarity, these methods can also be performed utilizing ubiquitin-like proteins and measuring/detecting the removal of the ubiquitin-like protein. The methods of the invention can be used to measure, for example, de-ubiquitination, de-SUMOylation, de-NEDDylation and de-ISGylation In another embodiment, provided herein is a method for identifying and/or measuring ubiquitinating activity of a sample (e.g., a cell lysate) by contacting a positionally addressable array comprising a plurality of polypeptides immobilized on a substrate, with a ubiquiton associated with a detectable moiety and a sample (e.g., a cell lysate); and detecting the detectable moiety. In some embodiments, the method is for identifying and/or measuring, for example, ubiquitination, SUMOylation, NEDDylation and ISGylation activity.

In another embodiment, provided herein is a method for identifying deubiquitinating activity of a sample (e.g., a cell lysate) by contacting a positionally addressable array comprising a plurality of polypeptides immobilized on a substrate with a ubiquiton associated with a detectable moiety and a ubiquitinating enzyme, (optionally detecting polypeptides that are associated with the detectable moiety), contacting the array with a sample (e.g., a cell lysate); detecting the detectable moiety, and identifying deubiquitination substrates, e.g., by comparing the polypeptides associated with the detectable moiety before and after contact with the cell lysate and/or comparing to a control array. In another embodiment, provided herein is a method for identifying deubiquitinating activity of a sample (e.g., a cell lysate) by contacting a positionally addressable array comprising a plurality of polypeptides immobilized on a substrate wherein the polypeptides comprise a ubiquiton (e.g., associated with a detectable moiety) with a sample (e.g., a cell lysate), (optionally detecting the detectable moiety), and identifying deubiquitination substrates, e.g., by comparing the polypeptides associated with the detectable moiety before and after contact with the cell lysate. In some embodiments, the polypeptides of the plurality of polypeptides comprise a ubiquitin associated with (e.g., fused as part of a fusion protein) a detectable moiety (e.g., a fluorescent protein).

The invention provides methods for identifying ubiquitinating or non-deubiquitinating activity of a sample (e.g., a cell lysate) that can be used to compare different samples (e.g., cell lysates from different populations of cells to further characterize the molecular differences of cells), for example, to identify biomarkers. In one embodiment, the different samples are derived from (e.g., are cell lysates of) different populations of cells. The different populations of cells can include cells of a different organism, different developmental state, different disease state, such as cancerous vs. benign vs. normal, exposed to different conditions, exposed to different compounds, cells from different organs and/or combinations thereof.

The detectable moiety can include, as a nonlimiting example, biotin, avidin, an epitope, or a fluorescent moiety. The detectable moiety can be covalently or non-covalently associated with the ubiquitin. In some embodiments, the detectable label is provided by an antibody labeled with a detectable moiety, e.g., a labeled antibody that binds ubiquitin or a ubiquitin-like protein.

Any of the methods that include polypeptide arrays provided herein, can include during contact with the ubiquitinating or deubiquitinating enzyme, contacting the enzyme and/or the polypeptides with a test compound.

The polypeptides for the protein array aspects of the invention can be immobilized on a substrate to form a positionally addressable array comprising a plurality of polypeptides, with each protein being at a different position on a solid support. The polypeptides can be immobilized in an array at a density, for example, of at least 100, 200, 250, 300, 400, 500, 1000, 2500, 5000, or 10,000 polypeptides per square centimeter. The polypeptides can include at least 100, 200, 250, 500, 1000, 2500, 5000, 7500, 10000, or all expressed polypeptides of a single species of organisms. The polypeptides can be structurally related and/or can be members of the same protein family. The polypeptides can include secondary modifications. The polypeptides can be in certain embodiments, at least 20, 25, 50, 100, 250, 500, or 1000 amino acids in length. The array can be formed by methods known in the art.

The protoarrays of the invention can also utilize RET as a means of detection. For example, two moieties can be utilized that are capable of RET (e.g., FRET or TR-FRET). In some embodiments, the plurality of polypeptides are associated with a member of a RET pair, e.g., a donor or acceptor moiety. In some embodiments, the plurality of polypeptides is associated with a fluorescent protein (e.g., a GFP) such as by being expressed as a fusion protein. In some embodiments, a ubiquitin or ubiquitin-like protein are associated with a member of a RET pair, e.g., a donor or acceptor moiety. In some embodiments, a ubiquitin or ubiquitin-like protein are labeled with a lanthanide metal complex. In some embodiments, a ubiquitin or ubiquitin-like protein is indirectly labeled utilizing an antibody labeled with a member of a RET pair.

In some embodiments, the method or assay involves two populations of a ubiquitin, two populations of a ubiquitin-like protein, or a population of a ubiquitin and a population of a ubiquitin-like protein, wherein one population is associated with a donor moiety and a second population is associated with an acceptor moiety. In some related embodiments, the polypeptides of the array are of a sufficient density that attachment of the two populations of ubiquitin or ubiquitin-like proteins results in RET. Therefore, various methods and assays described herein can utilize this format.

Assays and methods utilizing RET, may involve detecting an increase, decrease or no change of RET, an increase, decrease or no change of emission from the donor moiety, an increase, decrease or no change of emission from the acceptor moiety, or combinations and/or ratios thereof.

Some embodiments of the invention provide a method for detecting at least one substrate for at least one ubiquitination or ubiquitination-like enzyme comprising: a) contacting i) the at least one ubiquitination or ubiquitination-like enzyme with ii) polypeptides immobilized on a substrate and iii) at least one ubiquitin or ubiquitin-like protein comprising a detectable moiety, b) incubating (a) under conditions to allow for ubiquitin or ubiquitination-like activity, c) detecting the detectable moiety associated with any of the polypeptides on the substrate. Some embodiments of the invention provide a method for identifying or measuring deubiquitinating activity of a sample comprising: a) contacting i) the sample with ii) at least one or a plurality of polypeptides immobilized on a substrate, wherein the at least one or plurality of polypeptides comprise a ubiquitin or ubiquitin-like protein associated with a detectable moiety, wherein the deubiquitinating activity causes the dissociation of the detectable moiety from the substrate, b) incubating (a) under conditions to suitable for de-ubiquitination activity, c) detecting the detectable moiety associated with any of the polypeptides on the substrate.

Detection of Phosphodiesterase Activity

Figure 42:
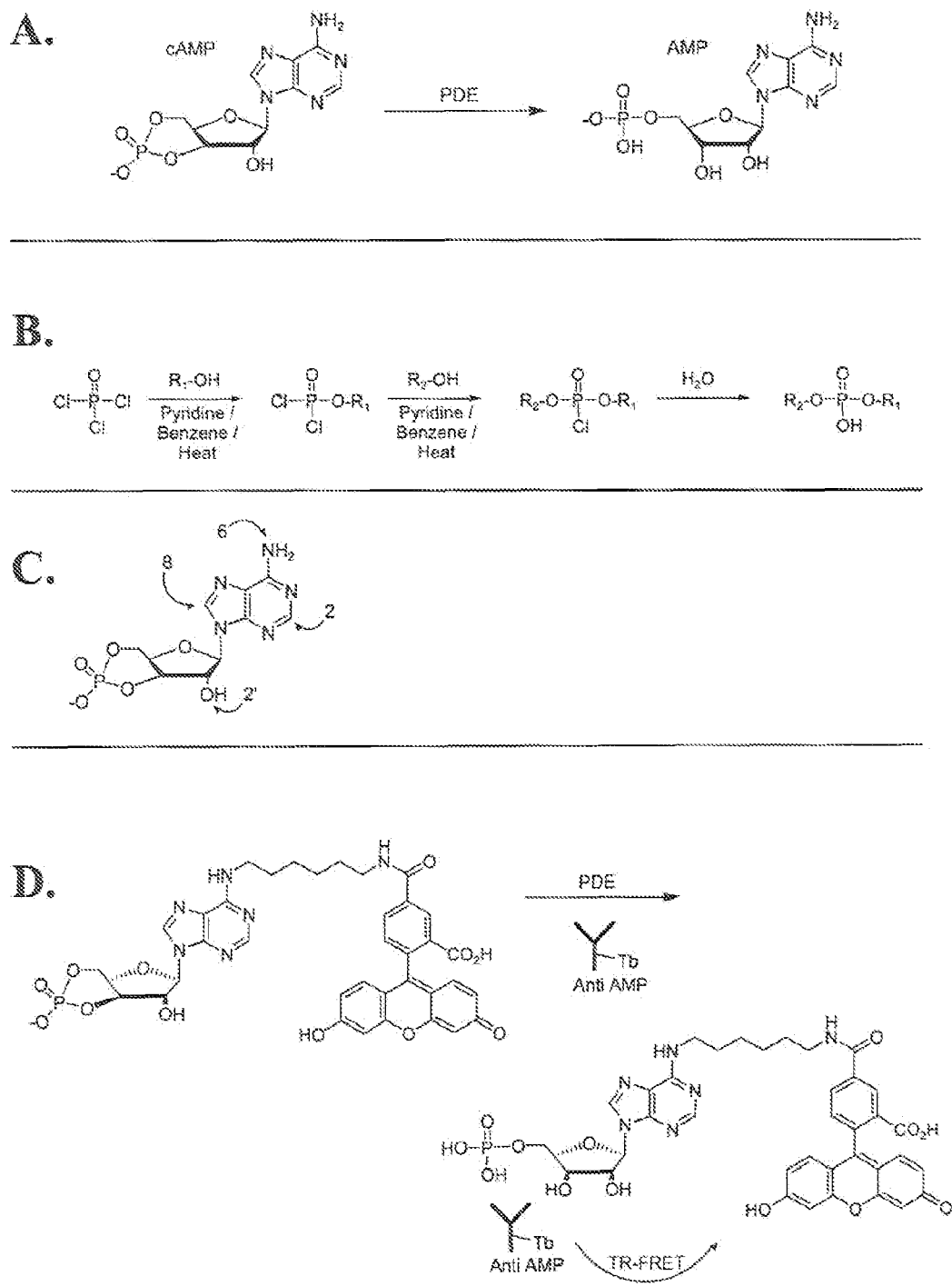
FIG. 42A shows cleavage of cAMP by phosphodiesterase to form AMP.
FIG. 42B shows a generic strategy for phosphodiester synthesis.
FIG. 42C depicts cAMP and shows analogs that are available with linkers attached at various positions.
FIG. 42D depicts detection of fluorescein labeled AMP using a Tb-anti AMP antibody.
FIG. 42E shows an exemplary method for detection of PDE activity using phosphotyrosine as the recognition element.
FIG. 42F shows an exemplary method for detection of PDE activity using bis-(fluorescein-tyrosine) phosphate as the substrate

Phosphodiesterases (PDEs) are an important class of enzymes that are of interest as pharmaceutical targets. Phosphodiesterases cleave a phosphodiester bond to form a phosphate and a hydroxyl group. In the case of cyclic nucleotide monophosphate substrates such as cAMP, the hydroxyl and the phosphate reside within the same molecule, and the cleavage of the phosphodiester forms the nucleotide monophosphate (e.g., AMP) as shown in FIG. 42A.

Phosphodiester synthesis is described in the scientific literature (e.g. Friedman et al., *J. Am. Chem. Soc.* 72(1): 624-625 (1950).) In general, phosphoryl chloride can be reacted with a hydroxyl containing compound in a pyridine/benzene mixture to form a dichloro phosphoryl ester, which can be reacted with a second equivalent of the same or different hydroxyl containing compound to form a mono-chloro phosphodiester, which can then be hydrolyzed with water to give the corresponding phosphodiester. An example of this is shown schematically in FIG. 42B.

Colorimetric assays for phosphodiesterases include the use of bis-(4-nitrophenyl) phosphate as substrate that forms para-nitrophenol and para-nitrophenol phosphate upon enzymatic cleavage. (Kelly et al. *Biochemistry*, 14(22):4983-8 (1975).) Para-nitrophenol is then detected by its absorbance at 410 nm. Berkessel and Riedl (Angew. *Chem., Int. Ed. Eng.*, 36:1481-1483 (1997)) have described the use of a quenched fluorescent substrate in which a naphthalene residue acts as the fluorophore, and an azobenzene moiety acts as the quencher. The naphthalene and the azobenzene are linked via a phosphodiester linkage that is cleaved by the phosphodiesterase, separating the quencher from the fluorophore. Takakusa and colleagues have described a FRET-based assay for phosphodiesterases that uses a substrate containing a FRET pair that is linked by a phosphodiester moiety. (Takakusa et al., *J Am Chem Soc*. 124(8):1653-7 (2002).) Their reported substrate, CPF4 (coumarin—phosphate—fluorescein) is capable of FRET between coumarin and fluorescein in the intact state, and decreased FRET upon cleavage by snake-venom phosphodiesterase I.

The present invention provides methods for the detection of phosphodiesterase activity. In some embodiments, these methods are based upon the specific recognition of the phosphate moiety (the phosphate monoester) by an antibody. In some embodiments, methods are based upon the specific recognition of the cyclic monoester/phosphate. In some embodiments, the antibody exhibits low binding affinity towards the uncleaved phosphodiester relative to its affinity for the phosphorylated product.

Neoepitope-based Assays

"Neoepitope" refers to an epitope that is uncovered, unmasked, or otherwise revealed in order to be recognized by an antibody. In some embodiments, prior to the event that allows the epitope to be bound by the antibody, there is decreased or no detectable binding. For example, the antibody demonstrates an affinity for a product of the reaction and less or no affinity for the starting compound(s). In some embodiments, the product comprises one member of a RET pair and the antibody comprises a second member of a RET pair and the antibody has binding specificity for the product.

Some embodiments of the invention utilize a strategy in which the phosphate generated upon phosphodiesterase mediated cleavage serves as an epitope for an antibody. Some embodiments of the invention provide a method of measuring/detecting phosphodiesterase by coupling the liberated phosphate to a first member of a RET pair (e.g. a fluorophore), and by labeling the antibody with a second member of the RET pair (e.g., terbium chelate), e.g., see FIGS. 42D and 42E. In some embodiments, a fluorescently modified cAMP is used as a substrate. In some embodiments, a fluorescently labeled phosphodiester that does not resemble or is not a cAMP is used as a substrate.

Cyclic AMP (cAMP) analogs containing amino-alkyl linkers attached to the 2, 6, 8, or 2' positions (FIG. 42C) are commercially available from e.g., Biolog (Bremen, Germany). Some embodiments of the invention utilize a fluorescein-labeled version of cAMP as a phosphodiesterase substrate. Ideally, a number of analogs may be prepared, in order to compare their ability to be utilized as a substrate for a phosphodiesterase, or their performance in a RET assay using, e.g., an anti-AMP antibody. Examples are also shown in FIG. 42D.

In one embodiment, a labeled (e.g., fluorescein) phosphodiesterase substrate is incubated with a phosphodiesterase, in the presence of a labeled (e.g., Terbium) anti-AMP antibody. In some embodiments, when the phosphodiester is cleaved, the AMP is recognized by the antibody, bringing the antibody's label (Tb) and the fluorescein into proximity so that FRET or TR-FRET may occur. The antibody can be added before, during or after the reaction. If the antibody is present during the reaction, then the reaction can be read in real time or in a kinetics mode. That way the progression and/or rate of the reaction can be measured.

Hohman et al. (*PNAS* 77(12):7410-7414 (1980)) describes a AMP-specific antibody.

Unmasking of Phosphotyrosine

Some embodiments of the invention are based upon using phosphotyrosine as the epitope that is generated upon phosphodiesterase activity utilizing known, readily available antibodies.

In one embodiment, a substrate consists of a phosphotyrosine labeled with a first member of a RET pair (e.g., fluorescein) that is coupled to another group through a phosphodiester linkage. The exact identity of the "another" group is unimportant, but it is expected that different groups could lead to differences in performance as a substrate, or increase substrate solubility, etc. FIG. 42E depicts an example of this type of assay. Depending on enzyme specificity, up to four products can be formed depending on the site of ester hydrolysis. This assay detects the product formed when the cleavage occurs at the phospho-ester site that is not attached to the tyrosine moiety, thereby leaving fluorescein labeled phosphotyrosine intact after enzyme activity. This molecule is then detected with an anti-phosphotyrosine antibody (e.g., such as PY20) labeled with a second member of a RET pair (e.g., terbium). RET is possible when the labeled antibody binds the fluorescein labeled phosphotyrosine.

Fluorescein labeled phosphotyrosine is recognized with high affinity by terbium-labeled PY20, and a high TR-FRET signal is generated upon this interaction (data not shown). In some embodiments for a fluorescein labeled phosphotyrosine substrate, if the site of enzymatic cleavage is at the oxygen attached to the tyrosine the generated fluorescein labeled molecule may not be recognized by the antibody, and therefore no RET (e.g., TR-FRET) signal would be generated.

In some embodiments of the invention, a substrate can be used to detect phosphodiesterase (PDE) activity by unmasking of phosphotyrosine as shown in FIG. 42F. This substrate, bis-(fluorescein-tyrosine) phosphate, will form two products, one of which will be recognized by the antibody. In this embodiment, both products are fluorescent, and therefore fluorescence background may be increased due to the presence of extra fluorescein. In some embodiments, two antibodies could be used: one directed towards phosphotyrosine, the other directed towards tyrosine.

Fluorescently labeled cAMP analogs modified at the 2, 6, 8, or 2' position of cAMP are readily synthesizable from commercially available starting materials, or are commercially available products (e.g., Alexa Fluor® 488 8-(6-aminohexyl)aminoadenosine 3',5'-cyclicmonophosphate, bis(triethylammonium) salt (Alexa Fluor® 488 cAMP), available as part #A35775 from Molecular Probes).

Antibodies labeled with terbium chelates are readily prepared using standard antibody labeling techniques and commercially available amine-reactive terbium chelates (such as Invitrogen's LanthaScreen™ Amine Reactive Tb Chelate, part #PV3581).

The related embodiments of the invention will provide assays that are more sensitive in terms of the amount of enzyme required to yield a suitable signal change.

Some embodiments of the invention include a substrate of the structure:

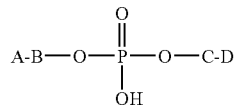

in which either A or D (or both) are fluorescent, and which, when cleaved by a hydrolytic enzyme, yields a product that is recognized by an antibody to which is attached a luminescent probe that can act as a partner in a RET assay with fluorescent moiety A or D.

The assays and methods described in this section "Detection of Phosphodiesterase Activity" can also be used to identify compounds/samples that modulate these reactions. For example, the compound is added to the reaction and e.g., the reaction is compared to a control to determine if the compound modulates the reaction. Modulation includes inhibiting or activating the reaction.

The assays and methods as described in this section "Detection of Phosphodiesterase Activity" can be run in formats similar to those described herein for other assays and methods as appropriate. Also, where an assay or method described herein utilizes an antibody, it is understood that the invention includes essentially any binding molecule with the same characteristics can be used as a replacement for or in addition to the antibody.

The present invention provides phosphodiesterase assays wherein a phosphodiesterase substrate is labeled with a first member of a RET pair, wherein upon cleavage by a phosphodiesterase, an epitope for an antibody to bind is exposed/created. An antibody labeled with a second member of the RET pair is contacted with the product(s) of the reaction wherein the antibody binds to the epitope an the product comprising the first member of the RET pair. Thus, allowing RET between the RET pair moieties upon e.g., exposure to the appropriate wavelengths of light. In some embodiments, a similar format is followed except that the cleavage by the phosphodiesterase removes/destroys an epitope for the antibody.

Some embodiments of the invention provide a method of detecting phosphodiesterase activity comprising: a) contacting i) a sample with ii) a substrate for a phosphodiesterase wherein the substrate comprises a first member of a RET pair to form a test sample; b) incubating (a) under conditions to suitable for the phosphodiesterase activity; c) contacting the test sample, either before, during or after (b), with a binding molecule with specificity of a cleavage product of the phosphodiesterase, wherein the binding molecule comprises a second member of the RET pair, wherein the cleavage product comprises the first member of a the RET pair; d) exposing the test sample to at least one wavelength of light; and e) measuring the fluorescence emission from the test sample. In some embodiments, the fluorescence emission from the test sample is compared to that of a control sample/reaction.

EXAMPLES

The invention is now described with reference to the following examples. The following examples are intended to illustrate but not limit the invention. These examples are provided for the purpose of illustration only and the invention should in no way be construed as being limited to these examples but rather should be construed to encompass any and all variations which become evident as a result of the teachings provided herein.

Example 1

Labeling of an Antibody with a Luminescent Metal Chelate 1 mg purified PY72 (anti-phosphotyrosine) IgG antibody, an antibody that preferentially binds amino acid sequences containing phosphorylated tyrosines (e.g., sequences phosphorylated by protein tyrosine kinases (PTKs)) and was dialyzed for 1.5 hours in a 100 mM sodium bicarbonate buffer, pH 9.5, using a 12-14,000 MWCO dialysis membrane. (PY72 hybridoma cells were obtained from the Salk Institute; the immunogen was phosphotyrosine conjugated to KLH. Ascites were produced by Harlan Bioproducts for Science, Indianapolis Ind. Ascites were purified with a protein G column (Pierce). Purified antibody is also available from Covance, Berkeley Calif. (Part #MMS414P).) The antibody was then removed from the dialysis membrane and concentrated to 48.8 uM (7.3 mg/mL) using a Centricon YM50 (Millipore) concentrator. 100 uL of this antibody solution was diluted to 5 mg/ml (33.4 uM) into the labeling reaction which consisted of 10 mM phenyl phosphate, and 660 µM carbostyril 124-diethylenetriaminepentaaceticacid-phenylalanine isothiocyanate *Tb(III)) (CS124-DTPA-Phe-NCS*Tb, see FIG. 3) (final concentrations) in 100 mM sodium bicarbonate buffer, pH 9.5. The reaction was incubated at room temperature for 4 hours with light vortexing every 30 minutes, and then dialyzed twice for 1.5 hours each against tris-buffered saline (TBS) to remove unreacted and/or hydrolyzed chelate. The amount of chelate bound to the antibody was quantitated by the absorbance of the CS124 moiety at 343 nm ($E_{340}$=11,440 $M^{-1}cm^{-1}$), and the amount of antibody quantitated by its absorbance at 280 nm ($E_{280}$=210,000 $M^{-1}cm^{-1}$), correcting for the absorbance of the CS124 at 280 nM (1.1 times its absorbance at 343 nM). From these measurements it was determined that the reaction produced an antibody labeled with an average of 5.8 chelates per antibody.

A monoclonal antibody with specificity for phosphorylated serines (anti-pSer; phosphorylated serines are products of Serine/Threonine kinase activity) was also prepared and labeled with a luminescent metal chelate, as described above.

Example 2

Binding Curve Experiment between Protein Tyrosine Kinase Product Tracer (PTK Tracer) and Anti-PTK Product (PY72) Antibody A direct binding curve (showing luminescent metal chelate-labeled PY72 antibody binding to fluorescent acceptor labeled tracer) was generated by incubating serial dilutions of the labeled antibody (10 nM to 9.8 pM in two fold dilutions) with 1 nM fluorescent acceptor-labeled tracer (PTK labeled tracer; sequence F-ADE(pY)LIPQQS, where F is fluorescein and pY is a phosphorylated tyrosine, SEQ ID NO:1; note that the tracer is a phosphorylated tyrosine derivative of a protein tyrosine kinase (PTK) substrate) in FP dilution buffer (part #P2839, Invitrogen, Carlsbad, Calif.). After a 30 minute incubation, the fluorescence polarization of each composition in the plate was read on a Tecan Ultra plate reader using a 485 nm excitation filter (20 nm bandpass) and 535 nm emission filters (25 nm bandpass). Data was collected using 10 flashes per well and a 40 µs integration time. The antibody was seen to bind to the tracer with an EC50 of slightly more than 1 nM.

A similar binding curve was performed with a luminescent metal chelated-labeled anti-pSer antibody and a fluorescent acceptor-labeled tracer (STK labeled tracer, sequence F-GR-PRTS(pS)FAEG, where F is a fluorescein and pS is a phosphorylated serine, SEQ ID NO:2; note that the tracer is a phosphorylated serine derivative of a S/T kinase (STK) substrate).

Example 3

Competition Curve between Labeled Kinase Product Tracer and Unlabeled Kinase Product A competition curve to show that the disruption of the antibody-tracer interaction could be monitored by both fluorescence polarization and time-resolved RET from the same sample was performed by incubating serial dilutions (10 µM to 19.5 nM in two-fold dilutions) of an unlabeled phosphotyrosine-containing peptide competitor (ADE(pY)LIPQQS, where pY is a phosphorylated tyrosine, SEQ ID NO:3) in the presence of 10 nM Tb-chelate labeled PY72 antibody and 1 nM labeled PTK labeled tracer, as described above. After a 30 minute incubation, the plate was read on a Tecan Ultra plate reader. Fluorescence polarization was measured using a 485 nm excitation filter (20 nm bandpass) and 535 nm emission filters (25 nm bandpass). Time-resolved RET was measured using a 340 nm excitation filter (35 nm bandpass) and 495 nm (10 nm bandpass) and 520 nm (25 nm bandpass) filters using a 200 μs integration window after a 100 μs post-flash delay with 10 flashes per well. The time-resolved RET value (ratio) was calculated by dividing the 520 nm signal by the 495 nm signal. The shapes of the curves generated by TR-RET or FP were seen to nearly overlap, indicating that the presence of a phosphopeptide (such as that generated by a kinase reaction) could be detected and quantitated using FP or TR-RET, or both.

Example 4

Screening of Test Compounds as Modulators of Kinase Activity using Multimode FP and TR-RET Measurements A chemical library screen to identify inhibitors of Lyn B Kinase, a member of the SRC family of protein tyrosine kinase (PTK) enzymes, was performed. The kinase reaction was performed in the presence of 10 μM of a Prestwick library compound (test compound; Prestwick Library available from Prestwick Chemical, Inc., Washington DC) in 20 mM HEPES pH 7.5, 5 mM $MgCl_2$, 150 nM poly(Gly:Tyr, 4:1) protein tyrosine kinase substrate, and 10 μM ATP using 1 ng of Lyn B kinase per reaction. The kinase reaction was allowed to proceed for 1 hour at room temperature and then stopped by adding 100 mM EDTA to a final concentration of 5 mM in a total volume of 40 μl. To detect the presence of phosphopeptide product, 10 μl of a solution containing 20 nM Tb-chelate labeled PY72 antibody and 10 nM PTK labeled tracer was added to each well and incubated for an additional 30 min. The plate was then read on a Tecan Ultra plate reader in both fluorescence polarization and time-resolved RET measurement modes. Fluorescence polarization was measured using a 485 nm excitation filter (20 nm bandpass) and 535 nm emission filters (25 nm bandpass). Time-resolved RET was measured using a 340 nm excitation filter (35 nm bandpass) and 495 nm (10 nm bandpass) and 520 nm (25 nm bandpass) filters using a 200 μs integration window after a 100 μs post-flash delay with 10 flashes per well. The time-resolved RET value (ratio) was calculated by dividing the 520 nm signal by the 495 nm signal. Kinase inhibitors were identified by wells that showed high polarization or 520:495 TR-RET ratios. The results of the screen of approximately 750 compounds are shown in Example 5

Conversion of FP Assay to Multiplex FP/TR-RET Assay

Because terbium-chelates are able to serve as donors to fluorophores such as fluorescein or rhodamine (and derivatives thereof) in TR-RET assays, and because fluorescein and rhodamine have excellent properties for use in FP assays, it is a simple matter to modify an FP assay such that it can be read in a dual-mode FP/TR-RET manner by labeling, for example, a binding partner such as a receptor protein or an antibody with a fluorescent terbium chelate. The use of multiplex modes (e.g., both FP and TR-RET) allows verification of data and elimination of false positive or false negative results. In addition, assays that are problematic in either the FP mode or TR-RET mode may be converted to robust assays using the other mode.

An FP assay to detect phosphorylation of Ser133 on the cyclic-AMP response element binding protein (CREB) by CREB kinase (a serine kinase) was designed. The assay required the identification of a fluorescein-labeled kinase product tracer containing a phosphorylated serine. In addition, the assay required an anti-CREB pSer133 antibody (available from Cell Signaling Technologies, Beverly, Mass.) capable of binding the tracer, four candidate tracer peptides were prepared, as shown below, and tested for binding to the anti-pSer133 antibody. The tracers differed in their length and in the position of the fluorophore on the peptide.

```
                                          (SEQ ID NO: 4)
Tracer 1: Fluorescein-LRREILSRRP(pS)YRK;

(SEQ ID NO: 5)
Tracer 2: Fluorescein-REILSRRP(pS)YRK (SEQ ID NO: 6)
Tracer 3: Fluorescein- ILSRRP(pS)YRK;
and (SEQ ID NO: 7)
Tracer 4: LRREILSRRP(pS)YRK-Fluorescein.
```

When tested in direct binding to the antibody in FP mode, two tracers were seen to bind with sub-nM Kd affinities, but neither showed a change in polarization greater than 100 mP between the free and bound state. The robustness of an FP assay is in part a function of the magnitude of this difference in polarization. As changes in polarization of greater than 30 mP, or greater than 50 mP, or greater than 100 mP, are generally preferred, an attempt was made to convert the assay to a TR-RET assay.

The anti-pSer133 antibody was labeled with CS124-DTPA-Phe-NCS*Tb (see Example 1 above) to yield an antibody with an average of 62 chelate molecules per antibody. When the four candidate tracer peptides were titrated separately against this labeled antibody, SEQ ID NO: 7 was seen to bind with sub-nM affinity and a 32-fold change in TR-RET value between free and bound forms.

Example 6

PKA Enzyme Titration Demonstrating Z'-Factor of TR-RET Assay

PKA (a serine kinase) was serially diluted across 24 wells of a 384 well plate and reacted with 1 μM peptide PKA substrate (LRREILSRRPSYRK, SEQ ID NO:8) in 50 mM Tris (pH 7.5) containing 10 mM $MgCl_2$, 50 μM $NaVO_4$, and 5 μM ATP. The final reaction volume was 10 μL per well. The reactions were allowed to proceed for 90 minutes at room temperature, after which a 10 μL quench/detection solution (containing labeled tracer identified in Example 5 above), Tb-chelate-labeled anti-pSer133 antibody, and EDTA) was added. The plate was covered and incubated at room temperature for 2 hours. The plate was then read on a TECAN Ultra 384 fluorescence plate reader using a 340/35 nm excitation filter and 520/25 and 495/10 nm emission filters (Chroma Technology Corp.). Data was collected using 10 flashes per well with a 100 μs delay and 200 μs integration window.

To assess assay robustness, a Z' value was determined from 48 20 μL wells containing Tb-chelate labeled anti-pSer133 antibody and labeled tracer (see above) in the presence (24 wells; "low signal" controls) or absence (24 wells, "high signal" controls) of 2.5 μM unlabeled tracer. The plate was covered and incubated for 2 hours at room temperature. The plate was then read on a TECAN Ultra 384 fluorescence plate reader using the parameters described above. The Z'-value was 0.92.

Example 7

Conversion of Nuclear Receptor FP Assay to Multiplex FP/TR-RET Assay

To demonstrate the generality of the ability to convert FP assays to FP/TR-RET assays using terbium chelates, an Estrogen Receptor β (ER-β) FP competition assay was converted by directly labeling the ER receptor with an amine-reactive terbium dictate; see Example 1 above, In the EP assay, displacement of a fluorescein-labeled tracer by a competitor causes a change in the observed polarization from high to low. In the TR-RET assay, the amount of labeled tracer bound to receptor is measured by RET between the terbium chelate on the receptor and the fluorescein on the tracer. In the absence of a competitor the RET signal is high, and as the competitor displaces the tracer this signal decreases. 12.5 nM unlabeled or Tb-chelate labeled ER-β protein were incubated with 1 nM labeled tracer (Fluormone ES2 (part#P2613, Invitrogen, Carlsbad, Calif.)) and titrated with serial dilutions of unlabeled estradiol, a known ER-β ligand. Both FP and TR-RET assays showed similar EC50 values for the competition curve. In addition, the TR-RET assay offers the advantage that it could be re-formatted, with similar results expected, using limiting concentrations of receptor and excess concentrations of tracer.

Example 8

Conversion of EGFR Kinase FP Assay to Multiplex FP/TR-RET Assay

The general method identified in Example 7 was used to screen for inhibitors of Epidermal Growth Factor Receptor (EGFR) Kinase (a protein tyrosine kinase) using the LOPAC (Sigma #L01280) compound library. Hits identified in both readout modes were all seen to be true hits, whereas hits that showed discrepancy between readout modes were seen to be false. These results indicate that by multiplexing readout modes within an assay, one can significantly improve the integrity of the determined results.

Anti p-Tyr antibody (anti-pY20 available from Zymed) was concentrated to 5 mg/mL in 100 mM sodium carbonate buffer, pH 9.5. CS124-DTPA-Phe-NCS*Tb (Tb-chelate) was added at a 5 to 40-fold molar excess relative to antibody, and the reaction incubated at room temperature for 4 hours with light vortexing every 30 minutes. After 4 hours, the antibody was dialyzed twice against PBS to remove unreacted and/or hydrolyzed chelate. The amount of chelate bound to the antibody was quantitated by the absorbance of the CS124 moiety at 343 nm ($E_{340}$=11,440 $M^{-1}cm^{-1}$), and the amount of antibody quantitated by its absorbance at 280 nm ($E_{280}$=210,000 $M^{-1}cm^{-1}$), correcting for the absorbance of the CS124 at 280 nM (1.1 × its absorbance at 343 nM).

To determine whether labeling of the antibody affected its affinity for a fluorescein-labeled phosphopeptide tracer (see Example 2), binding curves were performed as previously described. At a labeling ratio of less than 9 chelates per antibody, the affinity for the tracer was seen to vary by less than 2-fold.

Epidermal Growth Factor Receptor (EGFR) Tyrosine Kinase (available from #P2628, Invitrogen, Carlsbad, Calif.) was screened for activity against the LOPAC[128™] (Sigma #L01280) library (containing 1280 compounds) in 10 μL reaction volume (20 μL detection volume) in Corning low-volume 384-well plates (part #3676). The kinase reaction was performed in the presence of 10 μM library compound under the following reaction conditions: 20 mM HEPES pH 7.5, 5 mM $MgCl_2$, 2 mM $MnCl_2$, 0.05 mM $Na_3VO_4$, 1 mM DTT, 150 nM poly(GlyTyr) 4:1 poly-GT tyrosine kinase substrate, and 10 μM ATP using 0.1 unit of kinase per reaction. The reaction was allowed to proceed for 90 minutes at 30° C., after which a 10 μl solution of a 20 mM EDTA, 8 nM Tb-labeled anti-pTyr (anti pY72 antibody; see Examples 1 and 2) and 4 nM PTK labeled-tracer (see Example 2 above) in TR-RET dilution buffer (part#PV3152, Invitrogen, Carlsbad, Calif.) were added. The quenched reactions were then allowed to incubate for 1 hour at room temperature, after which they were read on a Tecan Ultra plate reader. Fluorescence Polarization was measured using a 485 nm excitation filter (20 nm bandpass) and 535 nm emission filters (25 nm bandpass). Time Resolved RET was measured using a 340 nm excitation filter (35 nm bandpass) and two emission filters; a 495 nm with a 10 nm band pass for a reference peak and 520 nm with a 25 nm band pass for signal change measurement, using a 200 μs integration window following a 100 μs post-flash delay. TR-RET filters were from Chroma Technology Corp. TR-RET values (ratios) were determined by dividing the intensity of the sample at 520 nm by the intensity of the sample at 495 nm.

Data from the FP and TR-RET reads were normalized and plotted on orthogonal axes. The difference in the percent inhibition as determined by FP and TR-RET was determined. Four compounds that fell outside of three standard deviations from this average (CB1954, GW5074, Ergocristine, Pyrocatechol) were identified for further analysis. In addition, two compounds (Tyrophostin AG 1478, GW2974) showing strong correlation between detection modes and strong inhibition were also selected for follow-up profiling.

The two identified inhibitors (Tyrphostin AG1478 and GW2974, which are known inhibitors of EGFR kinase) were assayed in a series of 3-fold dilutions, and the four poorly-correlating compounds in a series of two-fold dilutions, against EGFR kinase under conditions as described in the library screen. Follow-up screening identified GW2974 as the more potent inhibitor, with an EC50 of about 10-fold less than that seen for AG1478.

To demonstrate the ability of the TR-RET detection mode to identify true hits even in the presence of interfering background fluorescence (a useful criteria when identifying either hits that are intrinsically fluorescent, or when screening libraries of pooled compounds in which the presence of a fluorescent compound could mask the presence of a hit), the assay was performed against a dilution series of the inhibitor Tyrphostin AG1478 in the presence of 10 nM fluorescein. The TR-RET data was seen to be impervious to the presence of the background fluorescence signal, whereas the FP data was severely compromised.

Two compounds that showed poor correlation between the FP and TR-RET detection modes, GW5074 and Ergocristine, were seen to precipitate, suggesting that the spurious signal in the FP detection mode was likely an artifact of light scatter. Because the signal due to scatter has a short lifetime, it does not affect the TR-RET reading mode.

Two other compounds that showed poor correlation, CB-1954 and Pyrocatechol, were re-assayed and neither was seen to be an inhibitor. An examination of the screen showed that these compounds were in adjacent wells of the assay plate, suggesting a systematic error that led to the spurious results.

To assess the concentration of phosphorylated kinase product required to give a detectable change in signal, a serial dilution of an unlabeled phosphorylated PTK tracer (as competitor product to tracer) was incubated with 4 nM Tb-chelate labeled anti-pTyr antibody and 2 nM fluorescein-labeled PTK tracer in TR-RET dilution buffer (see above). The plate was then read in both FP and TR-RET modes as described previously. The amount of competitor required for half-maximal signal change was seen to be nearly identical between assay modes, indicating that both assays had similar sensitivities.

To assess assay robustness, 60 wells containing 4 nM Tb-chelate labeled anti-pTyr antibody and 2 nM fluorescein-labeled tracer (the "high value" controls), and 60 wells containing the same components in addition to 1 uM competitor peptide (the "low value" controls) were read in both FP and TR-RET detection modes as described previously. Z' values room-temperature, 50 μL of 50 mM dithiothreiotol (DTT) in 100 mM sodium acetate buffer, pH 4.5, was added and the reaction allowed to incubate an additional 30 minutes at room temperature. The reaction was then dialyzed twice for two hours each against 1 L degassed PBS buffer. After dialysis, 8 μL of a solution containing 4.2 mM TTHA-AMCA-(2-amioethyl)maleimide and 10 mM EuCl₃ in 1 M Tris, pH 8.0, was added to the antibody solution and allowed to incubate for 2 hours at room temperature. The labeled antibody was then dialyzed twice (first for two hours, then overnight) to remove excess and unreacted chelate.

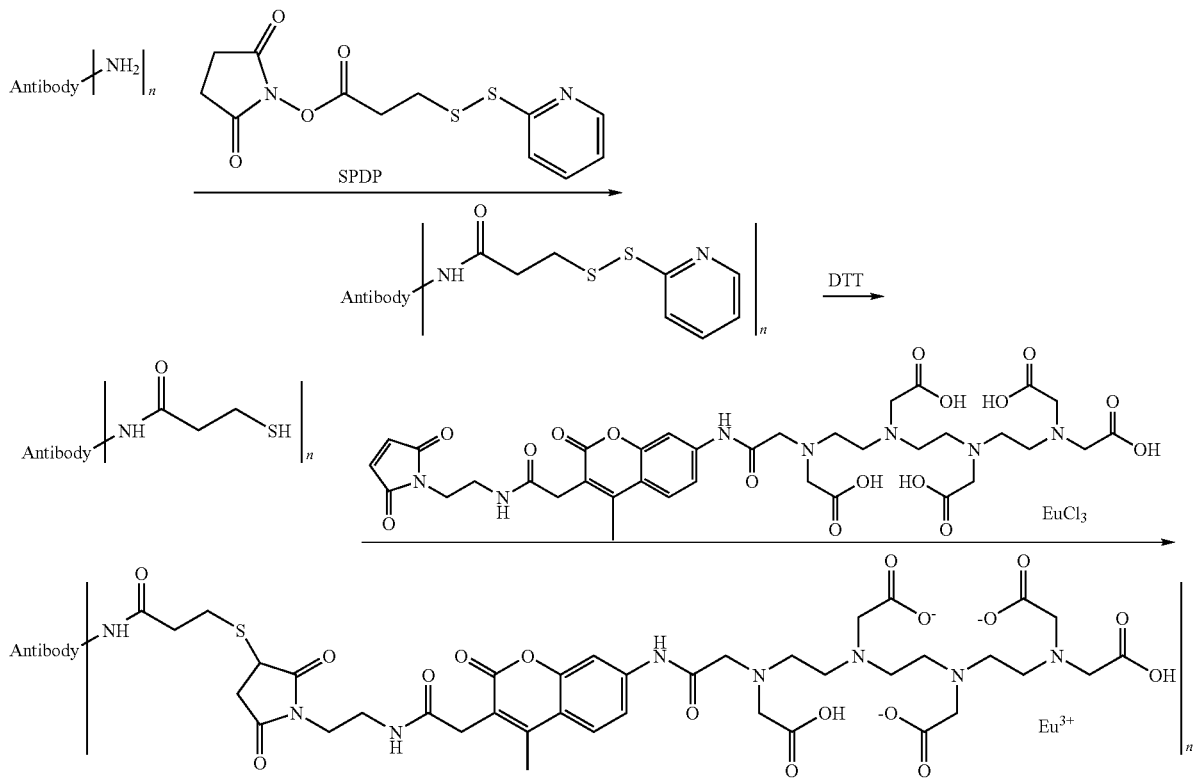

Labeling of PY72 antibody using SPDP and Eu-TTHA-AMCA-(2-aminoethyl)maleimide.

were calculated according to Zhang et al., "A Simple Statistical Parameter for Use in Evaluation and Validation of High Throughput Screening Assays," Journal of Biomolecular Screening 4(2):67-73 (1999). The Z'-factor was seen to be >0.8 for each assay mode.

Example 9

Multiplex FP/TR-RET Assay using an Eu(III)-Chelate-Labeled Binding Partner

Binding partners labeled with Eu-chelates can also be used in the methods of the present invention.

Europium(III)-chelate labeled PY72 (anti-phosphotyrosine) antibody (see Example 1) was prepared as follows. To 50 μL of a 28.4 μM solution of PY72 antibody in phosphate-buffered saline (PBS) was added 1 μL of 21.25 mM SPDP (N-Succinimidyl 3-(2-pyridyldithio) propionate, Pierce Chemical Company) in DMSO. After a one hour reaction at A competition curve to show that the disruption of an Eu-chelate labeled antibody-labeled tracer interaction by an unlabeled phosphopeptide (e.g., a product of a protein kinase enzymatic reaction) could be measured by fluorescence polarization and/or time-resolved RET from the same sample was performed by incubating serial dilutions of an unlabeled phosphotyrosine-containing peptide competitor (2 μM to 1 nM in two-fold dilutions; in the presence of 5 nM Eu-chelate labeled PY72 antibody and 1 nM luminescent tracer in FP dilution buffer (Part #P2839, Invitrogen, Carlsbad, Calif.). The luminescent labeled tracer was Alexa Fluor 633-CADE (pY)LIPQQS (SEQ ID NO:10), a peptide in which the C5 maleimide derivative of Alexa Fluor 633 (Molecular Probes, Eugene Oreg., Part #A20342) had been coupled to the terminal cysteine of the peptide using standard procedures (following the protocol included with the Alexa Fluor dye) and purified via HPLC using standard procedures. The peptide (CADE(pY)LIPQQS; SEQ ID NO:9) had been ordered by AnaSpec, San Jose Calif. Alexa Fluor 633 has a maximum excitation wavelength of approximately 622 nm and a maximum emission wavelength of approximately 640 nm in aqueous solution. After a 30 minute incubation, the plate was read on a Tecan Ultra plate reader in both FP and TR-RET formats. Fluorescence polarization was measured using a 590 nm excitation filter (20 nm bandpass) and 650 nm emission filters (40 nm bandpass). Time-resolved RET was measured using a 340 nm excitation filter (35 nm bandpass) and 615 nm (10 nm bandpass) and 665 nm (10 nm bandpass) emission filters using a 200 μs integration window after a 100 μs post-flash delay with 10 flashes per well. The time-resolved RET value (ratio) was calculated by dividing the 665 nm signal by the 615 nm signal. The shapes of the curves generated by TR-RET or FP were seen to nearly overlap, indicating that the presence of a competitor phosphopeptide (such as that generated by a kinase reaction) could be detected and quantitated using either FP or TR-RET modes.

Example 10

Detection of Histidine-Tagged Proteins using Multiplex Modes

A multiplex system for the detection of His-tagged proteins or peptides was developed. The basis of the assay was a competition between a Histidine-tagged analyte protein and a tracer consisting of fluorescein linked to a hexahistidine peptide for a terbium-chelate labeled anti-His-tag antibody. In the absence of analyte protein or peptide, the fluorescein-labeled hexahistidine peptide associates with the anti-His-tag antibody, and this interaction can be detected by TR-RET or FP. In the presence of increasing amounts of analyte protein, this tracer-antibody interaction is disrupted and the TR-RET signal or fluorescence polarization of the tracer decreases. Fluorescein-His6 peptide (fluorescein-HHHHHH, the "luminescent tracer;" SEQ ID NO:11) was synthesized by a commercial supplier (ResGen, Huntsville Ala.) and used as supplied. A commercial monoclonal antibody specific for the hexahistidine tag (Part MCA1396, Serotec, Raleigh, N.C.) was purchased and used as supplied with no additional purification. 0.25 mg antibody was concentrated in 100 mM sodium carbonate buffer, pH 9.5, to a final volume of 50 uL (5 mg/mL final concentration of antibody). To label the antibody, 30 ug of CS124-DTPA-Phe-NCS-Tb (a 20-fold molar excess relative to antibody) was added and the reaction allowed to proceed at room temperature for 4 hours with light vortexing every 30 minutes. After 4 hours, the antibody was dialyzed twice versus PBS to remove unreacted and/or hydrolyzed chelate. The amount of chelate bound to the antibody was quantitated by the absorbance of the CS124 moiety at 343 nm ($E_{340}$=11,440 $M^{-1}cm^{-1}$), and the amount of antibody quantitated by its absorbance at 280 nm ($E_{280}$=210,000 $M^{-1}cm^{-1}$), correcting for the absorbance of the CS124 at 280 nM (1.1 × its absorbance at 343 nM). From these measurements an average of 7.7 chelates per antibody was determined. The labeled antibody was seen to be stable for at least 6 months with no noticeable loss in performance.

A competitive binding assay was performed with 20 nM antibody and 2 nM tracer, with titration of increasing amounts of His-tagged peptide (sequence: Biotin-KGGHHHHHH, source: ResGen; SEQ ID NO:12) ranging from 3 uM to 1.5 nM in two-fold dilutions. The assay components were mixed in FP Dilution buffer (see above) and read after a 30 minute incubation on a Tecan Ultra plate reader using a 340 nm excitation filter (35 nm bandpass) and a 520 nm emission filter (25 nm bandpass). Data were collected using a 200 μs integration window after a 100 μs post-flash delay, with 10 flashes per well.

Example 11

Ubiquitin Fusion Proteins

*E. coli* expression plasmids for two de-ubiquinating (DUB) substrates are constructed using the pRSET(B) vector (Invitrogen, Cat#V351-20) such that the fusion proteins encoded are comprised of (N-terminal to C-terminal), a His-tag, Emerald green fluorescent protein (EmGFP), ubiquitin, a linker of variable sequence, and a C-terminal cysteine residue. The amino acid sequences of two such substrates constructed are MRGSHHHHHHGMASMTGGQQMGRDLYD-DDDKDRWGSEFATMVSKGEELFTGVV PILVELDGD-VNGHKFSVSGEGEGDATYGKLTLKFICT-TGKLPVPWPTLVTTLTYGVQ CFARYPDHMKQHDFFKSAMPEGYVQER-TIFFKDDGNYKTRAEVKFEGDTLVNRIEL KGID-FKEDGNILGHKLEYNYNSHKVYITAD-KQKNGIKVNFKTRHNIEDGSVQLADH YQQNTPIGDGPVLLPDNHYL STQ SAL SKDP-NEKRDHMVLLEFVTAAGITLGMDELY KLET-DQTSLYKKAGTMQIFVKTLTGKTI-TLEVEPSDTIENVKAKIQDKEGIPPDQQRLI FAGKQLEDGRTLSDYNIQKESTLHLVLRLRGGAC (SEQ ID NO:13) and MRGSHHHHHHGMASMTG-GQQMGRDLYDDDDKDRWGSEFATMVSK-GEELFTGVV PILVELDGDVNGHKFSVSGEGEG-DATYGKLTLKFICTTGKLPVPWPTLVTTLTYGVQ CFARYPDHMKQHDFFKSAMPEGYVQER-TIFFKDDGNYKTRAEVKFEGDTLVNRIEL KGID-FKEDGNILGHKLEYNYNSHKVYITAD-KQKNGIKVNFKTRHNIEDGSVQLADH YQQNTPIGDGPVLLPDNHYL STQ SAL SKDP-NEKRDHMVLLEFVTAAGITLGMDELY KLET-DQTSLYKKAGTMQIFVKTLTGKTI-TLEVEPSDTIENVKAKIQDKEGIPPDQQRLI FAGKQLEDGRTLSDYNIQKESTLHLVLR-LRGGFFGVGGEGAC (SEQ ID NO:14). These constructs are used to produce the substrates EmGFP-Ub-AC-Tb and EmGFP-Ub-FFG-X-Tb, respectively.

BL21 Star™ (DE3)pLysS cells (Invitrogen, Cat#C6020-03) are transformed with the expression plasmids for the DUB substrates and plated on LB agar with ampicillin and chloramphenicol. Single colonies are selected and grown overnight in 50 mL of LB (Luria Broth) medium with ampicillin (100 mg/L) and chloramphenicol (34 mg/L) at 37° C. and 225 rpm. 500 mL of Turbo Prime™ Broth (Athena Enzyme Systems, 0110) is inoculated with 5 mL of each overnight culture and grown at 37° C. at 225 rpm until the $OD_{595}$ reached approximately 0.3. The cultures are then shifted to 25° C. and grown for one hour followed by induction with 0.5 mM IPTG. The cells are harvested after 4 hours of additional growth by centrifugation and stored at −80° C. Cell pellets from 500 mL of culture are suspended in 200 mL of Lysis Buffer (25 mM Tris pH 7.5, 100 mM NaCl). The cells are disrupted by passing the suspension twice through a chilled high pressure homogenizer (Avestin EmulsifFlex C-50) at 10-15,000 pounds per square inch (PSI) and collected on ice. The lysates are then clarified by centrifugation at 28,000×g for 30 minutes at 4° C. The supernatants are batch bound to 2 mL of NiNTA agarose (Invitrogen) for 1 hour at 4° C. The resin is then collected by centrifugation at 153×g for 5 min. The supernatants are discarded and the resin is suspended in approximately 5 mL of Lysis Buffer and transferred to a disposable column. The columns are allowed to drain, and then are then washed with 20 mL of Lysis Buffer, followed by 10 mL of Lysis Buffer with 50 mM imidazole by gravity. The column is then eluted with 4 mL of 12.5 mM Tris, 50 mM NaCl, and 500 mM Imidazole pH 7.0 and a single fraction is collected, e.g., which is bright green. Dithiothreitol (DTT) is added to the eluted protein to a final concentration of 10 mM, which is then incubated at room temperature for 2 hours. 500 µL portions of protein are then desalted into HBS (137 mM NaCl, 2.7 mM KCl, and 10 mM Hepes pH 7.5) using a NAP-5 column (GE Healthcare 17-0853-01) and collected in a single 1 mL fraction per sample of protein. Thiol reactive terbium chelate (Invitrogen PV3580) is then dissolved in water to 1 mg/mL and added in 2-fold molar excess to the desalted protein, which is at 60 to 80 µM. The labeling reactions are allowed to proceed at room temperature for 3 hours, and the products are desalted over a NAP-5 column into HBS. These purified DUB substrates are quantified using the empirically determined extinction coefficient for GFP of 40,000 $M^{-1}cm^{-1}$ at 480 nm and stored at $-80°$ C. Labeling efficiency is calculated based on the extinction coefficient of the terbium chelate at 12,570 $M^{-1}cm^{-1}$.

Protease Reactions

Protease reactions are performed using the DUB substrates EmGFP-Ub-AC-Tb or EmGFP-Ub-FFG-X-Tb in 50 mM Tris pH 7.5, 5 mM DTT, 0.1 mg/mL bovine serum albumin (BSA), 0.5 mM ethylenediaminetetraacetic (EDTA) in 384-well low volume plates (Corning 3676). Reactions are started by addition of 10 µL of 200 nM DUB substrate to 10 µL of various concentrations of UCH-L3 (Boston Biochem E-325). Fluorescence measurements are captured after a one hour incubation at room temperature on a Tecan Ultra plate reader. Intensities are measured at 520 nm (20 nm bandwidth) and 495 nm (10 nm bandwidth), with excitation at 340 nm (30 nm bandwidth). Protease activity correlates with a decrease in emission intensity at 520 nm. See FIGS. 10, 11A-11F, and 12.

Example 12

Protease Reactions using the DUB Substrates

Preparation of YFP-ubiquitin-AC-terbium

An expression plasmid encoding a his-tagged YFP ("Topaz" (Cubitt et al., Cell Biol. 58:19-30 (1999)) variant)-ubiquitin fusion with a C-terminal alanine-cysteine (AC) addition (YFP-Ub-AC) was expressed and purified from *Escherichia coli* using standard methods. The encoded sequence was MRGSHHHHHHGMASMTGGQQMGRDLYD-DDDKDRWGSEFATMVSKGEELFTGVV PILVELDGD-VNGHKFSVSGEGEGDATYGKLTLKFICT-TGKLPVPWPTLVTTFGYGVQ CFARYPDHMRQHDFFKSAMPEGYVQER-TIFFKDDGNYKTRAEVKFEGDTLVNRIEL KGID-FKEDGNILGHKLEYNYNSHNVYIMAD-KQKNGIKVNFKIRHNIEDGSVQLADH YQQNTPIGDGPVLLPDNHYLSYQSAL-SKDPNEKRDHMVLLEFVTAAGITLGMDELY KLET-DQTSLYKKAGTMQIFVKTLTGKTI-TLEVEPSDTIENVKAKIQDKEGIPPDQQRLI FAGKQLEDGRTLSDYNIQKESTLHLVLRLRGGAC (SEQ ID NO:26).

Expression of YFP-Ub-AC:

The YFP-Ub-AC expression plasmid encodes an Alanine-Cysteine (AC) addition mutant to the C-terminus of YFP (Topaz)-ubiquitin. The expression plasmid was transferred into chemically competent BL21 Star (DE3) pLysS cells using the method supplied by the vendor; followed by plating onto LB agar plates containing 0.1 mg/mL ampicillin and 0.05 mg/mL chloramphenicol. A colony was selected to inoculate 50 mL of LB broth containing 0.1 mg/mL ampicillin and 0.05 mg/mL chloramphenicol that was grown overnight at 37° C. From the overnight culture, 5 mL was used to inoculate 500 mL of LB broth containing 0.1 mg/mL ampicillin and 0.05 mg/mL chloramphenicol and was grown at 37° C. until an optical density of 0.2 at 600 nm was reached. The temperature of the incubator was reduced to 25° C. and the culture continued to grow until an optical density of 0.6 at 600 nm was achieved. At this point, IPTG (isopropyl-β-D-thiogalactopyranoside) was added to a concentration of 1 mM to induce the T7 promoter on the expression plasmid and to stimulate production of YFP-Ub-AC. The cells were induced for 4 hrs at 25° C. The cells were harvested by centrifugation at 4200 rpm (in a JS-4.2 rotor) for 20 min at 4° C. The supernatant was discarded, and the cell paste was stored at $-80°$ C.

Extraction and Purification of YFP-Ub-AC:

The YFP-Ub-AC cell paste was resuspended in 25 mM Tris-HCl pH 7.5 with 100 mM NaCl and 30 mM Imidazole with a handheld polytron biohomogenizer. The resuspended cells were lysed by passing through an Avestin Emulsiflex C50 homogenizer at 10,000-15,000 psi at 4° C. The homogenized cells were centrifuged at 13,500 rpm (~28,000×g) for 30 min in a JA-14 rotor at 4° C. The supernatant was collected, and was batch bound to Ni-NTA agarose for 1 hr at 4° C. with gentle agitation. The Ni-NTA agarose was transferred to a disposable column and washed with 5 column volumes of lysis buffer to remove contaminating proteins. The YFP-Ub-AC was eluted from the Ni-NTA column with 25 mM Tris-HCl pH 7.5 with 100 mM NaCl and 400 mM Imidazole. The YFP-Ub-AC was diluted to 5 mg/mL (based upon absorbance at 280 nm; $\epsilon_{280}=33,350$ $M^{-1}$ $cm^{-1}$) with storage buffer (25 mM Tris-HCl pH 7.5 with 100 mM NaCl and 5% (v/v) glycerol) and DTT was added to a final concentration of 10 mM. The intermediate was stored at $-80°$ C. until required for labeling.

Labeling of YFP-Ub-AC:

One mL of the YFP-Ub-AC intermediate (5 mg/mL) was defrosted and placed over a Nap™ 10 desalting column to remove the DTT. The eluted protein was immediately combined with 200 µg of thiol reactive Tb-chelate (Invitrogen Corp., Carlsbad, Calif.), and allowed to react at room temperature for two hours. The reaction mixture was loaded into a Slide-A-Lyzer (10,000 MWCO) and dialyzed against Hepes Buffered Saline (HBS) to remove unreacted Tb chelate. The dialyzed YFP-Ub-AC is diluted with HBS to a final concentration of 20 µM (based upon absorbance at 280 nm) and stored at $-80°$ C.

Protease Assay Protocol

Proteases (UCH-L1, UCH-L3, USP-5, and USP-14) and ubiquitin aldehyde were purchased from Boston Biochem (Cambridge, Mass.). To assay relative activity of each DUB toward the YFP-ubiquitin-Tb substrate, serial dilutions of enzymes were prepared in 10 µl of assay buffer (20 mM Tris, pH 7.4, 0.01% Nonidet-P40, 10 mM DTT) in a black 384-well low-volume plate (Corning No. 3676). To each well was then added 10 µl of a 20 nM solution of YFP-ubiquitin-Tb substrate in the same buffer. After 50 min, the plate was read on a BMG Labtech Pherastar plate reader using the LanthaScreen filter module. The emission ratio was calculated as the raw acceptor intensity divided by the raw donor intensity when measured using a 200-µs signal integration window following a 100-µs delay. No background subtraction or cross talk correction was required. Kinetic reads were performed similarly against varying concentrations of UCH-L3, with the reactions read every minute for 90 min Inhibitor titrations were performed using 15 pM UCH-L3 and 10 nM YFP-ubiquitin-Tb in a 1 h reaction against a dilution series of ubiquitin aldehyde or ubiquitin as inhibitor. Z' values were determined at various percentage conversions of substrate, using different concentration of UCH-L3. In these experiments, 24 positive control wells and 24 negative control wells were measured and Z' was calculated according to the equation (Zhang et al., *J. Biomol. Screen.* 4:67-73 (1999). Z'=1− $[3\sigma_{c+}+3\sigma_{c-})/|\mu_{c+}-\mu_{c-}|]$, where $\sigma_{c+}$ and $\sigma_{c-}$ are the standard deviations of the positive and negative control wells on the assay plate, respectively, and $\mu_{c+}$ and $g_{c-}$ are average values for the positive and negative control wells on the assay plate, respectively. Negative control wells contained 50 nM ubiquitin-aldehyde to inhibit UCH-L3. Normalized emission ratios were calculated relative to wells that contained maximal and minimal FRET signal and then multiplied by 100. Time-resolved spectra and emission signal decay of intact and cleaved YFP-Ub-AC-Tb Time-resolved spectra of 10 nM YFP-ubiquitin-Tb that had been incubated with or without excess UCH-L3 were measured using a Tecan Safire² plate reader. Samples were 20 μL and were read in a white 384-well low-volume plate (Corning). Excitation was set to 332 nm (20 nm bandwidth), and emission measurements were collected from 475 to 650 nm in 1-nm increments using a 200-μs signal integration window following a 100-μs delay and averaged over 100 measurements (flashes) per wavelength. Emission signal decays were measured using a BMG Labtech Pherastar plate reader.
Titration of YFP-ubiquitin-Tb DUB Substrate into UCH-L3

A 400 nM solution of UCH-L3 (Bostonbiochem; Catalog #:E-325) in assay buffer (TR-FRET dilution buffer (PV3574) with 10 mM DTT) is prepared. Twenty microliters of the enzyme solution is added to the first column of a Corning black 384 low volume plate (#3676), and a serial dilution is performed across the plate with assay buffer (10 μL). A 20 nM solution of YFP-ubiquitin-Tb substrate is prepared with assay buffer, and 10 μL of this solution is added to each well. Final concentration of UCH-L3 in first well is 200 nM. Final concentration of YFP-ubiquitin-Tb substrate in the assay is 10 nM. The plate is allowed to equilibrate at room temperature for 40-50 min, and then read on a BMG LABTECH PHEARstar with the appropriate settings for LanthaScreen™. The collected data is graphed, and fit to a sigmodial dose response (variable slope) to obtain the $EC_{50}$ value. (FIG. 41C)
Results YFP-ubiquitin-Tb was tested as a substrate (at 10 nM) against UCH-L3, USP-2, USP-15, UCHL1, USP-5 and USP-14. USP-14 is not expected to show activity in the absence of association with components of the 26S proteasome. USP-2 and USP-15 are essentially indistinguishable. (FIG. 41A)

Figure 41:
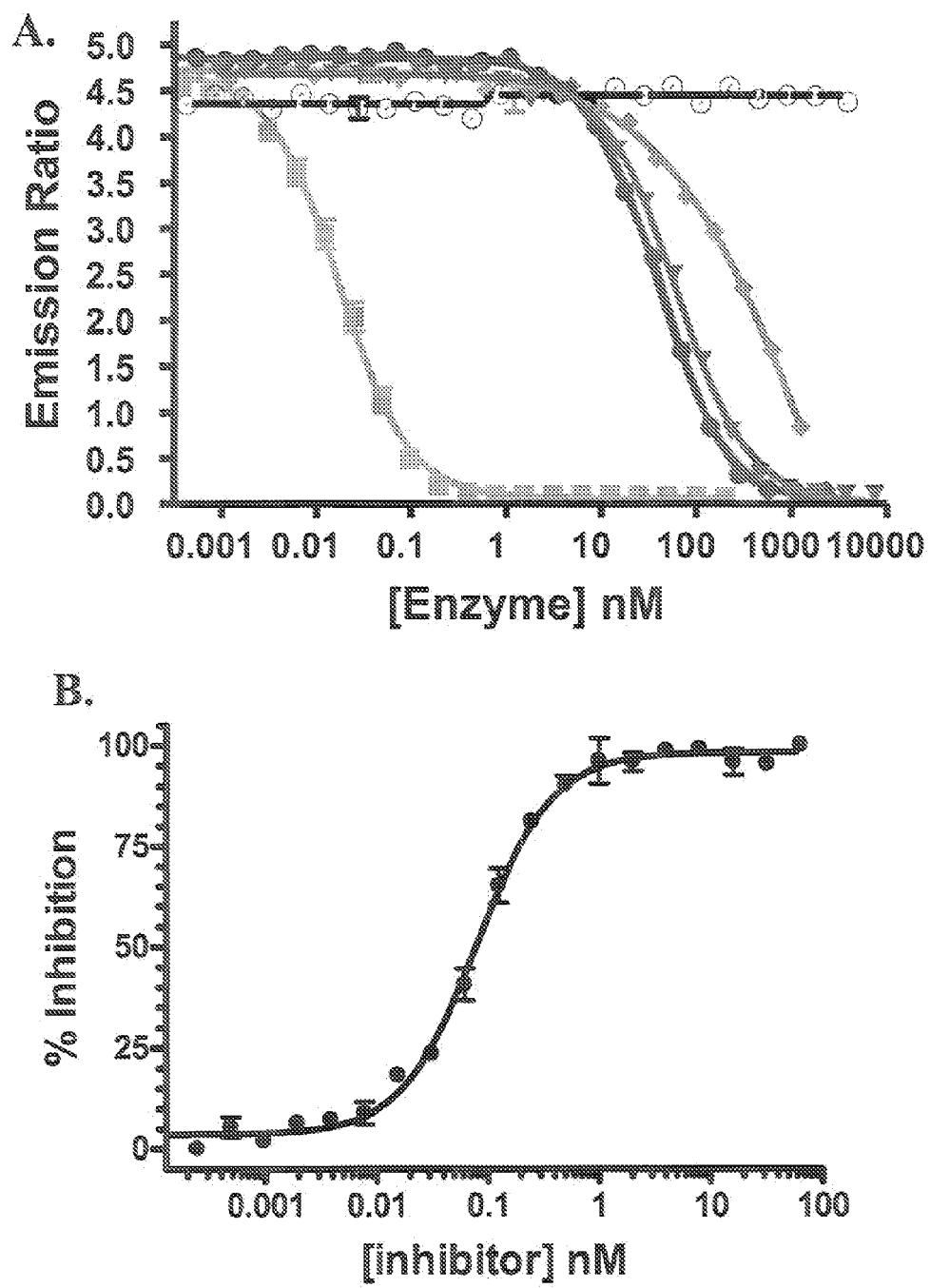
FIG. 41A shows the results when GFP-Ub-Tb was tested as a substrate (at 10 nM) against UCH-L3 (■), USP-2 (●), USP-15 (▲), UCH-L1 (▼), USP-5 (♦) and USP-14 (○). USP-14 is not expected to show activity in the absence of association with components of the 26S proteasome. USP-2 and USP-15 are indistinguishable.
FIG. 41B shows the results when tight-binding DUB inhibitor, ubiquitin aldehyde, was titrated against 0.1 nM UCH-L3 and 10 nM GFP-Ub-Tb and shown to inhibit the reaction with an IC50 of 0.2 nM.
FIG. 41C shows a sigmodial dose response (variable slope) to obtain the $EC_{50}$ value for a titration of a YFP-ubiquitin-Tb substrate as described in Example 12.
Figure 41:
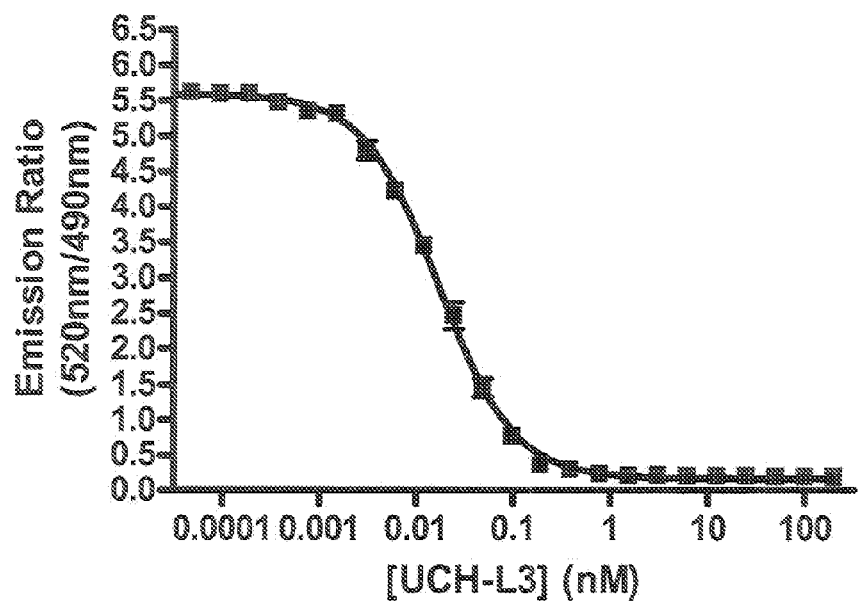

FIG. 41C shows a sigmodial dose response (variable slope) to obtain the $EC_{50}$ value for a titration of a YFP-ubiquitin-Tb substrate. The corresponding best fit values are: Bottom=0.1659; Top=5.595; $LogEC_{50}$=−1.765; Hillslope=−1.117; and $EC_{50}$=0.01717.

Example 13

Preparation of a MEK1 Conjugate

A fluorescein-MEK1 conjugate is prepared from wt MEK1 (inactive) (Invitrogen, cat#P3093). First, MEK1 samples are dialyzed against HBS (137 mM NaCl, 2.7 mM KCl, and 10 mM Hepes pH 7.5). Next, 5-IAF (5-iodoacetaminofluorescein) or 5-FAM, SE (5-carboxyfluorescein, succinimdyl ester) are added in either 10- or 50-fold molar excess to 10 μM MEK1 and the reactions are allowed to proceed at room temperature for 1 hour and 40 minutes. The reactive dyes are removed by desalting the MEK1 samples over using NAP-5 columns into HBS. The labeled MEK1 preparations are stored frozen at 80° C.

Although this study took advantage of the fact that MEK contains several surface-accessible thiol groups to which an acceptor fluorophore could be attached via an iodoacetamide-functionalized fluorescein derivative, amine-reactive isothiocyanate or activated ester derivatives of suitable fluorophores are equally appropriate. Additionally, although fluorescein was used in this study, other fluorophores with similar spectra (such as BODIPY-FL, Oregon green, or Alexa Fluor-488) would be equally suitable, and red shifted fluorophores may also be used by employing alternative filter sets.

Example 14

Construction and Preparation of GFP Fusions of Kinase Substrates

*E. coli* expression plasmids for GFP fusions of kinase substrates are constructed using the pRSET(B) vector (Invitrogen V351-20) such that the fusion proteins encoded are comprised of (N-terminal to C-terminal), a His-tag, EmGFP, and a kinase substrate. Two such substrates are EmGFP-ATF2 (19-96), and EmGFP-c-Jun(1-79). The amino acid sequence of EmGFP-c-Jun is MRGSHHHHHHGMASMTG-GQQMGRDLYDDDDKDRWGSEFATMVSK-GEELFTGVVP ILVELDGDVNGHKFSVSGEGEG-DATYGKLTLKFICTTGKLPVPWPTLVTTLTYGVQCF ARYPDHMKQHDFFKSAMPEGYVQER-TIFFKDDGNYKTRAEVKFEGDTLVNRIELKGI DFKEDGNILGHKLEYNYNSHKVYITAD-KQKNGIKVNFKTRHNIEDGSVQLADHYQQ NTPIGDGPVLLPDNHYLSTQSALSKDP-NEKRDHMVLLEFVTAAGITLGMDELYKLET DQTSLYKKAGSMTAKMETTFYDDALNAS-FLPSESGPYGYSNPKILKQSMTLNLADPV GSLKPHL-RAKNSDLLTSPDVGLLKLASPELERL (SEQ ID NO:15). The amino acid sequence of EmGFP-ATF2 is MRGSHHH-HHHGMASMTGGQQMGRDLYDDDDKDRWG-SEFATMVSKGEELFTGVVP ILVELDGDVNGHKFSVS-GEGEGDATYGKLTLKFICTTGKLPVPWPTLVTTLTYG VQCF ARYPDHMKQHDFFKSAMPEGYVQER-TIFFKDDGNYKTRAEVKFEGDTLVNRIELKGI DFKEDGNILGHKLEYNYNSHKVYITAD-KQKNGIKVNFKTRHNIEDGSVQLADHYQQ NTPIGDGPVLLPDNHYLSTQSALSKDP-NEKRDHMVLLEFVTAAGITLGMDELYKLET DQTSLYKKAGSMSDDKPFLCTAPGCGQR-FTNEDHLAVHKHKHEMTLKFGPARNDSV IVADQTPTPTRFLKNCEEVGLFNELASPFENEF (SEQ ID NO:16).

BL21 Star™ (DE3)pLysS cells (Invitrogen C6020-03) are transformed with the expression plasmids for the GFP-tagged kinase substrates and plated on LB agar with ampicillin and chloramphenicol. Single colonies are selected and grown in 500 mL of either LB (Luria Broth) or Turbo Prime™ Broth (Athena Enzyme Systems 0110) and are grown at 37° C. at 225 rpm until the OD595 reached approximately 0.3 to 1.0 prior to induction. The cultures are induced with IPTG (0.05 to 0.5 mM) and the cells are harvested after 4-16 hours of additional growth by centrifugation and stored at −80° C. Cell pellets from 500 mL of culture are suspended in 200 mL of Break Buffer (50 mM Tris pH 7.5, 200 mM NaCl, 0.1% Triton X-100, 20 µM leupeptin and 0.5 mM PMSF). The cells are disrupted by passing the suspension twice through a chilled high pressure homogenizer (Avestin EmulsifFlex C-50) at approximately 10,000 PSI and collected on ice. The lysates are then clarified by centrifugation at 28,000×g for 30 minutes at 4° C. The supernatants are batch bound to 2 mL of NiNTA agarose (Invitrogen) for 1 hour at 4° C. The resin is then collected by centrifugation at approximately 500×g for 5 min. The supernatants are discarded and the resin is suspended in approximately 5 mL of Lysis Buffer and transferred to disposable columns. The columns are allowed to drain, and then are washed with 25 mL of Break Buffer, followed by 10 mL of Break Buffer with 25 mM imidazole by gravity. The columns are then eluted with 5 mL of Break Buffer with 250 mM Imidazole and a single fraction is collected, which is bright green. These purified GFP-tagged substrates are quantified using the empirically determined extinction coefficient for GFP of 40,000 M−1cm−1 at 480 nm and stored at −80° C.

Terbium-labeled antibodies are produced by labeling of phospho-specific antibodies c-Jun [pS73] (Biosource 44-292) and ATF2 [pT71] (Biosource 44-294) with amine-reactive terbium chelate (Invitrogen) following the manufacturer's recommended conditions and using antibody preparations in phosphate buffer saline without BSA.

Example 15

Kinase Reactions and Assays

Kinase reactions are performed in Kinase Buffer (50 mM HEPES pH 7.5, 0.01% BRIJ-35, 10 mM MgCl2, and 1 mM EGTA; Invitrogen) in 384-well low volume plates (Corning 3676). Reactions are performed in a volume of 5 to 15 uL with 200 to 225 nM substrate, various concentrations of kinase, and 100 µM ATP. EmGFP-ATF2 is used as a substrate for JNK1 (Invitrogen PV3319), JNK2 (Invitrogen PV3620), p38α (Invitrogen PV3304), and p38β (Invitrogen PV3679). EmGFP-c-Jun is used as a substrate for JNK1 and JNK2. Fluorescein-MEK1 is used as a substrate for cRaf (Invitrogen PV3805), BRAF catalytic domain (Invitrogen PV3849), and BRAF (Invitrogen PV3848). Kinase reactions are incubated at ambient temperature for 1 hour, after which the appropriate terbium labeled phospho-specific antibody is added to a final concentration of 2.5 or 5 nM for the GFP-fusion substrates. For fluorescein-MEK1, an equal volume of a 1:10 dilution of an unlabeled phospho-specific antibody, Phospho-MEK1/2 (Ser217/221) (Cell Signalling Technology 9123S) is added to 5 µL kinase reactions, followed by 10 µL of 20 nM Tb-anti-Rabbit secondary Antibody (Invitrogen PV3773). All antibodies are diluted in TR-FRET dilution buffer (20 mM Tris, pH 7.5 and 0.01% NP-40; Invitrogen) prior to addition to the kinase reactions. Fluorescence measurements are captured after a one hour incubation at room temperature on a Tecan Ultra plate reader. Intensities are measured at 520 nm (20 nm bandwidth) and 495 nm (10 nm bandwidth), with excitation at 340 nm (30 nm bandwidth). Kinase activity correlates with an increase in emission intensity at 520 nm, and typically a decrease in emission intensity at 495 nm. See FIGS. 9, 13, 14, 15, 16, 17, 18 and 19.

Figure 20:
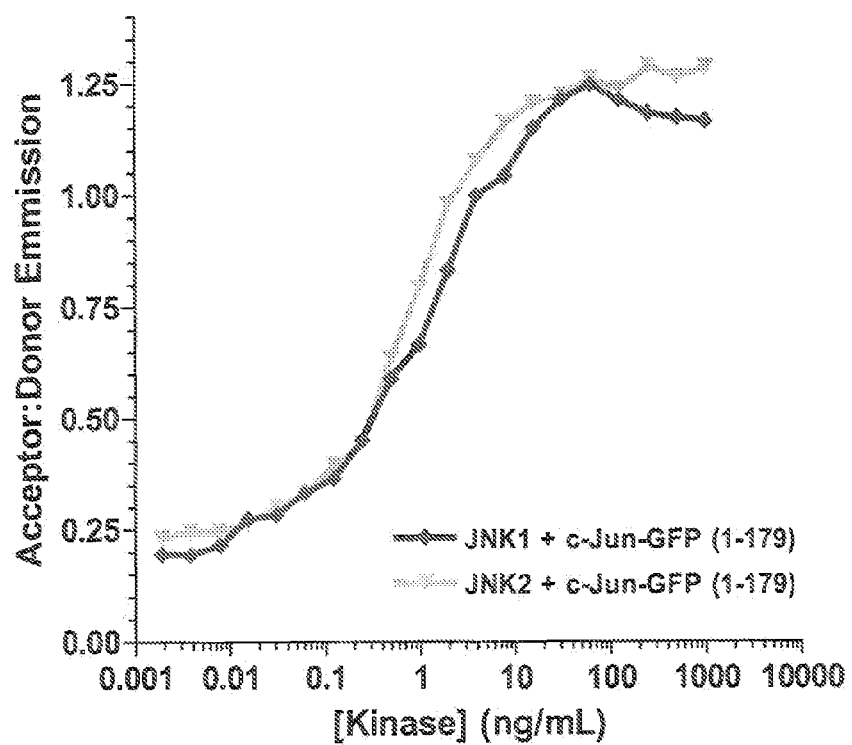
FIG. 20 shows the results of an assay of JNK1 and JNK2 using c-Jun-GFP fusion substrate.

Jun kinases (JNKs) phosphorylate a host of transcription factors including c-Jun in response to appropriate stimulation. Phosphorylated c-Jun then interacts with c-Fos to form the transcriptional activator, AP1. Activity of JNK activity is readily assayed using GFP-fusions of the native substrate in accordance with the present invention e.g., utilizing c-Jun when paired with terbium labeled antibodies specific for phosphorylated c-Jun. See FIG. 20.

c-Jun N-terminal kinases (JNKs) are members of the MAP kinase family that specifically phosphorylate c-Jun at Ser-63 and Ser-73 following UV irradiation or other stress stimuli. This phosphorylation is dependant on a "docking" event mediated by, e.g., residues 30-60 of the c-Jun substrate and residues within different domains near the JNK active site.

Example 16

Assay for Modulators of Kinase Reactions

SB202190 is a potent and selective p38 MAP kinase inhibitor. This compound inhibits p38α and p38β, but not the p38γ or p38δ isoforms, ERK2, other members of the MAP kinase family, or their upstream activators. This selectivity makes SB202190 a useful tool for dissecting the role of p38 in signaling pathways. SB202190 is reported to have an IC50 of 30 nM for p38α and p38β.

Figure 21:
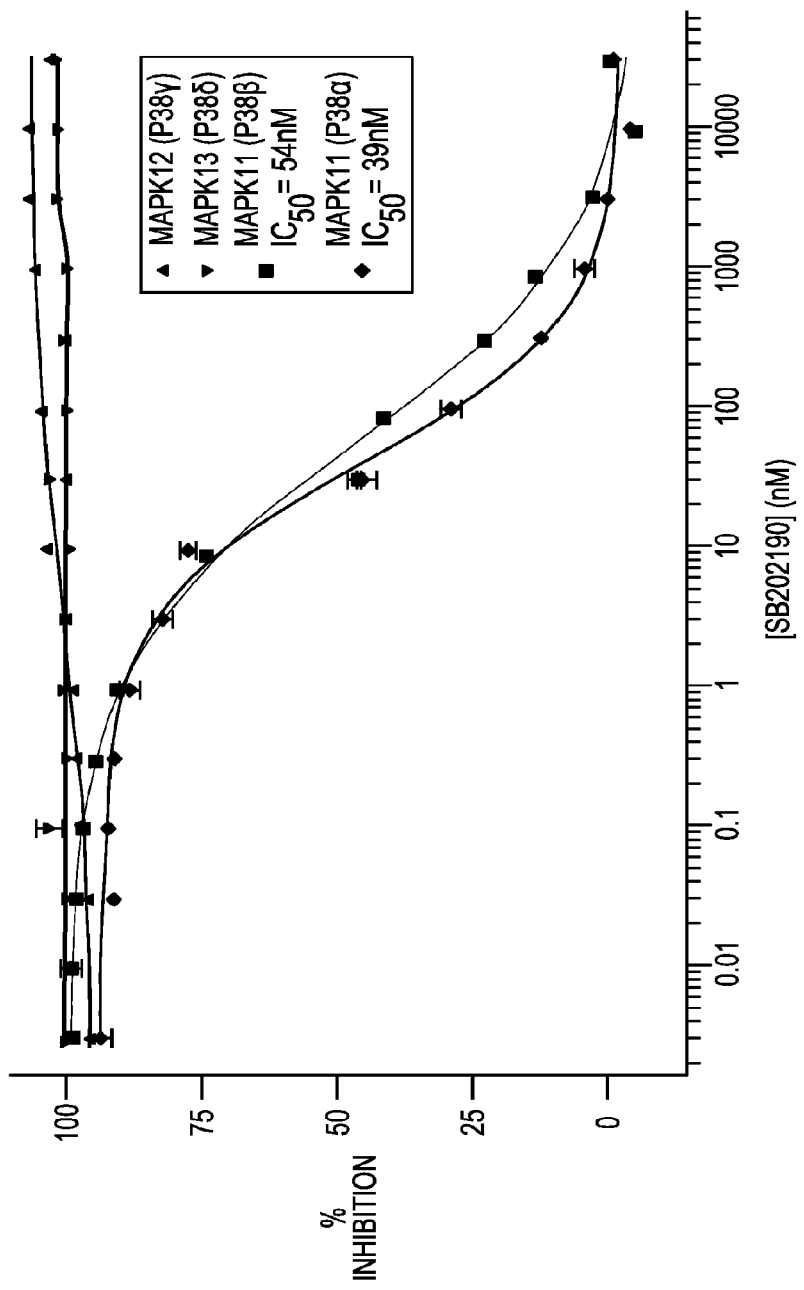
FIG. 21 shows an assay demonstrating selective inhibition of p38 isoforms using ATF2-GFP as a substrate.

The p38 MAP kinases, p38α, p38β, p38γ, and p38δ (Invitrogen, Madison, Wis.) are evaluated against the inhibitor SB202190 (BioSource, Camarillo, Calif.). Enzyme concentrations are based on EC80-values in the presence of 10 µM ATP, which corresponds to the ATP EC50 for the enzymes tested. Enzyme concentrations are 4.5 µg/mL (p38α), 1.2 µg/mL (p38β), 0.3 µg/mL (p38γ), and 1.3 µg/mL (p38δ). The inhibition curves are performed in Kinase buffer A (Invitrogen, Calif.) starting at 30 µM SB202190 using ½ log dilutions down to 3 pM. Inhibition data is generated using 400 nM ATF2-GFP fusion protein as the MAP kinase substrate. Reactions are allowed to proceed for 1 hour at 22° C. in a 10 µL volume. The reactions are stopped by a 10 µL addition of 20 mM EDTA and 5 nM terbium-labeled, anti-phosphospecific ATF2 antibody. The results are read 60 minutes later on a Tecan Ultra384 plate reader in TR-FRET mode. The excitation wavelength used is 340 nm and emission is monitored at 495 and 520 nm. The 520:495 ratio is plotted versus inhibitor concentration using Prism (GraphPad Software, San Diego, Calif.) to determine IC50 values. See FIG. 21.

Example 17

Expression, Extraction, Labeling and Purification of MCGG-Ubiquitin

The expression plasmid (pEXP14-Ub-MCGG) encodes a Methionine-Cysteine-Glycine-Glycine (MCGG) addition mutant to the N-terminus of ubiquitin. The pEXP14-Ub-MCGG vector was produced by PCR amplifying the Ub protein with recombination sites compatible with the entry vector pDonr221 (Invitrogen, Cat#12536-017). The PCR product was recombined into pDonr221. pDonr221 was used in a Gateway® reaction with the destination vector pDEST14 (Invitrogen, cat#11801-016). As will be apparent to one skilled in the art, essentially any compatible vector for expressing a Methionine-Cysteine-Glycine-Glycine (MCGG) addition mutant to the N-terminus of ubiquitin would be suitable for this procedure.

The expression plasmid is transferred into chemically competent DH5a cells using the method supplied by the vendor; followed by plating onto LB agar plates containing 0.1 mg/mL ampicillin. A colony is selected to inoculate 50 mL of LB broth containing 0.1 mg/mL ampicillin that is grown overnight at 37° C. From the overnight culture, 5 mL is used to inoculate 500 mL of LB broth containing 0.1 mg/mL ampicillin and is grown at 37° C. until an optical density of >0.6 at 600 nm is reached. At this point, IPTG (isopropyl-β-D-thiogalactopyranoside) is added to a concentration of 1 mM to induce the T7 promoter on the expression plasmid and to stimulate production of the MCGG-ubiquitin mutant protein. The cells are induced for 4 hrs at 37° C. The DH5a cells are harvested by centrifugation at 4200 rpm (in a JS-4.2 rotor) for 20 min at 4° C. The supernatant is discarded, and the cell paste is stored at −80° C.

The MCGG-ubiquitin cell paste is resuspended in Hepes Buffered Saline containing 1 mM EDTA and 10 mM DTT using a handheld polytron biohomogenizer. The resuspended cells are lysed by passing through an Avestin Emulsiflex C50 homogenizer at 10,000-15,000 psi. The homogenized cells are centrifuged at 8900 rpm (~12,000×g) for 20 min in a JA-14 rotor at 4° C. The supernatant is collected, and perchloric acid is added on ice to 3.5% (v/v) to precipitate contaminating proteins. The precipitate is removed by centrifugation at 8900 rpm (~12,000×g) for 20 min in a JA-14 rotor at 4° C. The supernatant is dialyzed against 50 mM Ammonia Acetate buffer pH 4.5 overnight in 3500 MWCO Spectra/Por3 dialysis membrane. The dialyzed sample is loaded onto a HiTrap SP HP column that is pre-equilibrated with 50 mM Ammonia Acetate buffer pH 4.5. MCGG-ubiquitin is eluted from the column with a salt gradient from 0-0.5 M sodium chloride monitoring at 280 nm (typical elution: between 0.14-0.22 M salt). Fractions containing the desired protein are pooled together and dialyzed against Hepes Buffered Saline pH 7.5 overnight in 3500 MWCO Spectra/Por3 dialysis membrane. The dialyzed fractions are stored at −80° C. until required for labeling.

The MCGG-Ubiquitin is defrosted and the concentration is determined by absorbance at 280 nm based upon the molar extinction coefficient of ubiquitin of 1280 M−1 cm−1 (molecular weight of MCGG-Ubiquitin: 8912 Da). Ten equivalents of tri-(2-carboxyethyl)phosphine hydrochloride (TCEP) is added to the MCGG-ubiquitin to reduce any disulfides, followed by five equivalents of either fluorescein-5-maleimide, the LanthaScreen™ thiol reactive Terbium chelate, or N-(biotinyl)-N'-(iodoacetyl)ehtylenediamine to produce fluorescein-ubiquitin, terbium-ubiquitin, and biotin-ubiquitin, respectively. The labeled ubiquitins are dialyzed against Hepes Buffered Saline overnight in 3500 MWCO Spectra/Por3 dialysis membrane to remove unreacted dye. The labeled proteins are purified on a HiLoad 26/60 Superdex 75 prepgrade column. The labeled proteins typically elute between 0.6-0.7 column volumes. Fractions containing the desired labeled protein are pooled together and concentrated with an Amicon Ultrafiltration cell with a Millipore 3000 NMWL membrane to a concentration between 0.5-1 mg/mL based upon absorption at 492 nm for fluorescein-ubiquitin (molar extinction coefficient at 492 nm: 83,000 M−1 cm−1), 343 nm for terbium-ubiquitin (molar extinction coefficient at 343 nm: 12,570 M−1 cm−1), and 280 nm for biotin-ubiquitin (molar extinction coefficient at 280 nm: 1280 M−1 cm−1). Molecular weight of fluorescein-ubiquitin: 9341 Da; Terbium-ubiquitin: 9912 Da; and biotin-ubiquitin: 9238 Da. The proteins are stored at −20° C.

Example 18

Intrachain TR-FRET Ubiquitination Reaction

The following solutions are combined in a black Corning 384 well low volume plate (Part #3676) for the Intrachain TR-FRET ubiquitination reaction:

| Solution | Stock Concentration | Volume (mL) | Final Concentration in reaction |
|---|---|---|---|
| Tris-HCl pH 8.0 | 1 M | 1 | 0.1 M |
| DTT | 10 mM | 1 | 1 mM |
| ATP Regeneration Solution * | 10X | 1 | 1 X |
| Fluorescein-Ubiquitin | 2.5 μM | 1.5 | 375 nM |
| Terbium-Ubiquitin | 500 nM | 0.5 | 25 nM |
| E1 | 450 nM | 0.5 | 22.5 nM |
| E2-25k (UbcH1) | 5.2 μM | 2 | 1 μM |
| diH₂0 | — | 2.5 | — |
| Total Volume | | 10 | |

The ATP Regeneration Solution is adapted from Yao, T.; Cohen, R. E. J. Biol. Chem. 2000, 275, 36862-36868.

The plate is sealed with foil to prevent evaporation and placed at 37° C. for 6-8 hours. Following the incubation, 10 μL of TR-FRET Dilution Buffer (20 mM Tris, pH 7.5 and 0.01% NP-40) is added to each well and the plate is read on either a Tecan Ultra or a BMG PheraStar with the recommended filter sets for LanthaScreen™. A graphical representation of the Intrachain TR-FRET Ubiquitination Assay is displayed in FIG. 22.

Example 19

Deconjugating Assay Using Different Ubiquitin-Like proteins (Ubl)

Ubl Fusion Proteins

BL21 Star™ (DE3) pLysS cells (Invitrogen, Cat#C6020-03) are transformed with the expression plasmids for the SUMO1/2/3 or Nedd8 substrates and plated on LB agar with ampicillin and chloramphenicol. Single colonies are selected and grown overnight in 50 mL of LB (Luria Broth) medium with ampicillin (100 mg/L) and chloramphenicol (34 mg/L) at 37° C. and 225 rpm. 500 mL of LB medium is inoculated with 5 mL of each overnight culture and grown at 37° C. at 225 rpm until the OD600 reached approximately 0.6. The cultures are then shifted to 25° C. and grown for an addition hour followed by induction with 1 mM IPTG. The cells are harvested after 4 hours of additional growth by centrifugation and stored at −80° C. Cell pellets from 500 mL of culture are suspended in 200 mL of Lysis Buffer (25 mM Tris pH 7.5, 100 mM NaCl). The cells are disrupted by passing the suspension twice through a chilled high pressure homogenizer (Avestin EmulsifFlex C-50) at 10-15,000 pounds per square inch (PSI) and collected on ice. The lysates are then clarified by centrifugation at 28,000×g for 20 minutes at 4° C. The supernatants are batch bound to 2 mL of NiNTA agarose (Invitrogen) for 1 hour at 4° C. The resin is collected by centrifugation at 153×g for 5 min. The supernatants are discarded and the resin is suspended in approximately 5 mL of Lysis Buffer and transferred to a disposable column. The columns are allowed to drain, and are then washed with 20 mL of Lysis Buffer, followed by 10 mL of Lysis Buffer with 30 mM imidazole by gravity. The column is then eluted with 4 mL of 25 mM Tris, 50 mM NaCl, and 300 mM Imidazole pH 7.5 and a single fraction is collected, e.g., which is bright green. Dithiothreitol (DTT) is added to the eluted protein to a final concentration of 10 mM.

Approximately 0.5-1 mg of protein is then desalted into HBS (137 mM NaCl, 2.7 mM KCl, and 10 mM Hepes pH 7.5) using a NAP-5 column (GE Healthcare 17-0853-01) and collected in a single 1 mL fraction per sample of protein. Thiol reactive terbium chelate (Invitrogen PV3580) is then dissolved in water to 1 mg/mL and added in 2-fold molar excess to the desalted protein. The labeling reactions are allowed to proceed at room temperature for 3 hours, and the products are desalted over a NAP-5 column or dialyzed overnight into HBS.

Primary Sequence Information

```
Topaz-SUMO1-AC:
                                            (SEQ ID NO: 17)
MRGSHHHHHHGMASMTGGQQMGRDLYDDDDKDRWGSEFATMVSKGEELFT

GVVPILVELDGDVNGHKFSVSGEGEGDATYGKLTLKFICTTGKLPVPWPT

LVTTFGYGVQCFARYPDHMRQHDFFKSAMPEGYVQERTIFFKDDGNYKTR

AEVKFEGDTLVNRIELKGIDFKEDGNILGHKLEYNYNSHNVYIMADKQKN

GIKVNFMRHNIEDGSVQLADHYQQNTPIGDGPVLLPDNHYLSYQSALSKD

PNEKRDHMVLLEFVTAAGITLGMDELYKLETDQTSLYKKAGTMSDQEAKP

STEDLGDKKEGEYIKIKVIGQDSSEIHFKVKMTTHLKKLKESYCQRQGVP

MNSLRFLFEGQRIADNHTPKELGMEEEDVIEVYQEQTGGAC

Topaz-SUMO2-AC:
                                            (SEQ ID NO: 18)
MRGSHHHHHHGMASMTGGQQMGRDLYDDDDKDRWGSEFATMVSKGEELFT

GVVPILVELDGDVNGHKFSVSGEGEGDATYGKLTLKFICTTGKLPVPWPT

LVTTFGYGVQCFARYPDHMRQHDFFKSAMPEGYVQERTIFFKDDGNYKTR

AEVKFEGDTLVNRIELKGIDFKEDGNILGHKLEYNYNSITNVYIMADKQK

NGIKVNFKIRHNIEDGSVQLADHYQQNTPIGDGPVLLPDNHYLSYQSALS

KDPNEKRDHMVLLEFVTAAGITLGMDELYKLETDQTSLYKKAGTMADEKP

KEGVKTENNDHINLKVAGQDGSVVQFKIKRHTPLSKLMKAYCERQGLSMR

QIRFRFDGQPINETDTPAQLEMEDEDTIDVFQQQTGGAC

Topaz-SUMO3-AC:
                                            (SEQ ID NO: 19)
MRGSHHHHHHGMASMTGGQQMGRDLYDDDDKDRWGSEFATMVSKGEELFT

GVVPILVELDGDVNGHKFSVSGEGEGDATYGKLTLKFICTTGKLPVPWPT

LVTTFGYGVQCFARYPDHMRQHDFFKSAMPEGYVQERTIFFKDDGNYKTR

AEVKFEGDTLVNRIELKGIDFKEDGNILGHKLEYNYNSHNVYIMADKQKN

GIKVNFHIRHNIEDGSVQLADHYQQNTPIGDGPVLLPDNHYLSYQSALSK

DPNEKRDHMVLLEFVTAAGITLGMDELYKIETDQTSLYKKAGTMSEEKPK

EGVKTENDHINLKVAGQDGSVVQFKIKRHTPLSKLMKAYCERQGLSMRQI

RFRFDGQPINETDTPAQLEMEDEDTIDVFQQQTGGAC

Topaz-Nedd8-AC:
                                            (SEQ ID NO: 20)
MRGSHHHHHHGMASMTGGQQMGRDLYDDDDKDRWGSEFATMVSKGEELFT

GVVPILVELDGDVNGHKFSVSGEGEGDATYGKLTLKFICTTGKLPVPWPT

LVTTFGYGVQCFARYPDHMRQHDFFKSAMPEGYVQERTIFFKDDGNYKTR

AEVKFEGDTLVNRIELKGIDFKEDGNILGHKLEYNYNSHNVYIMADKQKN

GIKVNFIRHNIEDGSVQLADHYQQNTPIGDGPVLLPDNHYLSYQSALSKD

PNEKRDHMVLLEFVTAAGITLGMDELYKIETDQTSLYKKAGTMLIKVKTL

TGKEIEIDIEPTDKVERIKERVEEKEGIPPQQQRLIYSGKQMNDEKTAAD

YKILGGSVLHLVLALRGGAC
```

Deconjugating Assays for the Ubiquitin-Like Proteins (Ubl)

Figure 39:
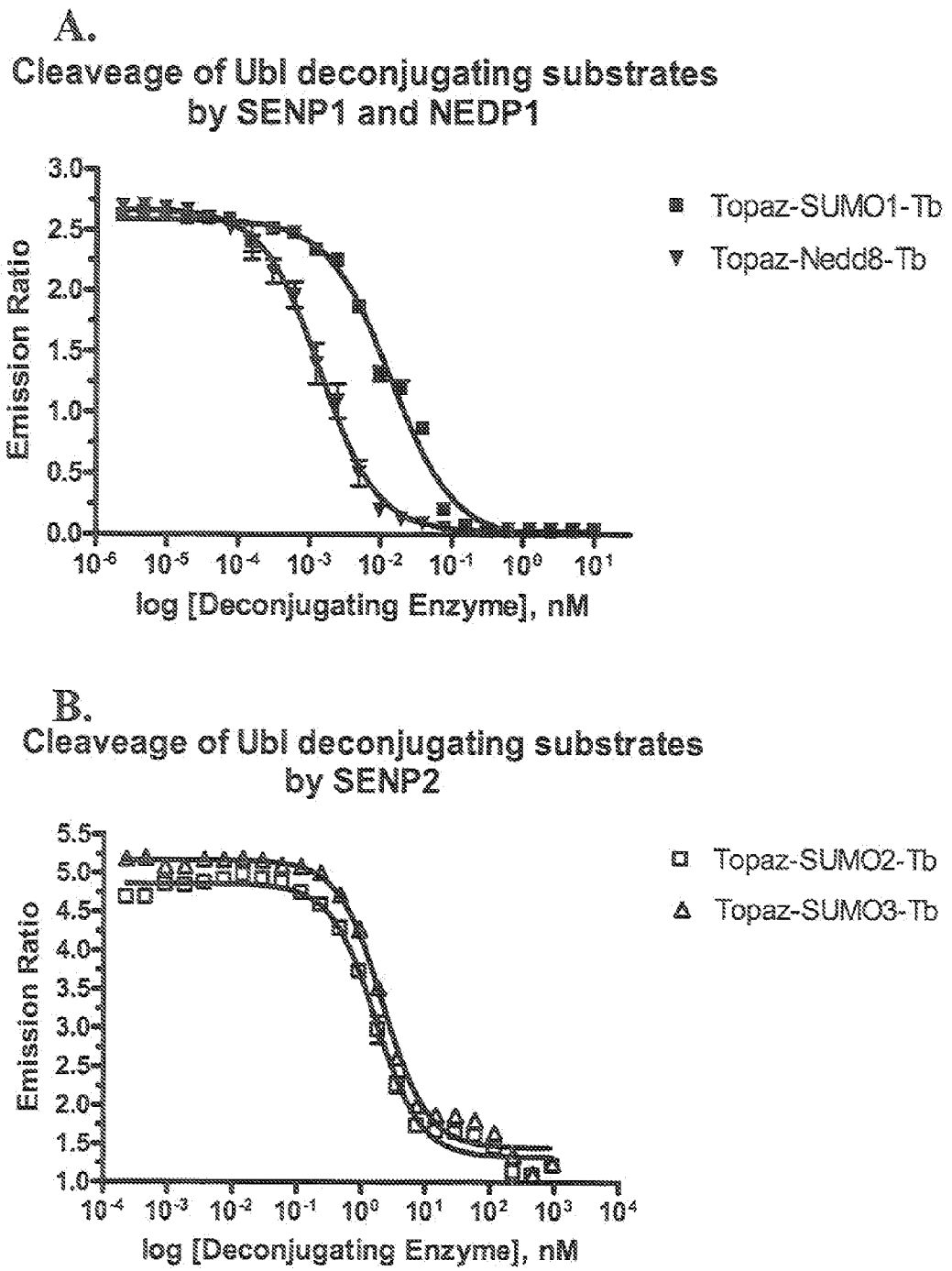
FIG. 39A shows cleavage of a SUMO1 deconjugating substrate (Topaz-SUMO1-Tb) and a Nedd8 deconjugating substrate (Topaz-Nedd8-Tb) by SENP1 and NEDP1, respectively.
FIG. 39B shows cleavage of a SUMO2 (Topaz-SUMO2-Tb) and a SUMO3 (Topaz-SUMO3-Tb) deconjugating substrate by SENP2.

A reaction buffer of TR-FRET Dilution Buffer with 2 mM DTT was used in these assays. A titration of SENP1, SENP2, or NEDP1 enzymes (Boston Biochem E-700, E-710, or E-800) was performed across the plate with a final volume of 10 μL in each well. To the respective enzyme, 10 μL of a 25 nM solution of the SUMO1, SUMO2, SUMO3, or Nedd8 deconjugating substrate was added. Fluorescence measurements were captured after a one hour incubation at room temperature on a BMG Labtech Pherastar plate reader. Intensities were measured at 520 nm (20 nm bandwidth) and 495 nm (10 nm bandwidth), with excitation at 340 nm (30 nm bandwidth). FIG. 39A shows cleavage of the SUMO1 deconjugating substrate (Topaz-SUMO1-Tb) and the Nedd8 deconjugating substrate (Topaz-Nedd8-Tb) by SENP1 and NEDP1, respectively. FIG. 39B shows cleavage of the SUMO2 (Topaz-SUMO2-Tb) and SUMO3 (Topaz-SUMO3-Tb) deconjugating substrate by SENP2

Example 20

Modulation Assay for JNK1 and JNK2

The inhibitor SP600125 (also called JNK inhibitor 1) is a potent and selective, ATP-competitive JNK inhibitor.

Jnk1 or Jnk2 (300 ng/mL and 650 ng/mL, respectively) are assayed against 200 nM GFP-ATF2 in the presence of 2 uM ATP and a 3 fold-dilution series of SP600125 (Calbiochem) ranging from 10 uM to 56.5 pM for 1 hour in a 10 uL reaction using kinase assay buffer (50 mM HEPES pH 7.5, 0.01% BRIJ-35, 10 mM MgCl2, and 1 mM EGTA; Invitrogen). Following the reaction, EDTA and Tb-labeled anti ATF2 (pT71) are added in TR-FRET dilution buffer (20 mM Tris, pH 7.5 and 0.01% NP-40; Invitrogen) to a final concentration of 10 mM and 2 nM, respectively in a final volume of 20 uL. After 1 hour the plate is read as described previously. Each reaction is performed in triplicate and the data tabulated.

In an assay ran with these conditions the EC50 values for SP600125 were 160 nM for JNK1 and 120 nM for JNK2. Also see Table 1.

TABLE 1

| [SP600125] | TR-FRET Values for | | | |
|---|---|---|---|---|
| (nM) | JNK1 | (SD) | JNK2 | (SD) |
| 10000 | 0.578457 | 0.016633 | 0.537319 | 0.020552 |
| 3333.333 | 0.563713 | 0.029295 | 0.503451 | 0.011045 |
| 1111.111 | 0.593834 | 0.022212 | 0.53796 | 0.025938 |
| 370.3704 | 0.749088 | 0.036247 | 0.650066 | 0.02006 |
| 123.4568 | 0.882975 | 0.03771 | 0.754911 | 0.00713 |
| 41.15226 | 1.069977 | 0.126997 | 0.899433 | 0.05813 |
| 13.71742 | 1.080586 | 0.018744 | 0.971719 | 0.050825 |
| 4.572474 | 1.131812 | 0.025132 | 1.035266 | 0.01501 |
| 1.524158 | 1.09941 | 0.020823 | 1.008316 | 0.025819 |
| 0.5080526 | 1.180712 | 0.066149 | 1.027086 | 0.034209 |
| 0.1693509 | 1.198769 | 0.021396 | 1.019811 | 0.022467 |
| 0.05645029 | 1.188235 | 0.073231 | 1.016772 | 0.050778 |

Example 21

Assay Miniaturization/Volumes and Interference Resistance

In triplicate 10 μL assay reactions, a dilution series of JNK1 kinase is assayed against 400 nM GFP-cJun (1-179) in the presence of 100 μM ATP. After 1 hour, a 10 μL solution of terbium-labeled anti phospho-cJun (pSer 73) and EDTA is added to each well, for a final concentration of 2 nM antibody and 10 mM EDTA. After a 1 hour incubation the plate is read and TR-FRET values calculated. For assay robustness (Z') and interfering compound experiments, a dilution series of JNK1 is first assayed in order to determine the concentration of kinase required to effect an 80% change in the TR-FRET value between non-phosphorylated and fully-phosphorylated product. This concentration of kinase is used for Z' and interfering compound experiments, and control wells containing 5-times this concentration of kinase are measured to verify that the experiments is performed near the EC80 for kinase. For Z' experiments, 48 positive control wells and 48 negative control (no ATP) wells are measured and Z' calculated. To approximate Z' values at lower assay volumes, 4 μL aliquots are removed from the control wells and placed into empty wells, and read following re-adjustment of the instrument's Z axis focal height. Interfering compound experiments are performed by measuring 6 positive and 6 negative control wells in the presence of interferant that is added subsequent to the kinase assay. NADPH, tartrazine, and allura red are added to a final concentration of 5 uM, coumarin and fluorescein to a final concentration of 100 nM, and non-dairy creamer to a final concentration of 0.5 mg/mL.

The Z' values were determined for an assay of JNK1 activity using GFP-cJun (1-179) as the substrate, using an EC80 concentration of JNK1. In a 20 μL final assay volume, a Z' of 0.93 was determined, using 48 positive and negative control wells in a low-volume 384-well plate. To simulate conditions for an assay (in the absence of liquid handling capacity to carry out such an assay), 4 μL of each control well was transferred to an empty well, and the Z' determined to be 0.88. Based upon these results, the assay can be readily miniaturized below at least 10 μL reaction final assay volume, given proper liquid handling abilities.

In addition to the Z' value, it is desirable to have fluorescence-based HTS assays that are resistant to optical interference from the high concentrations of library compounds that are present in HTS screens. Three common sources of interference are "color quenchers" (compounds that cause inner-filter effects by absorbing either excitation or emission light), autofluorescent compounds, and light scatter from precipitated compounds. To demonstrate the resistance of terbium-based TR-FRET assays to these common interferences, positive- and negative-control wells were spiked with interfering compounds prior to being read. Color quenchers (NADPH, tartrazine, and allura red) were present at a concentration of 5 μM, to mimic a concentration of 10 μM in a kinase assay. Tartrazine and allura red are the major chromophores in the food dies FD&C Yellow #5 and FD&C Red #40, respectively. NADPH absorbs strongly in the UV region in which the terbium chelate is excited ($\lambda$max=340 nm), tartrazine absorbs strongly in the region between terbium excitation and emission ($\lambda$max=425 nm), and allura red absorbs strongly in the region of fluorescein emission ($\lambda$max=524 nm). Highly fluorescent compounds coumarin and fluorescein were present at 100 nM, representing an assay concentration of 200 nM. This concentration of fluorescein represents 10-times the highest fluorescence intensity of any compound in the LOPAC 1280 library (Sigma) at 10 μM when read with a fluorescein filter set. Finally, non-dairy coffee creamer was used at 0.5 mg/mL as a light-scattering agent. At this concentration, the solution is visibly turbid. In all these cases, negligible effect was seen on the ratiometric assay readout. In the raw donor and acceptor intensity data (not shown), only the wells containing allura red showed a noticeable (~30% decrease) effect of interfering compound; however, the magnitude of this affect was similar in both data channels, and were corrected by "ratioing" the data. Interference from fluorescent or light-scattering compounds was avoided by the time-resolved nature of the readout: any interference had decayed to background levels long before the measurements were made.

Example 22

Assay of Kinase from Cell Lysate

RAW 264.7 cells (mouse macrophage cell line) were serum starved overnight and stimulated (or not) with 10 ug/ml of Anisomycin for 15 minutes prior to lysates being prepared. Lysates were prepared following a standard protocol, e.g., as described in the Kinase Activity Assay Kit protocol, Rev. A1 Dec. 9, 2005, Catalog#KNZ0031, BioSource (California). The protocol is outlined below.

Procedure for Extraction of Proteins From Cells

When using the Omnia™ Lysate Assay to determine MAP-KAP-K2 activity in cell lysates, the following procedure for sample preparation may be used. This protocol has been successfully applied to several cell lines of human and mouse origin.

1. Thaw Omnia Cell Extraction Buffer (BioSource, California) on ice.
2. Set up and stimulate cells as desired.
3. Collect cells in cold PBS by centrifugation (for non-adherent cells) or scraping from culture plates (for adherent cells).
4. Centrifuge the cells at 1,500 rpm for 5 minutes at 4° C.
5. Aspirate the PBS.
6. Resuspend the cell pellet in Omnia Cell Extraction Buffer and transfer the lysate to a 1.5 mL microcentrifuge tube. The volume of Omnia Cell Extraction Buffer depends on the cell number and expression level of MAPKAP-K2. The optimal protein concentration of lysate should be in the range of 5 to 10 mg/mL. Add an appropriate amount of protease and phosphatase inhibitor (typically provided as a 100× stock solution) before using. Under these conditions, using 0.005 mL (25-50 μg) of the clarified cell extract will be sufficient for measurement of MAPKAP-K2 activity.
7. Lyse the cells at 4° C. for 30 minutes on a rotator. Whole cell extract can then be briefly sonicated or put through a syringe and needle if desired.
8. Centrifuge at 13,000 rpm for 20-30 minutes at 4° C.
9. Transfer the clarified cell extracts to clean microcentrifuge tubes.
10. The clarified cell extract should be stored at −80° C. until ready for analysis. Avoid repeated freeze-thaw cycles. In preparation for performing the assay, allow the samples to thaw on ice. Mix well prior to analysis.

Lysate was serially diluted in buffer and 5 uL aliquots were assayed against 400 nM GFP-cJun in assay buffer containing 100 uM ATP. Assays were stopped by addition of EDTA and antibody, with a final anti-phospho cJun antibody concentration of 2 nM. The plate was read after 1 hour incubation and the data collected. See Table 2. Samples were performed in duplicates.

Western blot analysis of the lysate also showed phosphorylation of JNK upon stimulation (data not shown).

TABLE 2

| % Cell Lysate in 5 uL Addition | +Anisomycin | | −Anisomycin | |
|---|---|---|---|---|
| 100 | 0.979635 | 0.976799 | 0.377859 | 0.380806 |
| 50 | 0.9027 | 0.922563 | 0.260973 | 0.265696 |
| 25 | 0.847415 | 0.85707 | 0.201307 | 0.190043 |
| 12.5 | 0.748306 | 0.838366 | 0.158479 | 0.162943 |
| 6.25 | 0.591718 | 0.787767 | 0.154326 | 0.140817 |
| 3.125 | 0.570311 | 0.706959 | 0.139773 | 0.131134 |
| 1.5625 | 0.455359 | 0.568673 | 0.11984 | 0.125585 |
| 0.78125 | 0.372224 | 0.473877 | 0.132307 | 0.127491 |
| 0.390625 | 0.28128 | 0.342142 | 0.121477 | 0.12066 |
| 0.1953125 | 0.247363 | 0.314539 | 0.12562 | 0.123227 |
| 0.09765625 | 0.216065 | 0.228614 | 0.122899 | 0.130475 |
| 0.04882813 | 0.157244 | 0.189433 | 0.125412 | 0.136159 |
| 0.02441406 | 0.147868 | 0.153411 | 0.128357 | 0.130535 |
| 0.01220703 | 0.141944 | 0.142445 | 0.129685 | 0.133322 |
| 0.006103516 | 0.139507 | 0.133902 | 0.128934 | 0.134491 |
| 0.003051758 | 0.13083 | 0.131193 | 0.124874 | 0.131069 |

Example 23

Cellular (Living Cell) Ibiquitination Assay

As an example of one embodiment of the invention, this example utilizes two technologies, a LanthaScreen TR-FRET reagent (terbium-labeled, ubiquitin specific monoclonal antibody) that provides a donor label and a recombinant Green Fluorescent Protein (acceptor label) fused to a ubiquitination target (e.g., IκBα) expressed in a living cell.

Figure 32A:
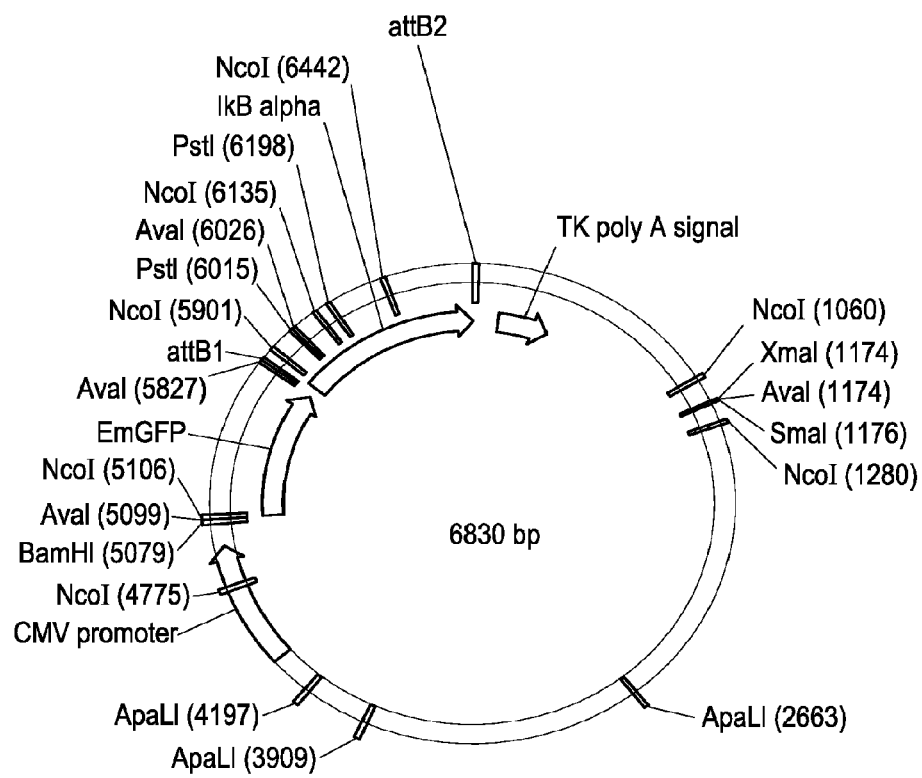
FIG. 32A depicts a map of pcDNA6.2-N-EmGFP-DEST.

A pcDNA-EmGFP-IkBa expression clone (CMV promoter, TK poly A) was generated by gateway cloning technology (Invitrogen). LR recombination reaction was performed using pcDNA6.2-N-EmGFP-DEST (FIG. 32A) and Ultimate ORF clone IOH4138 substrates. The coding sequence for EmGFP-IkBa is shown in FIG. 32B. This DNA construct was transfected into GripTite 293 cells using Lipofectamine 2000 transfection reagent (Invitrogen). Once the cells established stable resistance to blasticidin (and stable expression of GFP), cells were sorted by FACS and clones were isolated for further assay development.

This example describes a GFP-IκBαfusion protein expressing HEK293 cell line (isolated clonally by FACS). This cell line is responsive to the inflammatory effects of TNFα stimulation thru the NFκB pathway. It is believed that IκBα becomes ubiquitinated (e.g., poly-ubiquitinated) in response to TNFα treatment, thus freeing NFκB to translocate to the nucleus and stimulate transcription of target genes.

Monoclonal antibodies that specifically bind to ubiquitin or poly-ubiquitin chains were labeled with ITC-terbium chelate (roughly 7-10 labels/Ab). Amine-reactive ITC-Tb chelate (Invitrogen) was conjugated to monoclonal antibodies using the manufacture's protocol. Briefly, 500 ug of antibody (dialyzed into Hepes-buffered saline, pH 7.5) was reacted with 1:10 volume of 50ug ITC-Tb-chelate (resuspended in 1M Na-Bicarbonate buffer, pH 9.5). The conjugation was allowed to proceed overnight at room temperature and dialyzed into Hepes buffered saline on the following day. Tb labeling efficiency was determined using Absorbance methods.

Figure 30:
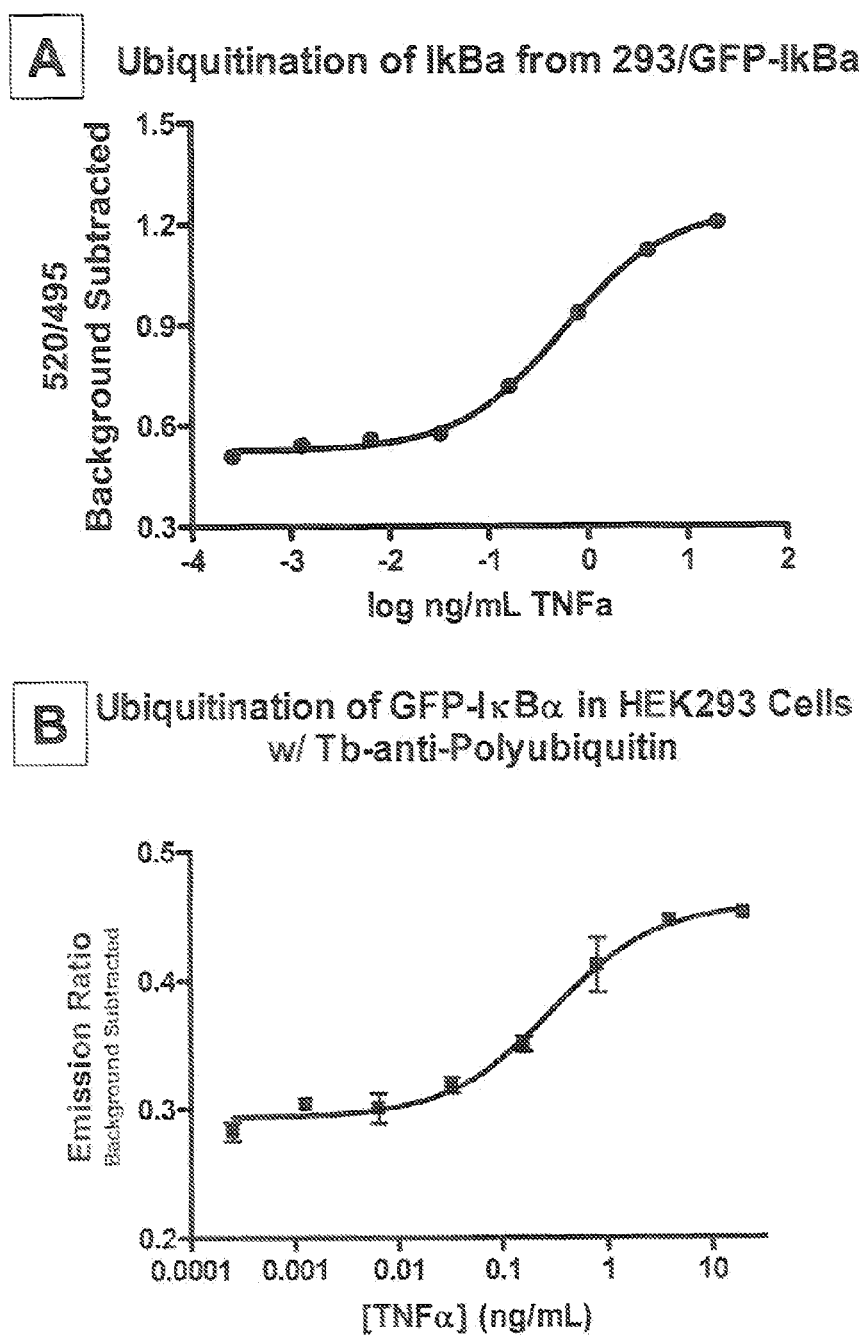
FIG. 30 shows data from a cellular ubiquitination assay as described herein, e.g., see Example 23 below. Panels A shows data using an anti-ubiquitin labeled antibody. Panel B shows data using an anti-polyubiquitin labeled antibody.

On the first day, $8\times10^4$ HEK293/GFP-IκBα cells were added per well in a 96 well, clear bottom plate (Costar). The cells were plated in DMEM+10% dFBS+pen/strep+25 mM HBS+Non-essential amino acids in a volume of 100uL/well. On day two, the cells were treated 1h with 10uL of dose-response of TNFα (Biosource, Catalog# PHC3015) starting with 20ng/mL TNF (final concentration), serial dilutions (1:5) were added to the cells, including a "zero" TNF control as a final data point. Serial dilutions of TNF were carried out in full growth media. Then the media was removed. The cells were lysed 30 minutes on ice with 50 uL of phospho-elisa lysis buffer (based on 20mM tris/1% NP40 with protease inhibitors added) and briefly agitated on tabletop plate mixer (Phospho-ELISA lysis buffer composition (1×): 20mM Tris-HCl pH7.4, 1% NP40, 5mM EDTA, 5mM NaPP, 150mM NaCl, 2mM VO4, 1:200 dilution of protease inhibitor cocktail (Sigma, P8340)). 20uL of cell lysates was transferred to a 384 well plate and 5ul of a 50nM antibody-Tb solution was added (final antibody concentration is roughly 1nM). The following monoclonal antibodies purchased from BioMol (Plymouth Meeting, Pa.) were used in these experiments: FK-1 (recognizing poly-ubiquitin chains, Catalog#PW8805) and FK-2 (recognizing ubiquitin, Catalog#PW8810). Complexes were allowed to form and equilibrate for 30 minutes at room temp and TR-FRET was determined using a Tecan ultra fluorescence plate reader (excitation at 340/emission 495 and 520, 100us lag time, 200us integration time). Emission values at 520 were divided by those at 340 to normalize against well-to-well variations in antibody concentrations. Ab fluorescence values at 520 were also subtracted from the 520 values of samples in order to obtain a "background subtracted" value for each sample. Examples of dose-response curve for TNFα stimulation of ubiquitination of GFP-IκBα are shown in FIGS. 30. FIG. 30A utilized a Tb-anti-ubiquitin antibody (FK-2). FIG. 30B shows data utilizing a Tb-anti-polyubiquitin antibody (FK-1).

In summary, GFP-IκBα/HEK293 cells were treated with TNFα in a dose-responsive manner and lysed using a tris/1% NP-40-based lysis buffer. Tb-antibodies were then tested for their ability to bind to the GFP-IκBα-Ub complexes, using a TR-FRET readout (excitation at 340/emission 495 and 520, 100us lag time, 200us integration time). This assay allows the user to assay an inflammation pathway (specifically), however the approach may be useful as a platform for a variety of targets from other disease pathways (e.g., ubiquitination of p53, caspases, etc.).

Example 24

Protein Ubiquitination on ProtoArray® Protein Microarrays

The following example demonstrates that protein ubiquitination assays, including those related to ubiquitination-like proteins (e.g., SUMOylation, NEDDylation and ISGylation) can be performed using protein arrays.

Materials and Methods

Protein Arrays

P53 (Biomol) and c-Jun (Biomol) were diluted in printing buffer and arrayed on to nitrocellulose coated slides (PATH, Gentel) using an arrayer (OmniGrid, Genomic Solutions) and stored at −20° C.

Ubiquitination Assay on ProtoArray® Protein Microarrays

Protein arrays were blocked in buffer (50 mM Tris pH 7.5, 5 mM MgSO4, 0.1% Tween 20) at 4° C. for 1 hour. Ubiquitination conjugation mix was prepared using a ubiquitin conjugation kit from Biomol. Briefly, for a 120 ul reaction, the following mix was prepared: (10 uls energy, 40 ul Fraction A, 40 uls of Fraction B with either 30 ul of biotin-ubiquitin (Invitrogen) or fluorescein-ubiquitin (Invitrogen). The ubiquitin conjugation reaction was added to the protein array under a HYBRISLIP™ hybridization cover and incubated at 25° C. for 90 minutes. Subsequently, the slides were washed three times with buffer (50 mM Tris pH 7.5, 5 mM MgSO4, 0.1% Tween 20). For the slides treated with fluorescein-ubiquitin, the slides were dried and scanned. For the biotin-ubiquitin treated slides, the arrays were incubated with streptavidin-AF647 (0.75 ug/ml) for 45 minutes at 4° C. The slides were then washed three times with buffer (50 mM Tris pH 7.5, 5 mM MgSO4, 0.1% Tween 20) dried and scanned. Data from the protein arrays were acquired with GENEPIX® PRO software (Molecular Devices) and the data processed in MICROSOFT® EXCEL® application.

Results

Figure 31A:
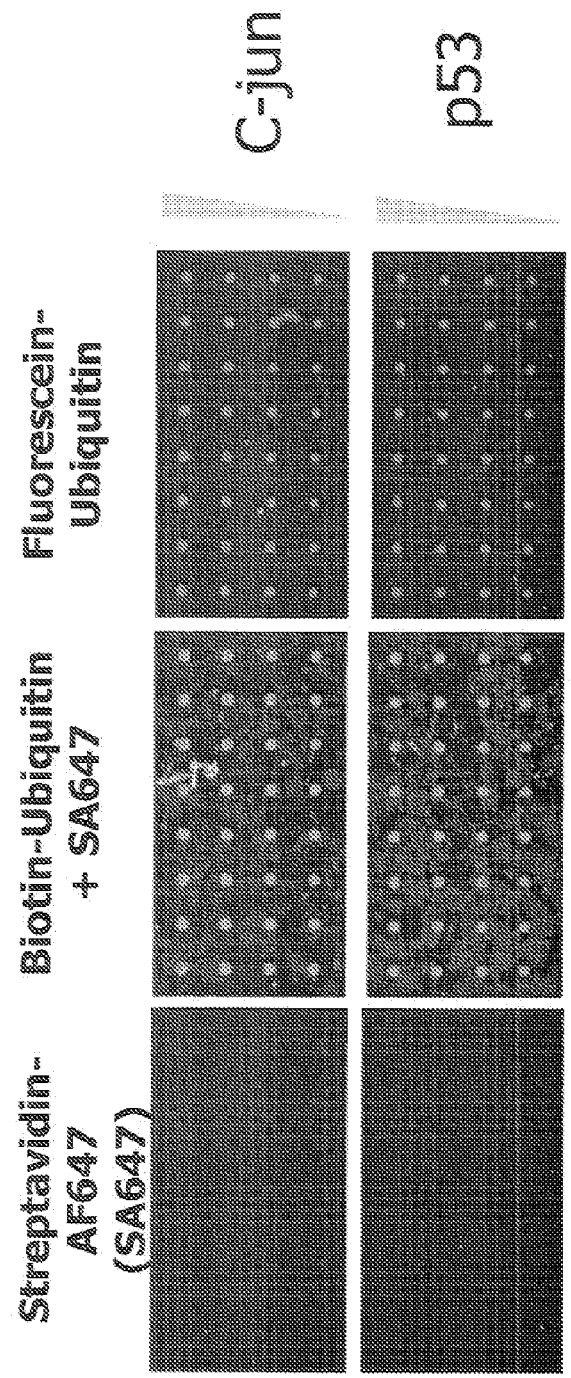
FIG. 31 depicts protein ubiquitination on protein arrays. (A) Protein arrays containing p53 and c-Jun proteins were incubated with enzymes for protein ubiquitination in the presence of fluorescein ubiquitin or biotin-ubiquitin. To detect ubiquitination for arrays treated with biotin-ubiquitin, arrays were also treated with streptavidin-AF647 (SA647). A negative control was also performed in which an array was treated with only SA647. (B) The data in A was quantified and plotted as a function of signal intensity (y-axis) versus the relative amount of protein spotted on the arrays (x-axis).
Figure 31B:
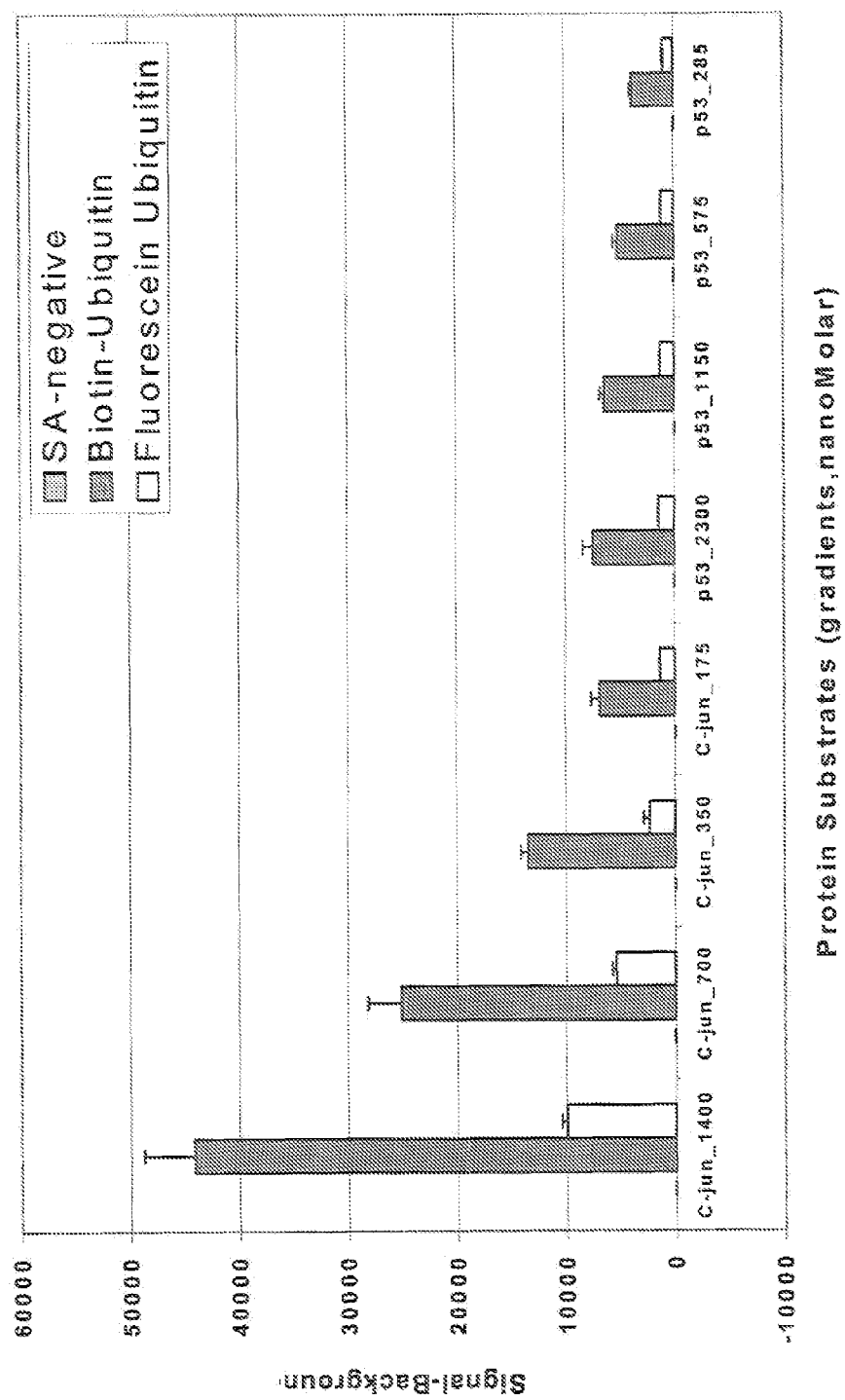

High content protein arrays (ProtoArray® Protein Microarrays, Invitrogen Corporation, Carlsbad, Calif.) present the opportunity to rapidly identify novel substrates for ubiquitin-protein ligases (E3). We performed an experiment to detect protein ubiquitination on protein arrays. To do so, protein arrays containing proteins (p53 and c-Jun), which are known to be ubiquitinated in vivo, were treated with an enzyme mixture containing the machinery for protein ubiquitination (Fuchs, S. Y. et al. *J Biol Chem* 272, 32163-8 (1997); and Auger et al. *Methods Enzymol* 399, 701-17 (2005)). We observed ubiquitination of both c-Jun and p53 immobilized on a modified glass slide. Detection of substrate ubiquitination was observed with both biotin-ubiquitin coupled to streptavidin-AlexaFluor647 (SA647) and Fluorescein-ubiquitin (FIG. 31A). The data for protein ubiquitination were quantified as a function of the amount of protein spotted on the arrays. A decrease in signals (fluorescence intensity of the spots on the microarray) is observed with a corresponding decrease in the amount of protein spotted (FIG. 31B).

This example demonstrates protein ubiquitination on protein arrays. High content protein arrays are likely to be useful tools for the identification of substrates of cell machinery that either ubiquitinate, SUMOylate or NEDDylate proteins, such as to facilitate degradation, a change in protein function or alter protein localization within a cell (Pray, T. R. et al. *Drug Resist Updat* 5: 249-58 (2002)).

Example 25

LPS Induced Phosphorylation of GFP-ATF2 in THP1 Cell Lysates

Figure 37:
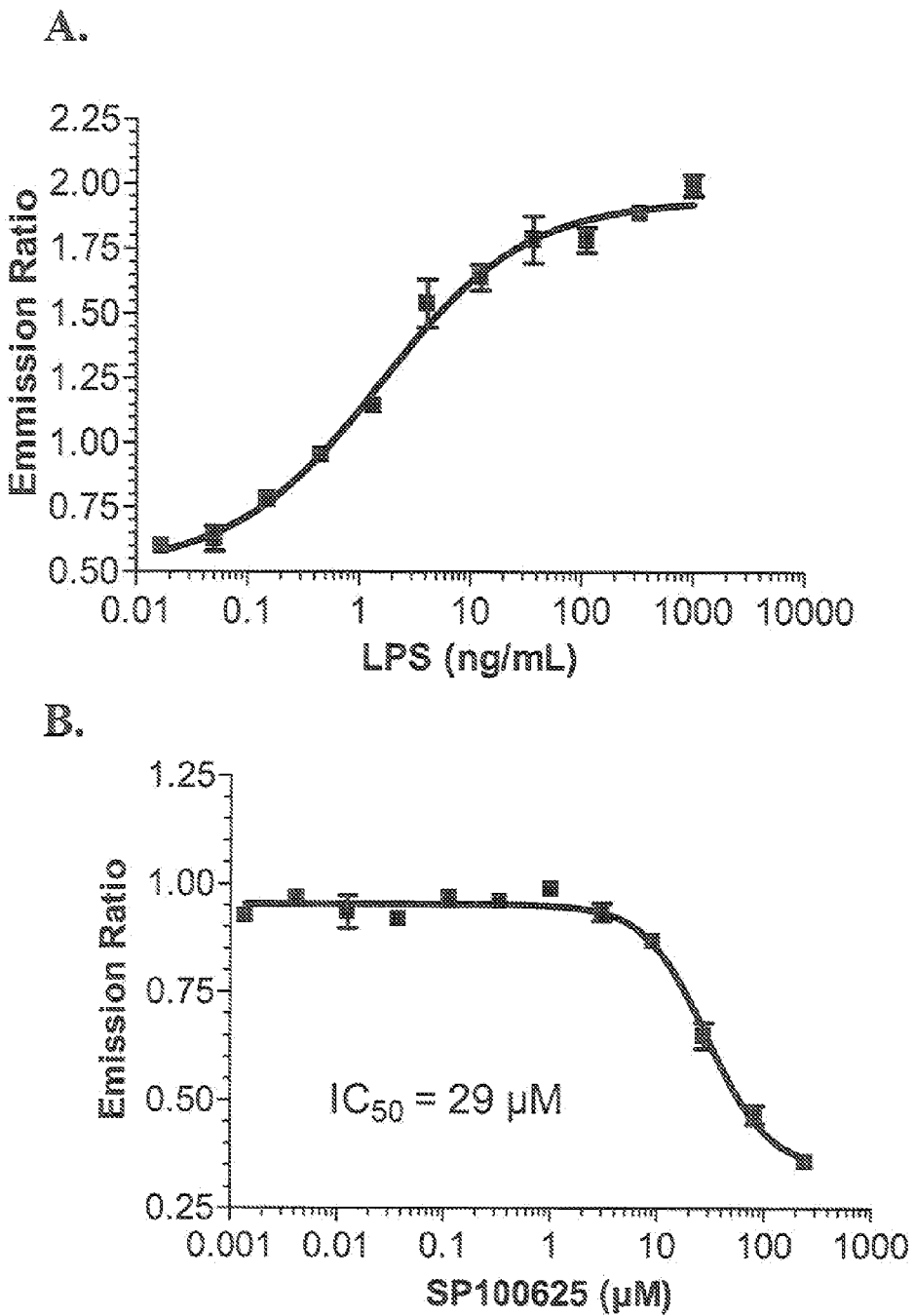
FIG. 37A shows results from an assay for LPS induced phosphorylation of GFP-ATF2 in THP1 cell lysates.
FIG. 37B shows results for inhibition of JNK activation by SP600125 measured in THP1 cell lysates.

THP1 (ATTC, Part #TIB-202) cells were stimulated by adding varying amounts of LPS (Calbiochem, part#437628) to the cells for 30 minutes. The cells were washed and lysed as in Example 22, and 5 µL, of lysate was added to 5 µL, of 400 nM GFP-ATF2 and 200 µM ATP. After 60 minutes, phosphorylated product was detected by adding Tb-anti-pATF2 (Invitrogen part #PV445) antibody and EDTA to quench the kinase reaction. Data was collected using a Tecan Ultra 384 plate reader (Tecan Group Ltd., Switzerland). Results are shown in FIG. 37A.

Example 26

Inhibition of JNK Activation by SP600125 Measured in THP1 Cell Lysates

THP1 cells were stimulated with LPS (60 ng/mL) in the presence of SP600125, a potent inhibitor of JNK activity, but a weak inhibitor of kinases that activate JNK. The assay was performed as described in Example 25. The observed IC50 values is consistent with published work suggesting that SP600125 acts at (but not up stream of) JNK activity. Results are shown in FIG. 37B.

Example 27

TNF-a Induced Phosphorylation of GFP-IkB-a in HEK293 GFP-IkB-a Cells

A mammalian expression vector for the stable expression of a HEK293-GFP-IkBa cell line was generated by subcloning the IkBα fragment into pCDNA™ 6.2/N-EmGFP Dest using Invitrogen's Gateway® technology. The resulting vector pCDNA™ 6.2-GFP-IkBa was validated by sequencing.

The expression vector was transfected into the HEC293 cell line using Lipofectamine™ LTX according to manufacturer's protocol. The transfected cells were selected with blasticidin S HCl (5 µg/ml) for 14 days and sorted for GFP expressing cells by flow cytometry. Individual clones were generated by single cell sorting and the best performing clone was selected for all subsequent experiments.

Figure 38:
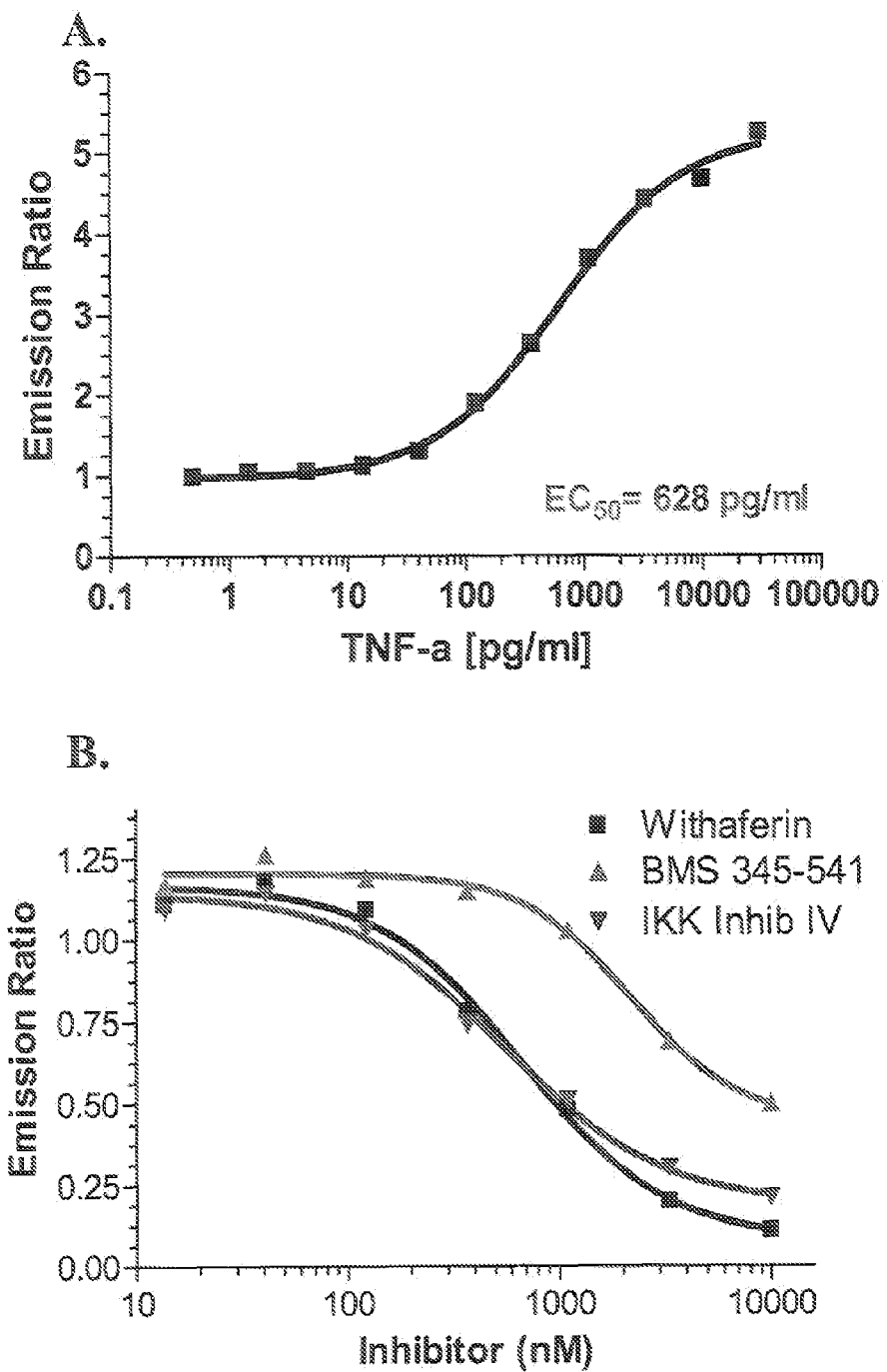
FIG. 38A shows TNF-α induced phosphorylation of GFP-Iκβ-α in HEK293 GFP-Iκβ-a cells.
FIG. 38B shows inhibition of TNF-α induced phosphorylation of GFP-IκBα.

HEK293-GFP-IkBa cells were stimulated for 30 min with varying amounts of TNF-α, after which the cells were washed and lysed (20 mM Tris, pH 7.4; 1% NP-40; 5 mM EDTA; 5 mM sodium pyrophosphate; 5 mM NaF; 150 mM NaCl; 2 mM VO4; 1:100 Phosphatase inhibitor mix 1 SIGMA P-2850; 1:100 Protease inhibitor mix SIGMA P-8340). To measure phosphorylation of GFP-IkBα, 20 µl of lysate was transferred to 384 well plate, followed by addition of a Tb-anti p532-IkBα antibody (Invitrogen, Part #PV3662). After a 20 minute incubation at RT, the samples were analyzed using a Tecan Ultra 384 plate reader. Results are shown in FIG. 38A.

Example 28

Inhibition of TNF-α Induced Phosphorylation of GFP-IκBα

This experiment was performed as described in Example 27, using a stimulation concentration of 1000 pg/mL LPS, with an additional 60 min incubation of the inhibitor preceding the stimulation with TNF-α. The inhibitors used were IKK-inhibitor IV, BMS-345541 and Withaferin. Results are shown in FIG. 38B.

Example 29

Conjugating Assay Using Different Ubiquitin-like Proteins (Ubl)

Expression/Labeling of CGG addition mutants of Ubls:

An expression plasmid (pEXP17-CGG-Ubl) was constructed to encode a Cysteine-Glycine-Glycine (CGG) insertion to the N-terminus of SUMO1/2/3 or Nedd8. The pEXP17-CGG-UBl vectors were produced by PCR amplifying the Ub-like protein with recombination sites compatible with the entry vector pDonr221 (Invitrogen, Cat#12536-017). The PCR product was recombined into pDonr221. pDonr221 was used in a Gateway® reaction with the destination vector pDEST17 (Invitrogen, cat#11803). As will be apparent to one skilled in the art, essentially any compatible vector for expressing a Cysteine-Glycine-Glycine (CGG) insertion to the N-terminus of SUMO1/2/3 or Nedd8 would be suitable for this procedure.

The expression plasmid is transferred into chemically competent BL21 STAR™ (DE3) cells using the method supplied by the vendor; followed by plating onto LB agar plates containing 0.1 mg/mL ampicillin A colony is selected to inoculate 50 mL of LB broth containing 0.1 mg/mL ampicillin that is grown overnight at 37° C. From the overnight culture, 5 mL is used to inoculate 500 mL of LB broth containing 0.1 mg/mL ampicillin and is grown at 37° C. until an optical density of >0.6 at 600 nm is reached. At this point, IPTG (isopropyl-β-D-thiogalactopyranoside) is added to a concentration of 1 mM to induce the T7 promoter on the expression plasmid and to stimulate production of the CGG Ubl addition mutant proteins. The cells are induced for 4 hrs at 25° C. The cells are harvested by centrifugation at 4200 rpm (in a JS-4.2 rotor) for 20 min at 4° C. The supernatant is discarded, and the cell paste is stored at -80° C.

The CGG-Ubl cell paste is resuspended in Hepes Buffered Saline containing 1 mM EDTA and 10 mM DTT using a handheld polytron biohomogenizer. The resuspended cells are lysed by passing through an Avestin Emulsiflex C50 homogenizer at 10,000-15,000 psi. The homogenized cells are centrifuged at 13,500 rpm (~28,000×g) for 20 min in a JA-14 rotor at 4° C. The collect supernatants are batch bound to 2 mL of Ni-NTA agarose (Invitrogen) for 1 hour at 4° C. The resin is then collected by centrifugation at 153×g for 5 min. The supernatants are discarded and the resin is suspended in approximately 5 mL of Lysis Buffer and transferred to a disposable column. The columns are allowed to drain, and then are then washed with 20 mL of Lysis Buffer, followed by 10 mL of Lysis Buffer with 30 mM imidazole by gravity. The column is then eluted with 4 mL of HBS with 300 mM imidazole pH 7.5. Dithiothreitol (DTT) is added to the eluted protein to a final concentration of 10 mM.

The protein is then loaded onto a HighTrap Q HP (SUMO1/2/3) (GE Healthcare 17-1153-01) or HighTrap SP HP (Nedd8) (GE Healthcare 17-1151-01) column. A linear gradient of 0 to 400 mM NaCl over 30 column volumes is performed by the AKTA purifier. The desired protein elutes between 150-300 mM NaCl. The fractions containing the desired protein (as determined by SDS-PAGE) are pooled and DTT is added to a final concentration of 10 mM.

To label, approximately 2 mg of protein is desalted into HBS (137 mM NaCl, 2.7 mM KCl, and 10 mM Hepes pH 7.5) using a NAP-5 column (GE Healthcare 17-0853-01) and collected in a single 1 mL fraction per sample of protein. For Terbium labeling of the proteins, thiol reactive terbium chelate (Invitrogen, PV3580) is dissolved in water and added in 2-fold molar excess to the desalted protein. For the fluorescein labeling of the proteins, thiol reactive fluorescein (Invitrogen, F-150) is dissolved in DMSO to 5 mg/mL and added in a 5 fold excess to the desalted protein. The labeling reactions are allowed to proceed at room temperature for 4 hours, and the products are desalted over a NAP-5 column or dialyzed overnight into HBS.

Primary Sequence Information

His-CGG-SUMO1:
(SEQ ID NO: 21)
MSYYHHHHHHLESTSLYKKAGTMCGGSDQEAKPSTEDLGDKKEGEYIKLK

VIGQDSSEIHFKVKMTTHLKKLKESYCQRQGVPMNSLRFLFEGQRIADNH

TPKELGMEEEDVIEVYQEQTGG

His-CGG-SUMO2:
(SEQ ID NO: 22)
MSYYHHHHHHLESTSLYKKAGTMCGGADEKPKEGVDKTENNDHINLKVAG

QGSVVQFKIKRHTPLSKLMKAYCERQGLSMRQIRFRFDGQPINETDTPAQ

LEMEDEDTIDVFQQQTGG

His-CGG-SUMO3:
(SEQ ID NO: 23)
MSYYHHHHHHLESTSLYKKAGTMCGGSEEKPKEGVKTENDHINLKVAGQD

GSVVQFKIKRHTPLSKLMKAYCERQGLSMRQIRFRFDGQPINETDTPAQL

EMEDEDTIDVFQQQTGG

His-CGG-Nedd8:
(SEQ ID NO: 24)
MSYYHHHHHHLESTSLYKKAGTMCGGLIKVKTLTGKEIEIDIEPTDKVER

IKERVEEKEGIPPQQQRLIYSGKQMNDEKTAADYKILGGSVLHLVLALRG

G

Anti-Epitope TR-FRET "SUMOylation" Assay:

The following solutions are combined in a black Corning 384 well low volume plate (Part #3676) for the Anti-epitope TR-FRET SUMOylation reaction:

| Solution | Final Concentration in reaction |
| --- | --- |
| Tris-HCl pH 7.5 | 50 mM |
| DTT | 2 mM |
| ATP | 5 mM |
| MgCl$_2$ | 10 mM |
| Fluorescein-SUMO1/2/3 | 100 nM |
| E1 | 25 ng (200 nM) |
| Ubc9 (E2) | 15 ng (37.5 nM) |
| GST-RanBP2 (E3) | 10 ng (8 nM) |
| GST-SP100 | 10 ng (12.5 nM) |
| Total Assay volume | 10 μL |

The following reagents were supplied by BioMol with the following SKU #: E1 (UW9330); Ubc9 (UW9320); GST-RanBP2 (UW9455); and GST-SP100 (UW9825).

Figure 40:
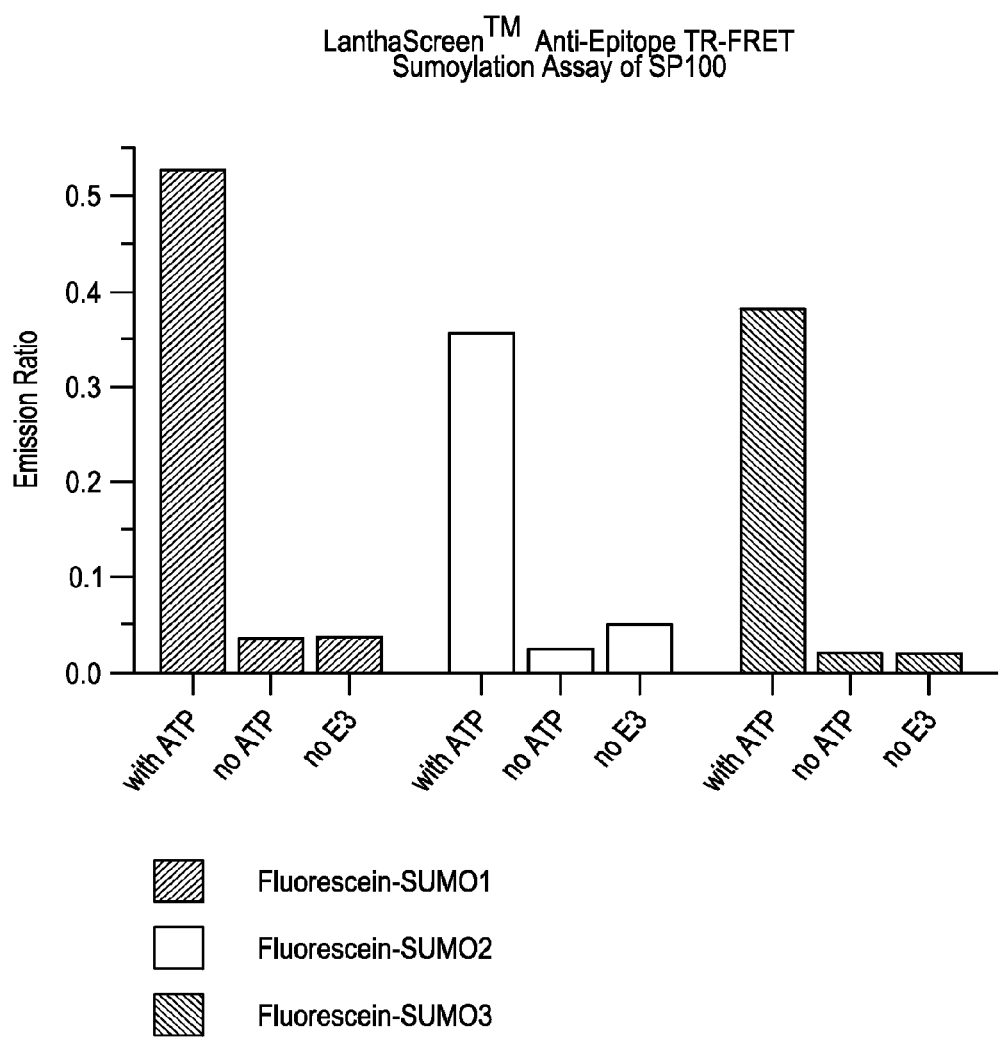
FIG. 40 shows representative data of an anti-epitope TR-FRET SUMOylation assay of GST-SP100 with a fluorescein-SUMO1/2/3 and a Tb-anti-GST antibody.

The plate is sealed with foil to prevent evaporation and placed at 37° C. for 1-3 hours. Following the incubation, 10 μL of TR-FRET Dilution Buffer (20 mM Tris, pH 7.5 and 0.01% NP-40) containing 40 nM Tb-anti-GST (Invitrogen, PV4216) is added to each well and the plate is allowed to equilibrate at room temperature for 30 minutes. The assay plate is read on either a Tecan Ultra 384 or a BMG Labtech PheraStar with the recommended filter sets for LanthaScreen™. FIG. 40 shows representative data of a Anti-epitope TR-FRET SUMOylation assay of GST-SP100 with a Fluorescein-SUMO1/2/3 and a Tb-anti-GST antibody.

Example 30

Deubiquitination Assays Using a Fusion Protein Between a GFP and a Ubiquitin

A reaction buffer of TR-FRET Dilution Buffer with 2 mM DTT was used in these assays. A titration of SENP1, SENP2, or NEDP1 enzymes (Boston Biochem E-700, E-710, or E-800) was performed across the plate with a final volume of 10 μL in each well. To the respective enzyme, 10 μL of a 25 nM solution of the SUMO1, SUMO2, SUMO3, or Nedd8 deconjugating substrate was added. Fluorescence measurements were captured after a one hour incubation at room temperature on a BMG Labtech Pherastar plate reader. Intensities were measured at 520 nm (20 nm bandwidth) and 495 nm (10 nm bandwidth), with excitation at 340 nm (30 nm bandwidth).

GFP-Ub-Tb was tested as a substrate (at 10 nM) against UCH-L3 (■), USP-2 (+), USP-15 (▲), UCH-L1 (▼), USP-5 (♦) and USP-14 (○). (UCH-L3 (BioMol; UW9745); USP-2 (BioMol; UW9850); USP-15 (BioMol; UW9845); UCH-L1 (BostonBiochem; E-340); USP-5 (BostonBiochem; E-322); USP-14 (BostonBiochem; E-342)) USP-14 is not expected to show activity in the absence of association with components of the 26S proteasome. USP-2 and USP-15 are indistinguishable. (FIG. 41A)

The tight-binding DUB inhibitor, ubiquitin aldehyde, was titrated against 0.1 nM UCH-L3 and 10 nM GFP-Ub-Tb and shown to inhibit the reaction with an IC50 of 0.2 nM. (FIG. 41B)

Excellent Z' at Low Turnover –Z' values were determined from 24 negative and 24 positive wells containing increasing amounts of DUB. A Z' of >0.5 was observed for 20% turnover of substrate to product, >0.75 was observed for 38% turnover of substrate to product and >0.8 was observed for 54% turnover of substrate to product.

Example 31

Exemplary Protocols and Literature of the Invention

This example provides exemplary literature related to compositions and methods of the invention and is meant to provide examples of non-limiting methods and compositions of the present invention. It shows an example of a User Guide for Lanthascreen™ Ubiquitin Assay Reagents. The methods and compositions described in Appendix A are exemplary methods and compositions of the present invention as described herein.

Sections 1.0 and 2.0 provide, inter alia, examples of reagents capable of use in the methods of the present invention and possible amounts (e.g., weights) of which these reagents can be packaged in.

Section 3.0 is an introduction describing, inter alia, FRET, TR-FRET and common lanthanides used in FRET, including TR-FRET.

Section 4.0 describes, inter alia, non-limiting examples of instrument settings and general principles related to the present invention.

Section 5.0 describes various non-limiting examples of assay formats related to detecting and/or measuring ubiquination. Section 5.0 includes sample assay conditions. One skilled in the art will recognize that these conditions are exemplary and the present invention includes other conditions that allow, in this case, a ubiquination reaction to occur and allows for detection of ubiquination as described herein. The conditions described for the anti-epitope ubiquination assay are provides as exemplary and/or optimal conditions. For example, a similar ubiquitination assay can be carried out wherein the antibody binds the protein (e.g., binds native protein sequences) and not necessarily an epitope tag incorporated into the protein or polypeptide.

Section 6.0 describes examples of ubiquination assays of the present invention involving GFP fusion proteins. The present invention is not limited to the use of GFP as a fluorescent protein or polypeptide. As discussed herein, the present invention includes the use of any compatible fluorescent protein or polypeptide. GFP is shown as an example of a fluorescent protein or polypeptide that is compatible with a terbium donor.

Section 7.0 demonstrates, inter alia, the robustness/data quality for exemplary methods of the present invention using ratiometric measurements.

LanthaScreen™ Ubiquitin Assay Reagents-User Guide
Table of Contents
1.0 Reagents Available
2.0 Introduction
3.0 Instrument Settings
4.0 High Throughput Screening Of Ubiquitination With Tr-Fret Reagents
5.0 Alternative Ubiquitination Assays With Gfp Fusion Proteins
6.0 Assessing Data Quality In Ratiometric Measurements
7.0 Related Products
8.0 Notice To Purchaser
1.0 Reagents Available

| REAGENTS | Size | Cat. No. |
| --- | --- | --- |
| LanthaScreen ™ Tb-Ubiquitin | 5 µg | PV4375 |
| | 25 µg | PV4376 |
| Fluorescein-Ubiquitin | 50 µg | PV4377 |
| | 500 µg | PV4378 |
| Biotin-Ubiquitin | 10 µg | PV4379 |
| | 100 µg | PV4380 |

2.0 Introduction

For screening libraries of compounds, time-resolved FRET (TR-FRET) is a recognized method for overcoming interference from compound autofluorescence or light scatter from precipitated compounds. The premise of a TR-FRET assay is the same as that of a standard FRET assay: when a suitable pair of fluorophores are brought within close proximity of one another, excitation of the first fluorophore (the donor) can result in energy transfer to the second fluorophore (the acceptor). This energy transfer is detected by an increase in the fluorescence emission of the acceptor, and a decrease in the fluorescence emission of the donor. In HTS assays, FRET is often expressed as a ratio of the intensities of the acceptor and donor fluorophores. The ratiometric nature of such a value corrects for differences in assay volumes between wells, and corrects for quenching effects due to colored compounds.

In contrast to standard FRET assays, TR-FRET assays use a long-lifetime lanthanide chelate as the donor species. Lanthanide chelates are unique in that their excited state lifetime (the average time that the molecule spends in the excited state after accepting a photon) can be on the order of a millisecond or longer. This is in sharp contrast to the lifetime of common fluorophores used in standard FRET assays, which are typically in the nanosecond range. Because interference from autofluorescent compounds or scattered light is also on the nanosecond timescale, these factors can negatively impact standard FRET assays. To overcome these interferences, TR-FRET assays are performed by measuring FRET after a suitable delay, typically 50 to 100 microseconds after excitation by a flashlamp excitation source in a microtiter plate reader. This delay not only overcomes interference from background fluorescence or light scatter, but also avoids interference from direct excitation due to the non-instantaneous nature of the flashlamp excitation source.

The most common lanthanides used in TR-FRET assays for HTS are terbium and europium. Terbium offers unique advantages over europium when used as the donor species in a TR-FRET assay. In contrast to europium based systems that employ APC as the acceptor, terbium-based TR-FRET assays can use common fluorophores such as fluorescein as the acceptor. In terbium-based TR-FRET assays, fluorescein-labeled reagents may be used rather than biotinylated molecules that must then be indirectly labeled via streptavidin-mediated recruitment of APC as is commonly performed in europium-based assays. The use of directly labeled molecules in a terbium-based TR-FRET assay reduces costs, improves kinetics, avoids problems due to steric interactions involving large APC conjugates, and simplifies assay development, since there are fewer independent variables requiring optimization in a directly labeled system.

3.0 Instrument Settings

The excitation and emission spectra of terbium and fluorescein are shown below in FIG. 6. As with other TR-FRET systems, the terbium donor is excited using a 340 nm excitation filter with a 30 nm bandwidth. However, the exact specifications of the excitation filter are not critical, and filters with similar specifications will work well. In general, excitation filters that work with europium-based TR-FRET systems will perform well with the LanthaScreen™ terbium chelates.

Figure 6:
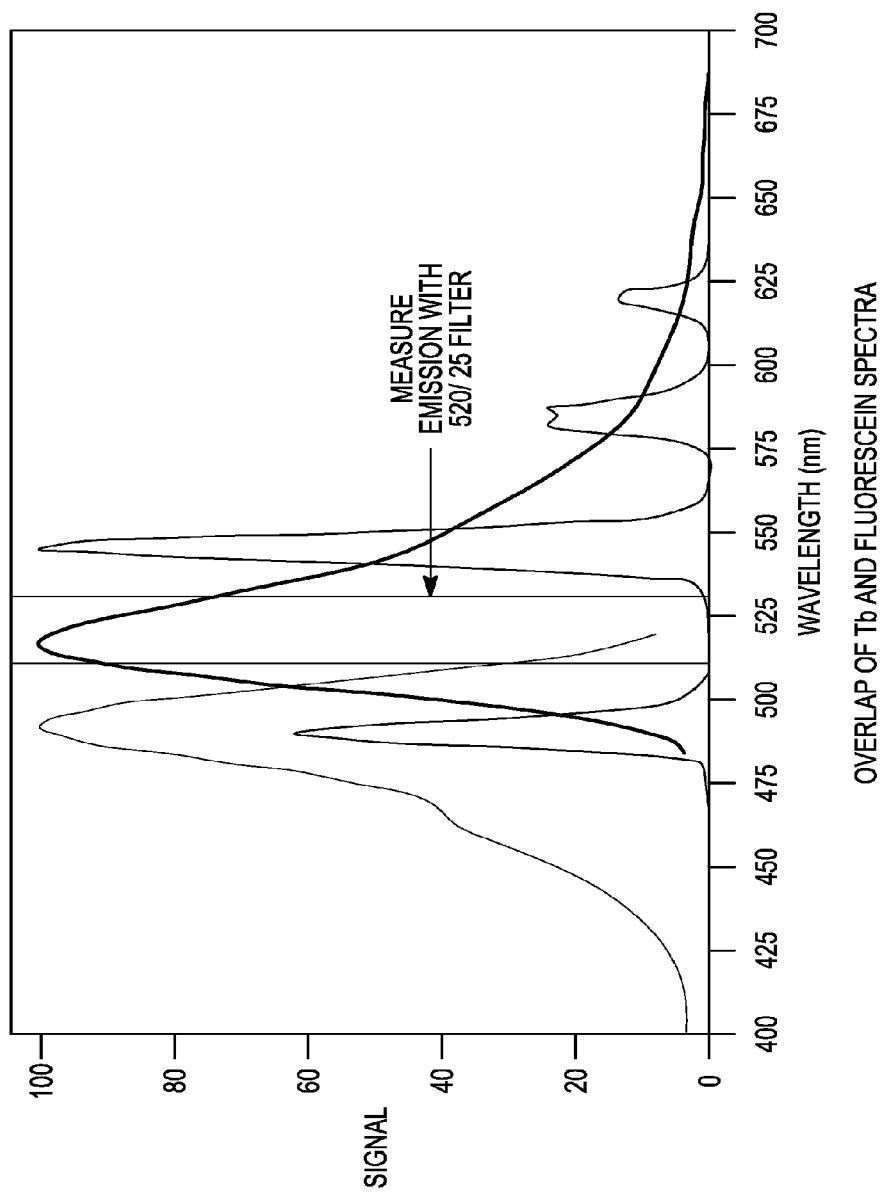
FIG. 6 demonstrates an overlap of the terbium chelate and fluorescein spectra.
Figure 7:
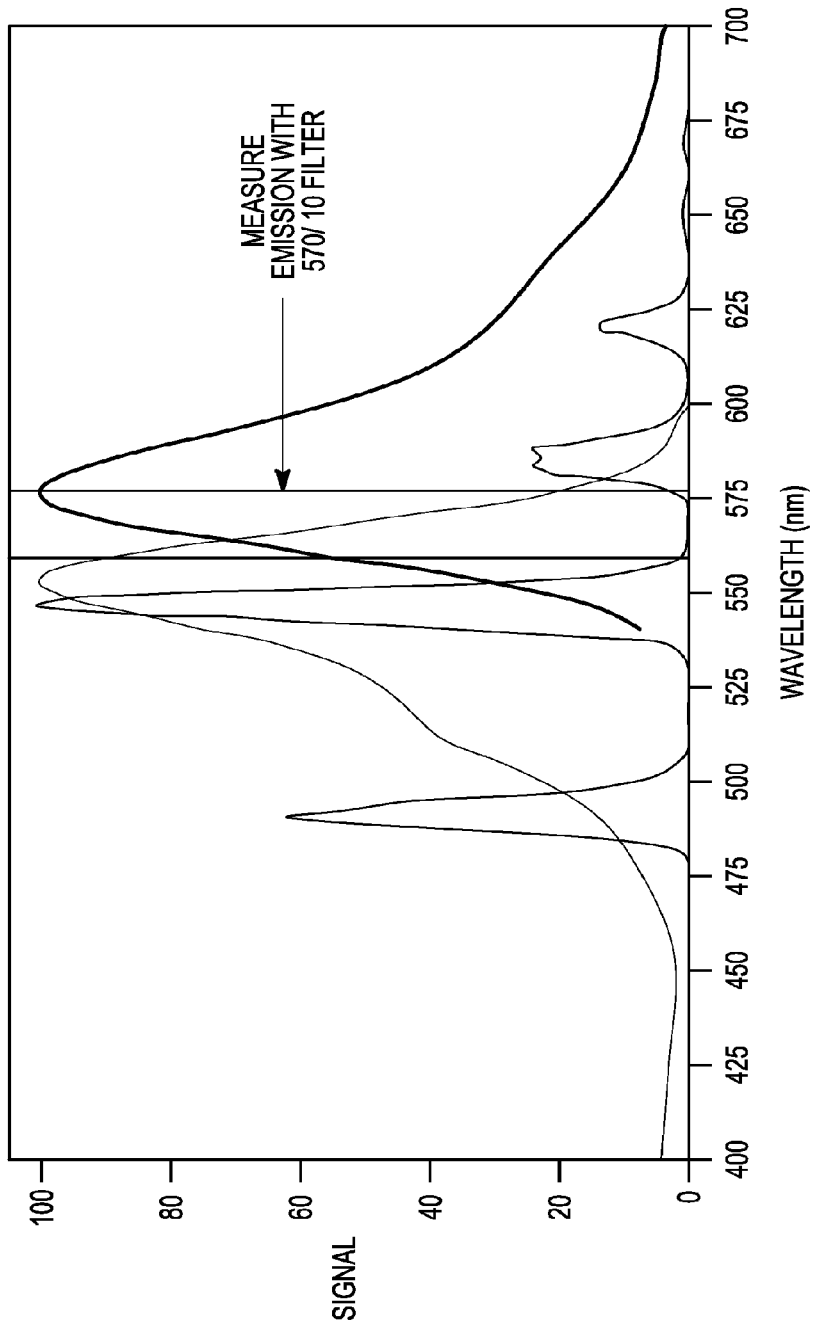
FIG. 7 demonstrates an overlap of the terbium chelate and rhodamine spectra.
Figure 8:
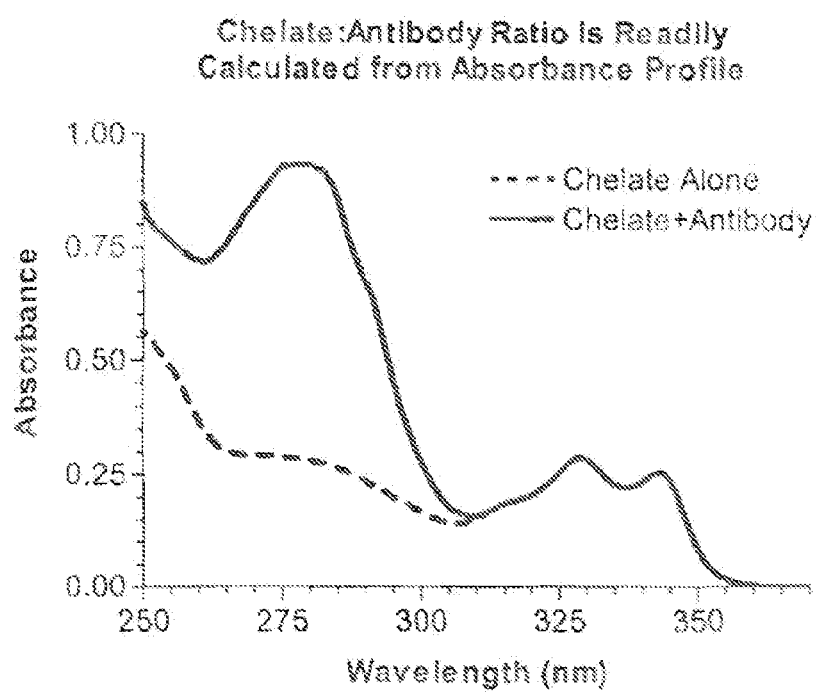
FIG. 8 demonstrates the absorbance profile of a chelate and a chelate-antibody conjugate.

As is shown in FIG. 6, the terbium emission spectrum is characterized by four sharp emission peaks, with silent regions between each peak. The first terbium emission peak (centered between approximately 485 and 505 nm) overlaps with the maximum excitation peak of fluorescein. Energy transfer to fluorescein is then measured in the silent region between the first two terbium emission peaks. Because it is important to measure energy transfer to fluorescein without interference from terbium, a filter centered at 520 nm with a 25 nm bandwidth is used for this purpose. The specifications of this filter are more significant than those of the excitation filter. In general, standard "fluorescein" filters may not be used, because such filters also pass light associated with the terbium spectra as well. The emission of fluorescein due to FRET is referenced (or "ratioed") to the emission of the first terbium peak, using a filter that isolates this peak. This is typically accomplished with a filter centered at 490 or 495 nm, with a 10 nm bandwidth. In general, a 490 nm filter will reduce the amount of fluorescein emission that "bleeds through" into this measurement, although instrument dichroic mirror choices (such as those on the Tecan Ultra instrument) may necessitate the use of a 495 nm filter. The effect on the quality of the resulting measurements is minimal in either case. Filters suitable for LanthaScreen™ assays are available from Chroma (Rockingham, Vt.) as filter set PV001, or from other vendors. A LanthaScreen™ filter module for the BMG LABTECH PHERAstar is available direct from BMG LABTECH (Durham, N.C.).

Aside from filter choices, instrument settings are typical to the settings used with europium-based technologies. In general, guidelines provided by the instrument manufacturer can be used as a starting point for optimization. A delay time of 100 µs, followed by a 200 µs integration time, would be typical for a LanthaScreen™ assay. The number of flashes or measurements per well is highly instrument dependent and should be set as advised by your instrument manufacturer. In general, LanthaScreen™ assays can be run on any filter-based instrument capable of time-resolved FRET, such as the Tecan Ultra, BMG LABTECH PHERAStar, Molecular Devices Analyst, or PerkinElmer Envision. LanthaScreen™ assays have also been performed successfully on the Tecan Safire$^2$ monochromator-based instrument and the Molecular Devices M5 instrument. Contact Invitrogen Technical Services for instrument-specific setup guidelines.

4.0 High Throughput Screening of Ubiquitination with TR-FRET Reagents

The LanthaScreen™ ubiquitination products provide sensitive HTS reagents to monitor changes in the rate of formation, or the amount of mono and polyubiquitination of proteins. By incorporating the TR-FRET donor (i.e. terbium) and acceptor (i.e. fluorescein) onto ubiquitin itself, universal assay reagents were created that can be used to rapidly develop screening assays for ubiquitin conjugating enzymes. Due to the selective labeling process, all of the lysines within ubiquitin are unmodified, and the labeled ubiquitin reagents are readily incorporated into ubiquitin-protein conjugates and poly-ubiquitin chains.

HTS Ubiquitination Assay Formats

For a typical HTS TR-FRET ubiquitination assay, fluorescein, terbium, or biotin-ubiquitin are incubated with ubiquitin conjugating enzymes (E1, E2, and E3), a target protein to be ubiquitinated, and ATP. The enzymes conjugate the labeled ubiquitins onto the target protein, resulting in mono or polyubiquitination. Depending upon the specific assay, a detection reagent (i.e. a Tb-anti-epitope tag antibody or LanthaScreen™ Tb-Streptavidin) may be added to the ubiquitination reaction to complete the TR-FRET pairing. See as examples FIGS. 10, 22, 26, 27 and 29.

The extent of target protein ubiquitination is directly related to the TR-FRET signal. In general, an increase in the TR-FRET signal signifies the ubiquitination of the target protein, whereas no increase in the TR-FRET signal would suggest that the target protein is not ubiquitinated. In HTS applications, a drug is introduced to measure the effectiveness of the compound to inhibit or promote the ubiquitination of the target protein. If the drug inhibits the ubiquitination reaction, a decrease in the TR-FRET signal (compared to control wells) would be observed due to a decrease in the ubiquitination of the target protein. Conversely, an increase in the TR-FRET signal would be observed if the drug promotes the ubiquitination of the target protein.

The availability of Tb-labeled anti-species antibodies from the LanthaScreen™ toolbox provides additional assay formats for detecting ubiquitination when a specific primary antibody to the target protein is available. The versatility of the LanthaScreen™ ubiquitination reagents allows one to easily construct a custom assay that will integrate the advantages of TR-FRET HTS with minimal development time.

Example Assay Conditions

Example assay conditions for the LanthaScreen TR-FRET ubiquitination assays are outlined below. The assay parameters were experimentally determined based upon the ubiquitin conjugating enzyme UbcH1 (E2-25k), and are provided as a starting point for optimization. The addition of dithiothreitol (DTT) is optional, and may be required to activate some ubiquitin conjugating enzymes. To stop the ubiquitination reaction, EDTA can be added at a concentration equal to the $Mg^{2+}$ concentration within the reaction to prevent ATP hydrolysis.

| Solution | Final Concentration Range in Reaction |
|---|---|
| Tris-HCl pH 8.0 | 100 mM |
| DTT | 1 mM |
| ATP Regeneration Solution* | 1 X |
| Ubiquitin | 300-400 nM |
| E1 | 10-30 nM |
| E2 | Assay Specific |
| diH$_2$0 | — |

*ATP Regeneration Solution (1X): 4 mM ATP, 5 mM MgCl$_2$, 5 mM creatine phosphate (Sigma; P7936), 0.03 mg/mL creatine phosphokinase (Sigma; C3755), and 0.3 units/mL inorganic pyrophosphatase (Sigma; I1643). Adapted from Yao, T.; Cohen, R. E. J. Biol. Chem. 2000, 275, 36862-36868. The 'ATP regeneration enzymes' are not required for a functional ubiquitination assay. A solution of only ATP and MgCl$_2$ is also an appropriate energy source for the ubiquitination assays.

Anti-epitope Ubiquitination Assay:

The anti-epitope ubiquitination assay can be used when the target protein contains an epitope tag. Since the TR-FRET donor (Tb) is located on the introduced antibody, this assay can be used for the detection of mono or polyubiquitination because ubiquitin chain formation is not required to complete the TR-FRET pairings (FIG. 27 (Fluorescein Anti-epitope/Terbium Ub)).

| Solution | Stock Concentration | Volume in assay | Final Concentration in Reaction |
|---|---|---|---|
| Tris-HCl pH 8.0 | 1 M | 1 µL | 100 mM |
| DTT | 10 mM | 1 µL | 1 mM |
| ATP Regeneration Solution | 10X | 1 µL | 1 X |
| Fluorescein-Ubiquitin | 2.33 µM | 1.5 µL | 350 nM |
| E1 | 50 nM | 2 µL | 10 nM |
| GST-UbcH1 (E2-25k) | 200 nM | 1 µL | 20 nM |
| diH$_2$0 | — | 2.5 µL | — |
| Total Assay Volume | | 10 µL | |

The solutions were combined in a Corning low volume 384 well plate (#3676) that was covered with aluminum sealing tape to prevent evaporation, and then placed at 37° C. for 8 hours. Experiments with other ubiquitin conjugating enzymes have shown the development of a TR-FRET signal with incubation times as little as 90 minutes. The ideal incubation time should be determined experimentally for optimal performance.

Figure 34A:
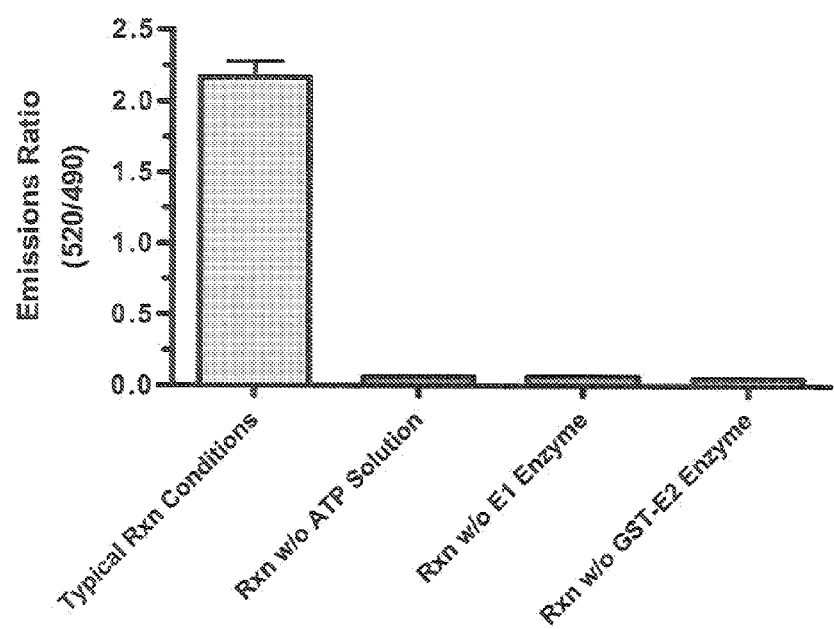
FIG. 34 shows representative data from an anti-epitope ubiquitination assay with GST-UbcH1. The anti-epitope ubiquitination assay has a good signal-to-background compared to controls (A), and methylated ubiquitin will compete with fluorescein-ubiquitin for attachment to the GST-UbcH1 (B). The results of 23 positive control wells (standard ubiquitination reaction conditions) and 23 negative controls wells (standard ubiquitination reaction without ATP) give a Z' value of 0.88 for the anti-epitope ubiquitination assay.
Figure 34B:
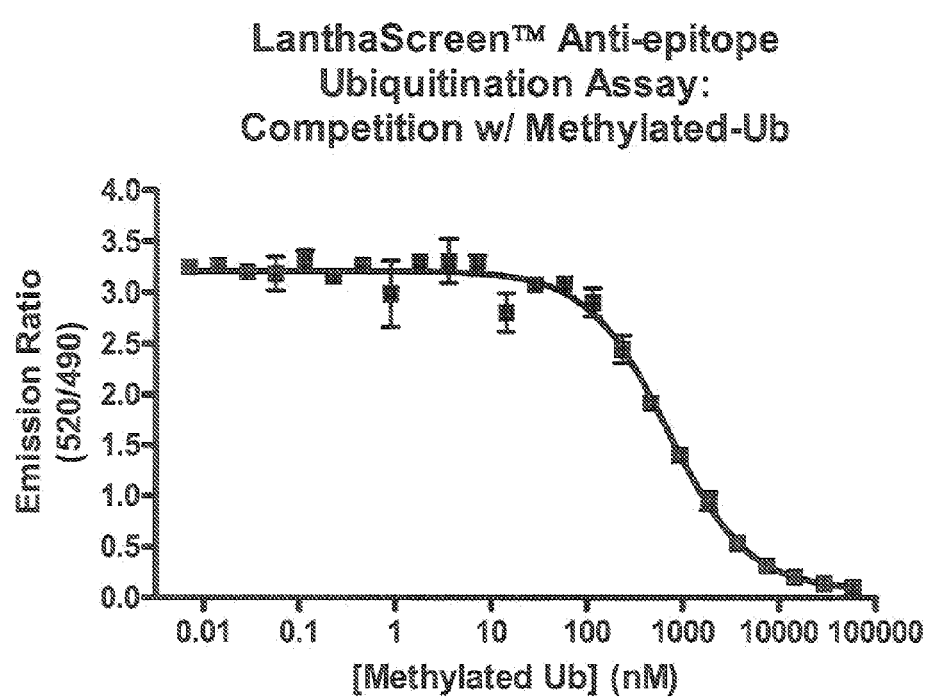

Following the incubation, 10 µL of TR-FRET Dilution Buffer (PV3574, Invitrogen, Carlsbad, Calif.) containing Tb-anti-GST (final concentration: 1 nM) was added to each well. The plate equilibrated at room temperature for 20 minutes, and was read on a BMG LABTECH PHERAstar with the recommended filter sets for LanthaScreen™. Representative data from an anti-epitope ubiquitination assay with GST-UbcH1 is shown in FIG. 34.

Intrachain Ubiquitination Assay:

The intrachain ubiquitination assay is used for detecting the polyubiquitination of a target protein. Since both the TR-FRET donor and acceptor are located on ubiquitin itself, no development step or reagent addition step is required. (FIG. 22) This allows the intrachain ubiquitination reaction to be used for real time ubiquitination readout (or ubiquitination kinetics), or as an endpoint assay. The conditions outlined below are for an endpoint assay readout.

| Solution | Stock Concentration | Volume in assay | Final Concentration in Reaction |
|---|---|---|---|
| Tris-HCl pH 8.0 | 1 M | 1 µL | 100 mM |
| DTT | 10 mM | 1 µL | 1 mM |
| ATP Regeneration Solution | 10X | 1 µL | 1 X |
| Fluorescein-Ubiquitin | 2 µM | 1.5 µL | 300 nM |
| LanthaScreen™ Tb-Ubiquitin | 500 nM | 0.5 µL | 25 nM |
| E1 | 440 nM | 0.5 µL | 22 nM |
| UbcH1 (E2-25k) | 5 µM | 2 µL | 1 µM |
| diH20 | — | 2.5 µL | — |
| Total Assay Volume | | 10 µL | |

Figure 23:
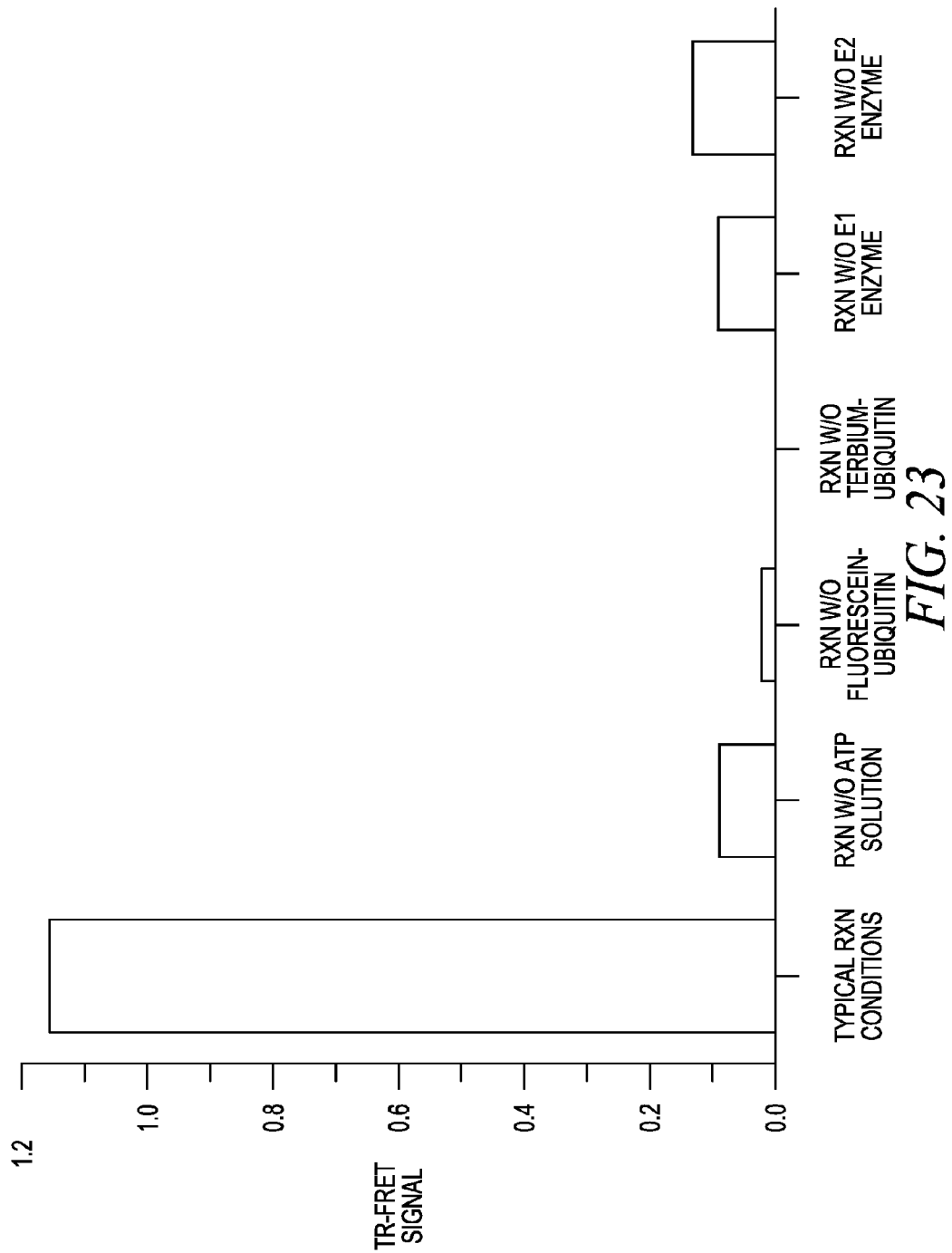
FIG. 23 shows a representative bar graph of the TR-FRET signal witnessed with a LanthaScreen™ Intrachain Ubiquitination reaction and the corresponding controls.
Figure 24:
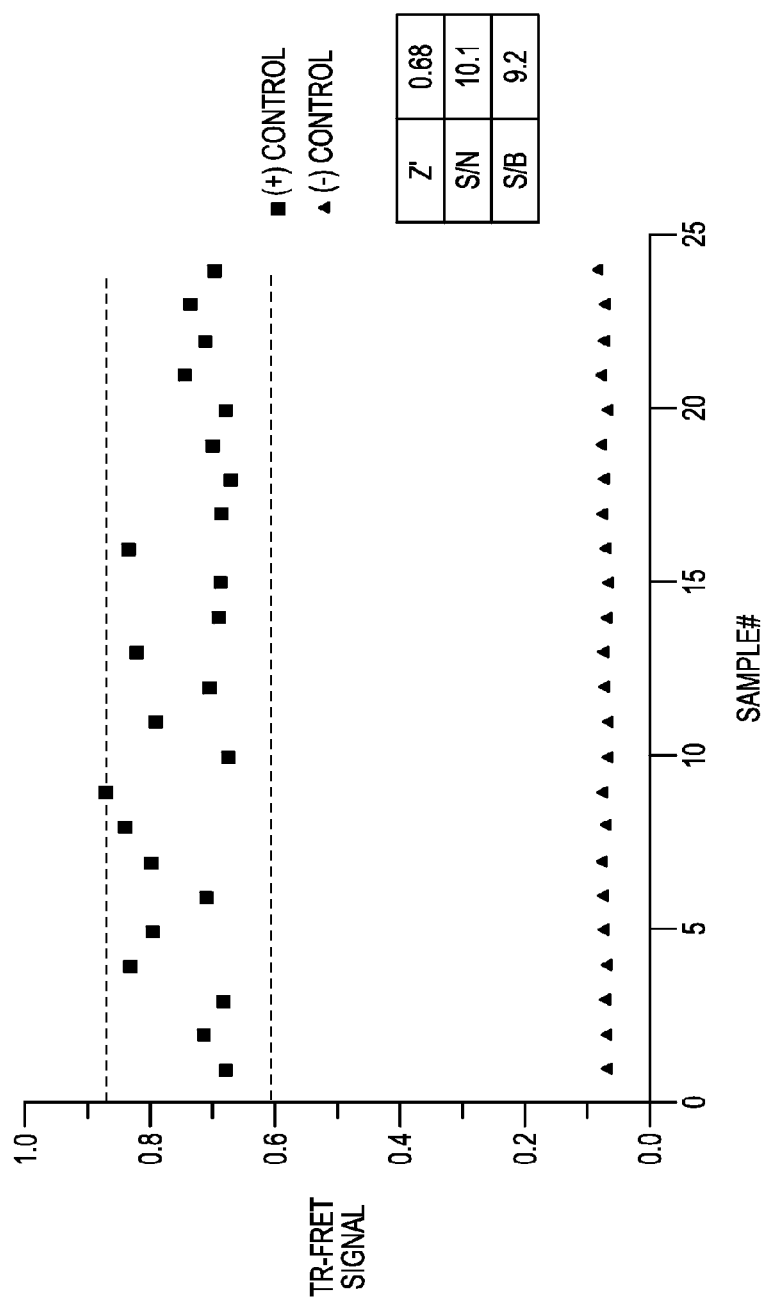
FIG. 24 shows representative Z' data for an Intrachain Ubiquitination reaction. The negative control (−) is the reaction mixture without the ATP solution. The dashed lines represent two standard deviations.
Figure 25:
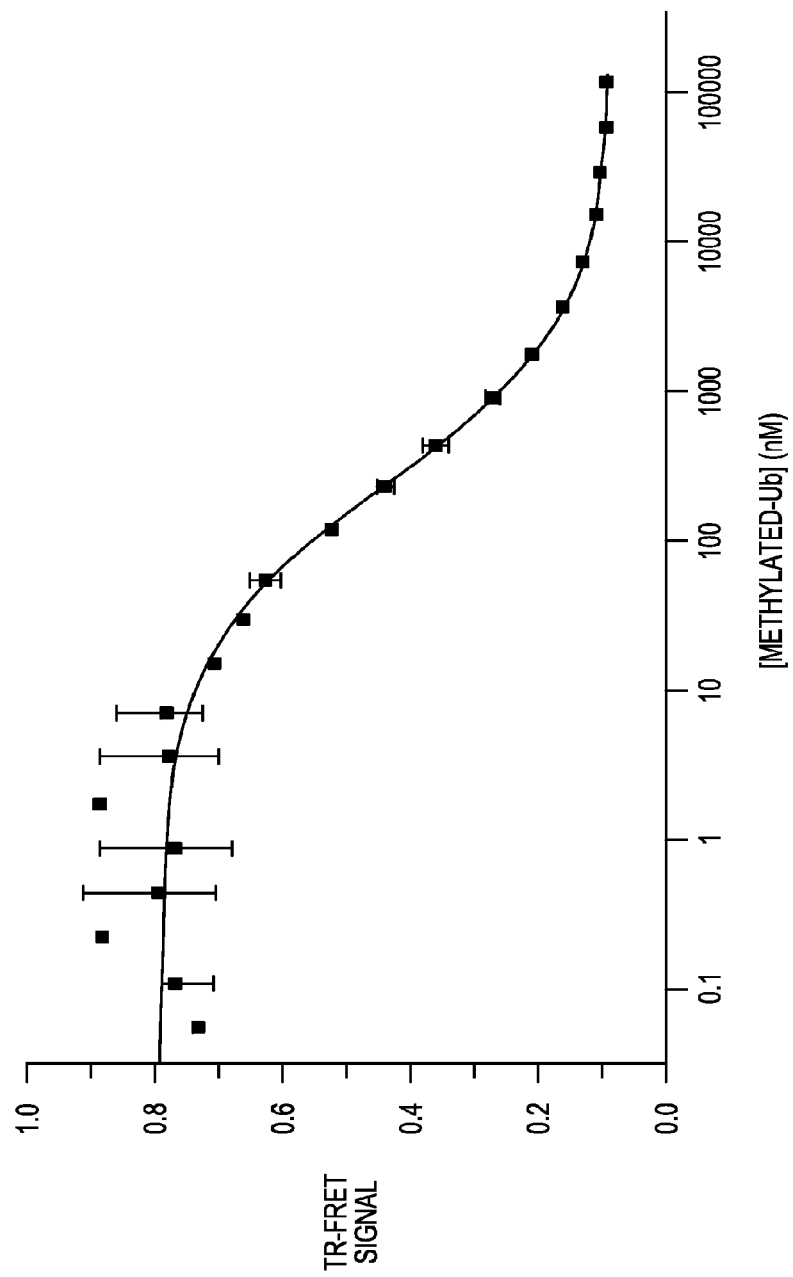
FIG. 25 shows an inhibition curve of an Intrachain TR-FRET Ubiquitination assay with methylated-ubiquitin. Methylated-ubiquitin is unable or has the decreased ability to form poly-ubiquitin chains due to the methylation of the lysine residues within the protein, therefore preventing or inhibiting the formation of intrachain TR-FRET pairs.
Figure 35:
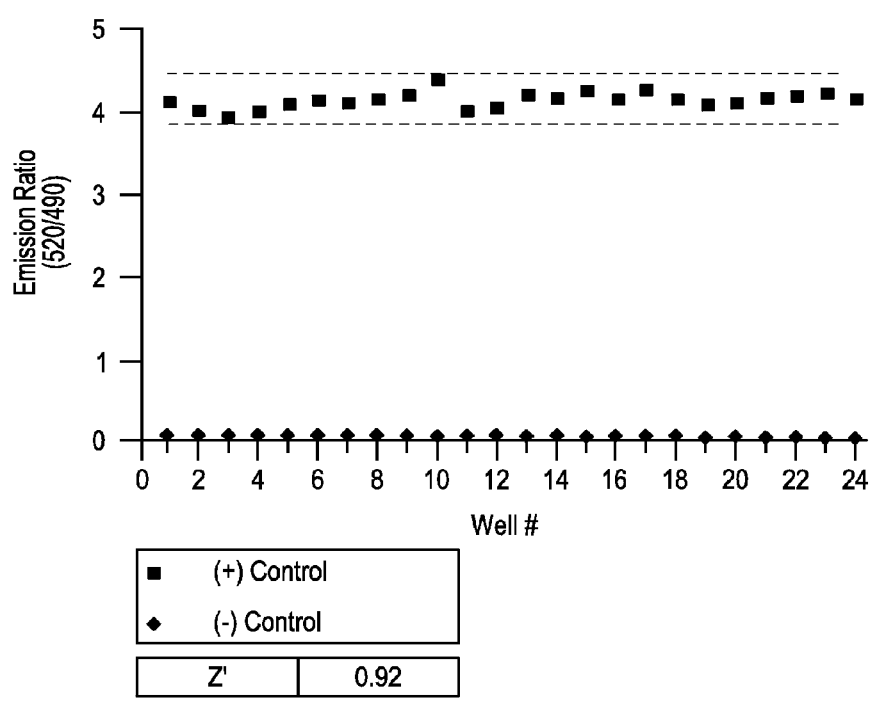
FIG. 35 shows representative data from an endpoint intrachain ubiquitination assay with UbcH1. The results of 24 positive control wells (standard ubiquitination reaction conditions) and 24 negative controls wells (standard ubiquitination reaction without ATP) gave a Z' value of 0.92 for the intrachain ubiquitination assay. The dashed lines represent ±3 standard deviations.

The solutions were combined in a Corning low volume 384 well plate (#3676) that was covered with aluminum sealing tape to prevent evaporation, and then placed at 37° C. for 8 hours. Following the incubation, 10 µL of TR-FRET dilution buffer (PV3574) was added to each well, and the plate was read on a BMG LABTECH PHERAstar with the recommended filter sets for LanthaScreen™. Representative data from an endpoint intrachain ubiquitination assay with UbcH1 is shown in FIGS. 23, 25 and 35.

In the real time intrachain ubiquitination assay, no development or reagent addition step is performed. To accommodate for the removal of the development step, the assay volume should be increased to 20 µL, and the concentration of the Fluorescein-Ubiquitin and LanthaScreen™ Tb-Ubiquitin should be decreased to 150 nM and 12.5 nM, respectively, to prevent the observation of diffusional enhanced FRET. The addition of a small amount of detergent (~0.01% Nonidet P-40) to the reaction is also recommended to prevent adsorption of the proteins to the plate.

Figure 33:
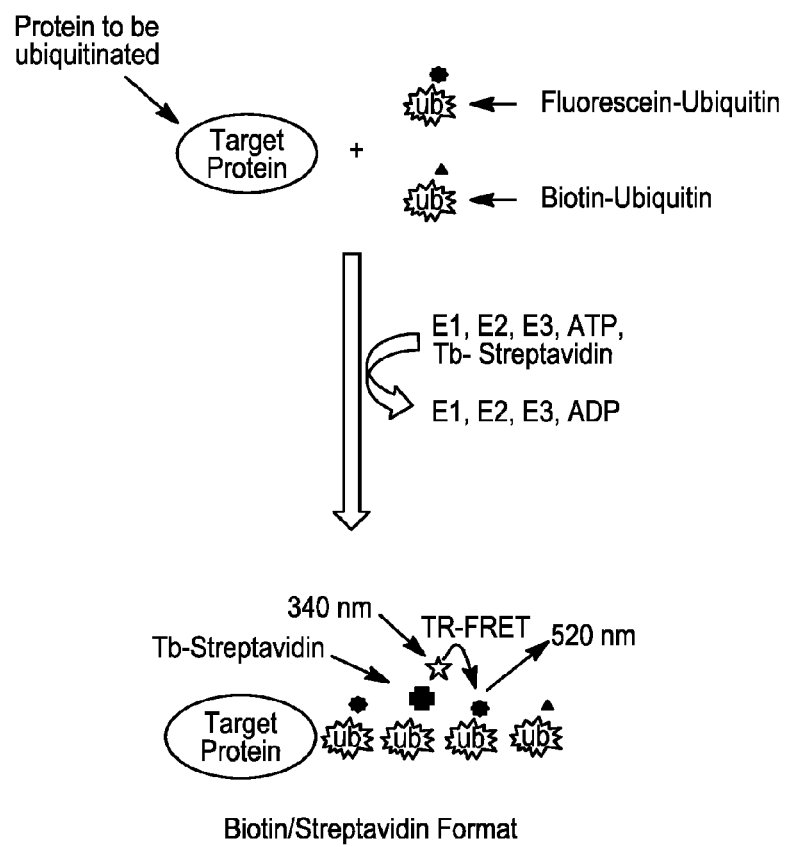
FIG. 33 depicts a biotin/streptavidin format for ubiquitination (e.g., polyubiquitination). This is a drawing of one exemplary format. In some embodiments, the streptavidin is attached to a Ub and a labeled biotin (e.g., Tb labeled) binds to the streptavidin-Ub. In some embodiments, a streptavidin/biotin complex can be on the target protein with the other member of the FRET pair on a Ub. In some embodiments, a streptavidin/biotin complex can be on a Ub with the other member of a FRET pair on a target protein. In some embodiments, the streptavidin complex contains a donor member of a FRET pair. In some embodiments, the streptavidin complex contains an acceptor member of a FRET pair.

Biotin/Streptavidin Ubiquitination Assay:

The Biotin/Streptavidin ubiquitination assay can also be used to detect the polyubiquitination of a target protein. In this assay, the TR-FRET donor (Tb) is introduced with the addition of LanthaScreen™ Tb-Streptavidin during the development step. (FIG. 33)

| Solution | Stock Concentration | Volume in assay | Final Concentration in Reaction |
|---|---|---|---|
| Tris-HCl pH 8.0 | 1 M | 1 µL | 100 mM |
| DTT | 10 mM | 1 µL | 1 mM |
| ATP Regeneration Solution | 10X | 1 µL | 1 X |
| Fluorescein-Ubiquitin | 2 µM | 1.5 µL | 300 nM |
| Biotin-Ubiquitin | 400 nM | 2.5 µL | 100 nM |
| E1 | 440 nM | 0.5 µL | 22 nM |
| UbcH1 (E2-25k) | 50 µM | 1 µL | 5 µM |
| diH$_2$0 | — | 1.5 µL | — |
| Total Assay Volume | | 10 µL | |

Figure 36A:
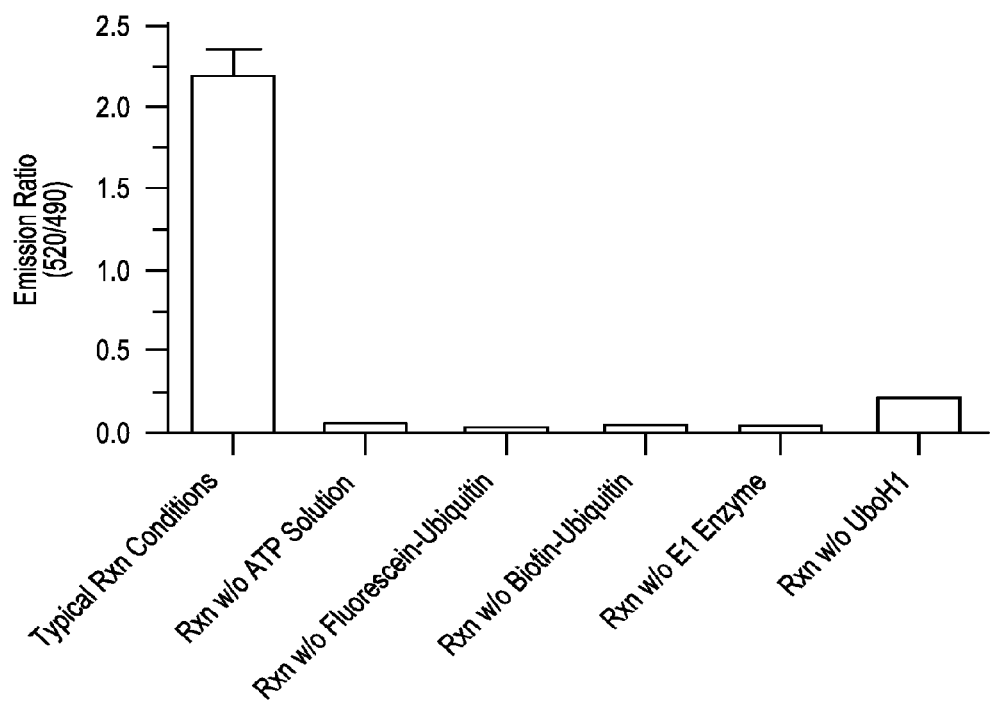
FIG. 36 shows representative data from a Biotin/Streptavidin ubiquitination assay with UbcHl. The Biotin/Streptavidin ubiquitination assay has a good signal-to-background compared to controls (A) and methylated ubiquitin will compete with the ability of biotin and fluorescein-ubiquitin to form polyubiquitin chains (B). The results of 21 positive control wells (standard ubiquitination reaction conditions) and 21 negative controls wells (standard ubiquitination reaction without ATP) give a Z' value of 0.8 for the Biotin/Streptavidin ubiquitination assay (C). The dashed lines represent ±3 standard deviations.
Figure 36B:
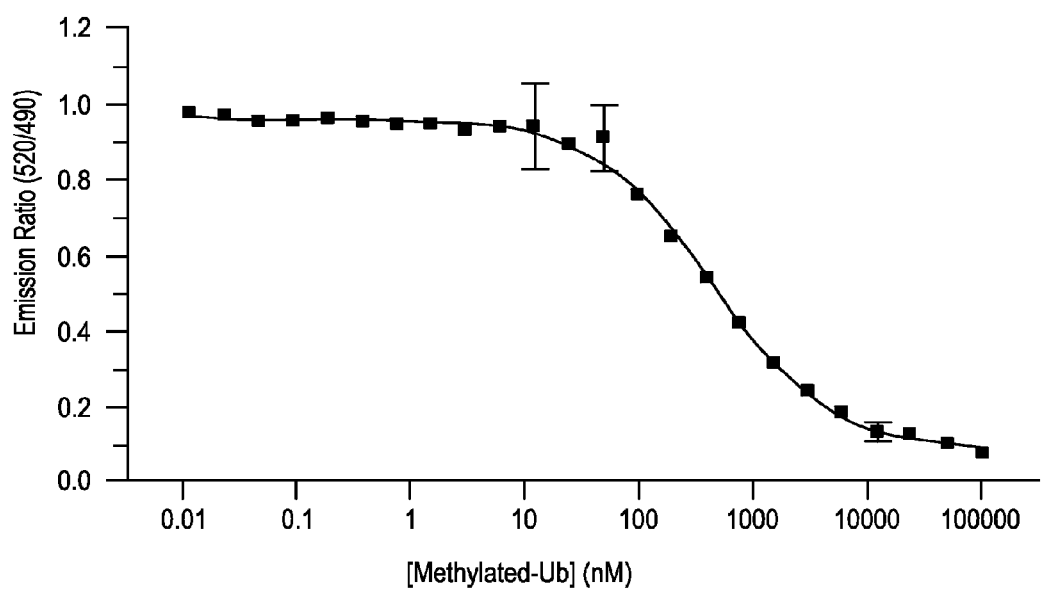
Figure 36C:
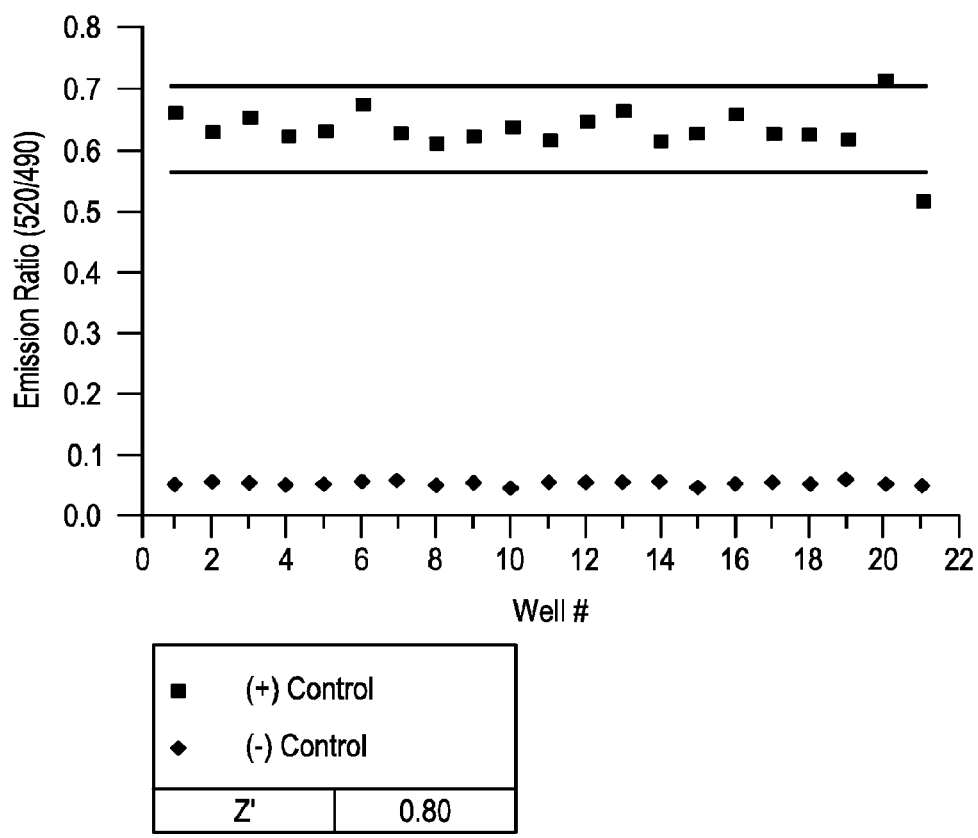

The solutions were combined in a Corning low volume 384 well plate (#3676) that was covered with aluminum sealing tape to prevent evaporation, and then placed at 37° C. for 8 hours. Following the incubation, 10 µL of TR-FRET Dilution Buffer (PV3574) containing LanthaScreen™ Tb-Streptavidin (final concentration: 2 nM) was added to each well. The plate equilibrated at room temperature for 20 minutes, and was read on a BMG LABTECH PHERAstar with the recommended filter sets for LanthaScreen™. Representative data from a Biotin/Streptavidin ubiquitination assay with UbcH1 is shown in FIG. 36.

Pre-Mixing of Solutions for Addition to Plate

Pre-mixing of the ubiquitination assay solutions for a single solution addition step resulted in minor variances in the TR-FRET signal. If pre-mixing is performed, higher Z' values were achieved when the ATP solution was added as a second step to initiate the ubiquitination reaction. Pre-mixing conditions should be assessed to identify optimal assay conditions.

Assay Stability and Read Window

For a given assay system, signal stability and read window should be assessed. In general, assays showed a stable signal for 12 hours following the development step. Experiments with ubiquitin conjugating enzymes other then UbcH1 have shown the development of a TR-FRET signal with incubation times as little as 90 minutes. Depending on the specific assay configuration, and the demands of the assay, these times may vary and should be determined experimentally for the given assay system.

Plate Selection

We recommend black Corning® 384-well, low-volume, round-bottom (non-binding surface) assay plates (#3676, Corning, N.Y.). Other black-walled, low-binding assay plates, while not tested, may be suitable.

5.0 Alternative Ubiquitination Assays With GFP Fusion Proteins

Green Fluorescent Protein (GFP) is an excellent FRET acceptor of the LanthaScreen™ terbium donor. Therefore, GFP-fusion proteins can be used in a ubiquitination assay with LanthaScreen™ Tb-Ubiquitin or Tb-Streptavidin/Biotin-Ubiquitin. See FIG. 26. In these particular assay formats, GFP replaces fluorescein as the TR-FRET acceptor, and can still be read with the standard LanthaScreen™ filter sets.

6.0 Assessing Data Quality in Ratiometric Measurements

The TR-FRET value is a unitless ratio derived from the underlying donor and acceptor signals. Because the underlying donor and acceptor signals are dependent on instrument settings (such as instrument gain), the TR-FRET ratio, signal-to-noise (S/N), signal-to-background (S/B), and the resulting "top" and "bottom" of an assay window will depend on these settings as well, and will vary from instrument to instrument. What is important in determining the robustness of an assay is not the size of the window as much as the size of the errors in the data relative to the difference in the maximum and minimum values. It is for this reason that the "Z prime" value (Z') proposed by Zhang and colleagues (*J Biomol Screen* 1999: 4(2) pp 67-73), which takes these factors into account, is the correct way to assess data quality in a TR-FRET assay. Shown below are two "Z prime" calculations that were preformed on the same ubiquitination assay samples, but on two different instruments. Even though each instrument shows a different TR-FRET signal and assay window, the Z' values are comparable. Typically, our ubiquitination assays have Z' values of greater than 0.7. The dashed lines represent ±3 standard deviations.

7.0 Related Products

| REAGENTS | Volume | Invitrogen Cat. No. |
|---|---|---|
| LanthaScreen ™ TR-FRET Dilution Buffer | 100 mL | PV3574 |
| LanthaScreen ™ Tb-Streptavidin, 1 mg/mL | 50 µg | PV3576 |
|  | 1 mg | PV3577 |
| LanthaScreen ™ Tb-anti-GST Antibody | 25 µg | PV4216 |
|  | 1 mg | PV4217 |
| LanthaScreen ™ Tb-anti-His-Tag Antibody | 25 µg | PV3568 |
|  | 1 mg | PV3569 |
| LanthaScreen ™ Tb-anti-Mouse Antibody | 25 µg | PV3765 |
|  | 1 mg | PV3767 |
| LanthaScreen ™ Tb-anti-Goat Antibody | 25 µg | PV3769 |
|  | 1 mg | PV3771 |
| LanthaScreen ™ Tb-anti-Rabbit Antibody | 25 µg | PV3773 |
|  | 1 mg | PV3775 |
| LanthaScreen ™ Tb-anti-Human Antibody | 25 µg | PV3777 |
|  | 1 mg | PV3779 |
|  | 10 µg | PV3583 |
| LanthaScreen ™ Amine Reactive Tb Chelate | 100 µg | PV3582 |
|  | 1 mg | PV3581 |
|  | 10 µg | PV3580 |
| LanthaScreen ™ Thiol Reactive Tb Chelate | 100 µg | PV3579 |
|  | 1 mg | PV3578 |

For a complete, up to date listing of products, contact Invitrogen (Carlsbad, Calif.).

Whereas, particular embodiments of the invention have been described above for purposes of description, it will be appreciated by those skilled in the art that numerous variations of the details may be made without departing from the invention as described in the appended claims.

All publications, patents and patent applications mentioned in this specification are herein incorporated by reference in their entirety into the specification to the same extent as if each individual publication, patent or patent application was specifically and individually indicated to be incorporated herein by reference.

What is claimed is:

1. A method for detecting at least one substrate for at least one ubiquitination or ubiquitination-like enzyme, the method comprising:
   a) contacting i) the at least one ubiquitination or ubiquitination-like enzyme with ii) polypeptides immobilized on a support, wherein the polypeptides are associated with a first detectable moiety, and iii) at least one ubiquiton comprising a second detectable moiety, wherein the first moiety and the second moiety comprise a resonance energy transfer (RET) pair,
   b) incubating (a) under conditions to allow for ubiquitination or ubiquitination-like activity,
   c) exposing the support to at least one wavelength of light, and
   d) detecting at least one substrate for at least one ubiquitination or ubiquitination-like enzyme by detecting resonance energy transfer from the support.

2. A method for identifying deubiquitinating activity of a sample, the method comprising:
   a) contacting i) the sample with ii) at least one or a plurality of polypeptides immobilized on a substrate, wherein the at least one or plurality of polypeptides is associated with a first detectable moiety and wherein the at least one or plurality of polypeptides comprise a ubiquitin or ubiquitin-like protein associated with a second detectable moiety, wherein the first moiety and the second moiety comprise a RET pair and wherein the deubiquitinating activity causes the dissociation of the detectable moiety from the substrate,
   b) incubating (a) under conditions suitable for de-ubiquitination activity,
   c) exposing the substrate to at least one wavelength of light, and
   d) detecting fluorescence emission from the substrate;
   wherein a decrease in RET between the first and second moiety indicates deubiquitinating activity in the sample.

3. The method of claim 1, wherein the first detectable moiety is a fluorescent protein.

4. The method of claim 1, wherein the polypeptides are associated with an antibody and the antibody comprises the first detectable moiety.

5. The method of claim 1, wherein the at least one ubiquiton is directly labeled with the second detectable moiety.

6. The method of claim 1, wherein the first detectable moiety comprises a luminescent metal complex and the second detectable moiety comprises a fluorescent acceptor moiety.

7. The method of claim 2, wherein the at least one or plurality of polypeptides is a fluorescent protein.

8. The method of claim 7, wherein the second detectable moiety comprises a luminescent metal complex.

9. The method of claim 2, wherein the at least one or plurality of polypeptides and the ubiquitin or ubiquitin-like protein are fused as part of a fusion protein.

10. The method of claim 2, wherein the second detectable moiety is covalently associated with the ubiquitin or ubiquitin-like protein.

11. The method of claim 2, wherein the first detectable moiety comprises a luminescent metal complex and the second detectable moiety comprises a fluorescent acceptor moiety or the first detectable moiety comprises a fluorescent acceptor moiety and the second detectable moiety comprises a luminescent metal complex.

12. A method for detecting at least one substrate for at least one ubiquitination or ubiquitination-like enzyme, the method comprising:
   a) contacting i) the at least one ubiquitination or ubiquitination-like enzyme with ii) polypeptides immobilized on a support, iii) at least one ubiquiton comprising a first detectable moiety, and iv) at least one ubiquiton comprising a second detectable moiety, wherein the first moiety and the second moiety comprise a resonance energy transfer (RET) pair,
   b) incubating (a) under conditions to allow for ubiquitination or ubiquitination-like activity,
   c) exposing the support to at least one wavelength of light, and
   d) detecting at least one substrate for at least one ubiquitination or ubiquitination-like enzyme by detecting resonance energy transfer from the support.

13. The method of claim 12, wherein the first detectable moiety is directly associated with the at least one ubiquiton.

14. The method of claim 13, wherein the second detectable moiety is indirectly associated with the at least one ubiquiton.

15. The method of claim 12, wherein the first detectable moiety comprises a luminescent metal complex and the second detectable moiety comprises a fluorescent acceptor.

16. A method for detecting at least one substrate for at least one ubiquitination or ubiquitination-like enzyme, the method comprising:
   a) contacting i) the at least one ubiquitination or ubiquitination-like enzyme with ii) a positionally addressable array comprising polypeptides immobilized on a support, iii) at least one ubiquiton comprising a first detectable moiety, and iv) at least one ubiquiton comprising a second detectable moiety, wherein the first moiety and the second moiety comprise a resonance energy transfer (RET) pair, wherein the detectable moiety comprises a fluorescent or luminescent label,
   b) incubating (a) under conditions to allow for ubiquitination or ubiquitination-like activity,
   c) exposing the array to at least one wavelength of light, and
   d) detecting at least one substrate for at least one ubiquitination or ubiquitination-like enzyme by detecting resonance energy transfer from the support.

17. The method of claim 16, wherein the detectable moiety is indirectly associated with the at least one ubiquiton.

* * * * *

SEQUENCE LISTING

```
<160> NUMBER OF SEQ ID NOS: 27

<210> SEQ ID NO 1
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: PHOSPHORYLATION

<400> SEQUENCE: 1

Ala Asp Glu Tyr Leu Ile Pro Gln Gln Ser
1               5                   10

<210> SEQ ID NO 2
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (7)..(7)
<223> OTHER INFORMATION: PHOSPHORYLATION
```

-continued

```
<400> SEQUENCE: 2

Gly Arg Pro Arg Thr Ser Ser Phe Ala Glu Gly
1               5                   10

<210> SEQ ID NO 3
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: PHOSPHORYLATION

<400> SEQUENCE: 3

Ala Asp Glu Tyr Leu Ile Pro Gln Gln Ser
1               5                   10

<210> SEQ ID NO 4
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

<400> SEQUENCE: 4

Leu Arg Arg Glu Ile Leu Ser Arg Arg Pro Ser Tyr Arg Lys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (9)..(9)
<223> OTHER INFORMATION: PHOSPHORYLATION

<400> SEQUENCE: 5

Arg Glu Ile Leu Ser Arg Arg Pro Ser Tyr Arg Lys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (7)..(7)
<223> OTHER INFORMATION: PHOSPHORYLATION

<400> SEQUENCE: 6

Ile Leu Ser Arg Arg Pro Ser Tyr Arg Lys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: synthetic construct
```

```
<220> FEATURE:
<221> NAME/KEY: MOD_RES
<222> LOCATION: (11)..(11)
<223> OTHER INFORMATION: PHOSPHORYLATION

<400> SEQUENCE: 7

Leu Arg Arg Glu Ile Leu Ser Arg Arg Pro Ser Tyr Arg Lys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: synthetic construct

<400> SEQUENCE: 8

Leu Arg Arg Glu Ile Leu Ser Arg Arg Pro Ser Tyr Arg Lys
1               5                   10

<210> SEQ ID NO 9
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (5)..(5)
<223> OTHER INFORMATION: PHOSPHORYLATION

<400> SEQUENCE: 9

Cys Ala Asp Glu Tyr Leu Ile Pro Gln Gln Ser
1               5                   10

<210> SEQ ID NO 10
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (5)..(5)
<223> OTHER INFORMATION: PHOSPHORYLATION

<400> SEQUENCE: 10

Cys Ala Asp Glu Tyr Leu Ile Pro Gln Gln Ser
1               5                   10

<210> SEQ ID NO 11
<211> LENGTH: 6
<212> TYPE: PRT
<213> ORGANISM: Artificial Sequence
<220> FEATURE:
<223> OTHER INFORMATION: synthetic construct

<400> SEQUENCE: 11

His His His His His His
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic construct

<400> SEQUENCE: 12
```

```
Lys Gly Gly His His His His His
  1               5
```

<210> SEQ ID NO 13
<211> LENGTH: 371
<212> TYPE: PRT
<213> ORGANISM: Artificial Sequence
<220> FEATURE:
<223> OTHER INFORMATION: synthetic fusion protein

<400> SEQUENCE: 13

```
Met Arg Gly Ser His His His His His His Gly Met Ala Ser Met Thr
  1               5                  10                  15

Gly Gly Gln Gln Met Gly Arg Asp Leu Tyr Asp Asp Asp Lys Asp
             20                  25                  30

Arg Trp Gly Ser Glu Phe Ala Thr Met Val Ser Lys Gly Glu Glu Leu
             35                  40                  45

Phe Thr Gly Val Val Pro Ile Leu Val Glu Leu Asp Gly Asp Val Asn
 50                  55                  60

Gly His Lys Phe Ser Val Ser Gly Glu Gly Glu Gly Asp Ala Thr Tyr
 65                  70                  75                  80

Gly Lys Leu Thr Leu Lys Phe Ile Cys Thr Thr Gly Lys Leu Pro Val
             85                  90                  95

Pro Trp Pro Thr Leu Val Thr Thr Leu Thr Tyr Gly Val Gln Cys Phe
            100                 105                 110

Ala Arg Tyr Pro Asp His Met Lys Gln His Asp Phe Phe Lys Ser Ala
            115                 120                 125

Met Pro Glu Gly Tyr Val Gln Glu Arg Thr Ile Phe Phe Lys Asp Asp
130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
            165                 170                 175

Ile Leu Gly His Lys Leu Glu Tyr Asn Tyr Asn Ser His Lys Val Tyr
            180                 185                 190

Ile Thr Ala Asp Lys Gln Lys Asn Gly Ile Lys Val Asn Phe Lys Thr
            195                 200                 205

Arg His Asn Ile Glu Asp Gly Ser Val Gln Leu Ala Asp His Tyr Gln
            210                 215                 220

Gln Asn Thr Pro Ile Gly Asp Gly Pro Val Leu Leu Pro Asp Asn His
225                 230                 235                 240

Tyr Leu Ser Thr Gln Ser Ala Leu Ser Lys Asp Pro Asn Glu Lys Arg
            245                 250                 255

Asp His Met Val Leu Leu Glu Phe Val Thr Ala Ala Gly Ile Thr Leu
            260                 265                 270

Gly Met Asp Glu Leu Tyr Lys Leu Glu Thr Asp Gln Thr Ser Leu Tyr
            275                 280                 285

Lys Lys Ala Gly Thr Met Gln Ile Phe Val Lys Thr Leu Thr Gly Lys
            290                 295                 300

Thr Ile Thr Leu Glu Val Glu Pro Ser Asp Thr Ile Glu Asn Val Lys
305                 310                 315                 320

Ala Lys Ile Gln Asp Lys Glu Gly Ile Pro Pro Asp Gln Gln Arg Leu
            325                 330                 335

Ile Phe Ala Gly Lys Gln Leu Glu Asp Gly Arg Thr Leu Ser Asp Tyr
            340                 345                 350

Asn Ile Gln Lys Glu Ser Thr Leu His Leu Val Leu Arg Leu Arg Gly
```

Gly Ala Cys
    370

<210> SEQ ID NO 14
<211> LENGTH: 379
<212> TYPE: PRT
<213> ORGANISM: Artificial Sequence
<220> FEATURE:
<223> OTHER INFORMATION: synthetic fusion protein

<400> SEQUENCE: 14

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Glu Phe Ala Thr Met Val Ser Lys Gly Glu Glu Leu
        35                  40                  45

Phe Thr Gly Val Val Pro Ile Leu Val Glu Leu Asp Gly Asp Val Asn
    50                  55                  60

Gly His Lys Phe Ser Val Ser Gly Glu Gly Glu Gly Asp Ala Thr Tyr
65                  70                  75                  80

Gly Lys Leu Thr Leu Lys Phe Ile Cys Thr Thr Gly Lys Leu Pro Val
                85                  90                  95

Pro Trp Pro Thr Leu Val Thr Thr Leu Thr Tyr Gly Val Gln Cys Phe
            100                 105                 110

Ala Arg Tyr Pro Asp His Met Lys Gln His Asp Phe Phe Lys Ser Ala
        115                 120                 125

Met Pro Glu Gly Tyr Val Gln Glu Arg Thr Ile Phe Phe Lys Asp Asp
    130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                165                 170                 175

Ile Leu Gly His Lys Leu Glu Tyr Asn Tyr Asn Ser His Lys Val Tyr
            180                 185                 190

Ile Thr Ala Asp Lys Gln Lys Asn Gly Ile Lys Val Asn Phe Lys Thr
        195                 200                 205

Arg His Asn Ile Glu Asp Gly Ser Val Gln Leu Ala Asp His Tyr Gln
    210                 215                 220

Gln Asn Thr Pro Ile Gly Asp Gly Pro Val Leu Leu Pro Asp Asn His
225                 230                 235                 240

Tyr Leu Ser Thr Gln Ser Ala Leu Ser Lys Asp Pro Asn Glu Lys Arg
                245                 250                 255

Asp His Met Val Leu Leu Glu Phe Val Thr Ala Ala Gly Ile Thr Leu
            260                 265                 270

Gly Met Asp Glu Leu Tyr Lys Leu Glu Thr Asp Gln Thr Ser Leu Tyr
        275                 280                 285

Lys Lys Ala Gly Thr Met Gln Ile Phe Val Lys Thr Leu Thr Gly Lys
    290                 295                 300

Thr Ile Thr Leu Glu Val Glu Pro Ser Asp Thr Ile Glu Asn Val Lys
305                 310                 315                 320

Ala Lys Ile Gln Asp Lys Glu Gly Ile Pro Pro Asp Gln Gln Arg Leu
                325                 330                 335

Ile Phe Ala Gly Lys Gln Leu Glu Asp Gly Arg Thr Leu Ser Asp Tyr
            340                 345                 350

-continued

Asn Ile Gln Lys Glu Ser Thr Leu His Leu Val Leu Arg Leu Arg Gly
            355                 360                 365

Gly Phe Phe Gly Val Gly Gly Glu Gly Ala Cys
370                 375

<210> SEQ ID NO 15
<211> LENGTH: 372
<212> TYPE: PRT
<213> ORGANISM: Artificial Sequence
<220> FEATURE:
<223> OTHER INFORMATION: synthetic fusion protein

<400> SEQUENCE: 15

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Arg Trp Gly Ser Glu Phe Ala Thr Met Val Ser Lys Gly Glu Glu Leu
        35                  40                  45

Phe Thr Gly Val Val Pro Ile Leu Val Glu Leu Asp Gly Asp Val Asn
50                  55                  60

Gly His Lys Phe Ser Val Ser Gly Glu Gly Glu Gly Asp Ala Thr Tyr
65                  70                  75                  80

Gly Lys Leu Thr Leu Lys Phe Ile Cys Thr Thr Gly Lys Leu Pro Val
                85                  90                  95

Pro Trp Pro Thr Leu Val Thr Thr Leu Thr Tyr Gly Val Gln Cys Phe
            100                 105                 110

Ala Arg Tyr Pro Asp His Met Lys Gln His Asp Phe Phe Lys Ser Ala
        115                 120                 125

Met Pro Glu Gly Tyr Val Gln Glu Arg Thr Ile Phe Phe Lys Asp Asp
130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                165                 170                 175

Ile Leu Gly His Lys Leu Glu Tyr Asn Tyr Asn Ser His Lys Val Tyr
            180                 185                 190

Ile Thr Ala Asp Lys Gln Lys Asn Gly Ile Lys Val Asn Phe Lys Thr
        195                 200                 205

Arg His Asn Ile Glu Asp Gly Ser Val Gln Leu Ala Asp His Tyr Gln
210                 215                 220

Gln Asn Thr Pro Ile Gly Asp Gly Pro Val Leu Leu Pro Asp Asn His
225                 230                 235                 240

Tyr Leu Ser Thr Gln Ser Ala Leu Ser Lys Asp Pro Asn Glu Lys Arg
                245                 250                 255

Asp His Met Val Leu Leu Glu Phe Val Thr Ala Ala Gly Ile Thr Leu
            260                 265                 270

Gly Met Asp Glu Leu Tyr Lys Leu Glu Thr Asp Gln Thr Ser Leu Tyr
        275                 280                 285

Lys Lys Ala Gly Ser Met Thr Ala Lys Met Glu Thr Thr Phe Tyr Asp
290                 295                 300

Asp Ala Leu Asn Ala Ser Phe Leu Pro Ser Glu Ser Gly Pro Tyr Gly
305                 310                 315                 320

Tyr Ser Asn Pro Lys Ile Leu Lys Gln Ser Met Thr Leu Asn Leu Ala
                325                 330                 335

-continued

Asp Pro Val Gly Ser Leu Lys Pro His Leu Arg Ala Lys Asn Ser Asp
        340                 345                 350

Leu Leu Thr Ser Pro Asp Val Gly Leu Leu Lys Leu Ala Ser Pro Glu
        355                 360                 365

Leu Glu Arg Leu
    370

<210> SEQ ID NO 16
<211> LENGTH: 371
<212> TYPE: PRT
<213> ORGANISM: Artificial Sequence
<220> FEATURE:
<223> OTHER INFORMATION: synthetic fusion protein

<400> SEQUENCE: 16

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Glu Phe Ala Thr Met Val Ser Lys Gly Glu Glu Leu
        35                  40                  45

Phe Thr Gly Val Val Pro Ile Leu Val Glu Leu Asp Gly Asp Val Asn
    50                  55                  60

Gly His Lys Phe Ser Val Ser Gly Glu Gly Glu Gly Asp Ala Thr Tyr
65                  70                  75                  80

Gly Lys Leu Thr Leu Lys Phe Ile Cys Thr Thr Gly Lys Leu Pro Val
                85                  90                  95

Pro Trp Pro Thr Leu Val Thr Thr Leu Thr Tyr Gly Val Gln Cys Phe
            100                 105                 110

Ala Arg Tyr Pro Asp His Met Lys Gln His Asp Phe Phe Lys Ser Ala
        115                 120                 125

Met Pro Glu Gly Tyr Val Gln Glu Arg Thr Ile Phe Phe Lys Asp Asp
    130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                165                 170                 175

Ile Leu Gly His Lys Leu Glu Tyr Asn Tyr Asn Ser His Lys Val Tyr
            180                 185                 190

Ile Thr Ala Asp Lys Gln Lys Asn Gly Ile Lys Val Asn Phe Lys Thr
        195                 200                 205

Arg His Asn Ile Glu Asp Gly Ser Val Gln Leu Ala Asp His Tyr Gln
    210                 215                 220

Gln Asn Thr Pro Ile Gly Asp Gly Pro Val Leu Leu Pro Asp Asn His
225                 230                 235                 240

Tyr Leu Ser Thr Gln Ser Ala Leu Ser Lys Asp Pro Asn Glu Lys Arg
                245                 250                 255

Asp His Met Val Leu Leu Glu Phe Val Thr Ala Ala Gly Ile Thr Leu
            260                 265                 270

Gly Met Asp Glu Leu Tyr Lys Leu Glu Thr Asp Gln Thr Ser Leu Tyr
        275                 280                 285

Lys Lys Ala Gly Ser Met Ser Asp Asp Lys Pro Phe Leu Cys Thr Ala
    290                 295                 300

Pro Gly Cys Gly Gln Arg Phe Thr Asn Glu Asp His Leu Ala Val His
305                 310                 315                 320

Lys His Lys His Glu Met Thr Leu Lys Phe Gly Pro Ala Arg Asn Asp

```
                        325                 330                 335
Ser Val Ile Val Ala Asp Gln Thr Pro Thr Pro Thr Arg Phe Leu Lys
            340                 345                 350

Asn Cys Glu Glu Val Gly Leu Phe Asn Glu Leu Ala Ser Pro Phe Glu
        355                 360                 365

Asn Glu Phe
    370

<210> SEQ ID NO 17
<211> LENGTH: 392
<212> TYPE: PRT
<213> ORGANISM: Artificial Sequence
<220> FEATURE:
<223> OTHER INFORMATION: synthetic fusion protein

<400> SEQUENCE: 17

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Glu Phe Ala Thr Met Val Ser Lys Gly Glu Glu Leu
        35                  40                  45

Phe Thr Gly Val Val Pro Ile Leu Val Glu Leu Asp Gly Asp Val Asn
    50                  55                  60

Gly His Lys Phe Ser Val Ser Gly Glu Gly Glu Gly Asp Ala Thr Tyr
65                  70                  75                  80

Gly Lys Leu Thr Leu Lys Phe Ile Cys Thr Thr Gly Lys Leu Pro Val
                85                  90                  95

Pro Trp Pro Thr Leu Val Thr Thr Phe Gly Tyr Gly Val Gln Cys Phe
            100                 105                 110

Ala Arg Tyr Pro Asp His Met Arg Gln His Asp Phe Phe Lys Ser Ala
        115                 120                 125

Met Pro Glu Gly Tyr Val Gln Glu Arg Thr Ile Phe Phe Lys Asp Asp
    130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                165                 170                 175

Ile Leu Gly His Lys Leu Glu Tyr Asn Tyr Asn Ser His Asn Val Tyr
            180                 185                 190

Ile Met Ala Asp Lys Gln Lys Asn Gly Ile Lys Val Asn Phe Lys Ile
        195                 200                 205

Arg His Asn Ile Glu Asp Gly Ser Val Gln Leu Ala Asp His Tyr Gln
    210                 215                 220

Gln Asn Thr Pro Ile Gly Asp Gly Pro Val Leu Leu Pro Asp Asn His
225                 230                 235                 240

Tyr Leu Ser Tyr Gln Ser Ala Leu Ser Lys Asp Pro Asn Glu Lys Arg
                245                 250                 255

Asp His Met Val Leu Leu Glu Phe Val Thr Ala Ala Gly Ile Thr Leu
            260                 265                 270

Gly Met Asp Glu Leu Tyr Lys Leu Glu Thr Asp Gln Thr Ser Leu Tyr
        275                 280                 285

Lys Lys Ala Gly Thr Met Ser Asp Gln Glu Ala Lys Pro Ser Thr Glu
    290                 295                 300

Asp Leu Gly Asp Lys Lys Glu Gly Glu Tyr Ile Lys Leu Lys Val Ile
305                 310                 315                 320
```

Gly Gln Asp Ser Ser Glu Ile His Phe Lys Val Lys Met Thr Thr His
                325                 330                 335

Leu Lys Lys Leu Lys Glu Ser Tyr Cys Gln Arg Gln Gly Val Pro Met
                340                 345                 350

Asn Ser Leu Arg Phe Leu Phe Glu Gly Gln Arg Ile Ala Asp Asn His
                355                 360                 365

Thr Pro Lys Glu Leu Gly Met Glu Glu Glu Asp Val Ile Glu Val Tyr
            370                 375                 380

Gln Glu Gln Thr Gly Gly Ala Cys
385                 390

<210> SEQ ID NO 18
<211> LENGTH: 388
<212> TYPE: PRT
<213> ORGANISM: Artificial Sequence
<220> FEATURE:
<223> OTHER INFORMATION: synthetic fusion protein

<400> SEQUENCE: 18

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Arg Trp Gly Ser Glu Phe Ala Thr Met Val Ser Lys Gly Glu Glu Leu
            35                  40                  45

Phe Thr Gly Val Val Pro Ile Leu Val Glu Leu Asp Gly Asp Val Asn
        50                  55                  60

Gly His Lys Phe Ser Val Ser Gly Glu Gly Glu Gly Asp Ala Thr Tyr
65                  70                  75                  80

Gly Lys Leu Thr Leu Lys Phe Ile Cys Thr Thr Gly Lys Leu Pro Val
                85                  90                  95

Pro Trp Pro Thr Leu Val Thr Thr Phe Gly Tyr Gly Val Gln Cys Phe
                100                 105                 110

Ala Arg Tyr Pro Asp His Met Arg Gln His Asp Phe Phe Lys Ser Ala
                115                 120                 125

Met Pro Glu Gly Tyr Val Gln Glu Arg Thr Ile Phe Phe Lys Asp Asp
            130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                165                 170                 175

Ile Leu Gly His Lys Leu Glu Tyr Asn Tyr Asn Ser His Asn Val Tyr
                180                 185                 190

Ile Met Ala Asp Lys Gln Lys Asn Gly Ile Lys Val Asn Phe Lys Ile
            195                 200                 205

Arg His Asn Ile Glu Asp Gly Ser Val Gln Leu Ala Asp His Tyr Gln
            210                 215                 220

Gln Asn Thr Pro Ile Gly Asp Gly Pro Val Leu Leu Pro Asp Asn His
225                 230                 235                 240

Tyr Leu Ser Tyr Gln Ser Ala Leu Ser Lys Asp Pro Asn Glu Lys Arg
                245                 250                 255

Asp His Met Val Leu Leu Glu Phe Val Thr Ala Ala Gly Ile Thr Leu
                260                 265                 270

Gly Met Asp Glu Leu Tyr Lys Leu Glu Thr Asp Gln Thr Ser Leu Tyr
            275                 280                 285

```
Lys Lys Ala Gly Thr Met Ala Asp Glu Lys Pro Lys Glu Gly Val Lys
            290                 295                 300

Thr Glu Asn Asn Asp His Ile Asn Leu Lys Val Ala Gly Gln Asp Gly
305                 310                 315                 320

Ser Val Val Gln Phe Lys Ile Lys Arg His Thr Pro Leu Ser Lys Leu
                325                 330                 335

Met Lys Ala Tyr Cys Glu Arg Gln Gly Leu Ser Met Arg Gln Ile Arg
                340                 345                 350

Phe Arg Phe Asp Gly Gln Pro Ile Asn Glu Thr Asp Thr Pro Ala Gln
                355                 360                 365

Leu Glu Met Glu Asp Glu Asp Thr Ile Asp Val Phe Gln Gln Gln Thr
    370                 375                 380

Gly Gly Ala Cys
385

<210> SEQ ID NO 19
<211> LENGTH: 387
<212> TYPE: PRT
<213> ORGANISM: Artificial Sequence
<220> FEATURE:
<223> OTHER INFORMATION: synthetic fusion protein

<400> SEQUENCE: 19

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
                20                  25                  30

Arg Trp Gly Ser Glu Phe Ala Thr Met Val Ser Lys Gly Glu Glu Leu
            35                  40                  45

Phe Thr Gly Val Val Pro Ile Leu Val Glu Leu Asp Gly Asp Val Asn
    50                  55                  60

Gly His Lys Phe Ser Val Ser Gly Glu Gly Glu Gly Asp Ala Thr Tyr
65                  70                  75                  80

Gly Lys Leu Thr Leu Lys Phe Ile Cys Thr Thr Gly Lys Leu Pro Val
                85                  90                  95

Pro Trp Pro Thr Leu Val Thr Thr Phe Gly Tyr Gly Val Gln Cys Phe
                100                 105                 110

Ala Arg Tyr Pro Asp His Met Arg Gln His Asp Phe Phe Lys Ser Ala
            115                 120                 125

Met Pro Glu Gly Tyr Val Gln Glu Arg Thr Ile Phe Phe Lys Asp Asp
    130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                165                 170                 175

Ile Leu Gly His Lys Leu Glu Tyr Asn Tyr Asn Ser His Asn Val Tyr
            180                 185                 190

Ile Met Ala Asp Lys Gln Lys Asn Gly Ile Lys Val Asn Phe Lys Ile
    195                 200                 205

Arg His Asn Ile Glu Asp Gly Ser Val Gln Leu Ala Asp His Tyr Gln
    210                 215                 220

Gln Asn Thr Pro Ile Gly Asp Gly Pro Val Leu Leu Pro Asp Asn His
225                 230                 235                 240

Tyr Leu Ser Tyr Gln Ser Ala Leu Ser Lys Asp Pro Asn Glu Lys Arg
                245                 250                 255

Asp His Met Val Leu Leu Glu Phe Val Thr Ala Ala Gly Ile Thr Leu
```

```
                260                 265                 270
Gly Met Asp Glu Leu Tyr Lys Leu Glu Thr Asp Gln Thr Ser Leu Tyr
                275                 280                 285
Lys Lys Ala Gly Thr Met Ser Glu Glu Lys Pro Lys Glu Gly Val Lys
                290                 295                 300
Thr Glu Asn Asp His Ile Asn Leu Lys Val Ala Gly Gln Asp Gly Ser
305                 310                 315                 320
Val Val Gln Phe Lys Ile Lys Arg His Thr Pro Leu Ser Lys Leu Met
                325                 330                 335
Lys Ala Tyr Cys Glu Arg Gln Gly Leu Ser Met Arg Gln Ile Arg Phe
                340                 345                 350
Arg Phe Asp Gly Gln Pro Ile Asn Glu Thr Asp Thr Pro Ala Gln Leu
                355                 360                 365
Glu Met Glu Asp Glu Asp Thr Ile Asp Val Phe Gln Gln Gln Thr Gly
                370                 375                 380
Gly Ala Cys
385

<210> SEQ ID NO 20
<211> LENGTH: 371
<212> TYPE: PRT
<213> ORGANISM: Artificial Sequence
<220> FEATURE:
<223> OTHER INFORMATION: synthetic fusion protein

<400> SEQUENCE: 20

Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
                20                  25                  30
Arg Trp Gly Ser Glu Phe Ala Thr Met Val Ser Lys Gly Glu Glu Leu
                35                  40                  45
Phe Thr Gly Val Val Pro Ile Leu Val Glu Leu Asp Gly Asp Val Asn
            50                  55                  60
Gly His Lys Phe Ser Val Ser Gly Glu Gly Glu Gly Asp Ala Thr Tyr
65                  70                  75                  80
Gly Lys Leu Thr Leu Lys Phe Ile Cys Thr Thr Gly Lys Leu Pro Val
                85                  90                  95
Pro Trp Pro Thr Leu Val Thr Thr Phe Gly Tyr Gly Val Gln Cys Phe
                100                 105                 110
Ala Arg Tyr Pro Asp His Met Arg Gln His Asp Phe Phe Lys Ser Ala
                115                 120                 125
Met Pro Glu Gly Tyr Val Gln Glu Arg Thr Ile Phe Phe Lys Asp Asp
            130                 135                 140
Gly Asn Tyr Lys Thr Arg Ala Glu Val Lys Phe Glu Gly Asp Thr Leu
145                 150                 155                 160
Val Asn Arg Ile Glu Leu Lys Gly Ile Asp Phe Lys Glu Asp Gly Asn
                165                 170                 175
Ile Leu Gly His Lys Leu Glu Tyr Asn Tyr Asn Ser His Asn Val Tyr
                180                 185                 190
Ile Met Ala Asp Lys Gln Lys Asn Gly Ile Lys Val Asn Phe Lys Ile
                195                 200                 205
Arg His Asn Ile Glu Asp Gly Ser Val Gln Leu Ala Asp His Tyr Gln
            210                 215                 220
Gln Asn Thr Pro Ile Gly Asp Gly Pro Val Leu Leu Pro Asp Asn His
225                 230                 235                 240
```

```
Tyr Leu Ser Tyr Gln Ser Ala Leu Ser Lys Asp Pro Asn Glu Lys Arg
            245                 250                 255

Asp His Met Val Leu Glu Phe Val Thr Ala Ala Gly Ile Thr Leu
        260                 265                 270

Gly Met Asp Glu Leu Tyr Lys Leu Glu Thr Asp Gln Thr Ser Leu Tyr
            275                 280                 285

Lys Lys Ala Gly Thr Met Leu Ile Lys Val Lys Thr Leu Thr Gly Lys
        290                 295                 300

Glu Ile Glu Ile Asp Ile Glu Pro Thr Asp Lys Val Glu Arg Ile Lys
305                 310                 315                 320

Glu Arg Val Glu Glu Lys Glu Gly Ile Pro Pro Gln Gln Arg Leu
            325                 330                 335

Ile Tyr Ser Gly Lys Gln Met Asn Asp Glu Lys Thr Ala Ala Asp Tyr
            340                 345                 350

Lys Ile Leu Gly Gly Ser Val Leu His Leu Val Leu Ala Leu Arg Gly
            355                 360                 365

Gly Ala Cys
    370

<210> SEQ ID NO 21
<211> LENGTH: 122
<212> TYPE: PRT
<213> ORGANISM: Artificial Sequence
<220> FEATURE:
<223> OTHER INFORMATION: synthetic construct

<400> SEQUENCE: 21

Met Ser Tyr Tyr His His His His His His Leu Glu Ser Thr Ser Leu
1               5                   10                  15

Tyr Lys Lys Ala Gly Thr Met Cys Gly Gly Ser Asp Gln Glu Ala Lys
            20                  25                  30

Pro Ser Thr Glu Asp Leu Gly Asp Lys Lys Glu Gly Tyr Ile Lys
        35                  40                  45

Leu Lys Val Ile Gly Gln Asp Ser Ser Glu Ile His Phe Lys Val Lys
    50                  55                  60

Met Thr Thr His Leu Lys Lys Leu Lys Glu Ser Tyr Cys Gln Arg Gln
65                  70                  75                  80

Gly Val Pro Met Asn Ser Leu Arg Phe Leu Phe Glu Gly Gln Arg Ile
                85                  90                  95

Ala Asp Asn His Thr Pro Lys Glu Leu Gly Met Glu Glu Glu Asp Val
            100                 105                 110

Ile Glu Val Tyr Gln Glu Gln Thr Gly Gly
        115                 120

<210> SEQ ID NO 22
<211> LENGTH: 118
<212> TYPE: PRT
<213> ORGANISM: Artificial Sequence
<220> FEATURE:
<223> OTHER INFORMATION: synthetic construct

<400> SEQUENCE: 22

Met Ser Tyr Tyr His His His His His His Leu Glu Ser Thr Ser Leu
1               5                   10                  15

Tyr Lys Lys Ala Gly Thr Met Cys Gly Gly Ala Asp Glu Lys Pro Lys
            20                  25                  30

Glu Gly Val Lys Thr Glu Asn Asn Asp His Ile Asn Leu Lys Val Ala
        35                  40                  45
```

```
Gly Gln Asp Gly Ser Val Val Gln Phe Lys Ile Lys Arg His Thr Pro
        50                   55                     60

Leu Ser Lys Leu Met Lys Ala Tyr Cys Glu Arg Gln Gly Leu Ser Met
65                      70                  75                  80

Arg Gln Ile Arg Phe Arg Phe Asp Gly Gln Pro Ile Asn Glu Thr Asp
                    85                  90                  95

Thr Pro Ala Gln Leu Glu Met Glu Asp Glu Asp Thr Ile Asp Val Phe
                100                 105                 110

Gln Gln Gln Thr Gly Gly
            115

<210> SEQ ID NO 23
<211> LENGTH: 117
<212> TYPE: PRT
<213> ORGANISM: Artificial Sequence
<220> FEATURE:
<223> OTHER INFORMATION: synthetic construct

<400> SEQUENCE: 23

Met Ser Tyr Tyr His His His His His His Leu Glu Ser Thr Ser Leu
1               5                   10                  15

Tyr Lys Lys Ala Gly Thr Met Cys Gly Gly Ser Glu Glu Lys Pro Lys
                20                  25                  30

Glu Gly Val Lys Thr Glu Asn Asp His Ile Asn Leu Lys Val Ala Gly
                35                  40                  45

Gln Asp Gly Ser Val Val Gln Phe Lys Ile Lys Arg His Thr Pro Leu
        50                   55                     60

Ser Lys Leu Met Lys Ala Tyr Cys Glu Arg Gln Gly Leu Ser Met Arg
65                      70                  75                  80

Gln Ile Arg Phe Arg Phe Asp Gly Gln Pro Ile Asn Glu Thr Asp Thr
                    85                  90                  95

Pro Ala Gln Leu Glu Met Glu Asp Glu Asp Thr Ile Asp Val Phe Gln
                100                 105                 110

Gln Gln Thr Gly Gly
            115

<210> SEQ ID NO 24
<211> LENGTH: 101
<212> TYPE: PRT
<213> ORGANISM: Artificial Sequence
<220> FEATURE:
<223> OTHER INFORMATION: synthetic construct

<400> SEQUENCE: 24

Met Ser Tyr Tyr His His His His His His Leu Glu Ser Thr Ser Leu
1               5                   10                  15

Tyr Lys Lys Ala Gly Thr Met Cys Gly Gly Leu Ile Lys Val Lys Thr
                20                  25                  30

Leu Thr Gly Lys Glu Ile Glu Ile Asp Ile Glu Pro Thr Asp Lys Val
            35                  40                  45

Glu Arg Ile Lys Glu Arg Val Glu Glu Lys Glu Gly Ile Pro Pro Gln
        50                   55                     60

Gln Gln Arg Leu Ile Tyr Ser Gly Lys Gln Met Asn Asp Glu Lys Thr
65                      70                  75                  80

Ala Ala Asp Tyr Lys Ile Leu Gly Gly Ser Val Leu His Leu Val Leu
                    85                  90                  95

Ala Leu Arg Gly Gly
            100
```

<210> SEQ ID NO 25
<211> LENGTH: 369
<212> TYPE: PRT
<213> ORGANISM: Artificial Sequence
<220> FEATURE:
<223> OTHER INFORMATION: synthetic fusion protein

<400> SEQUENCE: 25

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Glu Phe Ala Thr Met Val Ser Lys Gly Glu Glu Leu
        35                  40                  45

Phe Thr Gly Val Val Pro Ile Leu Val Glu Leu Asp Gly Asp Val Asn
    50                  55                  60

Gly His Lys Phe Ser Val Ser Gly Glu Gly Glu Gly Asp Ala Thr Tyr
65                  70                  75                  80

Gly Lys Leu Thr Leu Lys Phe Ile Cys Thr Thr Gly Lys Leu Pro Val
                85                  90                  95

Pro Trp Pro Thr Leu Val Thr Thr Phe Gly Tyr Gly Val Gln Cys Phe
            100                 105                 110

Ala Arg Tyr Pro Asp His Met Arg Gln His Asp Phe Phe Lys Ser Ala
        115                 120                 125

Met Pro Glu Gly Tyr Val Gln Glu Arg Thr Ile Phe Phe Lys Asp Asp
    130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                165                 170                 175

Ile Leu Gly His Lys Leu Glu Tyr Asn Tyr Asn Ser His Asn Val Tyr
            180                 185                 190

Ile Met Ala Asp Lys Gln Lys Asn Gly Ile Lys Val Asn Phe Lys Ile
        195                 200                 205

Arg His Asn Ile Glu Asp Gly Ser Val Gln Leu Ala Asp His Tyr Gln
    210                 215                 220

Gln Asn Thr Pro Ile Gly Asp Gly Pro Val Leu Leu Pro Asp Asn His
225                 230                 235                 240

Tyr Leu Ser Tyr Gln Ser Ala Leu Ser Lys Asp Pro Asn Glu Lys Arg
                245                 250                 255

Asp His Met Val Leu Leu Glu Phe Val Thr Ala Ala Gly Ile Thr Leu
            260                 265                 270

Gly Met Asp Glu Leu Tyr Lys Leu Glu Thr Asp Gln Thr Ser Leu Tyr
        275                 280                 285

Lys Lys Ala Gly Thr Met Gln Ile Phe Val Lys Thr Leu Thr Gly Lys
    290                 295                 300

Thr Ile Thr Leu Glu Val Glu Pro Ser Asp Thr Ile Glu Asn Val Lys
305                 310                 315                 320

Ala Lys Ile Gln Asp Lys Glu Gly Ile Pro Pro Asp Gln Gln Arg Leu
                325                 330                 335

Ile Phe Ala Gly Lys Gln Leu Glu Asp Gly Arg Thr Leu Ser Asp Tyr
            340                 345                 350

Asn Ile Gln Lys Glu Ser Thr Leu His Leu Val Leu Arg Leu Arg Gly
        355                 360                 365
```

Gly

```
<210> SEQ ID NO 26
<211> LENGTH: 371
<212> TYPE: PRT
<213> ORGANISM: Artificial Sequence
<220> FEATURE:
<223> OTHER INFORMATION: synthetic fusion protein

<400> SEQUENCE: 26
```

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Glu Phe Ala Thr Met Val Ser Lys Gly Glu Glu Leu
        35                  40                  45

Phe Thr Gly Val Val Pro Ile Leu Val Glu Leu Asp Gly Asp Val Asn
    50                  55                  60

Gly His Lys Phe Ser Val Ser Gly Glu Gly Glu Gly Asp Ala Thr Tyr
65                  70                  75                  80

Gly Lys Leu Thr Leu Lys Phe Ile Cys Thr Thr Gly Lys Leu Pro Val
                85                  90                  95

Pro Trp Pro Thr Leu Val Thr Thr Phe Gly Tyr Gly Val Gln Cys Phe
            100                 105                 110

Ala Arg Tyr Pro Asp His Met Arg Gln His Asp Phe Phe Lys Ser Ala
        115                 120                 125

Met Pro Glu Gly Tyr Val Gln Glu Arg Thr Ile Phe Phe Lys Asp Asp
    130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                165                 170                 175

Ile Leu Gly His Lys Leu Glu Tyr Asn Tyr Asn Ser His Asn Val Tyr
            180                 185                 190

Ile Met Ala Asp Lys Gln Lys Asn Gly Ile Lys Val Asn Phe Lys Ile
        195                 200                 205

Arg His Asn Ile Glu Asp Gly Ser Val Gln Leu Ala Asp His Tyr Gln
    210                 215                 220

Gln Asn Thr Pro Ile Gly Asp Gly Pro Val Leu Leu Pro Asp Asn His
225                 230                 235                 240

Tyr Leu Ser Tyr Gln Ser Ala Leu Ser Lys Asp Pro Asn Glu Lys Arg
                245                 250                 255

Asp His Met Val Leu Leu Glu Phe Val Thr Ala Ala Gly Ile Thr Leu
            260                 265                 270

Gly Met Asp Glu Leu Tyr Lys Leu Glu Thr Gln Thr Ser Leu Tyr
        275                 280                 285

Lys Lys Ala Gly Thr Met Gln Ile Phe Val Lys Thr Leu Thr Gly Lys
    290                 295                 300

Thr Ile Thr Leu Glu Val Glu Pro Ser Asp Thr Ile Glu Asn Val Lys
305                 310                 315                 320

Ala Lys Ile Gln Asp Lys Glu Gly Ile Pro Pro Asp Gln Gln Arg Leu
                325                 330                 335

Ile Phe Ala Gly Lys Gln Leu Glu Asp Gly Arg Thr Leu Ser Asp Tyr
            340                 345                 350

Asn Ile Gln Lys Glu Ser Thr Leu His Leu Val Leu Arg Leu Arg Gly
        355                 360                 365

Gly Ala Cys
370

<210> SEQ ID NO 27
<211> LENGTH: 1713
<212> TYPE: DNA
<213> ORGANISM: Artificial Sequence
<220> FEATURE:
<223> OTHER INFORMATION: synthetic coding sequence for a synthetic fusion protein

<400> SEQUENCE: 27

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccttcaccta cggcgtgcag tgcttcgccc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaag gtctatatca ccgccgacaa gcagaagaac | 480 |
| ggcatcaagg tgaacttcaa gacccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaagggc | 720 |
| tcgagcccat caacaagttt gtacaaaaaa gcaggcacca tgttccaggc ggccgagcgc | 780 |
| ccccaggagt gggccatgga gggccccccgc gacgggctga gaaggagcg gctactggac | 840 |
| gaccgccacg acagcggcct ggactccatg aaagacgagg agtacgagca gatggtcaag | 900 |
| gagctgcagg agatccgcct cgagccgcag gaggtgccgc gcggctcgga gccctggaag | 960 |
| cagcagctca ccgaggacgg ggactcgttc ctgcacttgg ccatcatcca tgaagaaaag | 1020 |
| gcactgacca tggaagtgat ccgccaggtg aagggagacc tggccttcct caacttccag | 1080 |
| aacaacctgc agcagactcc actccacttg gctgtgatca ccaaccagcc agaaattgct | 1140 |
| gaggcacttc tgggagctgg ctgtgatcct gagctccgag actttcgagg aaataccccc | 1200 |
| ctacaccttg cctgtgagca gggctgcctg ccagcgtgg gagtcctgac tcagtcctgc | 1260 |
| accaccccgc acctccactc catcctgaag gctaccaact acaatggcca cacgtgtcta | 1320 |
| cacttagcct ctatccatgg ctacctgggc atcgtggagc ttttggtgtc cttgggtgct | 1380 |
| gatgtcaatg ctcaggagcc ctgtaatggc cggactgccc ttcacctcgc agtggacctg | 1440 |
| caaaatcctg acctggtgtc actcctgttg aagtgtgggg ctgatgtcaa cagagttacc | 1500 |
| taccagggct attctcccta ccagctcacc tggggccgcc aagcacccg gatacagcag | 1560 |
| cagctgggcc agctgacact agaaaacctt cagatgctgc cagagagtga ggatgaggag | 1620 |
| agctatgaca cagagtcaga gttcacggag ttcacagagg acgagctgcc ctatgatgac | 1680 |
| tgtgtgtttg gaggccagcg tctgacgtta tag | 1713 |